US012679824B2

(12) United States Patent
Lerner et al.

(10) Patent No.: US 12,679,824 B2
(45) Date of Patent: Jul. 14, 2026

(54) IMIDAZOLE-PYRAZOLE DERIVATIVES

(71) Applicant: Hoffmann-La Roche Inc., Little Falls, NJ (US)

(72) Inventors: Christian Lerner, Bottmingen (CH); Mingming Li, Shanghai (CN); Yongqiang Liu, Shanghai (CN); Sébastien Schmitt, Hagenthal-le-Bas (FR); Jianhua Wang, Shanghai (CN); Min Wang, Shanghai (CN); Yongguang Wang, Shanghai (CN); Song Yang, Shanghai (CN); Chengang Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 594 days.

(21) Appl. No.: 18/115,767

(22) Filed: Feb. 28, 2023

(65) Prior Publication Data

US 2023/0295123 A1 Sep. 21, 2023

Related U.S. Application Data

(63) Continuation of application No. PCT/EP2021/073821, filed on Aug. 30, 2021.

(30) Foreign Application Priority Data

Sep. 1, 2020 (WO) ................ PCT/CN2020/112833
Jul. 26, 2021 (WO) ................ PCT/CN2021/108461

(51) Int. Cl.

| | |
|---|---|
| ***C07D 403/02*** | (2006.01) |
| ***A61P 31/04*** | (2006.01) |
| ***C07D 401/14*** | (2006.01) |
| ***C07D 471/08*** | (2006.01) |
| ***C07D 487/04*** | (2006.01) |
| ***C07D 487/08*** | (2006.01) |

(52) U.S. Cl.

CPC ............ *C07D 401/14* (2013.01); *A61P 31/04* (2018.01); *C07D 471/08* (2013.01); *C07D 487/04* (2013.01); *C07D 487/08* (2013.01)

(58) Field of Classification Search

CPC .................................................... C07D 403/02

See application file for complete search history.

(56) References Cited

U.S. PATENT DOCUMENTS

| | | | |
|---|---|---|---|
| 11,390,604 | B2 | 7/2022 | Blanc et al. |
| 2020/0290998 | A1 | 9/2020 | Blanc et al. |
| 2022/0396565 | A1 | 12/2022 | Cheng et al. |
| 2023/0017532 | A1 | 1/2023 | Cheng et al. |

FOREIGN PATENT DOCUMENTS

| | | | |
|---|---|---|---|
| EP | 2226322 | A | 9/2010 |
| WO | 2010/096462 | A1 | 8/2010 |
| WO | 2017/17631 | | 2/2017 |
| WO | 2019/016782 | A1 | 1/2019 |
| WO | 2020/126954 | A1 | 6/2020 |
| WO | 2020/182648 | A1 | 9/2020 |
| WO | 2021/148420 | A1 | 7/2021 |
| WO | 2022/043486 | A1 | 3/2022 |
| WO | 2022/167631 | A1 | 8/2022 |

OTHER PUBLICATIONS

International Preliminary Report on Patentability for PCT/EP2020/055987, issued Aug. 25, 2021, pp. 1-6.
International Search Report for PCT/EP2020/055987, mailed Apr. 29, 2020, pp. 1-3.
International Preliminary Report on Patentability for PCT/EP2021/073821, issued Mar. 7, 2023, pp. 1-7.
International Search Report for PCT/EP2021/073821, mailed Oct. 29, 2021, pp. 1-3.
International Preliminary Report on Patentability for PCT/EP2021/073722, issued Feb. 28, 2023, pp. 1-6.
International Search Report for PCT/EP2021/073722, mailed Dec. 23, 2021, pp. 1-4.
International Search Report for PCT/EP2022/052812 (w/ Written Opinion), mailed May 3, 2022, pp. 1-8.

*Primary Examiner* — John S Kenyon
(74) *Attorney, Agent, or Firm* — Genentech, Inc.

(57) ABSTRACT

The invention provides novel imidazole pyrazole derivatives having the general formula (I), and pharmaceutically acceptable salts thereof, wherein $R^1$-$R^7$ are as described herein:

(I)

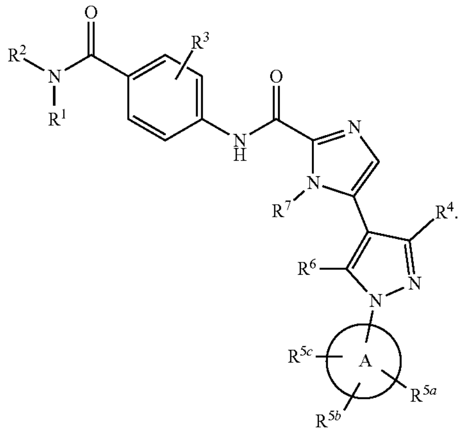

Further provided are pharmaceutical compositions including the compounds, processes of manufacturing the compounds and methods of using the compounds as medicaments, in particular methods of using the compounds as antibiotics for the treatment or prevention of bacterial infections and resulting diseases.

20 Claims, No Drawings

IMIDAZOLE-PYRAZOLE DERIVATIVES

CROSS-REFERENCE TO RELATED APPLICATIONS

This application is a Continuation of International Patent Application No. PCT/EP2021/073821, filed on Aug. 30, 2021, which claims benefit of priority to International Patent Application No. PCT/CN2021/108461, filed on Jul. 26, 2021, and International Patent Application No. PCT/CN2020/112833, filed on Sep. 1, 2020, each of which is incorporated herein by reference in its entirety.

BACKGROUND

The present invention relates to novel imidazole-pyrazole derivatives which exhibit antibacterial properties. The invention also relates to methods of using the compounds for the treatment or prevention of bacterial infections and resulting diseases, in particular for the treatment or prevention of infections with *Acinetobacter baumannii* and resulting diseases. *Acinetobacter baumannii* is a Gram-negative, aerobic, nonfermenting bacterium recognized over the last decades as an emerging pathogen with very limited treatment options. *A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents. *A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinants and shows an environmental persistence that allows its survival and spread in the nosocomial setting, making this organism a frequent cause of outbreaks of infection and an endemic, health care-associated pathogen.

Due to increasing antibiotic resistance to most if not all available therapeutic options, Muti-Drug Resistant (MDR) *A. baumannii* infections, especially those caused by Carbapenem resistant *A. baumannii*, are extremely difficult or even impossible to treat with high mortality rate as well as increased morbidity and length of stay in intensive care unit.

*Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii.*

The present invention provides novel compounds which exhibit activity against drug-susceptible as well as drug-resistant strains of *Acinetobacter baumannii.*

SUMMARY OF THE DISCLOSURE

In a first aspect, the present invention provides a compound of formula (I):

(I)

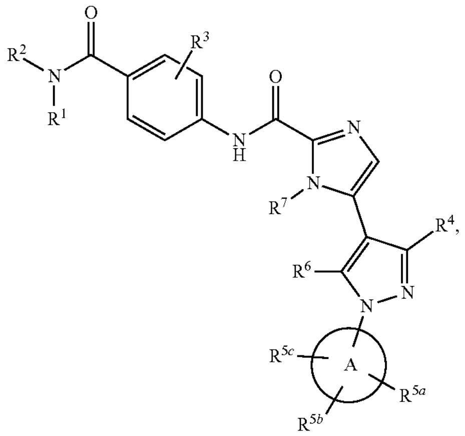

or a pharmaceutically acceptable salt thereof, wherein $R^1$-$R^7$ are as defined herein.

In one aspect, the present invention provides a process of manufacturing the compounds of formula (I) described herein.

In a further aspect, the present invention provides a compound of formula (I) as described herein, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a further aspect, the present invention provides a compound of formula (I) as described herein, or a pharmaceutically acceptable salt thereof, for use in the treatment or prevention of infections and resulting diseases caused by Gram-negative bacteria.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

DETAILED DESCRIPTION OF THE DISCLOSURE

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The following definitions are provided to facilitate understanding of certain terms used frequently herein and are not meant to limit the scope of the present disclosure. All references referred to herein are incorporated by reference in their entirety.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, sec-butyl, tert-butyl, and 2,2-dimethylpropyl. A particularly preferred, yet non-limiting example of alkyl is methyl.

The term "alkyldiyl" as used herein refers to a saturated linear or branched-chain divalent hydrocarbon radical of about 1 to 6 carbon atoms ($C_1$-$C_6$). Examples of alkyldiyl groups include, but are not limited to, methylene ($-CH_2-$), ethylene ($-CH_2CH_2-$), propylene ($-CH_2CH_2CH_2-$), and the like. An alkyldiyl group may also be referred to as an "alkylene" group.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "aminoalkyl" refers to an alkyl group, wherein at least one of the hydrogen atoms of the alkyl group has been replaced by an amino group. Preferably, "aminoalkyl" refers to an alkyl group wherein 1, 2 or 3 hydrogen atoms of the alkyl group have been replaced by an amino group. Preferred, yet non-limiting examples of aminoalkyl are aminomethyl and 1-aminoethyl.

The term "aminoalkoxy" refers to an alkoxy group, wherein at least one of the hydrogen atoms of the alkoxy group has been replaced by an amino group. Preferably, "aminoalkoxy" refers to an alkoxy group wherein 1, 2 or 3 hydrogen atoms of the alkoxy group have been replaced by an amino group. Preferred, yet non-limiting examples of aminoalkoxy are aminomethoxy and 1-aminoethoxy.

The term "heterocyclyl" refers to a saturated or partly unsaturated mono- or bicyclic, preferably monocyclic ring system of 3 to 10 ring atoms, preferably 3 to 8 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl, azetidin-2-yl, oxetan-3-yl, oxetan-2-yl, 1-piperidinyl, 2-piperidinyl, 3-piperidinyl, 4-piperidinyl, pyrrolidinyl (e.g. pyrrolidin-2-yl), morpholino, morpholin-2-yl, morpholin-3-yl, pyrrolidinyl (e.g., pyrrolidin-3-yl), piperazinyl (e.g., piperazin-1-yl), 3-azabicyclo[3.1.0]hexan-6-yl, or 2,5-diazabicyclo[2.2.1]heptan-2-yl. Particularly preferred, yet non-limiting examples of heterocyclyl include piperidyl, piperazinyl, pyrrolidinyl and 3-azabicyclo[3.1.0]hexan-6-yl.

The term "heteroaryl" refers to a mono- or multivalent, monocyclic or bicyclic, preferably bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O and N. Some preferred, yet non-limiting examples of heteroaryl include pyrimidinyl, pyrazolyl, pyridyl, pyrazinyl, imidazolyl, pyridazinyl, thiazolyl and 1H-pyrazolo[3,4-d]pyrimidin-6-yl. A particularly preferred, yet non-limiting examples of heteroaryl is pyridyl.

The term "hydroxy" refers to an $-OH$ group.

The term "amino" refers to an $-NH_2$ group.

The term "cyano" refers to a $-CN$ (nitrile) group.

The term "nitro" refers to a group $-NO_2$.

The term "carbamoyl" refers to a $-C(O)NH_2$ group.

The term "carbonyl" refers to a carbon radical having two of the four covalent bonds shared with an oxygen atom ($C=O$).

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Preferred, yet non-limiting examples of haloalkyl are trifluoromethyl, trifluoroethyl, 2-fluoroethyl, and 2,2-difluoroethyl. A particularly preferred, yet non-limiting example of haloalkyl is trifluoromethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy are difluoromethoxy and trifluoromethoxy.

The term "alkoxyalkoxy" refers to an alkoxy group, wherein at least one of the hydrogen atoms of the alkoxy group has been replaced by an alkoxy group, preferably methoxy. Preferably, "alkoxyalkoxy" refers to an alkoxy group wherein 1, 2 or 3 hydrogen atoms of the alkoxy group have been replaced by an alkoxy group, most preferably methoxy. A particularly preferred, yet non-limiting example of alkoxyalkoxy is 2-methoxyethoxy.

The term "alkoxyalkyl" refers to an alkyl group, wherein at least one of the hydrogen atoms of the alkyl group has been replaced by an alkoxy group. Preferably, "alkoxyalkyl" refers to an alkyl group wherein 1, 2 or 3 hydrogen atoms of the alkyl group have been replaced by an alkoxy group. A particular, yet non-limiting example of an alkoxyalkyl group is methoxymethyl.

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl, hydroxyethyl (e.g. 2-hydroxyethyl), and 3-hydroxy-3-methyl-butyl.

The term "carbamoylalkyl" refers to an alkyl group, wherein at least one of the hydrogen atoms of the alkyl group has been replaced by a carbamoyl group. Preferably, "carbamoylalkyl" refers to an alkyl group wherein 1, 2 or 3 hydrogen atoms, most preferably 1 hydrogen atom of the alkyl group have been replaced by a carbamoyl group. Preferred, yet non-limiting examples of carbamoylalkyl are 2-amino-2-oxo-ethyl, 3-amino-3-oxo-propyl and 4-amino-4-oxo-butyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochlorides, fumarates, lactates (in particular derived from L-(+)-lactic acid), tartrates (in particular derived from L-(+)-tartaric acid) and trifluoroacetates.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "mammal" as used herein includes both humans and non-humans and includes but is not limited to humans, non-human primates, canines, felines, murines, bovines, equines, and porcines. In a particularly preferred embodiment, the term "mammal" refers to humans.

The term "nosocomial infection" refers to a hospital-acquired infection (HAI), which is an infection that is acquired in a hospital or other health care facility. To emphasize both hospital and nonhospital settings, it is sometimes instead called a health care-associated infection (HAI or HCAI). Such an infection can be acquired in hospitals, nursing homes, rehabilitation facilities, outpatient clinics, or other clinical settings.

Compounds of the Invention

In a first aspect, the present invention provides a compound of formula (I):

(I)

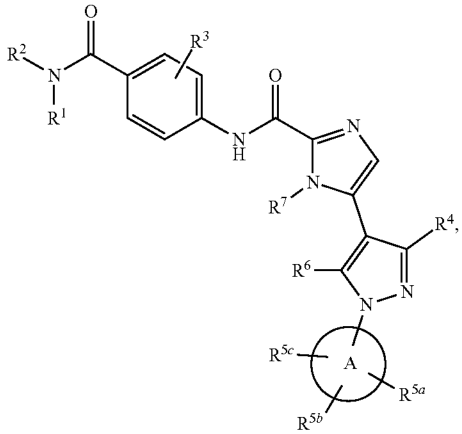

or a pharmaceutically acceptable salt thereof, wherein:

$R^1$ and $R^2$, taken together with the nitrogen atom to which they are attached, form a group of formula (II), (III) or (IV)

(II)

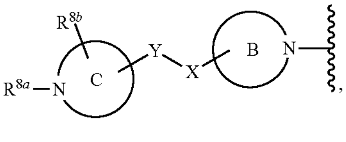

-continued (III)

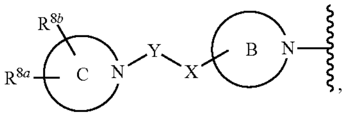

(IV)

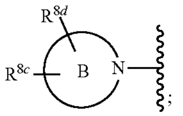

or $R^1$ is selected from $C_1$-$C_6$-alkyl, amino-$C_1$-$C_6$-alkyl, amino-$C_1$-$C_6$-alkoxy-$C_1$-$C_6$-alkyl, and a group

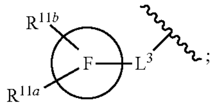

and $R^2$ is selected from hydrogen and $C_1$-$C_6$-alkyl;

$R^3$ is selected from hydrogen, halogen, $C_1$-$C_6$-alkyl and $C_1$-$C_6$-alkoxy;

$R^4$ and $R^6$ are each independently selected from hydrogen, $C_1$-$C_6$-alkyl, $C_1$-$C_6$-alkoxy, cyano, halo-$C_1$-$C_6$-alkyl and halo-$C_1$-$C_6$-alkoxy;

$R^{5a}$, $R^{5b}$ and $R^{5c}$ are each independently selected from hydrogen, halogen, hydroxy, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, (3- to 14-membered heterocyclyl)-C(O)—NH—, carbamoyl, and nitro;

$R^7$ is selected from hydrogen, $C_1$-$C_6$-alkyl and halo-$C_1$-$C_6$-alkyl;

$R^{8a}$ is selected from hydrogen, $C_1$-$C_6$-alkyl, carbamoyl-$C_1$-$C_6$-alkyl, and a group

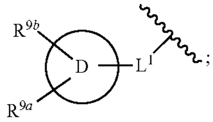

$R^{8b}$ is selected from hydrogen, hydroxy, oxo, hydroxy-$C_1$-$C_6$-alkyl, a group

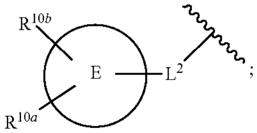

$R^{8c}$ is selected from hydrogen, $C_1$-$C_6$-alkyl, amino-$C_1$-$C_6$-alkyl, amino, $C_1$-$C_6$-alkyl-NH—, and $C_1$-$C_6$-alkoxy-$C_1$-$C_6$-alkyl;

$R^{8d}$ is hydrogen or $C_1$-$C_6$-alkyl;

$R^{9a}$, $R^{9b}$, $R^{10a}$, $R^{10b}$, $R^{12a}$ and $R^{12b}$ are each independently selected from hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro and hydroxy;

$R^{11a}$ and $R^{11b}$ are each independently selected from hydrogen, halogen, $C_1$-$C_6$-alkyl, $C_1$-$C_6$-alkoxy, halo-$C_1$-$C_6$-alkyl, amino-$C_1$-$C_6$-alkyl, hydroxy-$C_1$-$C_6$-alkyl, halo-$C_1$-$C_6$-alkoxy, amino, nitro, hydroxy and a group

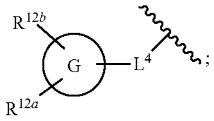

Y is carbonyl and X is selected from a covalent bond, NH, N($C_1$-$C_6$-alkyl), NH—$C_1$-$C_6$-alkyldiyl, and $C_1$-$C_6$-alkyldiyl; or X is carbonyl and Y is selected from a covalent bond, NH, N($C_1$-$C_6$-alkyl), NH—$C_1$-$C_6$-alkyldiyl, and $C_1$-$C_6$-alkyldiyl;

X is $C_1$-$C_6$-alkyldiyl and Y is a covalent bond;

$L^1$ and $L^3$ are each independently selected from a covalent bond, —C(O)—NH—$C_1$-$C_6$-alkyldiyl-, —$C_1$-$C_6$-alkyldiyl-NH—C(O)—, —C(O)—NH—$C_1$-$C_6$-alkoxy-$C_1$-$C_6$-alkyldiyl-, —$C_1$-$C_6$-alkoxy-$C_1$-$C_6$-alkyldiyl-NH—C(O)—, carbonyl and $C_1$-$C_6$-alkyldiyl;

$L^2$ and $L^4$ are each independently selected from a covalent bond, carbonyl, —O—, —NH—C(O)—, —C(O)—NH—, —C(O)—NH—$C_1$-$C_6$-alkyldiyl-, —$C_1$-$C_6$-alkyldiyl-NH—C(O)—, and $C_1$-$C_6$-alkyldiyl;

A is 5- to 14-membered heteroaryl;

B, C, D, E and G are each independently selected from 3- to 14-membered heterocyclyl and 5- to 14-membered heteroaryl; and F is selected from 3- to 14-membered heterocyclyl and $C_3$-$C_{10}$-cycloalkyl.

In one embodiment, the present invention provides a compound of formula (I) as described herein, or a pharmaceutically acceptable salt thereof, wherein $R^1$ and $R^2$, taken together with the nitrogen atom to which they are attached, form a group of formula (II), (III) or (IV):

(II)

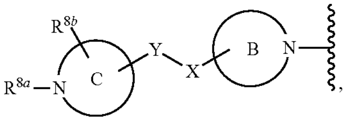

(III)

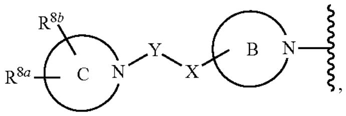

(IV)

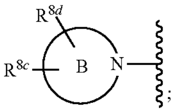

or $R^1$ is selected from $C_1$-$C_6$-alkyl, amino-$C_1$-$C_6$-alkyl, amino-$C_1$-$C_6$-alkoxy-$C_1$-$C_6$-alkyl, and a group

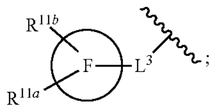

and $R^2$ is selected from hydrogen and $C_1$-$C_6$-alkyl;

$R^{9a}$ is hydrogen or hydroxy;

$R^{9b}$, $R^{10b}$, and $R^{12b}$ are each hydrogen;

$R^{8a}$ is selected from hydrogen, $C_1$-$C_6$-alkyl, carbamoyl-$C_1$-$C_6$-alkyl and a group

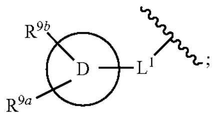

$R^{8b}$ is selected from hydrogen, hydroxy, oxo, hydroxy-$C_1$-$C_6$-alkyl, and a group

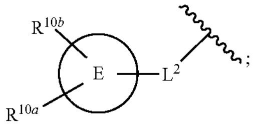

$R^{8c}$ is selected from hydrogen, $C_1$-$C_6$-alkyl, amino-$C_1$-$C_6$-alkyl, amino, $C_1$-$C_6$-alkyl-NH—, and $C_1$-$C_6$-alkoxy-$C_1$-$C_6$-alkyl;

$R^{8d}$ is hydrogen or $C_1$-$C_6$-alkyl;

$R^{10a}$ is selected from amino and nitro;

$R^{10a}$ is selected from hydrogen, amino-$C_1$-$C_6$-alkyl, hydroxy-$C_1$-$C_6$-alkyl, amino, hydroxy and a group

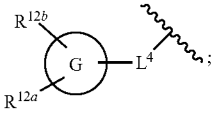

$R^{11b}$ is selected from hydrogen, halo-$C_1$-$C_6$-alkyl, and hydroxy-$C_1$-$C_6$-alkyl;

$R^{12a}$ is selected from hydrogen and hydroxy;

X is carbonyl and Y is a covalent bond or $C_1$-$C_6$-alkyldiyl; or

X is selected from NH, N($C_1$-$C_6$-alkyl), and NH—$C_1$-$C_6$-alkyldiyl; and Y is carbonyl; or X is $C_1$-$C_6$-alkyldiyl and Y is a covalent bond;

$L^1$ is $C_1$-$C_6$-alkyldiyl;

$L^2$ is —O—;

$L^3$ is selected from a covalent bond, C(O)—NH—$C_1$-$C_6$-alkyldiyl-, —C(O)—NH—$C_1$-$C_6$-alkoxy-$C_1$-$C_6$-alkyldiyl-, and $C_1$-$C_6$-alkyldiyl;

$L^4$ is selected from carbonyl, —C(O)—NH—, and —C(O)—NH—$C_1$-$C_6$-alkyldiyl-;

B, C, D and G are each independently 3- to 14-membered heterocyclyl;

E is 5- to 14-membered heteroaryl; and

F is selected from 5- to 14-membered heteroaryl, $C_3$-$C_{10}$-cycloalkyl, and 3- to 14-membered heterocyclyl.

In a preferred embodiment, the present invention provides a compound of formula (I) as described herein, or a pharmaceutically acceptable salt thereof, wherein $R^1$ and $R^2$, taken together with the nitrogen atom to which they are attached, form a group of formula (II), (III) or (IV):

(II)

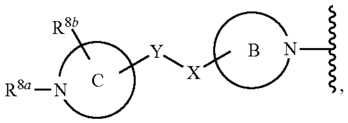

(III)

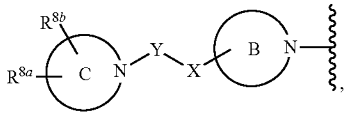

(IV)

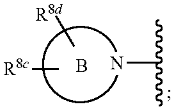

or $R^1$ is a group

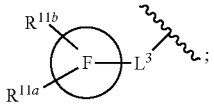

and $R^2$ is $C_1$-$C_6$-alkyl;

$R^{8a}$ is selected from hydrogen and $C_1$-$C_6$-alkyl;

$R^{8b}$ is selected from hydrogen and hydroxy;

$R^{8c}$ is hydrogen or $C_1$-$C_6$-alkyl-NH—;

$R^{8d}$ is hydrogen;

$R^{11a}$ is a group

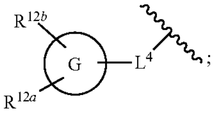

$R^{11b}$ is hydrogen;

$R^{12a}$ is hydroxy;

$R^{12b}$ is hydrogen;

X is carbonyl;

Y is a covalent bond or $C_1$-$C_6$-alkyldiyl;

$L^3$ is a covalent bond;

$L^4$ is carbonyl; and

B, C, F and G are each independently 3- to 14-membered heterocyclyl.

In a particularly preferred embodiment, the present invention provides a compound of formula (I) as described herein, or a pharmaceutically acceptable salt thereof, wherein $R^1$ and $R^2$, taken together with the nitrogen atom to which they are attached, form a group of formula (II), (III) or (IV):

(II)

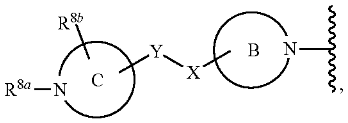

-continued (III)

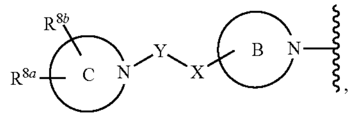

(IV)

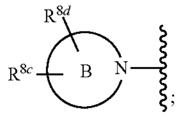

or $R^1$ is a group

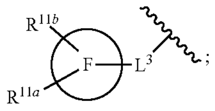

and $R^2$ is methyl;

$R^{8a}$ is selected from hydrogen and methyl;

$R^{8b}$ is selected from hydrogen and hydroxy;

$R^{8c}$ is hydrogen or methyl-NH—;

$R^{8d}$ is hydrogen;

$R^{11a}$ is a group

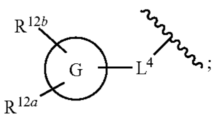

$R^{11b}$ is hydrogen $R^{12a}$ is hydroxy;

$R^{12b}$ is hydrogen;

X is carbonyl;

Y is a covalent bond or —$CH_2$—;

$L^3$ is a covalent bond;

$L^4$ is carbonyl;

B is selected from piperazinyl, piperidyl, and 2,8-diazaspiro[4.5]decan-8-yl;

C is selected from piperidyl and pyrrolidinyl;

F is piperidyl; and

G is pyrrolidinyl.

In one embodiment, the present invention provides a compound of formula (I) as described herein, or a pharmaceutically acceptable salt thereof, wherein A is 5- to 14-membered heteroaryl;

$R^{5a}$ is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, (3- to 14-membered heterocyclyl)-C(O)—NH—, carbamoyl and nitro;

$R^{5b}$ is selected from hydrogen, halogen, and amino; and $R^{5c}$ is hydrogen.

In a preferred embodiment, the present invention provides a compound of formula (I) as described herein, or a pharmaceutically acceptable salt thereof, wherein A is 5- to 14-membered heteroaryl;

$R^{5a}$ is selected from halogen, $C_1$-$C_6$-alkyl, $C_1$-$C_6$-alkoxy, hydroxy-$C_1$-$C_6$-alkyl, amino-$C_1$-$C_6$-alkyl, $C_1$-$C_6$-alkyl-NH—, amino-$C_1$-$C_6$-alkyl-NH—, and amino;

$R^{5b}$ is hydrogen or amino; and $R^{5c}$ is hydrogen.

In a particularly preferred embodiment, the present invention provides a compound of formula (I) as described herein, or a pharmaceutically acceptable salt thereof, wherein A is pyridyl;

$R^{5a}$ is selected from fluoro, methyl, methoxy, hydroxymethyl, methylamino, 2-aminoethyl-NH—, and amino;

$R^{5b}$ is hydrogen or amino; and $R^{5c}$ is hydrogen.

In one embodiment, the present invention provides a compound of formula (I) as described herein, or a pharmaceutically acceptable salt thereof, wherein:

$R^1$ and $R^2$, taken together with the nitrogen atom to which they are attached, form a group of formula (II), (III) or (IV):

(II)

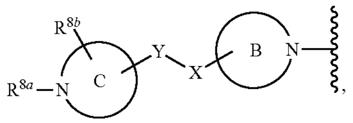

(III)

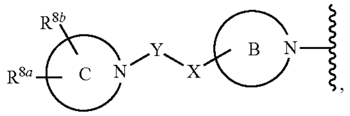

(IV)

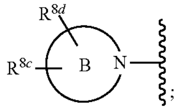

or $R^1$ is selected from $C_1$-$C_6$-alkyl, amino-$C_1$-$C_6$-alkyl, amino-$C_1$-$C_6$-alkoxy-$C_1$-$C_6$-alkyl, and a group

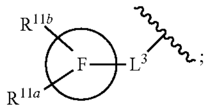

and $R^2$ is selected from hydrogen and $C_1$-$C_6$-alkyl;

$R^3$ is halogen or $C_1$-$C_6$-alkyl;

$R^4$ is selected from $C_1$-$C_6$-alkyl, $C_1$-$C_6$-alkoxy, cyano and halo-$C_1$-$C_6$-alkyl;

$R^{5a}$ is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, (3- to 14-membered heterocyclyl)-C(O)—NH—, carbamoyl and nitro;

$R^{5b}$ is selected from hydrogen, halogen, and amino;

$R^{5c}$ is hydrogen;

$R^6$ is selected from hydrogen and halo-$C_1$-$C_6$-alkyl;

$R^7$ is $C_1$-$C_6$-alkyl;

$R^{8a}$ is selected from hydrogen, $C_1$-$C_6$-alkyl, carbamoyl-$C_1$-$C_6$-alkyl and a group

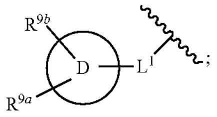

$R^{8b}$ is selected from hydrogen, hydroxy, oxo, hydroxy-$C_1$-$C_6$-alkyl, and a group

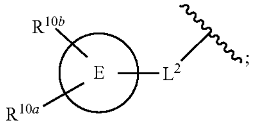

$R^{8c}$ is selected from hydrogen, $C_1$-$C_6$-alkyl, amino-$C_1$-$C_6$-alkyl, amino, $C_1$-$C_6$-alkyl-NH—, and $C_1$-$C_6$-alkoxy-$C_1$-$C_6$-alkyl;

$R^{8d}$ is hydrogen or $C_1$-$C_6$-alkyl;

$R^{9a}$ is hydrogen or hydroxy;

$R^{9b}$, $R^{10b}$, and $R^{12b}$ are each hydrogen;

$R^{10a}$ is selected from amino and nitro;

$R^{11a}$ is selected from hydrogen, amino-$C_1$-$C_6$-alkyl, hydroxy-$C_1$-$C_6$-alkyl, amino, hydroxy and a group

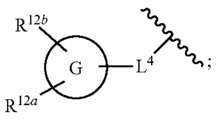

$R^{11b}$ is selected from hydrogen, halo-$C_1$-$C_6$-alkyl, and hydroxy-$C_1$-$C_6$-alkyl;

$R^{12a}$ is selected from hydrogen and hydroxy;

X is carbonyl and Y is a covalent bond or $C_1$-$C_6$-alkyldiyl; or

X is selected from NH, N($C_1$-$C_6$-alkyl), and NH—$C_1$-$C_6$-alkyldiyl; and Y is carbonyl; or X is $C_1$-$C_6$-alkyldiyl and Y is a covalent bond;

$L^1$ is $C_1$-$C_6$-alkyldiyl;

$L^2$ is —O—;

$L^3$ is selected from a covalent bond, C(O)—NH—$C_1$-$C_6$-alkyldiyl-, —C(O)—NH—$C_1$-$C_6$-alkoxy-$C_1$-$C_6$-alkyldiyl-, and $C_1$-$C_6$-alkyldiyl;

$L^4$ is selected from carbonyl, —C(O)—NH—, and —C(O)—NH—$C_1$-$C_6$-alkyldiyl-;

A is 5- to 14-membered heteroaryl;

B, C, D and G are each independently 3- to 14-membered heterocyclyl;

E is 5- to 14-membered heteroaryl; and

F is selected from 5- to 14-membered heteroaryl, $C_3$-$C_{10}$-cycloalkyl, and 3- to 14-membered heterocyclyl.

In a preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II), (III) or (IV):

(II)

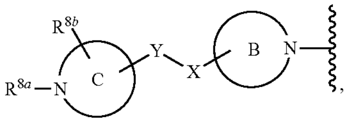

(III)

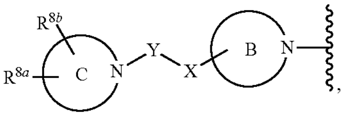

(IV)

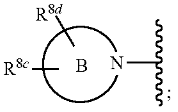

or $R^1$ is a group

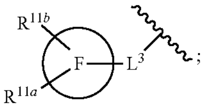

and $R^2$ is $C_1$-$C_6$-alkyl;

$R^3$ is halogen;

$R^4$ is halo-$C_1$-$C_6$-alkyl;

$R^{5a}$ is selected from halogen, $C_1$-$C_6$-alkyl, $C_1$-$C_6$-alkoxy, hydroxy-$C_1$-$C_6$-alkyl, amino-$C_1$-$C_6$-alkyl, $C_1$-$C_6$-alkyl-NH—, amino-$C_1$-$C_6$-alkyl-NH—, and amino;

$R^{5b}$ is hydrogen or amino;

$R^{5c}$ and $R^6$ are hydrogen;

$R^7$ is $C_1$-$C_6$-alkyl;

$R^{8a}$ is selected from hydrogen and $C_1$-$C_6$-alkyl;

$R^{8b}$ is selected from hydrogen and hydroxy;

$R^{8c}$ is hydrogen or $C_1$-$C_6$-alkyl-NH—;

$R^{8d}$ is hydrogen;

$R^{11a}$ is a group

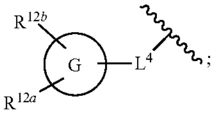

$R^{11b}$ is hydrogen;

$R^{12a}$ is hydroxy;

$R^{12b}$ is hydrogen;

X is carbonyl;

Y is a covalent bond or $C_1$-$C_6$-alkyldiyl;

$L^3$ is a covalent bond;

$L^4$ is carbonyl;

A is 5- to 14-membered heteroaryl;

B, C, F and G are each independently 3- to 14-membered heterocyclyl.

In a particularly preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II), (III) or (IV):

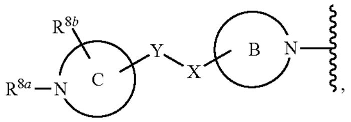

(II)

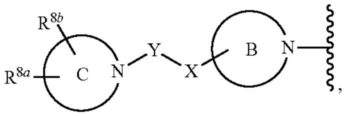

(III)

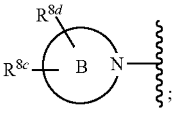

(IV)

or $R^1$ is a group

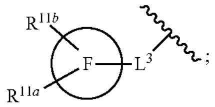

and $R^2$ is methyl;

$R^3$ is chloro;

$R^4$ is $CF_3$;

$R^{5a}$ is selected from fluoro, methyl, methoxy, hydroxymethyl, methylamino, 2-aminoethyl-NH—, and amino;

$R^{5b}$ is hydrogen or amino;

$R^{5c}$ and $R^6$ are hydrogen;

$R^7$ is methyl;

$R^{8a}$ is selected from hydrogen and methyl;

$R^{8b}$ is selected from hydrogen and hydroxy;

$R^{8c}$ is hydrogen or methyl-NH—;

$R^{8d}$ is hydrogen;

$R^{11a}$ is a group

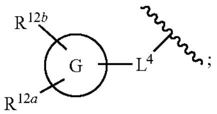

$R^{11b}$ is hydrogen $R^{12a}$ is hydroxy;

$R^{12b}$ is hydrogen;

X is carbonyl;

Y is a covalent bond or —$CH_2$—;

$L^3$ is a covalent bond;

$L^4$ is carbonyl;

A is pyridyl;

B is selected from piperazinyl, piperidyl, and 2,8-diazaspiro[4.5]decan-8-yl;

C is selected from piperidyl and pyrrolidinyl;

F is piperidyl; and

G is pyrrolidinyl.

In one embodiment, the present invention provides a compound of formula (I) as described herein, or a pharmaceutically acceptable salt thereof, wherein the compound of formula (I) is selected from the specific examples provided herein, in particular:

N-[3-Chloro-4-[4-(piperidine-4-carbonyl)piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(4-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-(5-chloro-2-pyridyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(5-methoxypyrimidin-2-yl)-3-(trifluoromethyl)pyrazol-4-yl]-1-methyl-imidazole-2-carboxamide;

5-[1-(5-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-[5-(2-methoxyethoxy)pyrimidin-2-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(5-fluoropyrimidin-2-yl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-(1h-pyrazolo[3,4-d]pyrimidin-6-yl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[3-(trifluoromethyl)-1-[3-(trifluoromethyl)-2-pyridyl]pyrazol-4-yl]imidazole-2-carboxamide;

N-[3-chloro-4-[4-(piperidine-4-carbonyl)piperazine-1-carbonyl]phenyl]-1-methyl-5-[1-(2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-(4-methoxy-2-pyridyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide;

5-[1-[4-(2-aminoethoxy)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(4-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-1-methyl-5-[1-[4-(methylamino)pyrimidin-2-yl]-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[4-(dimethylamino)pyrimidin-2-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[4-(dimethylamino)pyrimidin-2-yl]-5-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[4-(2-methoxyethylamino)pyrimidin-2-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-pyrazin-2-yl-3-(trifluoromethyl)pyrazol-4-yl]imidazole-2-carboxamide;

N-[3-Chloro-4-[4-(piperidine-4-carbonyl)piperazine-1-carbonyl]phenyl]-5-[1-[5-(dimethylamino)pyrimidin-2-yl]-3-(trifluoromethyl)pyrazol-4-yl]-1-methyl-imidazole-2-carboxamide;

5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-[6-(dimethylamino)pyridazin-3-yl]-3-(trifluoromethyl)pyrazol-4-yl]-1-methyl-imidazole-2-carboxamide;

5-[1-(5-Amino-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-[5-(2-methoxyethylamino)-2-pyridyl]-3-(trifluoromethyl)pyrazol-4-yl]-1-methyl-imidazole-2-carboxamide;

5-[1-[5-[(3-amino-3-oxo-propyl)amino]-2-pyridyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(4-hydroxypiperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-(4-methoxypyrimidin-2-yl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(2-methoxypyrimidin-4-yl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[[1-(piperidine-4-carbonyl)-4-piperidyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S)-morpholine-3-carbonyl]piperazine-1-carbonyl]phenyl]-1-methyl-imidazole-2-carboxamide;

5-[1-(5-amino-2-pyridyl)-3-(difluoromethyl)pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-methoxy-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-cyano-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-methyl-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-ethyl-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(6-aminopyridazin-3-yl)-3-(trifluoromethyl)pyrazol-4-yl]-N-[3-chloro-4-[4-(1-methylpiperidine-4-carbonyl)piperazine-1-carbonyl]phenyl]-1-methyl-imidazole-2-carboxamide;

N-[3-chloro-4-[4-(1-methylpiperidine-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide;

5-[1-(5-amino-2-pyridyl)-3-(trifluoromethyl)pyrazol-4-yl]-N-[3-chloro-4-[4-[2-(3-hydroxypyrrolidin-1-yl)acetyl]piperazine-1-carbonyl]phenyl]-1-methyl-imidazole-2-carboxamide;

N-[3-chloro-4-[4-[(2S,3S)-3-hydroxypyrrolidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(4-hydroxypiperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[(2S,3S)-3-hydroxypyrrolidine-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[2-(3-hydroxypyrrolidin-1-yl)acetyl]piperazine-1-carbonyl]phenyl]-1-methyl-5-[1-[5-(methylamino)-2-pyridyl]-3-(trifluoromethyl)pyrazol-4-yl]imidazole-2-carboxamide;

1-methyl-5-[1-[5-(methylamino)-2-pyridyl]-3-(trifluoromethyl)pyrazol-4-yl]-N-[3-methyl-4-[4-(piperidine-4-carbonyl)piperazine-1-carbonyl]phenyl]imidazole-2-carboxamide;

N-[3-chloro-4-[4-[(2S,4R)-4-hydroxypyrrolidine-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[1-(2-methoxyethyl)pyrazol-4-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[1-(2-methoxyethyl)-5-methyl-pyrazol-4-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[1-(2-methoxyethyl)imidazol-4-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-(1-methylimidazol-4-yl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(5-methyl-1H-pyrazol-4-yl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(4-methyl-1H-pyrazol-5-yl)-3-(trifluoromethyl)pyrazol-4-yl]imidazole-2-carboxamide;

N-[4-[4-[(1R,5S)-3-Azabicyclo[3.1.0]hexane-6-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

N-[3-chloro-4-[[(1R,5S)-3-[(2S,4R)-4-hydroxypyrrolidine-2-carbonyl]-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide;

N-[3-chloro-4-[[(1S,5R)-3-(piperidine-4-carbonyl)-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide;

N-[3-chloro-4-[4-[(3S,4R)-3-hydroxypiperidine-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[4-[4-[1-(Azetidin-3-ylmethyl)piperidine-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

5-[1-(5-Amino-2-pyridyl)-3-(trifluoromethyl)pyrazol-4-yl]-N-[3-chloro-4-[4-(piperazine-1-carbonyl)piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[3-(hydroxymethyl)piperazine-1-carbonyl]piperidine-1-carbonyl]phenyl]-1-methyl-imidazole-2-carboxamide;

5-[1-(5-Amino-2-pyridyl)-3-(trifluoromethyl)pyrazol-4-yl]-N-[3-chloro-4-[4-[(2-oxopiperazin-1-yl)methyl]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(1H-pyrazol-3-ylmethylcarbamoyl)phenyl]-1-methyl-imidazole-2-carboxamide;

N-[3-Chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide;

N-[4-[(3R)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide;

N-[4-(3-aminopropylcarbamoyl)-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(4-piperidylmethylcarbamoyl)phenyl]-1-methyl-imidazole-2-carboxamide;

5-[1-(5-amino-2-pyridyl)-3-(trifluoromethyl)pyrazol-4-yl]-N-[3-chloro-4-(4-piperidylmethylcarbamoyl)phenyl]-1-methyl-imidazole-2-carboxamide;

5-[1-(5-amino-2-pyridyl)-3-(trifluoromethyl)pyrazol-4-yl]-N-[3-chloro-4-[4-(methylamino)piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[(3-methylolpyrrolidin-3-yl)carbamoyl]phenyl]-1-methyl-imidazole-2-carboxamide;

N-[4-[[1-(aminomethyl)cyclopropyl]carbamoyl]-3-chloro-phenyl]-5-[1-(5-amino-2-pyridyl)-3-(trifluoromethyl)pyrazol-4-yl]-1-methyl-imidazole-2-carboxamide;

N-[4-[(3S)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(2,8-diazaspiro[4.5]decane-8-carbonyl)phenyl]-1-methyl-imidazole-2-carboxamide;

N-[3-chloro-4-[4-(1-methylpiperidine-4-carbonyl)piperazine-1-carbonyl]phenyl]-5-[1-[4-(methoxymethyl)-1H-pyrazol-3-yl]-3-(trifluoromethyl)pyrazol-4-yl]-1-methyl-imidazole-2-carboxamide;

5-[1-(6-amino-3-pyridyl)-3-(trifluoromethyl)pyrazol-4-yl]-N-[3-chloro-4-(4-isonipecotoylpiperazine-1-carbonyl)phenyl]-1-methyl-imidazole-2-carboxamide;

N-[4-[cis-(3-aminocyclobutyl)carbamoyl]-3-chloro-phenyl]-5-[1-(5-amino-2-pyridyl)-3-(trifluoromethyl)pyrazol-4-yl]-1-methyl-imidazole-2-carboxamide;

N-[4-(2,3,3a,4,6,6a-hexahydro-1H-pyrrolo[3,4-c]pyrrole-5-carbonyl)-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[methyl(4-piperidyl)carbamoyl]phenyl]-1-methyl-imidazole-2-carboxamide;

N-[4-[4-(aminomethyl)piperidine-1-carbonyl]-3-chloro-phenyl]-5-[1-(5-amino-2-pyridyl)-3-(trifluoromethyl)pyrazol-4-yl]-1-methyl-imidazole-2-carboxamide;

N-[4-[[3-(aminomethyl)-3-(chloromethyl)cyclobutyl]carbamoyl]-3-chloro-phenyl]-5-[1-(5-amino-2-pyridyl)-3-(trifluoromethyl)pyrazol-4-yl]-1-methyl-imidazole-2-carboxamide;

N-[4-[[(trans-3-aminocyclopentyl]carbamoyl]-3-chloro-phenyl]-5-[1-(5-amino-2-pyridyl)-3-(trifluoromethyl)pyrazol-4-yl]-1-methyl-imidazole-2-carboxamide;

N-[4-(2-aminoethylcarbamoyl)-3-chloro-phenyl]-5-[1-(5-amino-2-pyridyl)-3-(trifluoromethyl)pyrazol-4-yl]-1-methyl-imidazole-2-carboxamide;

N-[4-[(2-aminocyclopropyl)methylcarbamoyl]-3-chloro-phenyl]-5-[1-(5-amino-2-pyridyl)-3-(trifluoromethyl)pyrazol-4-yl]-1-methyl-imidazole-2-carboxamide;

N-[4-[trans-(3-aminocyclobutyl)carbamoyl]-3-chloro-phenyl]-5-[1-(5-amino-2-pyridyl)-3-(trifluoromethyl)pyrazol-4-yl]-1-methyl-imidazole-2-carboxamide;

N-[4-(4-aminopiperidine-1-carbonyl)-3-chloro-phenyl]-5-[1-(5-amino-2-pyridyl)-3-(trifluoromethyl)pyrazol-4-yl]-1-methyl-imidazole-2-carboxamide;

N-[4-[2-(2-aminoethoxy)ethylcarbamoyl]-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[2-[(2S,4R)-4-hydroxyprolyl]-2,8-diazaspiro[4.5]decane-8-carbonyl]phenyl]-1-methyl-imidazole-2-carboxamide;

5-[1-(5-amino-2-pyridyl)-3-(trifluoromethyl)pyrazol-4-yl]-N-[3-chloro-4-[[(1R,3R)-3-[[(2S,4R)-4-hydroxyprolyl]amino]cyclopentyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[4-[[(2S,4R)-4-hydroxyprolyl]amino]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[6-[[(2S,4R)-4-hydroxyprolyl]amino]-2-azaspiro[3.3]heptane-2-carbonyl]phenyl]-1-methyl-imidazole-2-carboxamide;

5-[1-(5-amino-2-pyridyl)-3-(trifluoromethyl)pyrazol-4-yl]-N-[3-chloro-4-[3-[[(2S,4R)-4-hydroxyprolyl]amino]propylcarbamoyl]phenyl]-1-methyl-imidazole-2-carboxamide;

5-[1-(5-aminopyridin-2-yl)-3-(trifluoromethyl)pyrazol-4-yl]-N-[3-chloro-4-[[4-(hydroxymethyl)-1-[rac-(2R,4S)-4-hydroxypyrrolidine-2-carbonyl]pyrrolidin-3-yl]carbamoyl]phenyl]-1-methylimidazole-2-carboxamide;

N-[4-(5-aminopentylcarbamoyl)-3-chloro-phenyl]-5-[1-(5-amino-2-pyridyl)-3-(trifluoromethyl)pyrazol-4-yl]-1-methyl-imidazole-2-carboxamide;

5-[1-(5-aminopyrazin-2-yl)-3-(trifluoromethyl)pyrazol-4-yl]-N-[3-chloro-4-(4-isonipecotoylpiperazine-1-carbonyl)phenyl]-1-methyl-imidazole-2-carboxamide;

N-[3-chloro-4-[4-[(2S,4R)-4-hydroxyprolyl]piperazine-1-carbonyl]phenyl]-5-[1-(6-chloro-3-pyridyl)-3-(trifluoromethyl)pyrazol-4-yl]-1-methyl-imidazole-2-carboxamide;

N-[3-chloro-4-(4-isonipecotoylpiperazine-1-carbonyl)phenyl]-5-[1-(6-methoxy-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(piperazine-1-carbonyl)phenyl]-1-methyl-imidazole-2-carboxamide;

5-[1-(5-amino-2-pyridyl)-3-(trifluoromethyl)pyrazol-4-yl]-N-[3-chloro-4-[2-[[(2S,4R)-4-hydroxyprolyl]amino]ethylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[[1-[(2S,4R)-4-hydroxyprolyl]-4-piperidyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[[1-[(2S,4R)-4-hydroxyprolyl]-4-piperidyl]-methyl-carbamoyl]phenyl]-1-methyl-imidazole-2-carboxamide;

5-[1-(5-amino-2-pyridyl)-3-(trifluoromethyl)pyrazol-4-yl]-N-[3-chloro-4-[[2-[[(2S,4R)-4-hydroxyprolyl]amino]cyclopropyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[5-[(2S,4R)-4-hydroxyprolyl]-1,3,3a,4,6,6a-hexahydropyrrolo[3,4-c]pyrrole-2-carbonyl]phenyl]-1-methyl-imidazole-2-carboxamide;

5-[1-(5-amino-2-pyridyl)-3-(trifluoromethyl)pyrazol-4-yl]-N-[3-chloro-4-[trans-[3-[[(2S,4R)-4-hydroxyprolyl]amino]cyclobutyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[(3S)-3-[[[(2S,4R)-4-hydroxyprolyl]amino]methyl]pyrrolidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[2-[2-[[(2S,4R)-4-hydroxyprolyl]amino]ethoxy]ethylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[[(7S)-2-[(2S,4R)-4-hydroxyprolyl]-5-oxa-2-azaspiro[3.4]octan-7-yl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[cis-[3-[[(2S,4R)-4-hydroxyprolyl]amino]cyclobutyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[[1-[[(2S,4R)-4-hydroxyprolyl]amino]cyclopropyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[(3R)-3-[[[(2S,4R)-4-hydroxyprolyl]amino]methyl]pyrrolidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[[[(2S,4R)-4-hydroxyprolyl]amino]methyl]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[[(2S,4R)-4-hydroxyprolyl]-methyl-amino]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[[3-[[(2S,4R)-4-hydroxyprolyl]amino]-1-bicyclo[1.1.1]pentanyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[[(1S,3S)-3-[[(2S,4R)-4-hydroxyprolyl]amino]cyclopentyl]carbamoyl]phenyl]-1-methyl-imidazole-2-carboxamide;

N-[3-chloro-4-(4-isonipecotoylpiperazine-1-carbonyl)phenyl]-5-[1-(6-methoxypyrimidin-4-yl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(2-chloropyridin-4-yl)-3-(trifluoromethyl)pyrazol-4-yl]-1-methylimidazole-2-carboxamide;

5-[1-(5-amino-2-pyridyl)-3-(trifluoromethyl)pyrazol-4-yl]-N-[3-chloro-4-(4,7-diazaspiro[2.5]octane-7-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(3R)-3-methyl-1,4-diazepane-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,9-diazabicyclo[3.3.1]nonane-3-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2S,6R)-2,6-dimethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,6-diazabicyclo[3.1.1]heptane-6-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2S)-2-methylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,3-dimethylpiperazine-1-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(3S)-3-isopropylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,6-diazabicyclo[3.2.0]heptane-3-carbonyl)phenyl]-1-methyl-imidazole-2-carboxamide;

5-[1-(5-amino-2-pyridyl)-3-(trifluoromethyl)pyrazol-4-yl]-N-[3-chloro-4-(1,4-diazepane-1-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(3S)-3-methylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,8-diazabicyclo[3.2.1]octane-8-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2R)-2-ethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[(2S)-2-ethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(2-piperazinoethylcarbamoyl)phenyl]-1-methyl-imidazole-2-carboxamide;

5-[1-(5-amino-2-pyridyl)-3-(trifluoromethyl)pyrazol-4-yl]-N-[3-chloro-4-[(1R,4R)-2,5-diazabicyclo[2.2.1]heptane-2-carbonyl]phenyl]-1-methyl-imidazole-2-carboxamide;

5-[1-(5-amino-2-pyridyl)-3-(trifluoromethyl)pyrazol-4-yl]-N-[3-chloro-4-(4,7-diazaspiro[2.5]octane-4-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2S,3R)-2,3-dimethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[3-(methoxymethyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[(1R,5R)-3,6-diazabicyclo[3.2.0]heptane-3-carbonyl]phenyl]-1-methyl-imidazole-2-carboxamide;

5-[1-(5-amino-3-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-6-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-(4-isonipecotoylpiperazine-1-carbonyl)phenyl]-5-[1-(2-methoxy-4-pyridyl)-3-(trifluoromethyl)pyrazol-4-yl]-1-methyl-imidazole-2-carboxamide;

5-[1-(6-amino-5-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-(4-isonipecotoylpiperazine-1-carbonyl)phenyl]-5-[1-(6-methoxy-3-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(diethylcarbamoyl)phenyl]-1-methyl-imidazole-2-carboxamide;

5-[1-(6-amino-5-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(6-amino-4-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(6-amino-2-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-4-chloro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-4-chloro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-3-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-4-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-2-fluoro-4-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(6-amino-2-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(4-amino-5-nitro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-6-methylpyridin-2-yl)-3-(trifluoromethyl)pyrazol-4-yl]-N-[3-chloro-4-[4-(piperidine-4-carbonyl)piperazine-1-carbonyl]phenyl]-1-methylimidazole-2-carboxamide;

N-[3-chloro-4-[4-(piperidine-4-carbonyl)piperazine-1-carbonyl]phenyl]-5-[1-(4,5-diamino-2-pyridyl)-3-(trifluoromethyl)pyrazol-4-yl]-1-methyl-imidazole-2-carboxamide;

N-[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]isonipecotamide; and 5-[1-[5-(2-aminoethylamino)-2-pyridyl]-3-(trifluoromethyl)pyrazol-4-yl]-N-[3-chloro-4-(4-isonipecotoylpiperazine-1-carbonyl)phenyl]-1-methyl-imidazole-2-carboxamide.

In one embodiment, the present invention provides a compound of formula (I) as described herein, or a pharmaceutically acceptable salt thereof, wherein:

$R^1$ and $R^2$, taken together with the nitrogen atom to which they are attached, form a group of formula (II) or (III):

(II)

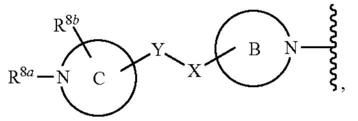

(III)

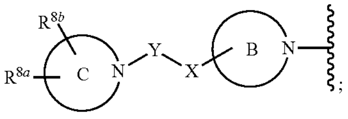

$R^1$ is a group

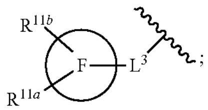

and $R^2$ is selected from hydrogen and $C_1$-$C_6$-alkyl;

$R^3$ is selected from hydrogen, halogen, $C_1$-$C_6$-alkyl and $C_1$-$C_6$-alkoxy;

$R^4$ and $R^6$ are each independently selected from hydrogen, $C_1$-$C_6$-alkyl, $C_1$-$C_6$-alkoxy, cyano, halo-$C_1$-$C_6$-alkyl and halo-$C_1$-$C_6$-alkoxy;

$R^{5a}$, $R^{5b}$ and $R^{5c}$ are each independently selected from hydrogen, halogen, hydroxy, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, ($C_1$-$C_6$-alkyl)$_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, carbamoyl and nitro;

$R^7$ is selected from hydrogen, $C_1$-$C_6$-alkyl and halo-$C_1$-$C_6$-alkyl;

$R^{8a}$ is selected from hydrogen, $C_1$-$C_6$-alkyl, carbamoyl-$C_1$-$C_6$-alkyl, and a group

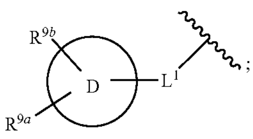

;

$R^{8b}$ is selected from hydrogen, hydroxy, oxo, hydroxy-$C_1$-$C_6$-alkyl, a group

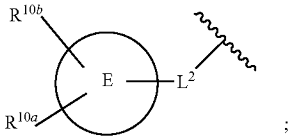

;

$R^{9a}$, $R^{9b}$, $R^{10a}$, $R^{10b}$, $R^{12a}$ and $R^{12b}$ are each independently selected from hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro and hydroxy;

$R^{11a}$ and $R^{11b}$ are each independently selected from hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro, hydroxy and a group

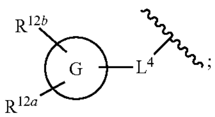

;

X is carbonyl and Y is a covalent bond or $C_1$-$C_6$-alkyldiyl; or

X is $C_1$-$C_6$-alkyldiyl and Y is a covalent bond;

$L^1$ and $L^3$ are each independently selected from a covalent bond, carbonyl and $C_1$-$C_6$-alkyldiyl;

$L^2$ and $L^4$ are each independently selected from a covalent bond, carbonyl, —O—, —NH—C(O)—, —C(O)—NH— and $C_1$-$C_6$-alkyldiyl;

A is 5- to 14-membered heteroaryl; and

B, C, D, E, F and G are each independently selected from 3- to 14-membered heterocyclyl and 5- to 14-membered heteroaryl.

In one embodiment, said compound of formula (I) is a compound of formula (I-I), or a pharmaceutically acceptable salt thereof, (I-I)

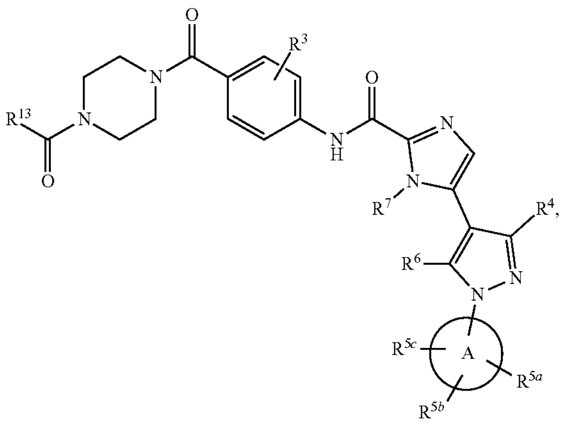

wherein:

$R^{13}$ is a group

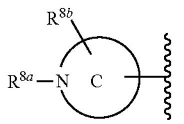

or a group

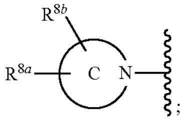

;

and

A, C, $R^3$, $R^4$, $R^{5a}$, $R^{5b}$, $R^{5c}$, $R^6$, $R^7$, $R^{8a}$ and $R^{8b}$ are as defined herein.

In one embodiment, said compound of formula (I) is a compound of formula (I-II), or a pharmaceutically acceptable salt thereof, (I-II)

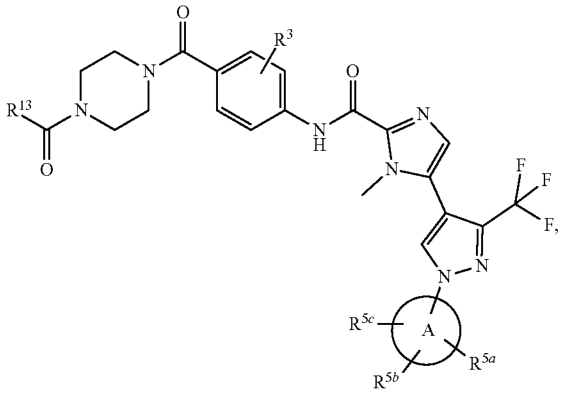

wherein:

$R^{13}$ is a group

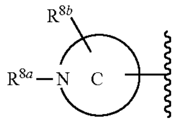

or a group

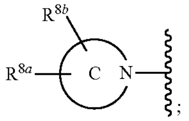

and

A, C, $R^3$, $R^{5a}$, $R^{5b}$, $R^{5c}$, $R^{8a}$ and $R^{8b}$ are as defined herein.

In one embodiment, said compound of formula (I) is a compound of formula (I-III), or a pharmaceutically acceptable salt thereof, (I-III)

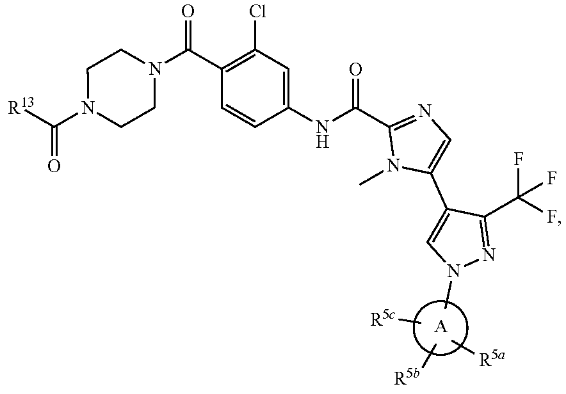

wherein:

$R^{13}$ is a group

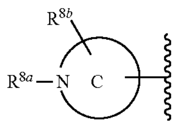

or a group

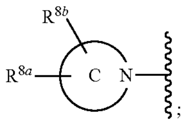

and

A, C, $R^3$, $R^{5a}$, $R^{5b}$, $R^{5c}$, $R^{8a}$ and $R^{8b}$ are as defined herein.

In one embodiment, the present invention provides a compound of formula (I) as described herein, or a pharmaceutically acceptable salt thereof, wherein:

$R^1$ and $R^2$, taken together with the nitrogen atom to which they are attached, form a group of formula (II) or (III):

(II)

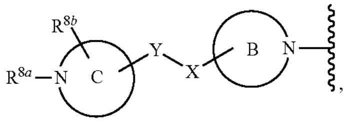

(III)

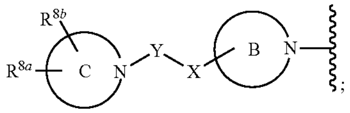

or $R^1$ is a group

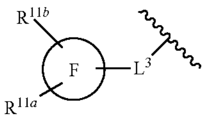

and $R^2$ is hydrogen;

$R^{9a}$, $R^{9b}$, $R^{10b}$, $R^{11b}$ and $R^{12b}$ are each hydrogen;

$R^{8a}$ is selected from hydrogen, $C_1$-$C_6$-alkyl, carbamoyl-$C_1$-$C_6$-alkyl and a group

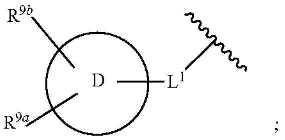

$R^{8b}$ is selected from hydrogen, hydroxy, oxo, hydroxy-$C_1$-$C_6$-alkyl, and a group

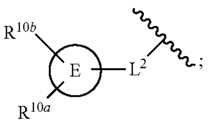

$R^{10a}$ is selected from amino and nitro;

$R^{11a}$ is a group

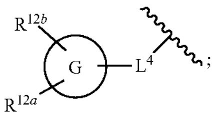

$R^{12a}$ is selected from hydrogen and hydroxy;

X is carbonyl and Y is a covalent bond or $C_1$-$C_6$-alkyldiyl; or

X is $C_1$-$C_6$-alkyldiyl and Y is a covalent bond;

$L^1$ is $C_1$-$C_6$-alkyldiyl;

$L^2$ is —O—;

$L^3$ is selected from a covalent bond and $C_1$-$C_6$-alkyldiyl;

$L^4$ is carbonyl;

B, C, D and G are each independently 3- to 14-membered heterocyclyl;

E is 5- to 14-membered heteroaryl; and

F is selected from 5- to 14-membered heteroaryl and 3- to 14-membered heterocyclyl.

In a preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II) or (III):

(II)

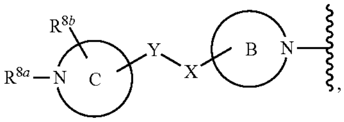

(III)

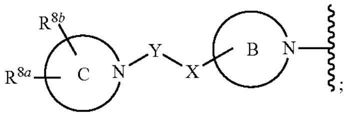

$R^{8a}$ is selected from hydrogen and $C_1$-$C_6$-alkyl;

$R^{8b}$ is selected from hydrogen and hydroxy;

X is carbonyl;

Y is a covalent bond or $C_1$-$C_6$-alkyldiyl; and

B and C are each independently 3- to 14-membered heterocyclyl.

In a particularly preferred embodiment, the present invention provides a compound of formula (I) as described herein, or a pharmaceutically acceptable salt thereof, wherein:

$R^1$ and $R^2$, taken together with the nitrogen atom to which they are attached, form a group of formula (II) or (III):

(II)

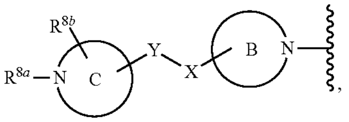

(III)

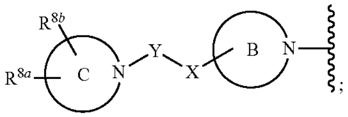

$R^{8a}$ is selected from hydrogen and methyl;

$R^{8b}$ is selected from hydrogen and hydroxy;

X is carbonyl;

Y is a covalent bond or —$CH_2$—;

B is piperazinyl; and

C is selected from piperidyl and pyrrolidinyl.

In one embodiment, the present invention provides a compound of formula (I) as described herein, or a pharmaceutically acceptable salt thereof, wherein $R^3$ is halogen or $C_1$-$C_6$-alkyl.

In a preferred embodiment, the present invention provides a compound of formula (I) as described herein, or a pharmaceutically acceptable salt thereof, wherein $R^3$ is halogen.

In a particularly preferred embodiment, the present invention provides a compound of formula (I) as described herein, or a pharmaceutically acceptable salt thereof, wherein $R^3$ is chloro.

In one embodiment, the present invention provides a compound of formula (I) as described herein, or a pharmaceutically acceptable salt thereof, wherein:

$R^4$ is selected from $C_1$-$C_6$-alkyl, $C_1$-$C_6$-alkoxy, cyano and halo-$C_1$-$C_6$-alkyl; and $R^6$ is selected from hydrogen and halo-$C_1$-$C_6$-alkyl.

In a preferred embodiment, the present invention provides a compound of formula (I) as described herein, or a pharmaceutically acceptable salt thereof, wherein:

$R^4$ is halo-$C_1$-$C_6$-alkyl; and $R^6$ is hydrogen.

In a particularly preferred embodiment, the present invention provides a compound of formula (I) as described herein, or a pharmaceutically acceptable salt thereof, wherein:

$R^4$ is $CF_3$; and $R^6$ is hydrogen.

In a preferred embodiment, the present invention provides a compound of formula (I) as described herein, or a pharmaceutically acceptable salt thereof, wherein A is a 5- to 9-membered heteroaryl and the other substituents of formula (I) are as defined in any of the other embodiments herein.

In a further preferred embodiment, the present invention provides a compound of formula (I) as described herein, or a pharmaceutically acceptable salt thereof, wherein A is a 5- to 9-membered heteroaryl selected from pyrimidinyl, pyrazolyl, pyridyl, pyrazinyl, imidazolyl, pyridazinyl, thiazolyl and 1H-pyrazolo[3,4-d]pyrimidin-6-yl and the other substituents of formula (I) are as defined in any of the other embodiments herein.

In a particularly preferred embodiment, the present invention provides a compound of formula (I) as described herein, or a pharmaceutically acceptable salt thereof, wherein A is a 5- to 9-membered heteroaryl selected from pyrimidinyl, pyrazolyl, pyridyl, pyrazinyl, imidazolyl, pyridazinyl and 1H-pyrazolo[3,4-d]pyrimidin-6-yl and the other substituents of formula (I) are as defined in any of the other embodiments herein.

In one embodiment, the present invention provides a compound of formula (I) as described herein, or a pharmaceutically acceptable salt thereof, wherein:

A is 5- to 14-membered heteroaryl;

$R^5$, is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, carbamoyl and nitro; and $R^{5b}$ and $R^{5c}$ are both hydrogen.

In a preferred embodiment, the present invention provides a compound of formula (I) as described herein, or a pharmaceutically acceptable salt thereof, wherein:

A is 5- to 14-membered heteroaryl;

$R^5$, is selected from $C_1$-$C_6$-alkoxy, hydroxy-$C_1$-$C_6$-alkyl, $C_1$-$C_6$-alkyl-NH— and amino; and $R^{5b}$ and $R^{5c}$ are both hydrogen.

In a particularly preferred embodiment, the present invention provides a compound of formula (I) as described herein, or a pharmaceutically acceptable salt thereof, wherein:

A is pyridyl;

$R^{5a}$ is selected from methoxy, hydroxymethyl, methylamino and amino; and $R^{5b}$ and $R^{5c}$ are both hydrogen.

In a preferred embodiment, the present invention provides a compound of formula (I) as described herein, or a pharmaceutically acceptable salt thereof, wherein $R^7$ is $C_1$-$C_6$-alkyl.

In a particularly preferred embodiment, the present invention provides a compound of formula (I) as described herein, or a pharmaceutically acceptable salt thereof, wherein $R^7$ is methyl.

In one embodiment, the present invention provides a compound of formula (I) as described herein, wherein:

$R^1$ and $R^2$, taken together with the nitrogen atom to which they are attached, form a group of formula (II) or (III):

(II)

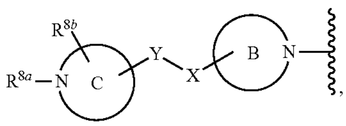

(III)

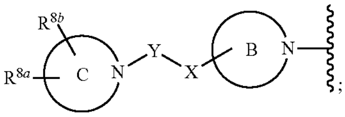

or $R^1$ is a group

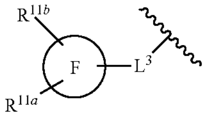

and $R^2$ is hydrogen;

$R^3$ is halogen or $C_1$-$C_6$-alkyl;

$R^4$ is selected from $C_1$-$C_6$-alkyl, $C_1$-$C_6$-alkoxy, cyano and halo-$C_1$-$C_6$-alkyl;

$R^{5a}$ is selected from hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, carbamoyl and nitro;

$R^{5b}$, $R^{5c}$, $R^{9a}$, $R^{9b}$, $R^{10b}$, $R^{11b}$ and $R^{12b}$ are each hydrogen;

$R^6$ is selected from hydrogen and halo-$C_1$-$C_6$-alkyl;

$R^7$ is $C_1$-$C_6$-alkyl;

$R^{8a}$ is selected from hydrogen, $C_1$-$C_6$-alkyl, carbamoyl-$C_1$-$C_6$-alkyl and a group

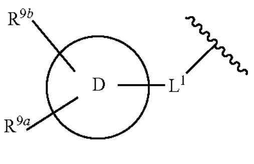

;

$R^{8c}$ is selected from hydrogen, hydroxy, oxo, hydroxy-$C_1$-$C_6$-alkyl, and a group

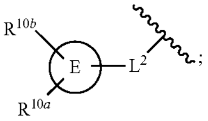

$R^{10a}$ is selected from amino and nitro;

$R^{11a}$ is a group

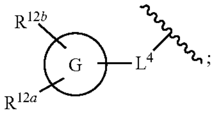

$R^{12a}$ is selected from hydrogen and hydroxy;

X is carbonyl and Y is a covalent bond or $C_1$-$C_6$-alkyldiyl; or

X is $C_1$-$C_6$-alkyldiyl and Y is a covalent bond;

$L^1$ is $C_1$-$C_6$-alkyldiyl;

$L^2$ is —O—;

$L^3$ is selected from a covalent bond and $C_1$-$C_6$-alkyldiyl;

$L^4$ is carbonyl;

A is 5- to 14-membered heteroaryl;

B, C, D and G are each independently 3- to 14-membered heterocyclyl;

E is 5- to 14-membered heteroaryl; and

F is selected from 5- to 14-membered heteroaryl and 3- to 14-membered heterocyclyl.

In a preferred embodiment, the present invention provides a compound of formula (I) as described herein, wherein:

$R^1$ and $R^2$, taken together with the nitrogen atom to which they are attached, form a group of formula (II) or (III):

(II)

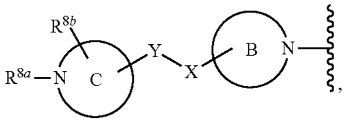

(III)

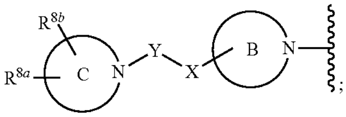

$R^3$ is halogen;

$R^4$ is halo-$C_1$-$C_6$-alkyl;

$R^{5a}$ is selected from $C_1$-$C_6$-alkoxy, hydroxy-$C_1$-$C_6$-alkyl, $C_1$-$C_6$-alkyl-NH— and amino;

$R^{5b}$, $R^{5c}$ and $R^6$ are hydrogen;

$R^7$ is $C_1$-$C_6$-alkyl;

$R^{8a}$ is selected from hydrogen and $C_1$-$C_6$-alkyl;

$R^{8b}$ is selected from hydrogen and hydroxy;

X is carbonyl;

Y is a covalent bond or $C_1$-$C_6$-alkyldiyl;

A is 5- to 14-membered heteroaryl; and

B and C are each independently 3- to 14-membered heterocyclyl.

In a particularly preferred embodiment, the present invention provides a compound of formula (I) as described herein, wherein:

$R^1$ and $R^2$, taken together with the nitrogen atom to which they are attached, form a group of formula (II) or (III):

(II)

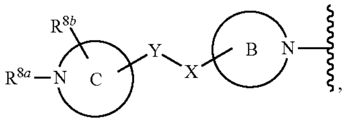

-continued

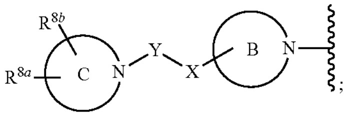

(III)

$R^3$ is chloro;

$R^4$ is $CF_3$;

$R^5$, is selected from methoxy, hydroxymethyl, methylamino and amino;

$R^{5b}$, $R^{5c}$ and $R^6$ are hydrogen;

$R^{8a}$ is selected from hydrogen and methyl;

$R^{8b}$ is selected from hydrogen and hydroxy;

X is carbonyl;

Y is a covalent bond or —$CH_2$—;

A is pyridyl;

B is piperazinyl; and

C is selected from piperidyl and pyrrolidinyl.

In one embodiment, the present invention provides a compound of formula (I) as described herein, wherein said compound of formula (I) is selected from:

Example A1

N-[3-Chloro-4-[4-(piperidine-4-carbonyl)piperazine-1-carbonyl]phenyl]-1-methyl-5-[1-pyrimidin-2-yl-3-(trifluoromethyl)pyrazol-4-yl]imidazole-2-carboxamide; formic acid Example A2

N-[3-chloro-4-[4-(piperidine-4-carbonyl)piperazine-1-carbonyl]phenyl]-1-methyl-5-[1-(4-pyridyl)-3-(trifluoromethyl)pyrazol-4-yl]imidazole-2-carboxamide; formic acid Example A3

N-[3-chloro-4-[4-(piperidine-4-carbonyl)piperazine-1-carbonyl]phenyl]-5-[1-(5-chloro-2-pyridyl)-3-(trifluoromethyl)pyrazol-4-yl]-1-methyl-imidazole-2-carboxamide; formic acid Example A4

N-[3-chloro-4-[4-(piperidine-4-carbonyl)piperazine-1-carbonyl]phenyl]-5-[1-(5-methoxypyrimidin-2-yl)-3-(trifluoromethyl)pyrazol-4-yl]-1-methyl-imidazole-2-carboxamide; formic acid Example A5

5-[1-(5-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid Example A6

N-[3-chloro-4-[4-(piperidine-4-carbonyl)piperazine-1-carbonyl]phenyl]-5-[1-[5-(2-methoxyethoxy)pyrimidin-2-yl]-3-(trifluoromethyl)pyrazol-4-yl]-1-methyl-imidazole-2-carboxamide; formic acid Example A7

N-[3-chloro-4-[4-(piperidine-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide; formic acid Example A8

N-[3-chloro-4-[4-(piperidine-4-carbonyl)piperazine-1-carbonyl]phenyl]-5-[1-(5-fluoropyrimidin-2-yl)-3-(trifluoromethyl)pyrazol-4-yl]-1-methyl-imidazole-2-carboxamide; formic acid Example A9

N-[3-chloro-4-[4-(piperidine-4-carbonyl)piperazine-1-carbonyl]phenyl]-1-methyl-5-[1-(1h-pyrazolo[3,4-d]pyrimidin-6-yl)-3-(trifluoromethyl)pyrazol-4-yl]imidazole-2-carboxamide; formic acid Example A10

N-[3-chloro-4-[4-(piperidine-4-carbonyl)piperazine-1-carbonyl]phenyl]-1-methyl-5-[3-(trifluoromethyl)-1-[3-(trifluoromethyl)-2-pyridyl]pyrazol-4-yl]imidazole-2-carboxamide; formic acid Example A11

N-[3-chloro-4-[4-(piperidine-4-carbonyl)piperazine-1-carbonyl]phenyl]-1-methyl-5-[1-(2-pyridyl)-3-(trifluoromethyl)pyrazol-4-yl]imidazole-2-carboxamide; formic acid Example A12

N-[3-chloro-4-[4-(piperidine-4-carbonyl)piperazine-1-carbonyl]phenyl]-5-[1-(4-methoxy-2-pyridyl)-3-(trifluoromethyl)pyrazol-4-yl]-1-methyl-imidazole-2-carboxamide; formic acid Example A13

N-[3-chloro-4-[4-(piperidine-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide; formic acid Example A14

5-[1-[4-(2-aminoethoxy)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid Example A15

5-[1-(4-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; 2,2,2-trifluoroacetic acid Example A16

N-[3-chloro-4-[4-(piperidine-4-carbonyl)piperazine-1-carbonyl]phenyl]-1-methyl-5-[1-[4-(methylamino)pyrimidin-2-yl]-3-(trifluoromethyl)pyrazol-4-yl]imidazole-2-carboxamide; 2,2,2-trifluoroacetic acid Example A17

N-[3-chloro-4-[4-(piperidine-4-carbonyl)piperazine-1-carbonyl]phenyl]-5-[1-[4-(dimethylamino)pyrimidin-2-yl]-3-(trifluoromethyl)pyrazol-4-yl]-1-methyl-imidazole-2-carboxamide; 2,2,2-trifluoroacetic acid Example A18

N-[3-chloro-4-[4-(piperidine-4-carbonyl)piperazine-1-carbonyl]phenyl]-5-[1-[4-(dimethylamino)pyrimidin-2-yl]-5-(trifluoromethyl)pyrazol-4-yl]-1-methyl-imidazole-2-carboxamide; 2,2,2-trifluoroacetic acid Example A19

N-[3-chloro-4-[4-(piperidine-4-carbonyl)piperazine-1-carbonyl]phenyl]-5-[1-[4-(2-methoxyethylamino)pyrimidin-2-yl]-3-(trifluoromethyl)pyrazol-4-yl]-1-methyl-imidazole-2-carboxamide; 2,2,2-trifluoroacetic acid Example A20

N-[3-chloro-4-[4-(piperidine-4-carbonyl)piperazine-1-carbonyl]phenyl]-1-methyl-5-[1-pyrazin-2-yl-3-(trifluoromethyl)pyrazol-4-yl]imidazole-2-carboxamide; 2,2,2-trifluoroacetic acid Example B1

N-[3-Chloro-4-[4-(piperidine-4-carbonyl)piperazine-1-carbonyl]phenyl]-5-[1-[5-(dimethylamino)pyrimidin-2-yl]-3-(trifluoromethyl)pyrazol-4-yl]-1-methyl-imidazole-2-carboxamide; formic acid Example B2

5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid Example B3

N-[3-chloro-4-[4-(piperidine-4-carbonyl)piperazine-1-carbonyl]phenyl]-5-[1-[6-(dimethylamino)pyridazin-3-yl]-3-(trifluoromethyl)pyrazol-4-yl]-1-methyl-imidazole-2-carboxamide; formic acid Example C1

5-[1-(5-Amino-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid Example C2

N-[3-chloro-4-[4-(piperidine-4-carbonyl)piperazine-1-carbonyl]phenyl]-5-[1-[5-(2-methoxyethylamino)-2-pyridyl]-3-(trifluoromethyl)pyrazol-4-yl]-1-methyl-imidazole-2-carboxamide; formic acid Example C3

5-[1-[5-[(3-amino-3-oxo-propyl)amino]-2-pyridyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid Example C4

5-[1-(5-amino-2-pyridyl)-3-(trifluoromethyl)pyrazol-4-yl]-N-[3-chloro-4-[4-(4-hydroxypiperidine-4-carbonyl)piperazine-1-carbonyl]phenyl]-1-methyl-imidazole-2-carboxamide; formic acid Example C5

N-[3-chloro-4-[4-(piperidine-4-carbonyl)piperazine-1-carbonyl]phenyl]-5-[1-(4-methoxypyrimidin-2-yl)-3-(trifluoromethyl)pyrazol-4-yl]-1-methyl-imidazole-2-carboxamide; formic acid Example C6

N-[3-chloro-4-[4-(piperidine-4-carbonyl)piperazine-1-carbonyl]phenyl]-5-[1-(2-methoxypyrimidin-4-yl)-3-(trifluoromethyl)pyrazol-4-yl]-1-methyl-imidazole-2-carboxamide; formic acid Example C7

5-[1-(5-amino-2-pyridyl)-3-(trifluoromethyl)pyrazol-4-yl]-N-[3-chloro-4-[[1-(piperidine-4-carbonyl)-4-piperidyl]methylcarbamoyl]phenyl]-1-methyl-imidazole-2-carboxamide; formic acid Example C8

5-[1-(5-amino-2-pyridyl)-3-(trifluoromethyl)pyrazol-4-yl]-N-[3-chloro-4-[4-[(3S)-morpholine-3-carbonyl]piperazine-1-carbonyl]phenyl]-1-methyl-imidazole-2-carboxamide; formic acid Example C9

5-[1-(5-amino-2-pyridyl)-3-(difluoromethyl)pyrazol-4-yl]-N-[3-chloro-4-[4-(1-methylpiperidine-4-carbonyl)piperazine-1-carbonyl]phenyl]-1-methyl-imidazole-2-carboxamide Example C10

5-[1-(5-amino-2-pyridyl)-3-methoxy-pyrazol-4-yl]-N-[3-chloro-4-[4-(1-methylpiperidine-4-carbonyl)piperazine-1-carbonyl]phenyl]-1-methyl-imidazole-2-carboxamide Example C11

5-[1-(5-amino-2-pyridyl)-3-cyano-pyrazol-4-yl]-N-[3-chloro-4-[4-(1-methylpiperidine-4-carbonyl)piperazine-1-carbonyl]phenyl]-1-methyl-imidazole-2-carboxamide Example C12

5-[1-(5-amino-2-pyridyl)-3-methyl-pyrazol-4-yl]-N-[3-chloro-4-[4-(1-methylpiperidine-4-carbonyl)piperazine-1-carbonyl]phenyl]-1-methyl-imidazole-2-carboxamide Example C13

5-[1-(5-amino-2-pyridyl)-3-ethyl-pyrazol-4-yl]-N-[3-chloro-4-[4-(1-methylpiperidine-4-carbonyl)piperazine-1-carbonyl]phenyl]-1-methyl-imidazole-2-carboxamide; 2,2,2-trifluoroacetic acid Example C14

5-[1-(6-aminopyridazin-3-yl)-3-(trifluoromethyl)pyrazol-4-yl]-N-[3-chloro-4-[4-(1-methylpiperidine-4-carbonyl)piperazine-1-carbonyl]phenyl]-1-methyl-imidazole-2-carboxamide; 2,2,2-trifluoroacetic acid Example C15

N-[3-chloro-4-[4-(1-methylpiperidine-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide; 2,2,2-trifluoroacetic acid Example C16

5-[1-(5-amino-2-pyridyl)-3-(trifluoromethyl)pyrazol-4-yl]-N-[3-chloro-4-[4-[2-(3-hydroxypyrrolidin-1-yl)acetyl]piperazine-1-carbonyl]phenyl]-1-methyl-imidazole-2-carboxamide; formic acid Example C17

N-[3-chloro-4-[4-[(2S,3S)-3-hydroxypyrrolidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide Example D1

N-[3-chloro-4-[4-(piperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example D2

5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid Example D3

N-[3-chloro-4-[4-(4-hydroxypiperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example D4

N-[3-chloro-4-[4-[(2S,3S)-3-hydroxypyrrolidine-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example D5

N-[3-chloro-4-[4-[2-(3-hydroxypyrrolidin-1-yl)acetyl]piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example D6

1-methyl-5-[1-[5-(methylamino)-2-pyridyl]-3-(trifluoromethyl)pyrazol-4-yl]-N-[3-methyl-4-[4-(piperidine-4-carbonyl)piperazine-1-carbonyl]phenyl]imidazole-2-carboxamide; formic acid Example D7

N-[3-chloro-4-[4-[(2S,4R)-4-hydroxypyrrolidine-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example E1

N-[3-chloro-4-[4-(piperidine-4-carbonyl)piperazine-1-carbonyl]phenyl]-5-[1-[1-(2-methoxyethyl)pyrazol-4-yl]-3-(trifluoromethyl)pyrazol-4-yl]-1-methyl-imidazole-2-carboxamide; formic acid Example E2

N-[3-chloro-4-[4-(piperidine-4-carbonyl)piperazine-1-carbonyl]phenyl]-5-[1-[1-(2-methoxyethyl)-5-methyl-pyrazol-4-yl]-3-(trifluoromethyl)pyrazol-4-yl]-1-methyl-imidazole-2-carboxamide; formic acid Example E3

N-[3-chloro-4-[4-(piperidine-4-carbonyl)piperazine-1-carbonyl]phenyl]-5-[1-[1-(2-methoxyethyl)imidazol-4-yl]-3-(trifluoromethyl)pyrazol-4-yl]-1-methyl-imidazole-2-carboxamide; formic acid Example E4

N-[3-chloro-4-[4-(piperidine-4-carbonyl)piperazine-1-carbonyl]phenyl]-1-methyl-5-[1-(1-methylimidazol-4-yl)-3-(trifluoromethyl)pyrazol-4-yl]imidazole-2-carboxamide; formic acid Example E5

N-[3-chloro-4-[4-(piperidine-4-carbonyl)piperazine-1-carbonyl]phenyl]-1-methyl-5-[1-(5-methyl-1H-pyrazol-4-yl)-3-(trifluoromethyl)pyrazol-4-yl]imidazole-2-carboxamide; formic acid Example E6

N-[3-chloro-4-[4-(piperidine-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide; formic acid Example E7

N-[3-chloro-4-[4-(piperidine-4-carbonyl)piperazine-1-carbonyl]phenyl]-1-methyl-5-[1-(4-methyl-1H-pyrazol-5-yl)-3-(trifluoromethyl)pyrazol-4-yl]imidazole-2-carboxamide; 2,2,2-trifluoroacetic acid Example F1

N-[4-[4-[(1R,5S)-3-Azabicyclo[3.1.0]hexane-6-carbonyl]piperazine-1-carbonyl]-3-chloro-phenyl]-1-methyl-5-[1- pyrimidin-2-yl-3-(trifluoromethyl)pyrazol-4-yl]imidazole-2-carboxamide; formic acid Example F2

N-[3-chloro-4-[[(1R,5S)-3-[(2S,4R)-4-hydroxypyrrolidine-2-carbonyl]-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide; formic acid Example F3

N-[3-chloro-4-[[(1S,5R)-3-(piperidine-4-carbonyl)-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide; formic acid Example F4

N-[3-chloro-4-[4-[(3S,4R)-3-hydroxypiperidine-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide; formic acid Example G1

N-[4-[4-[1-(Azetidin-3-ylmethyl)piperidine-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formic acid Example H1

5-[1-(5-Amino-2-pyridyl)-3-(trifluoromethyl)pyrazol-4-yl]-N-[3-chloro-4-[4-(piperazine-1-carbonyl)piperidine-1-carbonyl]phenyl]-1-methyl-imidazole-2-carboxamide; formic acid Example H2

5-[1-(5-amino-2-pyridyl)-3-(trifluoromethyl)pyrazol-4-yl]-N-[3-chloro-4-[4-[3-(hydroxymethyl)piperazine-1-carbonyl]piperidine-1-carbonyl]phenyl]-1-methyl-imidazole-2-carboxamide; formic acid Example I1

5-[1-(5-Amino-2-pyridyl)-3-(trifluoromethyl)pyrazol-4-yl]-N-[3-chloro-4-[4-[(2-oxopiperazin-1-yl)methyl]piperidine-1-carbonyl]phenyl]-1-methyl-imidazole-2-carboxamide; formic acid Example I2

5-[1-(5-amino-2-pyridyl)-3-(trifluoromethyl)pyrazol-4-yl]-N-[3-chloro-4-(1H-pyrazol-3-ylmethylcarbamoyl)phenyl]-1-methyl-imidazole-2-carboxamide Example J1

N-[3-Chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide; formic acid; and Example K1

N-[3-chloro-4-[4-(piperidine-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide; formic acid.

In a preferred embodiment, the present invention provides a compound of formula (I) as described herein, wherein said compound of formula (I) is selected from:

Example A7

N-[3-chloro-4-[4-(piperidine-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide; formic acid Example B3

N-[3-chloro-4-[4-(piperidine-4-carbonyl)piperazine-1-carbonyl]phenyl]-5-[1-[6-(dimethylamino)pyridazin-3-yl]-3-(trifluoromethyl)pyrazol-4-yl]-1-methyl-imidazole-2-carboxamide; formic acid Example C1

5-[1-(5-Amino-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid Example C16

5-[1-(5-amino-2-pyridyl)-3-(trifluoromethyl)pyrazol-4-yl]-N-[3-chloro-4-[4-[2-(3-hydroxypyrrolidin-1-yl)acetyl]piperazine-1-carbonyl]phenyl]-1-methyl-imidazole-2-carboxamide; formic acid Example D1

N-[3-chloro-4-[4-(piperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example D3

N-[3-chloro-4-[4-(4-hydroxypiperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example D7

N-[3-chloro-4-[4-[(2S,4R)-4-hydroxypyrrolidine-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide; formic acid Example E6

N-[3-chloro-4-[4-(piperidine-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide; formic acid; and Example F4

N-[3-chloro-4-[4-[(3S,4R)-3-hydroxypiperidine-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide; formic acid.

In one embodiment, the present invention provides pharmaceutically acceptable salts of the compounds of formula (I) as described herein, especially pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present invention provides compounds according to formula (I) as described herein (i.e., as "free bases" or "free acids", respectively).

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

In one aspect, the present invention provides a process of manufacturing the compounds of formula (I) described herein.

In a further aspect, the present invention provides a compound of formula (I) as described herein, or a pharmaceutically acceptable salt thereof, when manufactured according to the processes disclosed herein.

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 3rd Edition*, Richard C. Larock. John Wiley & Sons, New York, NY. 2018). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The following abbreviations are used herein:

CN or MeCN Acetonitrile

BINAP 2,2'-Bis(diphenylphosphino)-1,1'-binaphthalene

CFU colony-forming unit d day

DCM dichloromethane

DIPEA N,N-diisopropylethylamine

EtOAc or EA Ethyl acetate

FA Formic acid h(s) or hr(s) hour

HATU: 1-[Bis(dimethylamino)methylene]-1H-1,2,3-triazolo[4,5-b]pyridinium 3-oxid hexafluorophosphate HPLC: high performance liquid chromatography HPLC-UV: high performance liquid chromatography with ultraviolet detector IC50 half maximal inhibitory concentration IC90 90% inhibitory concentration NaBH3CN Sodium cyanoborohydride PE petroleum ether PdCl2(DPPF) [1,1'-Bis(diphenylphosphino)ferrocene]dichloropalladium(II)

Pd2(dba)3 Tris(dibenzylideneacetone)dipalladium(0)

PG Protective group

Precat precatalyst prep-HPLC preparative high performance liquid chromatography rt room temperature sat saturated SEM 2-methoxyethyl(trimethyl)silane FA Formic acid TEMPO (2,2,6,6-Tetramethylpiperidin-1-yl)oxyl TFA Trifluoroacetic Acid wt weight X-PHOS 2-Dicyclohexylphosphino-2',4',6'-triisopropylbiphenyl Scheme 1

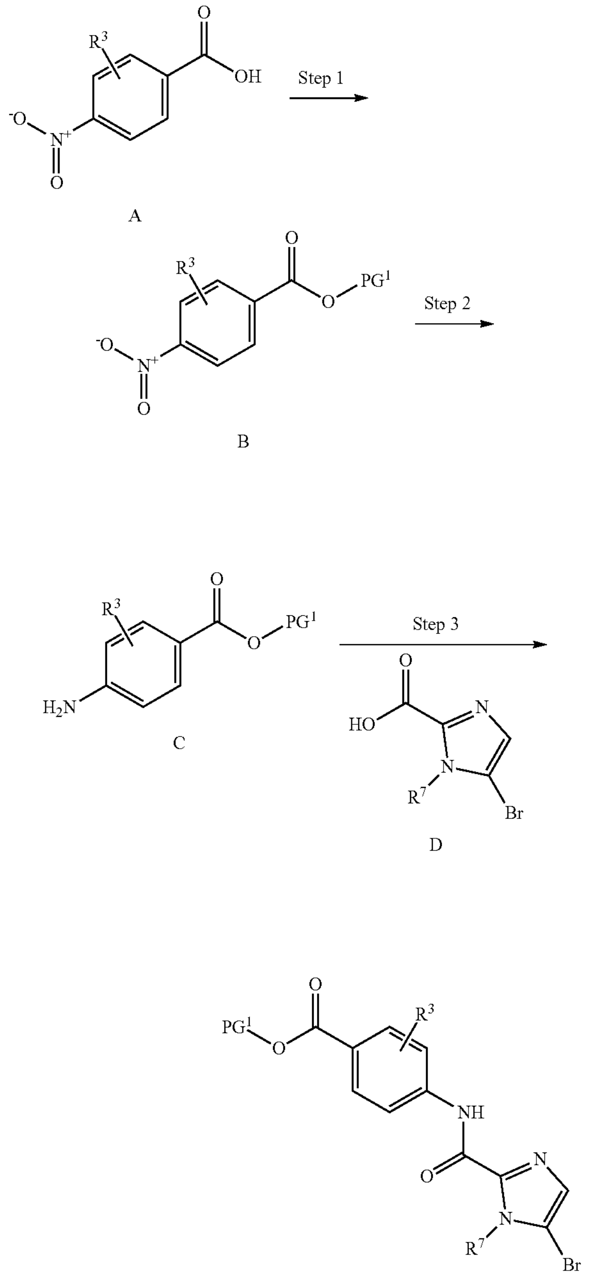

A

B

C

D

Intermediate B1

Wherein $PG^1$ is a protective group, e.g. a Boc protective group; and $R^3$ and $R^7$ are as described herein.

Compound of formula Intermediate B1 can be prepared according to Scheme 1. Protection of $R^3$-substituted 4-nitrobenzoic acid A with e.g. $(Boc)_2O$ gives compound B. Reduction of nitro group of compound B can be achieved under various conditions, like using an ammonium chloride/iron system at room temperature to give amine C. Coupling of D and amine C using a condensing agent, such as HATU/DIPEA in DMSO, affords the compound of formula Intermediate B1.

Scheme 2

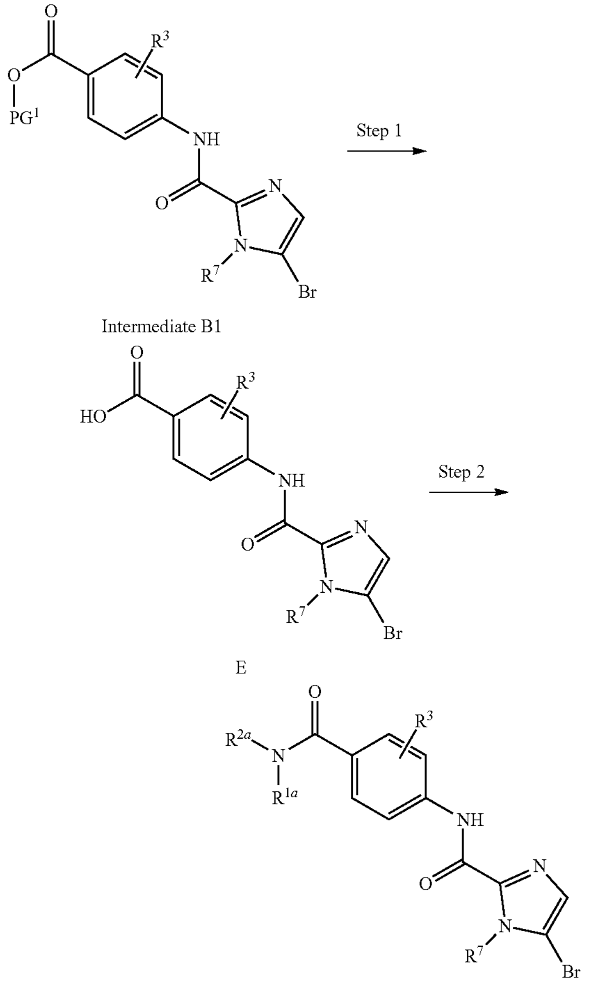

Intermediate B1

E

Intermediate B

Wherein $PG^1$, $PG^2$ and $PG^3$ are protective groups, e.g. a Boc group;

$R^{1a}$ and $R^{2a}$, taken together with the nitrogen atom to which they are attached, form a group of formula (IV), (V) or (VI):

(IV)

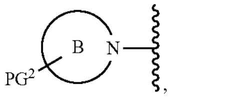

, (V)

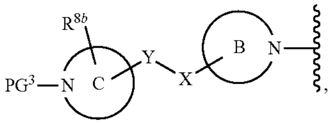

, (III)

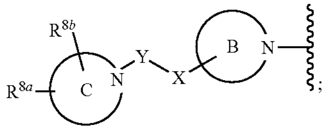

;

or $R^{1a}$ is a group

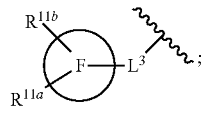

and $R^{2a}$ is selected from hydrogen and $C_1$-$C_6$-alkyl; and $R^3$, $R^7$, $R^{8a}$, $R^{8b}$, $R^{11a}$, $R^{11b}$, B, C, F, X, Y and $L^3$ are as described herein.

Compound of formula Intermediate B can be prepared according to Scheme 2. Hydrolysis of Intermediate B1 gives acid E, which can be coupled with diverse amines using a condensing agent, such as HATU/DIPEA in a solvent such as DMSO to afford Intermediate B.

-continued (III)

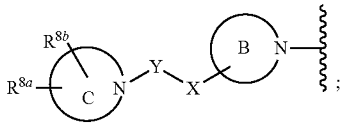

or $R^{1a}$ is a group

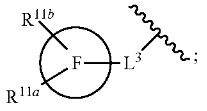

Scheme 3

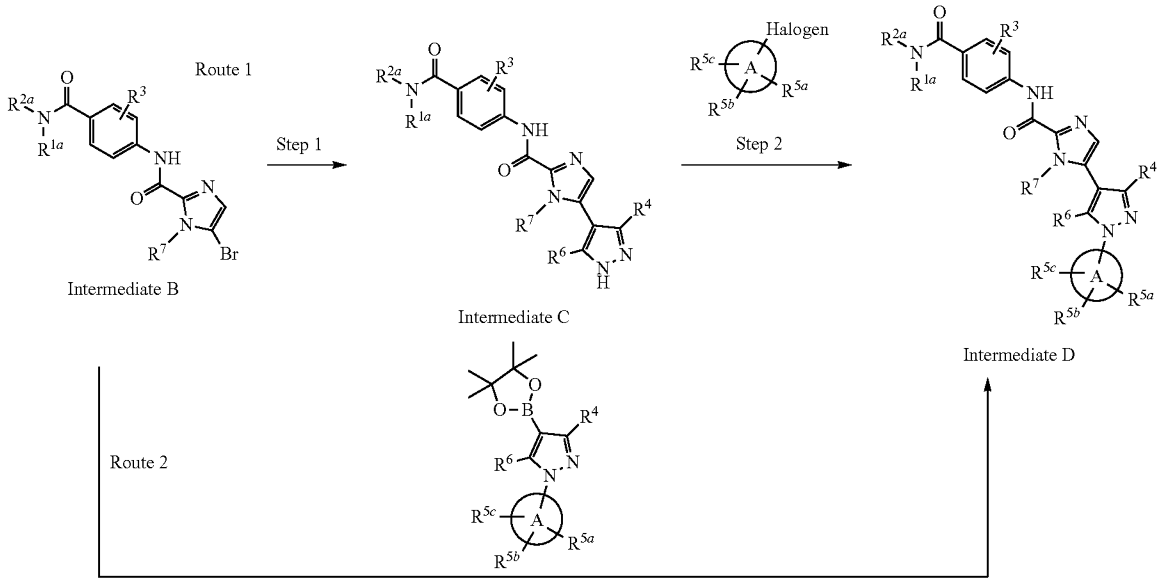

Wherein $PG^1$, $PG^2$ and $PG^3$ are protective groups, e.g. a Boc group;

$R^{1a}$ and $R^{2a}$, taken together with the nitrogen atom to which they are attached, form a group of formula (IV), (V) or (VI):

(IV)

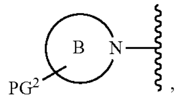

(V)

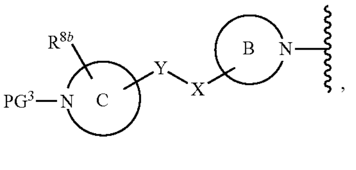

and $R^{2a}$ is selected from hydrogen and $C_1$-$C_6$-alkyl; and $R^3$, $R^4$, $R^{5a}$, $R^{5b}$, $R^{5c}$, $R^6$, $R^7$, $R^{8a}$, $R^{8b}$, $R^{11a}$, $R^{11b}$, A, B, C, F, X, Y and $L^3$ are as described herein.

Compound of formula Intermediate C and D can be prepared according to Scheme 3. Suzuki coupling of Intermediate B with pyrazole bronic esters can be achieved using conditions known in the art, e.g. using palladium precatalysts and phosphine ligands to give Intermediate C. This intermediate can be coupled further with halogen substituted heteroaryls under condition known in the art, for example microwave heating in the presence of a base, such as $K_2CO_3$, in a solvent, such as MeCN, to give Intermediate D (Route 1 in Scheme 3). Alternatively this coupling can also be achieved by well known palladium or copper catalyzed cross couplings. Another way is to use the halogen substituted heteroaryls in the presence of 2-(2,6-dimethylanilino)-2-oxo-acetic acid and a copper(I) source like copper(I) iodide and a suitable base like potassium phosphate.

Alternatively Intermediates D can also be prepared by Chan Lam type couplings using the corresponding boronate substituted heteroaryls in the presence of a copper(II) source and an oxidant like oxygen.

Intermediate D can also be prepared through a Suzuki coupling reaction of Intermediate B with a heteroaryl substituted pyrazole bronic esters (Route 2 in Scheme 3).

In some instances employed

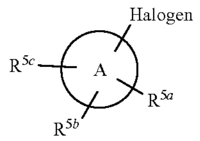

are not commercially available and have to be synthesized. One possibility is to start with compound which contains precursors of $R5^{a-c}$ and modify those, for example by substitution with benzophenone imine. An explicit procedure is given in the preparation of Intermediate Y3.

In some instances, employed

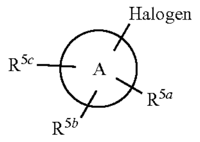

or

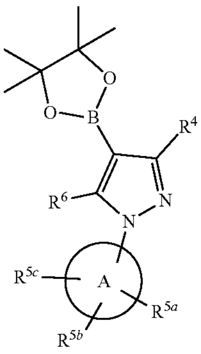

can contain precursors of $R5^{a-c}$ which can be further modified. An example would be protecting groups like Boc or SEM-Group which can be cleaved by various known methods. Another example would be a nitro group, which can be subsequently reduced by generally known methods like palladium catalysted hydrogenation or "Bechamp"-like procedures using zinc or iron powder in presence of a strong acid like HCl or weaker acids like ammonium chloride. The resulting amino group can be further modified by methods like alkylation, amidation or reductive amination to ultimately generate the desired $R5^{a-c}$ Scheme 3a In some instances, employed

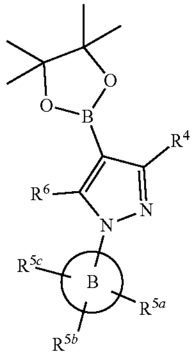

are not commercially available and may be prepared by the following steps in various appropriate order. An example is given in Scheme 3a

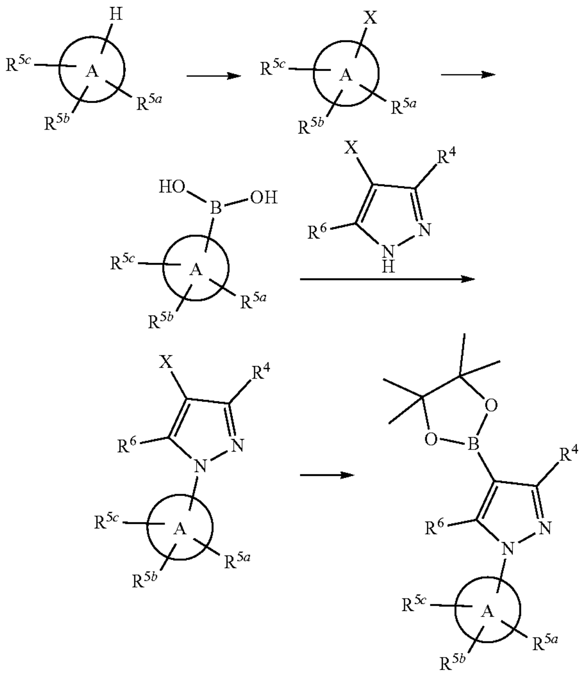

The corresponding "A" ring is halogenated, for example by deprotonation with a suitable strong base like LDA and then halogenate with a suitable X-electrophile. Subsequent transformation of the X substituent to the corresponding boronic acid or boronic acid ester via palladium catalyzed borylation yields an A-ring boronate. Then

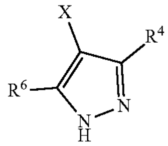

can be N-arylated with the obtained boronate using for example a Chan-Lam procedure employing a copper(II)

source under oxygen. Subsequent borylation as above then yields the desired building block to use in Scheme 3.

An explicit example for such a process is given with intermediate Y2.

The methods described in Scheme 3a, can of course also be used in transformations of Scheme 3.

In some cases, the sequence of the arylation in Scheme 3 and the saponification and/or amidation reaction in Scheme 2 could be reversed.

Scheme 4

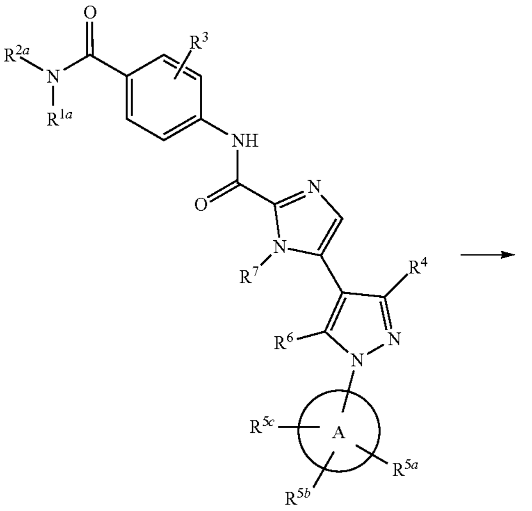

Intermediate D

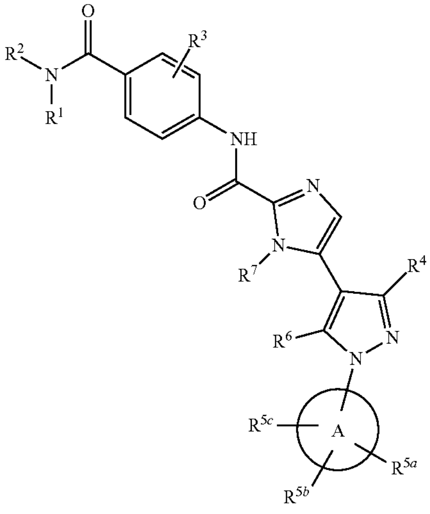

Example A to L

Wherein $PG^1$, $PG^2$ and $PG^3$ are protective groups, e.g. a Boc group;

$R^{1a}$ and $R^{2a}$, taken together with the nitrogen atom to which they are attached, form a group of formula (IV), (V) or (VI):

(IV)

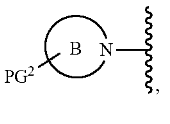

-continued (V)

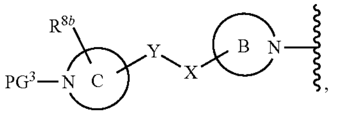

(III)

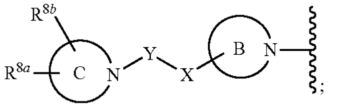

or $R^{1a}$ is a group

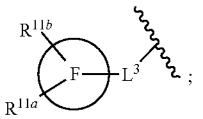

and $R^{2a}$ is selected from hydrogen and $C_1$-$C_6$-alkyl; and $R^1$, $R^2$, $R^3$, $R^4$, $R^{5a}$, $R^{5b}$, $R^{5c}$, $R^6$, $R^7$, $R^{8a}$, $R^{8b}$, $R^{11a}$, $R^{11b}$, A, B, C, F, X, Y and $L^3$ are as described herein.

Compound of formula Example A to L can be prepared according to Scheme 4 by removing the protective group in Intermediate D.

Using the Compounds of the Invention

As illustrated in the experimental section, the compounds of formula (I) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii.*

The compounds of formula (I) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii.*

The compounds of formula (I) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii.*

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In one aspect, the present invention provides compounds of formula (I) or their pharmaceutically acceptable salts as described herein for use as therapeutically active substances.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a particular embodiment, said nosocomial infections and resulting diseases are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by Gram-negative bacteria.

In a particular embodiment, said infections and resulting diseases caused by Gram-negative bacteria are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present invention provides a method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, which method comprises administering a compound of formula (I) as described herein, or a pharmaceutically acceptable salt thereof, to a mammal.

In a further aspect, the present invention provides the use of a compound of formula (I) as described herein, or a pharmaceutically acceptable salt thereof, as an antibiotic.

In a further aspect, the present invention provides the use of a compound of formula (I) as described herein, or a pharmaceutically acceptable salt thereof, for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present invention provides the use of a compound of formula (I) as described herein, or a pharmaceutically acceptable salt thereof, for the preparation of medicaments useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a particular embodiment, said infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, are selected from bacteremia, pneumonia, meningitis, urinary tract infection and wound infection, or a combination thereof.

In a further aspect, the present invention provides compounds of formula (I) or their pharmaceutically acceptable salts as defined above for use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In a further aspect, the present invention provides a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering a compound of formula (I) or a pharmaceutically acceptable salt thereof as defined above to a mammal.

In a further aspect, the present invention provides the use of compounds of formula (I) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In a further aspect, the present invention provides the use of compounds of formula (I) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.* Such medicaments comprise compounds of formula (I) or their pharmaceutically acceptable salts as defined above.

Pharmaceutical Compositions and Administration

In one aspect, the present invention provides pharmaceutical compositions comprising compounds of formula (I) or their pharmaceutically acceptable salts as defined above and one or more pharmaceutically acceptable excipients. Exemplary pharmaceutical compositions are described in Examples 1 to 4.

In a further aspect, the present invention relates to pharmaceutical compositions comprising compounds of formula (I) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

The compounds of formula (I) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

Co-Administration of Compounds of Formula (I) and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with an antibiotic, in particular with an antibiotic for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

The term "co-administering" refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including antibiotic agents. If the administration is not simultaneous, the compounds are administered in a close time proximity to each other. Furthermore, it does not matter if the compounds are administered in the same dosage form, e.g. one compound may be administered intravenously and another compound may be administered orally.

Typically, any agent that has antimicrobial activity may be co-administered. Particular examples of such agents are Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified e.g. in WO 2017072062 A1, WO 2019185572 A1 and WO 2019206853 A1, and Macrolides (erythromycin).

In one aspect, the present invention provides a pharmaceutical composition described herein, further comprising an additional therapeutic agent.

In one aspect, the present invention provides a pharmaceutical combination comprising a compound of formula (I) described herein and an additional therapeutic agent.

In one embodiment, said additional therapeutic agent is an antibiotic agent.

In one embodiment, said additional therapeutic agent is an antibiotic agent that is useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In one embodiment, said additional therapeutic agent is an antibiotic agent selected from Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified in WO 2017072062 A1, WO 2019185572 A1 and WO 2019206853 A1, and Macrolides (erythromycin).

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Intermediate A1 tert-Butyl (2-chloropyrimidin-5-yl)carbamate

To a 25 mL microwave vial was added 2-chloropyrimidin-5-amine (250 mg, 1.93 mmol), $Boc_2O$ (1.26 g, 1.34 mL, 5.79 mmol), DIPEA (748 mg, 1.01 mL, 5.79 mmol) and DMAP (23.6 mg, 193 μmol) in THF (10 mL). The vial was capped and heated under microwave at 50° C. for 2 h. The crude reaction mixture was concentrated in vacuum. The crude material was purified by flash chromatography to afford tert-butyl (2-chloropyrimidin-5-yl)carbamate (440 mg). MS [M+H]. 230.0.

Intermediate A2.1

2-Chloro-5-(2-methoxyethoxy)pyrimidine

In a 50 mL round-bottomed flask, 2-chloropyrimidin-5-ol (200 mg, 1.53 mmol), 1-bromo-2-methoxyethane (319 mg, 2.3 mmol) and $K_2CO_3$ (318 mg, 2.3 mmol) were combined with DMF (5 mL) to give a light brown solution. The reaction mixture was heated to 50° C. and stirred for 3 h. The reaction mixture was poured into 20 mL $H_2O$ and extracted with EtOAc (25 mL×3). The organic layers were combined, washed with sat NaCl (25 mL×3), The organic layers were dried over $Na_2SO_4$ and concentrated in vacuum to afford 2-chloro-5-(2-methoxyethoxy)pyrimidine (280 mg). MS $[M+H]^+$: 189.4.

The following intermediates were prepared in analogy of Intermediate B4.1.

| Ex# | Name | MS ESI [M + H]+ | Starting Material |
|---|---|---|---|
| Intermediate A2.2 | 2-fluoro-5-(2-methoxyethoxy)-pyridine | 172.3 | 6-fluoropyridin-3-ol and 1-bromo-2-methoxyethane |

Intermediate A3

6-Chloro-1-(tetrahydro-2H-pyran-2-yl)-pyrazolo[3,4-d]pyrimidine

To a 25 mL microwave vial was added 6-chloro-1H-pyrazolo[3,4-d]pyrimidine (200 mg, 1.29 mmol), DHP (142 mg, 154 μl, 1.68 mmol) and p-TsOH (24.6 mg, 129 μmol) in THF (10 mL). The vial was capped and heated at 60° C. for 1 h. The crude reaction mixture was concentrated in vacuum. The crude material was purified by flash chromatography (silica gel, 12 g, 0% to 5% MeOH in DCM) to afford 6-chloro-1-(tetrahydro-2H-pyran-2-yl)-pyrazolo[3,4-d]pyrimidine (200 mg). MS $[M+H]^+$: 238.8.

Intermediate A4.1

4-Iodo-1-(2-methoxyethyl)pyrazole

To a 25 mL microwave vial was added 4-iodo-1H-pyrazole (500 mg, 2.58 mmol), 1-bromo-2-methoxyethane (537 mg, 3.87 mmol) and $K_2CO_3$ (712 mg, 5.16 mmol) in MeCN (10 mL). The vial was capped and heated at 100° C. for 2 h. The reaction mixture was filtered through glass fiber paper. The filtrate was concentrated in vacuum. The crude material was purified by flash chromatography to afford 4-iodo-1-(2-methoxyethyl)-pyrazole (459 mg). MS $[M+H]^+$: 252.9.

The following intermediates were prepared in analogy of Intermediate A4.1.

| Ex# | Name | MS ESI [M + H]+ | Starting Material |
|---|---|---|---|
| Intermediate A4.2 | 4-iodo-1-(2-methoxyethyl)-5-methyl-pyrazole | 266.9 | 4-iodo-3-methyl-1H-pyrazole and 1-bromo-2-methoxyethane |
| Intermediate 4.3 | 4-iodo-1-(2-methoxyethyl)-imidazole | 252.9 | 4-iodo-1H-imidazole and 1-bromo-2-methoxyethane |

Intermediate A5

2-(2-Chloropyrimidin-4-yl)oxyethanol

To a solution of 2,4-dichloropyrimidine (1 g, 6.7 mmol) in MeCN (33.6 mL) were added tert-butyl (2-hydroxyethyl) carbamate (1.1 g, 6.7 mmol) and cesium carbonate (3.3 g, 10.1 mmol), The reaction mixture was stirred for 48 hours at 80° C. After cooled to room temperature, saturated $NaHCO_3$ was added and the products extracted into EtOAc. The organic extract was dried, filtered and concentrated in vacuum. Purification of the residue by flash chromatography gave the title product as light yellow oil, 283 mg. MS $[M+H]^+$: 274.1.

Intermediate A6.1 tert-Butyl N-tert-butoxycarbonyl-N-(2-chloropyrimidin-4-yl)carbamate 2-chloropyrimidin-4-amine (500 mg, 3.9 mmol), di-tert-butyl dicarbonate (1.0 g, 1.1 mL, 4.6 mmol) and N,N-dimethylpyridin-4-amine (47.2 mg, 386 μmol) were stirred in acetonitrile (15.4 mL) at rt for 3 h. After completion, silica gel (100-200 mesh) was added to absorb the material, and the sample was purified by flash chromatography to give the title compound as colorless oil, 505 mg. MS $[M-Boc-{}^tBu+H]^+$: 179.3.

The following intermediates were prepared in analogy of Intermediate A6.

| Ex# | Name | MS ESI [M + H]+ | Starting Material |
|---|---|---|---|
| Intermediate A6.2 | tert-butyl N-(2-chloropyrimidin-4-yl)-N-(2-methoxyethyl)carbamate | 288.1 | 2-chloro-N-(2-methoxyethyl)pyrimidin-4-amine and (Boc)2O |
| Intermediate A6.3 | tert-butyl N-(2-chloropyrimidin-4-yl)-N-methyl-carbamate | 244.1 | 2-chloro-N-methylpyrimidin-4-amine and (Boc)2O |

Intermediate A7

9H-Fluoren-9-ylmethyl N-(3-amino-3-oxo-propyl)-N-(6-bromo-3-pyridyl)carbamate

Step 1: 6-bromo-N-[3-[tert-butyl(dimethyl)silyl]oxypropyl]pyridin-3-amine (6-bromo-3-pyridyl)amine (2.4 g, 14.2 mmol), 3-[tert-butyl(dimethyl)silyl]oxypropionaldehyde (2.7 g, 14.2 mol) and acetic acid (170.1 mg, 162.1 uL, 2.8 mmol) were dissolved in dichloromethane (50 mL). To this solution was added sodium triacetoxyborohydride (3.6 g, 17.0 mmol) portionwise. The mixture was stirred at rt for 1 h after addition. The mixture was poured into 100 mL water and extracted with DCM (50 mL×2). The extracts were combined, washed with brine and dried over sodium sulfate. The solvent was removed in vacuum and the residue was purified by flash chromatography to give the title compound as light yellow solid, 3.0 g. MS $[M+H]^+$: 345.6.

Step 2: 9H-fluoren-9-ylmethyl N-(6-bromo-3-pyridyl)-N-(3-hydroxypropyl)carbamate (6-bromo-3-pyridyl)-[3-[tert-butyl(dimethyl)silyl]oxypropyl]amine (3.0 g, 8.7 mmol) was dissolved in 5 mL toluene and this solution was added dropwise to a solution of chlorocarbonic acid 9H-fluoren-9-ylmethyl ester (2.2 g, 8.7 mmol) in anhydrous toluene, extra dry (20 mL) at 0° C. After addition, the mixture was stirred at 0° C. for 1 h and then at rt for another 1 h. Yellow precipitate formed. The mixture was left overnight. The solvent was removed in vacuum, and the residue was purified by flash chromatography to give the title compound as light yellow oil, 2.0 g. MS $[M+H]^+$: 453.1.

Step 3: 3-[(6-bromo-3-pyridyl)-(9H-fluoren-9-yl-methoxycarbonyl)amino]propanoic acid Iodobenzene diacetate (703.4 mg, 2.2 mmol), TEMPO (62.4 mg, 0.4 mmol) and N-(6-bromo-3-pyridyl)-N-(3-hydroxypropyl)carbamic acid 9H-fluoren-9-ylmethyl ester (900 mg, 2.0 mmol) were combined in a reaction vessel, and to this mixture was added acetonitrile (11 mL) and water (6 mL). The reaction mixtures were stirred for 3 h before another batch of iodobenzene diacetate (703.4 mg, 2.2 mmol) was added. The stirring was continued overnight (~18 h). The solvent was removed in vacuum and the residue was purified by flash chromatography to give the title compound as light yellow foam, 778 mg. MS $[M+H]^+$: 467.1.

Step 4: 9H-fluoren-9-ylmethyl N-(3-amino-3-oxo-propyl)-N-(6-bromo-3-pyridyl)carbamate 3-[(6-bromo-3-pyridyl)-(9H-fluoren-9-ylmethoxycarbonyl)amino]propionic acid (142 mg, 0.3 mmol), ammonium chloride (32.5 mg, 0.6 mmol) and DIEA (196.4 mg, 265.4 uL, 1.5 mmol) were stirred in N,N-dimethylacetamide (5 mL) for 1 min. HATU (138.6 mg, 0.4 mmol) was added to the mixture, and the resulting solution was stirred at 25° C. for 1 h. The mixture was poured into 100 mL water and extracted with EtOAc (50 mL×3). The extracts were combined, washed with 50 mL brine, dried over sodium sulfate and concentrated in vacuum. The residue was purified by flash chromatography to give the title compound as light yellow oil, 114 mg. MS $[M+H]^+$: 466.1.

Intermediate A8

Benzyl 2-[3-oxo-4-(4-piperidylmethyl)piperazin-1-yl]acetate

Step 1: tert-butyl 4-[[4-(2-benzyloxy-2-oxo-ethyl)-2-oxo-piperazin-1-yl]methyl]piperidine-1-carboxylate 3-ketopiperazine-1-carboxylic acid benzyl ester (1.0 g, 4.3 mmol) was dissolved in N,N-dimethylformamide, extra dry (28.5 mL). The solution was cooled to 0° C. To this solution was added portion wise NaH (204.9 mg, 5.1 mmol). The mixture was stirred for 1 h at the same temperature after addition. Then the ice bath was removed and the stirring was continued at rt for 1 h. Then 4-(iodomethyl)piperidine-1-carboxylic acid tert-butyl ester (1.7 g, 5.1 mmol) was added in one time. The stirring was continued for 18 h at rt. The mixture was poured into 100 mL water and extracted with EtOAc (50 mL×3). The extracts were combined, washed with 50 mL brine, dried over sodium sulfate and concentrated in vacuum. The residue was purified by flash chromatography to yield the title compound as light yellow oil, 854 mg. MS $[M+H]^+$: 454.2.

Step 2: benzyl 2-[3-oxo-4-(4-piperidylmethyl)piperazin-1-yl]acetate

4-[(1-tert-butoxycarbonyl-4-piperidyl)methyl]-3-keto-piperazine-1-carboxylic acid benzyl ester (850 mg, 2.0 mmol) was dissolved in dichloromethane (4 mL) and 1 mL TFA. The solvent was stirred at rt for 3 h. The solvent was removed in vacuum and the residue was used in the coming step without further purification, light yellow oil, 600 mg. MS $[M+H]^+$: 332.4.

Intermediate A9.1

4-Methoxy-2-[4-(4,4,5,5-tetramethyl-1,3,2-dioxaborolan-2-yl)-3-(trifluoromethyl)pyrazol-1-yl]pyrimidine Step 1: 2-[4-bromo-3-(trifluoromethyl)pyrazol-1-yl]-4-methoxy-pyrimidine To a solution of 2-chloro-4-methoxypyrimidine (134 mg, 930 μmol) and 4-bromo-3-(trifluoromethyl)-1H-pyrazole (200 mg, 930 μmol) in MeCN (4.7 mL) were added N-ethyl-N-isopropylpropan-2-amine (180 mg, 243 μL, 1.4 mmol) and cesium carbonate (455 mg, 1.4 mmol). After heating at 100° C. for 3 h, the mixture was cooled to rt. 100-200 mesh silica gel was added to absorb the material, and the sample was purified by purified by flash chromatography to give 300 mg white powder. MS $[M+H]^+$: 322.9.

Step 2: 4-methoxy-2-[4-(4,4,5,5-tetramethyl-1,3,2-dioxaborolan-2-yl)-3-(trifluoromethyl)pyrazol-1-yl]pyrimidine 2-(4-bromo-3-(trifluoromethyl)-pyrazol-1-yl)-4-methoxypyrimidine (300 mg, 929 μmol), 4,4,4',4',5,5,5',5'-octamethyl-2,2'-bi(1,3,2-dioxaborolane) (283 mg, 1.11 mmol), [1,1'-Bis(diphenylphosphino)ferrocene]dichloropalladium(II), complex with dichloromethane (37.9 mg, 46.4 μmol), potassium acetate (273 mg, 2.8 mmol) and dry DMSO (4.6 mL) were placed in a microwave tube. The vial was sealed, evacuated and backfilled with nitrogen for 5 times. The mixture was heated at 80° C. for 18 h. Then the temperature was raised to 100° C. and the stirring was continued for 18 h. The reaction was cooled to rt and poured into 100 mL water. The aqueous phase was extracted with EtOAc (60 mL×4). The organic layers were combined, washed with brine (50 mL), dried over sodium sulfate and concentrated in vacuum. The residue was purified by flash chromatography to give the title compound as white powder, 58 mg. MS $[M+H]^+$:370.5.

The following intermediates were prepared in analogy of Intermediate A9.1.

| Ex# | Name | MS ESI $[M + H]^+$ | Starting Material |
|---|---|---|---|
| Intermediate A9.2 | 2-methoxy-4-[4-(4,4,5,5-tetramethyl-1,3,2-dioxaborolan-2-yl)-3-(trifluoromethyl)pyrazol-1-yl]pyrimidine | 370.5 | 4-bromo-3-(trifluoromethyl)-1H-pyrazole and 4-chloro-2-methoxypyrimidine |

Intermediate A9.3

6-[3-(Difluoromethyl)-4-(4,4,5,5-tetramethyl-1,3,2-dioxaborolan-2-yl)pyrazol-1-yl]pyridin-3-amine Step 1: 2-[4-bromo-3-(difluoromethyl)pyrazol-1-yl]-5-nitro-pyridine To a solution of 4-bromo-3-(difluoromethyl)-1H-pyrazole (800.0 mg, 4.06 mmol) in DMF (20.0 mL) was added sodium hydride (243.7 mg, 6.09 mmol) at 0° C. The mixture was stirred at 0° C. for 30 min. Then 2-chloro-5-nitro-pyridine (772.7 mg, 4.87 mmol) was added and the mixture was stirred at 0° C. for 1 h. The mixture was poured into water (50.0 mL) and filtered, the filter cake was washed with water (20.0 mL×3), dried in depressed pressure to give 2-[4-bromo-3-(difluoromethyl)pyrazol-1-yl]-5-nitro-pyridine (1.0 g, 3.13 mmol, 77% yield) as a brown solid. MS $[M+2+H]^+$: 320.9.

Step 2: 6-[4-bromo-3-(difluoromethyl)pyrazol-1-yl]pyridin-3-amine

To a solution of 2-[4-bromo-3-(difluoromethyl)pyrazol-1-yl]-5-nitro-pyridine (1.0 g, 3.13 mmol) in Acetic acid (50.0 mL) was added iron (1.7 g, 31.34 mmol). The mixture was stirred at 20° C. for 3 h. The reaction mixture was filtered and the filter cake was washed with DCM (20.0 mL). The filtrate was concentrated in vacuum to give a residue, which was purified by silica gel column to give 6-[4-bromo-3-(difluoromethyl)pyrazol-1-yl]pyridin-3-amine (700.0 mg, 2.42 mmol) as a brown solid. MS $[M+2+H]^+$: 290.9.

Step 3: 6-[3-(difluoromethyl)-4-(4,4,5,5-tetramethyl-1,3,2-dioxaborolan-2-yl)pyrazol-1-yl]pyridin-3-amine To a solution of 6-[4-bromo-3-(difluoromethyl)pyrazol-1-yl]pyridin-3-amine (300.0 mg, 1.04 mmol) and bis(pinacolato)diboron (289.9 mg, 1.14 mmol) in 1,4-dioxane (10.0 mL) was added potassium acetate (203.7 mg, 2.08 mmol) and Pd(dppf)$Cl_2$ (113.8 mg, 0.17 mmol) under argon in glove box. The mixture was stirred at 100° C. for 16 h. The reaction mixture was filtered and the filtrate was concentrated in vacuum to give a residue, which was purified by flash column (0.1% FA as additive) and dried by lyophilization to give 6-[3-(difluoromethyl)-4-(4,4,5,5-tetramethyl-1,3,2-dioxaborolan-2-yl)pyrazol-1-yl]pyridin-3-amine (150.0 mg, 0.45 mmol) as a yellow solid. MS $[M+H]^+$: 337.1.

Intermediate A9.4 tert-Butyl N-[6-[3-methoxy-4-(4,4,5,5-tetramethyl-1,3,2-dioxaborolan-2-yl)pyrazol-1-yl]-3-pyridyl]carbamate Step 1: 2-(3-methoxypyrazol-1-yl)-5-nitro-pyridine To a solution of 3-methoxy-1H-pyrazole (0.9 g, 9.17 mmol) in DMF (20.0 mL) was added sodium hydride (550.5 mg, 13.76 mmol) at 0° C. The mixture was stirred at 0° C. for 30 min. 2-chloro-5-nitro-pyridine (1.7 g, 11.01 mmol) was added and the mixture was stirred at 0° C. for 1 h. The reaction mixture was poured into water (50.0 mL) and filtered, The filter cake was washed with water (20.0 mL) and then dried in depressed pressure tp give 2-(3-methoxypyrazol-1-yl)-5-nitro-pyridine (1.8 g, 8.18 mmol) as a yellow solid. MS $[M+H]^+$: 220.9.

Step 2: 2-(4-bromo-3-methoxy-pyrazol-1-yl)-5-nitro-pyridine

To a solution of 2-(3-methoxypyrazol-1-yl)-5-nitro-pyridine (0.8 g, 3.63 mmol) in DCM (1.0 mL) was added N-bromosuccinimide (0.8 g, 4.49 mmol). The mixture was stirred at 20° C. for 12 h. The reaction mixture was poured into aq. $Na_2S_2O_3$ (10.0 mL) and extracted with EA (100.0 mL×3). The organics was washed with water (50.0 mL×2) then saturated brine solution (50.0 mL). The organics were then separated and dried ($MgSO_4$) before concentration to dryness to give 2-(4-bromo-3-methoxy-pyrazol-1-yl)-5-nitro-pyridine (1.0 g, 3.34 mmol) as a yellow solid. MS$[M+2+H]^+$: 300.9.

Step 3: 6-(4-bromo-3-methoxy-pyrazol-1-yl)pyridin-3-amine

To a solution of 2-(4-bromo-3-methoxy-pyrazol-1-yl)-5-nitro-pyridine (1.0 g, 3.34 mmol) in Acetic acid (30.0 mL) was added iron (1.9 g, 33.44 mmol). The mixture was stirred at 20° C. for 12 h. The reaction mixture was filtered, the filter cake was washed with DCM (20.0 mL×3) and then the filtrate was concentrated in vacuum and purified by silica gel to give 6-(4-bromo-3-methoxy-pyrazol-1-yl)pyridin-3-amine (800.0 mg, 2.97 mmol) as a brown solid. MS $[M+H]^+$: 268.9.

Step 4: tert-butyl N-[6-(4-bromo-3-methoxy-pyrazol-1-yl)-3-pyridyl]carbamate

To a solution of give 6-(4-bromo-3-methoxy-pyrazol-1-yl)pyridin-3-amine (350.0 mg, 1.30 mmol) in methanol (30.0 mL) was added di-t-butyldicarbonate (567.7 mg, 2.60 mmol). The mixture was stirred at 20° C. for 12 h. The reaction mixture was filtered, the filter cake was washed with DCM (20.0 mL×3) and then the filtrate was concentrated in vacuum and purified by silica gel column to give tert-butyl N-[6-(4-bromo-3-methoxy-pyrazol-1-yl)-3-pyridyl]carbamate (450.0 mg, 1.22 mmol) as a brown solid. MS $[M+H]^+$: 369.2.

Step 5: tert-butyl N-[6-[3-methoxy-4-(4,4,5,5-tetramethyl-1,3,2-dioxaborolan-2-yl)pyrazol-1-yl]-3-pyridyl]carbamate To a solution of tert-butyl N-[6-(4-bromo-3-methoxy-pyrazol-1-yl)-3-pyridyl]carbamate (450.0 mg, 1.22 mmol) and 4,4,5,5-tetramethyl-2-(4,4,5,5-tetramethyl-1,3,2-dioxaborolan-2-yl)-1,3,2-dioxaborolane (340.4 mg, 1.34 mmol) in 1,4-dioxane (10.0 mL) was added potassium acetate (239.2 mg, 2.44 mmol) and Pd(dppf)$Cl_2$ (133.6 mg, 0.18 mmol) under argon in glove box. The mixture was stirred at 100° C. for 16 h. The reaction mixture was filtered and the filtrate was concentrated in vacuum. Purified by flash column (0.1% FA as additive) to give tert-butyl N-[6-[3-methoxy-4-(4,4,5,5-tetramethyl-1,3,2-dioxaborolan-2-yl)pyrazol-1-yl]-3-pyridyl]carbamate (150.0 mg, 0.36 mmol) as a yellow solid. MS $[M+H]^+$: 417.3.

Intermediate A9.5 tert-Butyl N-[6-[3-cyano-4-(4,4,5,5-tetramethyl-1,3,2-dioxaborolan-2-yl)pyrazol-1-yl]-3-pyridyl]carbamate Step 1: 4-bromo-1-(5-nitro-2-pyridyl)pyrazole-3-carbonitrile To a solution of compound 4-bromo-1H-pyrazole-3-carbonitrile (1.0 g, 5.81 mmol) in DMF (8.0 mL) was added N,N-diisopropylethylamine (2.0 mL, 11.63 mmol) and 2-chloro-5-nitro-pyridine (0.7 mL, 6.40 mmol). The mixture was stirred at 80° C. for 12 h under $N_2$. The reaction mixture was quenched by water (10 mL), the residue was filtrated and concentrated under reduced pressure to give 4-bromo-1-(5-nitro-2-pyridyl)pyrazole-3-carbonitrile (1.2 g, 4.08 mmol) as brown solid.

Step 2: 1-(5-amino-2-pyridyl)-4-bromo-pyrazole-3-carbonitrile

To a solution of 4-bromo-1-(5-nitro-2-pyridyl)pyrazole-3-carbonitrile (1.5 g, 5.10 mmol) in acetic acid (20.0 mL) was added Fe (1.4 g, 25.50 mmol). The mixture was stirred at 25° C. for 6 h under $N_2$. The reaction mixture was filtered and the filtrate was concentrated under reduced pressure to remove the solvent, and the crude was purified by chromatography column flash and concentrated to give 1-(5-amino-2-pyridyl)-4-bromo-pyrazole-3-carbonitrile (0.5 g, 1.89 mmol 0) as a white solid. MS $[M+H]^+$: 263.9.

Step 3: tert-butyl N-[6-(4-bromo-3-cyano-pyrazol-1-yl)-3-pyridyl]carbamate

To a solution of 1-(5-amino-2-pyridyl)-4-bromo-pyrazole-3-carbonitrile (0.5 g, 1.89 mmol,) in DMF (5.0 mL) was added di-t-butyldicarbonate (619.8 mg, 2.80 mmol). The mixture was stirred at 25° C. for 12 h under $N_2$, The reaction mixture was added water (25 mL), extracted with EtOAc (20 mL×3). The combined organic layers were washed brine (10 mL), dried over $Na_2SO_4$ and concentrated under reduced pressure to remove the solvent. The crude was then purified by chromatography column flash and concentrated to give tert-butyl N-[6-(4-bromo-3-cyano-pyrazol-1-yl)-3-pyridyl]carbamate (0.5 g, 1.37 mmol) as yellow oil. MS $[M+H]^+$: 366.

Step 4: [1-[5-(tert-butoxycarbonylamino)-2-pyridyl]-3-cyano-pyrazol-4-yl]boronic acid A mixture of compound tert-butyl N-[6-(4-bromo-3-cyano-pyrazol-1-yl)-3-pyridyl]carbamate (0.5 g, 1.37 mmol), 4,4,5,5-tetramethyl-2-(4,4,5,5-tetramethyl-1,3,2-dioxaborolan-2-yl)-1,3,2-dioxaborolane (418.4 mg, 1.65 mmol), potassium acetate (0.2 mL, 2.75 mmol) and 1,1'-bis(diphenylphosphino)ferrocene-palladium(II)dichloride dichloromethane complex (112.0 mg, 0.14 mmol) in a flask. 1,4-dioxane (5.0 mL) was added by injector to the mixture. The mixture was stirred at 90° C. for 2 h under $N_2$. The reaction mixture was filtered and the filtrate was concentrated under reduced pressure to remove the solvent. The product was purified by reversed-phase chromatography (0.1% FA as additive) and dried to give [1-[5-(tert-butoxycarbonylamino)-2-pyridyl]-3-cyano-pyrazol-4-yl]boronic acid (268.0 mg, 0.81 mmol,) as a white solid. MS $[M+H]^+$: 330.1.

Intermediate A9.6 tert-Butyl N-[6-[3-methyl-4-(4,4,5,5-tetramethyl-1,3,2-dioxaborolan-2-yl)pyrazol-1-yl]-3-pyridyl]carbamate Step 1: 2-(4-bromo-3-methyl-pyrazol-1-yl)-5-nitro-pyridine To a solution of 4-bromo-3-methyl-1H-pyrazole (1.0 g, 6.21 mmol) in DMF (8.0 mL) was added NaH (871.3 mg, 9.32 mmol) and 2-chloro-5-nitro-pyridine (0.7 mL, 6.83 mmol) at 0° C. The mixture was stirred at 25° C. for 3 h under $N_2$. The reaction mixture was quenched by water (10 mL), filtered on celite and the filtrate was washed with water and concentrated to give crude product 2-(3-bromopyrazol-1-yl)-5-nitro-pyridine (1.5 g, 5.58 mmol) as yellow solid. MS $[M+H]^+$: 282.9.

Step 2: 6-(4-bromo-3-methyl-pyrazol-1-yl)pyridin-3-amine

To a solution of 2-(3-bromopyrazol-1-yl)-5-nitro-pyridine (1.6 g, 5.83 mmol) in acetic acid (20.0 mL) was added Fe (2.6 g, 46.63 mmol). The mixture was stirred at 25° C. for 12 h under $N_2$. The reaction mixture was filtered and the filtrate was concentrated under reduced pressure to remove the solvent, and the crude was purified by chromatography column flash and concentrated to give 6-(4-bromo-3-methyl-pyrazol-1-yl)pyridin-3-amine (0.6 g, 2.37 mmol) as yellow solid. MS $[M+H]^+$: 254.9.

Step 3: tert-butyl N-[6-(4-bromo-3-methyl-pyrazol-1-yl)-3-pyridyl]carbamate

To a solution of give 6-(4-bromo-3-methyl-pyrazol-1-yl)pyridin-3-amine (250.0 mg, 0.99 mmol) in methanol (0.5 mL) was added di-t-butyldicarbonate (0.3 mL, 1.48 mmol). The mixture was stirred at 25° C. for 12 h under $N_2$. The reaction mixture was concentrated under reduced pressure to remove the solvent to give crude product tert-butyl N-[6-(4-bromo-3-methyl-pyrazol-1-yl)-3-pyridyl]carbamate (280.0 mg, 0.79 mmol). MS $[M+H]^+$: 353.0.

Step 4: tert-butyl N-[6-[3-methyl-4-(4,4,5,5-tetramethyl-1,3,2-dioxaborolan-2-yl)pyrazol-1-yl]-3-pyridyl]carbamate A mixture of tert-butyl N-[6-(4-bromo-3-methyl-pyrazol-1-yl)-3-pyridyl]carbamate (250.0 mg, 0.71 mmol), bis(pinacolato)diboron (179.7 mg, 0.71 mmol), potassium acetate (0.09 mL, 1.42 mmol) and 1,1'-bis(diphenylphosphino)ferrocene-palladium(II)dichloride dichloromethane complex (57.8 mg, 0.07 mmol) in a flask. 1,4-dioxane (5.0 mL) was added by injector to the mixture. The flask was degassed and purged with $N_2$ gas for four times. The mixture was stirred at 90° C. for 2 h under $N_2$. The reaction mixture was filtered and the filtrate was concentrated under reduced pressure to remove the solvent, then the product was purified by reversed-phase chromatography (0.1% FA as additive) and dried to give tert-butyl N-[6-[3-methyl-4-(4,4,5,5-tetramethyl-1,3,2-dioxaborolan-2-yl)pyrazol-1-yl]-3-pyridyl]carbamate (120.0 mg, 0.30 mmol) as white solid. MS $[M+H]^+$: 317.1.

Intermediate A9.7 tert-Butyl N-[6-[3-ethyl-4-(4,4,5,5-tetramethyl-1,3,2-dioxaborolan-2-yl)pyrazol-1-yl]-3-pyridyl]carbamate Step 1: 2-(3-bromopyrazol-1-yl)-5-nitro-pyridine To a solution of 3-bromo-1H-pyrazole (1.0 g, 6.8 mmol) in THF (20.0 mL) was added sodium hydride, 60% in oil (299.3 mg, 7.48 mmol) slowly at 0° C. After addition, this reaction mixture was stirred at 0° C. for 0.5 h. 2-chloro-5-nitro-pyridine (1.2 g, 7.48 mmol) was added into this mixture at 0° C. The reaction mixture was stirred at 25° C. for 2.5 h. This reaction was quenched by saturated aqueous $NH_4Cl$ (50.0 mL) and was extracted by EtOAc (30.0 mL×3). The combined organic layers were dried over $Na_2SO_4$ and concentrated to get the crude product. This crude product was purified by silica gel chromatography (PE:EtOAc=20:1) to get 2-(3-bromopyrazol-1-yl)-5-nitro-pyridine (1.5 g, 5.58 mmol) as yellow solid. MS $[M+H]^+$: 268.8.

Step 2: 5-nitro-2-(3-vinylpyrazol-1-yl)pyridine

To a solution of 2-(3-bromopyrazol-1-yl)-5-nitro-pyridine (900.0 mg, 3.35 mmol), 4,4,5,5-tetramethyl-2-vinyl-1,3,2-dioxaborolane (772.7 mg, 5.02 mmol) and potassium carbonate (924.6 mg, 6.69 mmol) in 1,4-dioxane (25.0 mL) and water (2.5 mL) was added [1,1'-bis(diphenylphosphino) ferrocene]dichloropalladium(II) (244.7 mg, 0.33 mmol) in one portion under $N_2$. This reaction mixture was stirred at 100° C. for 16 h. This reaction mixture was filtered, and the filtrate was concentrated to get the residue. This residue was diluted with EtOAc (100.0 mL) and was washed by brine (20.0 mL×2). The organic layer was dried over $Na_2SO_4$ and concentrated to get the crude product. This crude product was purified by silica gel chromatography to get 5-nitro-2-(3-vinylpyrazol-1-yl)pyridine (1.1 g, 5.09 mmol) as yellow solid. MS $[M+H]^+$: 217.1.

Step 3: 6-(3-ethylpyrazol-1-yl)pyridin-3-amine

To a solution of 5-nitro-2-(3-vinylpyrazol-1-yl)pyridine (900.0 mg, 4.16 mmol) in methanol (5.0 mL) was added palladium on carbon (10%) (443.0 mg, 0.42 mmol) in one portion under $N_2$. $H_2$ was introduced into this system. This reaction mixture was stirred at 25° C. for 4 h. This reaction mixture was filtered, and the filtrate was concentrated to get 6-(3-ethylpyrazol-1-yl)pyridin-3-amine (740.0 mg, 3.93 mmol) as colorless oil, which would be used in the next step directly without further purification. MS $[M+H]^+$: 189.2.

Step 4: tert-butyl N-[6-(3-ethylpyrazol-1-yl)-3-pyridyl]carbamate

To a solution of 6-(3-ethylpyrazol-1-yl)pyridin-3-amine (900.0 mg, 4.78 mmol) and triethylamine (1.33 mL, 9.56 mmol) in ACN (20.0 mL) was added di-t-butyldicarbonate (1.32 mL, 5.74 mmol) in one portion. This reaction mixture was stirred at 60° C. for 2 h. This reaction mixture was concentrated to get the crude product. This crude product was purified by silica gel chromatography to get tert-butyl N-[6-(3-ethylpyrazol-1-yl)-3-pyridyl]carbamate (800.0 mg, 2.77 mmol) as yellow oil. MS $[M+H]^+$: 289.2.

Step 5: tert-butyl N-[6-(4-bromo-3-ethyl-pyrazol-1-yl)-3-pyridyl]carbamate

To a solution of tert-butyl N-[6-(3-ethylpyrazol-1-yl)-3-pyridyl]carbamate (700.0 mg, 2.43 mmol) in ACN (20.0 mL) was added N-bromosuccinimide (432.0 mg, 2.43 mmol) in one portion. This reaction mixture was stirred at 25° C. for 2 h. This reaction was quenched by saturated aqueous $Na_2SO_3$ (20.0 mL) and extracted by EtOAc (30.0 mL×2). The combined organic layers were dried over $Na_2SO_4$ and concentrated to get the crude product. This crude product was purified by Prep-HPLC (neutral) to get tert-butyl N-[6-(4-bromo-3-ethyl-pyrazol-1-yl)-3-pyridyl] carbamate (220.0 mg, 0.6 mmol) as red solid. MS $[M+H]^+$: 367.2.

Step 6: tert-butyl N-[6-[3-ethyl-4-(4,4,5,5-tetramethyl-1,3,2-dioxaborolan-2-yl)pyrazol-1-yl]-3-pyridyl]carbamate To a solution of bis(pinacolato)diboron (138.3 mg, 0.54 mmol), tert-butyl N-[6-(4-bromo-3-ethyl-pyrazol-1-yl)-3-pyridyl]carbamate (100.0 mg, 0.27 mmol) and potassium acetate (66.8 mg, 0.68 mmol) in 1,4-dioxane (2.0 mL) was added [1,1'-bis(diphenylphosphino)ferrocene]dichloropalladium(II) (19.9 mg, 0.03 mmol) in one portion under $N_2$. This reaction mixture was stirred at 100° C. for 2 h. This reaction mixture was filtered, and the filtrate was concentrate to get the crude product. This crude product was purified by Prep-TLC (PE:EtOAc=1:1) to get tert-butyl N-[6-[3-ethyl-4-(4,4,5,5-tetramethyl-1,3,2-dioxaborolan-2-yl)pyrazol-1-yl]-3-pyridyl]carbamate (120.0 mg, 0.29 mmol, 38% yield) as yellow oil. MS $[M+H]^+$: 289.2.

Intermediate A9.8 tert-Butyl N-[6-[4-(4,4,5,5-tetramethyl-1,3,2-dioxaborolan-2-yl)-3-(trifluoromethyl)pyrazol-1-yl] pyridazin-3-yl]carbamate Step 1: tert-butyl N-(6-chloropyridazin-3-yl)carbamate To a solution of 6-chloropyridazin-3-amine (6.0 g, 46.31 mmol), triethylamine (9.68 mL, 69.47 mmol) and 4-dimethylaminopyridine (2.8 g, 23.16 mmol) in ACN (20.0 mL) was added di-t-butyldicarbonate (15.1 g, 69.47 mmol) in one portion. This reaction mixture was stirred at 80° C. for 16 h. This reaction was quenched by saturated aqueous $Na_2CO_3$ (50.0 mL) and was extracted by EtOAc (100.0 mL×2). The combined organic layers were dried over $Na_2SO_4$ and concentrated to get the crude product. This crude product was purified silica gel chromatography to get tert-butyl N-(6-chloropyridazin-3-yl)carbamate (5.6 g, 24.38 mmol) as light yellow solid. MS $[M+H-C_4H_8]^+$:174.1.

Step 2: 6-[4-bromo-3-(trifluoromethyl)pyrazol-1-yl] pyridazin-3-amine

To a solution of tert-butyl N-(6-chloropyridazin-3-yl) carbamate (2.2 g, 9.3 mmol) and potassium carbonate (1.9 g, 13.96 mmol) in DMF (40.0 mL) was added tert-butyl N-(6-chloropyridazin-3-yl)carbamate (2.0 g, 9.3 mmol) and cesium fluoride (141.3 mg, 0.930 mmol) in one portion. This reaction mixture was stirred at 120° C. for 48 h. This reaction mixture was diluted with EtOAc (200.0 mL) and was washed by brine (50.0 mL×3). The organic layer was dried over $Na_2SO_4$ and concentrated to get the crude product. This crude product was purified by Prep-HPLC (TFA) to get 6-[4-bromo-3-(trifluoromethyl)pyrazol-1-yl] pyridazin-3-amine (350.0 mg, 1.14 mmol) as yellow solid. MS ($[M+H]^+$: 308.0.

Step 3: tert-butyl N-[6-[4-bromo-3-(trifluoromethyl) pyrazol-1-yl]pyridazin-3-yl]carbamate To a solution of 6-[4-bromo-3-(trifluoromethyl)pyrazol-1-yl]pyridazin-3-amine (350.0 mg, 1.14 mmol), triethylamine (0.48 mL, 3.41 mmol) and 4-dimethylaminopyridine (138.8 mg, 1.14 mmol) in DMF (10.0 mL) was added di-t-butyldicarbonate (297.5 mg, 1.36 mmol) in one portion. This reaction mixture was stirred at 80° C. for 16 h. This reaction mixture was diluted with brine (20.0 mL) and extracted by EtOAc (10.0 mL×3). The combined organic layers were dried over $Na_2SO_4$ and concentrated to get the crude product. This crude product was purified by Prep-HPLC (FA) to get tert-butyl N-[6-[4-bromo-3-(trifluoromethyl)pyrazol-1-yl]pyridazin-3-yl]carbamate (90.0 mg, 0.22 mmol) as yellow solid. MS $[M+2+H]^+$: 410.0.

Step 4: tert-butyl N-[6-[4-(4,4,5,5-tetramethyl-1,3,2-dioxaborolan-2-yl)-3-(trifluoromethyl)pyrazol-1-yl] pyridazin-3-yl]carbamate To a solution of tert-butyl N-[6-[4-bromo-3-(trifluoromethyl)pyrazol-1-yl]pyridazin-3-yl]carbamate (90.0 mg, 0.220 mmol), bis(pinacolato)diboron (83.9 mg, 0.33 mmol) and potassium acetate (43.2 mg, 0.44 mmol) in 1,4-dioxane (2.0 mL) was added [1,1'-bis(diphenylphosphino)ferrocene] dichloropalladium(II) (16.1 mg, 0.02 mmol) in one portion under $N_2$. This reaction mixture was stirred at 100° C. for 4 h. This reaction mixture was filtered, and the filtrate was concentrated to get the crude product. This crude product was purified by Prep-TLC (PE:EtOAc=4:1) to get tert-butyl N-[6-[4-(4,4,5,5-tetramethyl-1,3,2-dioxaborolan-2-yl)-3-(trifluoromethyl)pyrazol-1-yl]pyridazin-3-yl]carbamate (100.0 mg, 0.22 mmol, 42% yield) as yellow solid. MS $[M+H]^+$: 456.2.

Intermediate A9.9

Trimethyl-[2-[[4-methyl-3-[4-(4,4,5,5-tetramethyl-1,3,2-dioxaborolan-2-yl)-3-(trifluoromethyl)pyrazol-1-yl]pyrazol-1-yl]methoxy]ethyl]silane Step 1: trimethyl-[2-[(4-methylpyrazol-1-yl) methoxy]ethyl]silane A solution of 4-methyl-1H-pyrazole (5.0 g, 60.9 mmol) in THF (50.0 mL) was degassed and purged with $N_2$ for 3 times. Then sodium hydride (60%) (3.65 g, 91.35 mmol) was added into the mixture at 0° C. This mixture was stirred at 0° C. for 0.5 h. Then 2-(trimethylsilyl)ethoxymethyl chloride (12.9 mL, 73.08 mmol) was added into the mixture at 0° C. The reaction mixture was stirred at 20° C. for 2 h under $N_2$ atmosphere. This reaction was quenched by saturates aqueous $NH_4Cl$ (100 mL) and extracted with EtOAc (100.0 mL×3). The combined organic layers were washed with brine (100 mL), dried over $Na_2SO_4$, and concentrated under reduced pressure affording the crude product trimethyl-[2-[(4-methylpyrazol-1-yl)methoxy]ethyl]silane (15.0 g, 70.63 mmol) as a yellow solid, which would be used in the next step directly. MS $[M+H]^+$: 213.3.

Step 2: 2-[(3-bromo-4-methyl-pyrazol-1-yl) methoxy]ethyl-trimethyl-silane

A solution of trimethyl-[2-[(4-methylpyrazol-1-yl) methoxy]ethyl]silane (5.0 g, 23.54 mmol) in ACN (50 mL) was degassed and purged with $N_2$ for 3 times. Then N-bromosuccinimide (5.0 g, 28.25 mmol) was added into the mixture. The reaction mixture was stirred at 20° C. for 16 h under $N_2$ atmosphere. The mixture was extracted with EtOAc (100.0 mL×3). The combined organic layers were washed with brine (100 mL), dried over $Na_2SO_4$, and concentrated under reduced pressure affording the crude product. The crude product was purified by silica gel chromatography (PE:EtOAc=50/1~20/1) to get 2-[(3-bromo-4-methyl-pyrazol-1-yl)methoxy]ethyl-trimethyl-silane (4.4 g, 15.11 mmol) as a yellow oil. MS($[M+H]^+$: 293.0.

Step 3: [4-methyl-1-(2-trimethylsilylethoxymethyl) pyrazol-3-yl]boronic acid

A mixture of 2-[(3-bromo-4-methyl-pyrazol-1-yl) methoxy]ethyl-trimethyl-silane (2.5 g, 8.58 mmol), bis(pinacolato)diboron (5.4 g, 21.46 mmol), potassium acetate (1.61 mL, 25.75 mmol) and X-PHOS (409.1 mg, 0.86 mmol) in 1,4-dioxane (40.0 mL) was degassed and purged with $N_2$ for 3 times. Then tris(dibenzylideneacetone)dipalladium (0) (393.0 mg, 0.43 mmol) was added into the mixture. The reaction mixture was stirred at 100° C. for 16 h under $N_2$ atmosphere. The mixture was filtered and concentrated under reduced pressure affording the crude product. The crude product was purified by Prep-HPLC (TFA) to get [4-methyl-1-(2-trimethylsilylethoxymethyl)pyrazol-3-yl]boronic acid (970.0 mg, 3.79 mmol) as a yellow solid. MS $[M+H]^+$: 257.2.

Step 4: 2-[[3-[4-bromo-3-(trifluoromethyl)pyrazol-1-yl]-4-methyl-pyrazol-1-yl]methoxy]ethyl-trimethyl-silane To a solution of 4-bromo-3-(trifluoromethyl)-1H-pyrazole (400.0 mg, 1.86 mmol), [4-methyl-1-(2-trimethylsilylethoxymethyl)pyrazol-3-yl]boronic acid (572.0 mg, 2.23 mmol), Molecularsieves, 4 A (400.0 mg) and pyridine (0.3 mL, 3.72 mmol) in 1,2-dichloroethane (20.0 mL) was added copper(II) acetate monohydrate (74.3 mg, 0.37 mmol) in one portion. Then 02 (15 psi) was introduced into this system. The reaction mixture was stirred at 60° C. for 6 h. This reaction mixture was filtered, and the filtrate was concentrated to get the crude product. This crude product was purified by silica gel chromatography (PE:EtOAc=100:1~50:1) to get 2-[[3-[4-bromo-3-(trifluoromethyl)pyrazol-1-yl]-4-methyl-pyrazol-1-yl]methoxy]ethyl-trimethyl-silane (360.0 mg, 0.85 mmol, 39% yield) as yellow oil. MS $[M+H]^+$: 425.0.

Step 5: trimethyl-[2-[[4-methyl-3-[4-(4,4,5,5-tetramethyl-1,3,2-dioxaborolan-2-yl)-3-(trifluoromethyl) pyrazol-1-yl]pyrazol-1-yl]methoxy]ethyl]silane To a solution of bis(pinacolato)diboron (322.4 mg, 1.27 mmol), 2-[[3-[4-bromo-3-(trifluoromethyl)pyrazol-1-yl]-4-methyl-pyrazol-1-yl]methoxy]ethyl-trimethyl-silane (360.0 mg, 0.85 mmol) and potassium acetate (166.1 mg, 1.69 mmol) in 1,4-dioxane (10.0 mL) was added [1,1'-bis(diphenylphosphino)ferrocene]dichloropalladium(II) (61.9 mg, 0.08 mmol) in one portion under $N_2$. This reaction mixture was stirred at 100° C. for 16 h. This reaction mixture was filtered, and the filtrate was concentrated to get the crude product. This crude product was purified by Prep-TLC (PE:EtOAc=20:1) to get trimethyl-[2-[[4-methyl-3-[4-(4,4,5,5-tetramethyl-1,3,2-dioxaborolan-2-yl)-3-(trifluoromethyl)pyrazol-1-yl]pyrazol-1-yl]methoxy]ethyl]silane (300.0 mg, 0.64 mmol, 40% yield) as yellow oil. MS($[M+H]^+$: 473.0.

Intermediate A10

9H-Fluoren-9-ylmethyl N-(6-bromo-3-pyridyl)-N-(2-methoxyethyl)carbamate

Step 1: 6-bromo-N-(2-methoxyethyl)pyridin-3-amine 6-bromopyridin-3-amine (500 mg, 2.89 mmol), sodium iodide (216.6 mg, 1.45 mmol) and 1-bromo-2-methoxyethane (482.02 mg, 325.91 uL) were dissolved in anhydrous tetrahydrofuran (28.9 mL). The solution was cooled to 0° C. To this solution was added NaH (138.72 mg, 3.47 mmol) portionwise. The mixture was stirred at 0° C. for 4 h. Then another portion of NaH (138.72 mg, 3.47 mmol) was added, and the mixture was refluxed at 70° C. for 2 h. Then the mixture was cooled to r.t and concentrated in vacuum. The residue was purified by flash chromatography to afford 6-bromo-N-(2-methoxyethyl)pyridin-3-amine (373 mg). MS $[M+H]^+$: 231.1.

Step 2: 9H-fluoren-9-ylmethyl N-(6-bromo-3-pyridyl)-N-(2-methoxyethyl)carbamate

A mixture of 6-bromo-N-(2-methoxyethyl)pyridin-3-amine (3.7 g, 16.01 mmol), 9H-fluoren-9-ylmethyl carbonochloridate (4.56 g, 17.61 mmol) and $NaHCO_3$ (2.02 g, 24.02 mmol) were stirred in 1,4-dioxane (80.06 mL) at 0° C. for 18 h. The solvent was removed in vacuum, and the residue was purified by flash chromatography to afford 9H-fluoren-9-ylmethyl N-(6-bromo-3-pyridyl)-N-(2-methoxyethyl)carbamate (6.2 g) as a yellow oil. MS $[M+H]^+$: 453.2.

Intermediate A11.1

2-[(5-Iodo-4-methyl-pyrazol-1-yl)methoxy]ethyl-trimethyl-silane

At room temperature, a mixture of 5-iodo-4-methyl-1H-pyrazole (2 g, 9.62 mmol), 2-(chloromethoxy)ethyl-trimethyl-silane (1.92 g, 2.04 mL, 11.5 mmol) and DIPEA (1.86 g, 2.51 mL, 14.4 mmol) were stirred in DCM (45 mL) for 2 h. Then the solution was poured into water and acidified to pH=5-6 with 1N HCl aqueous solution. The organic layer was washed with brine, dried over anhydrous $Na_2SO_4$ and concentrated to afford the the mixture of 2-[(5-iodo-4-methyl-pyrazol-1-yl)methoxy]ethyl-trimethyl-silane and 2-[(3-iodo-4-methyl-pyrazol-1-yl)methoxy]ethyl-trimethyl-silane (1.9 g) as an oil.

The following intermediates were prepared in analogy of Intermediate A11.1.

| Ex# | Name | MS ESI $[M + H]^+$ | Starting Material |
|---|---|---|---|
| Intermediate A11.2 | 2-[(4-iodo-3-methyl-pyrazol-1-yl)methoxy]ethyl-trimethyl-silane | 339.0 | 4-iodo-3-methyl-1H-pyrazole and SEM-Cl |

Intermediate A12

5-Nitro-2-[4-(4,4,5,5-tetramethyl-1,3,2-dioxaborolan-2-yl)-3-(trifluoromethyl)pyrazol-1-yl]pyridine To a solution of 4-(4,4,5,5-tetramethyl-1,3,2-dioxaborolan-2-yl)-3-(trifluoromethyl)-1H-pyrazole (7.8 g, 30 mmol) in dimethyl sulfoxide (100 mL) and triethyl amine (3.0 mL) was added 2-chloro-5-nitro-pyridine (4.8 g, 30 mmol). Then the mixture was stirred for 3 h at 130° C. The mixture was poured into water and the aqueous solution was extracted with DCM. The combined organic layers were washed with water and brine, dried over anhydrous $Na_2SO_4$. The organic layer was concentrated in vacuum and the residue was purified by flash column to afford 5-nitro-2-[4-(4,4,5,5-tetramethyl-1,3,2-dioxaborolan-2-yl)-3-(trifluoromethyl)pyrazol-1-yl]pyridine (10 g) as a yellow solid. MS $[M+H]^+$: 385.1.

Intermediate B1.1 tert-Butyl 4-[(5-bromo-1-methyl-imidazole-2-carbonyl)amino]-2-chloro-benzoate

Step 1: tert-butyl 2-chloro-4-nitro-benzoate

To a mixture of 2-chloro-4-nitro-benzoic acid (15.0 g, 74.42 mmol), N,N-dimethylpyridin-4-amine (2.73 g, 22.33 mmol) and N,N-diethylethanamine (31.12 mL, 223.26 mmol) in THF (80 mL) was added a solution of tert-butoxycarbonyl tert-butyl carbonate (24.36 g, 111.63 mmol) in THF (20 mL) at −10° C. The resulting mixture was warmed to 25° C. and stirred for another 14 h. The mixture was concentrated. The residue was treated with EA (50 mL) and $H_2O$ (50 mL). The mixture was extracted with EA. The combined organic layers were concentrated. The crude was then purified by flash column chromatography to afford tert-butyl 2-chloro-4-nitro-benzoate (18.8 g) as a colorless solid.

Step 2: tert-butyl 4-amino-2-chloro-benzoate

To a mixture of tert-butyl 2-chloro-4-nitro-benzoate (18.8 g, 72.96 mmol) and Ammonium chloride (19.51 g, 364.81 mmol) in ethanol (200 mL) and water (200 mL) was added Iron (20.37 g, 364.81 mmol). The mixture was stirred at 25° C. for 14 h. The mixture was filtered by Celite. The filtrate was concentrated to remove ethanol. The mixture was extracted with EA. The combined organic layers were dried over anhydrous $Na_2SO_4$ and concentrated to afford tert-butyl 4-amino-2-chloro-benzoate (16.31 g) as a light yellow solid. MS $[M+H]^+$: 228.1.

Step 3: tert-butyl 4-[(5-bromo-1-methyl-imidazole-2-carbonyl)amino]-2-chloro-benzoate A mixture of 5-bromo-1-methyl-imidazole-2-carboxylic acid hydrochloride (7.0 g, 28.99 mmol), tert-butyl 4-amino-2-chloro-benzoate (6.0 g, 26.35 mmol), HATU (13.23 g, 34.79 mmol) and DIPEA (16.16 mL, 92.77 mmol) in DMF (15 mL) was stirred at 25° C. for 3 h. The mixture was added water (10 mL) and extracted with EA. The combined organic layers were concentrated. The crude was purified by FCC to afford tert-butyl 4-[(5-bromo-1-methyl-imidazole-2-carbonyl)amino]-2-chloro-benzoate (8 g, 19.29 mmol) as a white solid. MS $[M+H]^+$: 414.0

The following intermediate was prepared in analogy of Intermediate B1.1.

| Ex# | Name | MS ESI $[M + H]^+$ | Starting Material |
|---|---|---|---|
| Intermediate B1.2 | tert-butyl 4-[(5-bromo-1-methyl-imidazole-2-carbonyl)amino]-2-methyl-benzoate | 394.1 | 2-methyl-4-nitro-benzoic acid and 5-bromo-1-methyl-imidazole-2-carboxylic acid |

Intermediate B2.1

5-Bromo-N-[3-chloro-4-(piperazine-1-carbonyl)phenyl]-1-methyl-imidazole-2-carboxamide

Step 1: 4-(5-bromo-1-methyl-imidazole-2-carboxamido)-2-chlorobenzoic acid

In a 250 mL round-bottomed flask, tert-butyl 4-(5-bromo-1-methyl-imidazole-2-carboxamido)-2-chlorobenzoate (5 g, 12.1 mmol) was combined with $CH_2Cl_2$ (30 mL) to give a light brown solution. TFA (41.2 g, 27.9 mL, 362 mmol) was added. The reaction was stirred at room temperature for 1 h. The crude reaction mixture was concentrated in vacuum. The crude product was directly used to the next step, to afford 4-(5-bromo-1-methyl-imidazole-2-carboxamido)-2-chlorobenzoic acid (4.32 g). MS $[M+H]^+$: 359.8.

Step 2: tert-butyl 4-(4-(5-bromo-1-methyl-imidazole-2-carboxamido)-2-chlorobenzoyl)piperazine-1-carboxylate In a 100 mL round-bottomed flask, 4-(5-bromo-1-methyl-imidazole-2-carboxamido)-2-chlorobenzoic acid (2 g, 5.58 mmol), tert-butyl piperazine-1-carboxylate (1.19 g, 6.41 mmol,) and DIEA (2.16 g, 2.92 mL, 16.7 mmol) were combined with DMF (15 mL) to give a colorless solution. HATU (2.76 g, 7.25 mmol) was added. The mixture was stirred at room temperature for 1 h. The reaction mixture was poured into 150 mL $H_2O$ and extracted with EtOAc (75 mL×3). The organic layers were combined, washed with sat NaCl (75 mL×1), The organic layers were dried over $Na_2SO_4$ and concentrated in vacuum. to afford tert-butyl 4-(4-(5-bromo-1-methyl-imidazole-2-carboxamido)-2-chlorobenzoyl)piperazine-1-carboxylate (2.94 g). MS $[M+H]^+$: 527.9.

The following intermediates were prepared in analogy of Intermediate B2.1.

| Ex# | Name | MS ESI $[M + H]^+$ | Starting Material |
|---|---|---|---|
| Intermediate B2.2 | tert-butyl 1-[4-[(5-bromo-1-methyl-imidazole-2-carbonyl)amino]-2-chloro-benzoyl]piperidine-4-carboxylate | 527.1 | Intermediate B1.1 and TFA and isonipecotic acid tert-butyl ester |
| Intermediate B2.3 | tert-butyl 4-[4-[(5-bromo-1-methyl-imidazole-2-carbonyl)amino]-2-methyl-benzoyl]piperazine-1-carboxylate | 506.2 | Intermediate B1.2 and TFA and tert-butyl piperazine-1-carboxylate |
| Intermediate B2.4 | tert-butyl 4-[[[4-[(5-bromo-1-methyl-imidazole-2-carbonyl)amino]-2-chloro-benzoyl]amino]methyl]piperidine-1-carboxylate | 554.1 | Intermediate B1.1 and TFA and 4-(aminomethyl)piperidine-1-carboxylic acid tert-butyl ester |

Intermediate B3.1

5-Bromo-N-(3-chloro-4-(piperazine-1-carbonyl)phenyl)-1-methyl-imidazole-2-carboxamide In a 100 mL round-bottomed flask, tert-butyl 4-(4-(5-bromo-1-methyl-imidazole-2-carboxamido)-2-chlorobenzoyl)piperazine-1-carboxylate (2.94 g, 5.58 mmol) was combined with THF (20 mL) to give a light brown solution. HCl (in water) (11.6 mL, 140 mmol) was added. The reaction was stirred at room temperature for 1 h. The reaction mixture was concentrated in vacuum. The crude product was directly used to the next step, to afford 5-bromo-N-(3-chloro-4-(piperazine-1-carbonyl)phenyl)-1-methyl-imidazole-2-carboxamide (2.38 g). MS $[M+H]^+$: 427.8.

The following intermediates were prepared in analogy of Intermediate B3.1.

| Ex# | Name | MS ESI $[M + H]^+$ | Starting Material |
|---|---|---|---|
| Intermediate B3.2 | 5-bromo-1-methyl-N-[3-methyl-4-(piperazine-1-carbonyl)phenyl] imidazole-2-carboxamide | 406.2 | Intermediate B2.3 and HCl |
| Intermediate B3.3 | 5-bromo-N-[3-chloro-4-(4-piperidylmethylcarbamoyl) phenyl]-1-methyl-imidazole-2-carboxamide | 454.1 | Intermediate B2.4 and HCl |

Intermediate B4.1 tert-Butyl 4-(4-(4-(5-bromo-1-methyl-imidazole-2-carboxamido)-2-chlorobenzoyl)piperazine-1-carbonyl)piperidine-1-carboxylate In a 100 mL round-bottomed flask, 5-bromo-N-(3-chloro-4-(piperazine-1-carbonyl)phenyl)-1-methyl-imidazole-2-carboxamide (2.38 g, 5.58 mmol), 1-(tert-butoxycarbonyl) piperidine-4-carboxylic acid (2.05 g, 8.92 mmol) and DIEA (2.16 g, 2.92 mL, 16.7 mmol) were combined with DMF (15 mL) to give a light brown solution. HATU (3.39 g, 8.92 mmol) was added. The reaction was stirred at room temperature for 1 h. The reaction mixture was poured into 150 mL $H_2O$ and extracted with EtOAc (50 mL×3). The organic layers were combined, washed with sat NaCl (75 mL×1), The organic layers were dried over $Na_2SO_4$ and concentrated in vacuum. tert-butyl 4-(4-(4-(5-bromo-1-methyl-imidazole-2-carboxamido)-2-chlorobenzoyl)piperazine-1-carbonyl)piperidine-1-carboxylate (3.56 g). MS $[M+H]^+$: 638.9.

The following intermediates were prepared in analogy of Intermediate B4.1.

| Ex# | Name | MS ESI $[M + H]^+$ | Starting Material |
|---|---|---|---|
| Intermediate B4.2 | tert-butyl (3S,4R)-4-[4-[4-[(5-bromo-1-methyl-imidazole-2-carbonyl)amino]-2-chloro-benzoyl]piperazine-1-carbonyl]-3-hydroxy-piperidine-1-carboxylate | 655.3 | Intermediate B3.1 and (3S,4R)-1-tert-butoxycarbonyl-3-hydroxy-piperidine-4-carboxylic acid |
| Intermediate B4.3 | tert-butyl 4-[4-[4-[(5-bromo-1-methyl-imidazole-2- | 653.2 | Intermediate B3.1 and 1-tert-butoxycarbonyl-4-hydroxy-piperidine-4-carboxylic acid |

-continued

| Ex# | Name | MS ESI $[M + H]^+$ | Starting Material |
|---|---|---|---|
| | carbonyl)amino]-2-chloro-benzoyl]piperazine-1-carbonyl]-4-hydroxy-piperidine-1-carboxylate | | |
| Intermediate D27 | tert-butyl (25,3S)-2-[4-[2-chloro-4-[[1-methyl-5-[1-(5-nitro-2-pyridyl)-3-(trifluoromethyl)pyrazol-4-yl]imidazole-2-carbonyl]amino]benzoyl] piperazine-1-carbonyl]-3-hydroxy-pyrrolidine-1-carboxylate | 817.2 | Intermediate E1 and (2S,3S)-1-tert-butoxycarbonyl-3-hydroxy-pyrrolidine-2-carboxylic acid |
| Intermediate B4.5 | tert-butyl 4-[4-[4-[(5-bromo-1-methyl-imidazole-2-carbonyl)amino]-2-methyl-benzoyl]piperazine-1-carbonyl]piperidine-1-carboxylate | 617.1 | Intermediate B3.2 and 1-(tert-butoxycarbonyl) piperidine-4-carboxylic acid |
| Intermediate B4.6 | tert-butyl 4-[4-[[[4-[(5-bromo-1-methyl-imidazole-2-carbonyl)amino]-2-chloro-benzoyl]amino]methyl] piperidine-1-carbonyl]piperidine-1-carboxylatecarbonyl] piperidine-1-carboxylate | 665.2 | Intermediate B3.3 and 1-(tert-butoxycarbonyl) piperidine-4-carboxylic acid |
| Intermediate B4.7 | tert-butyl (3S)-3-[4-[4-[(5-bromo-1-methyl-imidazole-2-carbonyl)amino]-2-chloro-benzoyl]piperazine-1-carbonyl]morpholine-4-carboxylate | 639.1 | Intermediate B3.1 and (3S)-4-tert-butoxycarbonylmorpholine-3-carboxylic acid |
| Intermediate B4.8 | tert-butyl (2S,4R)-2-[4-[4-[(5-bromo-1-methyl-imidazole-2-carbonyl)amino]-2-chloro-benzoyl]piperazine-1-carbonyl]-4-hydroxy-pyrrolidine-1-carboxylate | 639.1 | Intermediate B3.1 and (2S,4R)-1-tert-butoxycarbonyl-4-hydroxy-pyrrolidine-2-carboxylic acid |
| Intermediate B4.9 | 5-bromo-N-[3-chloro-4-[4-(1-methylpiperidine-4-carbonyl)piperazine-1-carbonyl]phenyl]-1-methyl-imidazole-2-carboxamide | 553.1 | Intermediate B3.1 and 1-methylpiperidine-4-carboxylic acid |

Intermediate C1 tert-Butyl 2-chloro-4-[[1-methyl-5-[3-(trifluoromethyl)-1H-pyrazol-4-yl]imidazole-2-carbonyl]amino] benzoate In a 100 mL round-bottomed flask, tert-butyl 4-(5-bromo-1-methyl-imidazole-2-carboxamido)-2-chlorobenzoate (2 g, 4.82 mmol), 4-(4,4,5,5-tetramethyl-1,3,2-dioxaborolan-2-yl)-3-(trifluoromethyl)-1H-pyrazole (1.64 g, 6.27 mmol), 1,1'-bis(di-tert-butylphosphino)ferrocene palladium dichloride (314 mg, 482 mol) and $Na_2CO_3$ (1.53 g, 14.5 mmol) were combined with 1,4-Dioxane (30 mL) Water (3 mL) and stirred for 15 h under $N_2$. The filtrate was concentrated in vacuum. The crude material was purified by flash chromatography (silica gel, 20 g, 0% to 10% MeOH in DCM) to afford tert-butyl 2-chloro-4-(1-methyl-5-(3-(trifluoromethyl)-1H-pyrazol-4-yl)-imidazole-2-carboxamido)benzoate (2 g). MS $[M+H]^+$: 470.7.

The following intermediates were prepared in analogy of Intermediate C1.

| Ex# | Name | MS ESI $[M + H]^+$ | Starting Material |
|---|---|---|---|
| Intermediate C2 | tert-butyl 4-(2-chloro-4-(1-methyl-5-(3-(trifluoromethyl)-1H-pyrazol-4-yl)-imidazole-2- | 582.2 | Intermediate B2.1 and 4-(4,4,5,5-tetramethyl-1,3,2-dioxaborolan-2-yl)-3-(trifluoromethyl)-1H-pyrazole |

-continued

| Ex# | Name | MS ESI $[M + H]^+$ | Starting Material |
|---|---|---|---|
| | carboxamido)benzoyl) piperazine-1-carboxylate | | |
| Intermediate C3 | tert-butyl 4-(4-(2-chloro-4-(1-methyl-5-(3-(trifluoromethyl)-1H-pyrazol-4-yl)-imidazole-2-carboxamido)benzoyl) piperazine-1-carbonyl) piperidine-1-carboxylate | 693.3 | Intermediate B4.1 and 4-(4,4,5,5-tetramethyl-1,3,2-dioxaborolan-2-yl)-3-(trifluoromethyl)-1H-pyrazole |
| Intermediate C4 | tert-butyl (3S,4R)-4-[4-[2-chloro-4-[[1-methyl-5-[3-(trifluoromethyl)-1H-pyrazol-4-yl]imidazole-2-carbonyl]amino]benzoyl] piperazine-1-carbonyl]-3-hydroxy-piperidine-1-carboxylate | 709.5 | Intermediate B4.2 and 4-(4,4,5,5-tetramethyl-1,3,2-dioxaborolan-2-yl)-3-(trifluoromethyl)-1H-pyrazole |
| Intermediate D11 | tert-butyl 1-[2-chloro-4-[1-methyl-5-[1-(5-nitro-2-pyridyl)-3-(trifluoromethyl)pyrazol-4-yl]imidazole-2-carbonyl]amino]benzoyl] piperidine-4-carboxylate | 703.1 | Intermediate B2.2 and intermediate A12 |
| Intermediate D12 | tert-butyl 2-chloro-4-[[1-methyl-5-[1-(5-nitro-2-pyridyl)-3-(trifluoromethyl)pyrazol-4-yl]imidazole-2-carbonyl]amino]benzoate | 592.2 | Intermediate B1 and intermediate A12 |
| Intermediate D13 | tert-butyl 4-[4-[2-chloro-4-[[1-methyl-5-[1-(5-nitro-2-pyridyl)-3-(trifluoromethyl)pyrazol-4-yl]imidazole-2-carbonyl]amino]benzoyl] piperazine-1-carbonyl]-4-hydroxy-piperidine-1 -carboxylate | 831.2 | Intermediate B4.3 and intermediate A12 |
| Intermediate D14 | tert-butyl 4-[4-[2-chloro-4-[[5-[1-(4-methoxypyrimidin-2-yl)-3-(trifluoromethyl)pyrazol-4-yl]-1-methyl-imidazole-2-carbonyl]amino]benzoyl] piperazine-1-carbonyl]piperidine-1-carboxylate | 801.4 | Intermediate B4.1 and Intermediate A9.1 |
| Intermediate D15 | tert-butyl 4-[4-[2-chloro-4-[5-[1-(2-methoxypyrimidin-4-yl)-3-(trifluoromethyl)pyrazol-4-yl]-1-methyl-imidazole-2-carbonyl]amino]benzoyl] piperazine-1-carbonyl]piperidine-1-carboxylate | 801.4 | Intermediate B4.1 and Intermediate A9.2 |
| Intermediate D16 | tert-butyl 4-[4-[2-methyl-4-[1-methyl-5-[1-(5-nitro-2-pyridyl)-3-(trifluoromethyl)pyrazol-4-yl]imidazole-2-carbonyl]amino]benzoyl] piperazine-1-carbonyl]piperidine-1-carboxylate | 795.3 | Intermediate B4.5 and intermediate A12 |
| Intermediate D17 | tert-butyl 4-[4-[[[2-chloro-4-[[1-methyl-5-[1-(5-nitro-2-pyridyl)-3-(trifluoromethyl)pyrazol-4-yl]imidazole-2-carbonyl]amino]benzoyl] amino]methyl]piperidine-1-carbonyl]piperidine-1-carboxylate | 843.2 | Intermediate B4.6 and intermediate A12 |

-continued

| Ex# | Name | MS ESI [M + H]$^+$ | Starting Material |
|---|---|---|---|
| Intermediate D18 | tert-butyl (3S)-3-[4-[2-chloro-4-[[1-methyl-5-[1-(5-nitro-2-pyridyl)-3-(trifluoromethyl)pyrazol-4-yl]imidazole-2-carbonyl]amino]benzoyl] piperazine-1-carbonyl]morpholine-4-carboxylate | 817.3 | Intermediate B4.7 and intermediate A12 |
| Intermediate D19 | tert-butyl (2S,4R)-2-[4-[2-chloro-4-[[1-methyl-5-[1-(5-nitro-2-pyridyl)-3-(trifluoromethyl)pyrazol-4-yl]imidazole-2-carbonyl]amino]benzoyl] piperazine-1-carbonyl]-4-hydroxy-pyrrolidine-1-carboxylate | 817.0 | Intermediate B4.8 and intermediate A12 |
| Intermediate D20 | 5-[1-(5-amino-2-pyridyl)-3-(difluoromethyl)pyrazol-4-yl]-N-[3-chloro-4-[4-(1-methylpiperidine-4-carbonyl)piperazine-1-carbonyl]phenyl]-1-methyl-imidazole-2-carboxamide | 681.2 | Intermediate B4.9 and Intermediate A9.3 |
| Intermediate D21 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-methoxy-pyrazol-1-yl]-3-pyridyl]carbamate | 761.4 | Intermediate B4.9 and Intermediate A9.4 |
| Intermediate D22 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-cyano-pyrazol-1-yl]-3-pyridyl]carbamate | 756.2 | Intermediate B4.9 and Intermediate A9.5 |
| Intermediate D23 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-methyl-pyrazol-1-yl]-3-pyridyl]carbamate | 745.3 | Intermediate B4.9 and Intermediate A9.6 |
| Intermediate D24 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-ethyl-pyrazol-1-yl]-3-pyridyl]carbamate | 759.0 | Intermediate B4.9 and Intermediate A9.7 |
| Intermediate D25 | tert-butyl N-[6-[4-[2-[[3-chloro-4-[4-(1-methylpiperidine-4-carbonyl)piperazine-1-carbonyl]phenyl]carbamoyl]-3-methyl-imidazol-4-yl]-3-(trifluoromethyl)pyrazol-1-yl]pyridazin-3-yl]carbamate | 800.2 | Intermediate B4.9 and Intermediate A9.8 |
| Intermediate D26 | N-[3-chloro-4-[4-(1-methylpiperidine-4-carbonyl)piperazine-1-carbonyl]phenyl]-1-methyl-5-[1-[4-methyl-1-(2-trimethylsilylethoxymethyl) pyrazol-3-yl]-3-(trifluoromethyl)pyrazol-4-yl]imidazole-2-carboxamide | 817.3 | Intermediate B4.9 and Intermediate A9.9 |

Intermediate D1 tert-Butyl 4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carboxylate Step 1: tert-butyl 4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carboxylate To a 25 mL microwave vial was added tert-butyl 4-(2-chloro-4-(1-methyl-5-(3-(trifluoromethyl)-1H-pyrazol-4-yl)-imidazole-2-carboxamido)benzoyl)piperazine-1-carboxylate (1.5 g, 2.58 mmol), 2-chloro-5-nitropyridine (531 mg, 3.35 mmol) and $K_2CO_3$ (712 mg, 5.15 mmol) in MeCN (18 mL). The vial was capped and heated at 100° C. for 2 h. The crude reaction mixture was concentrated in vacuum. The reaction mixture was filtered through glass fiber paper. The filtrate was concentrated in vacuum. The crude material was purified by flash chromatography (silica gel, 40 g, 0% to 10% MeOH in DCM) to afford tert-butyl 4-(2-chloro-4-(1-methyl-S-(1-(5-nitropyridin-2-yl)-3-(trifluoromethyl)-pyrazol-4-yl)-imidazole-2-carboxamido)benzoyl)piperazine-1-carboxylate (1.4 g). MS $[M+H]^+$: 704.2.

The following intermediates were prepared in analogy of Intermediate D1.

| Ex# | Name | MS ESI $[M + H]^+$ | Starting Material |
|---|---|---|---|
| Intermediate D2 | tert-butyl 2-chloro-4-[[1-methyl-5-[1-pyrimidin-2-yl-3-(trifluoromethyl)pyrazol-4-yl]imidazole-2-carbonyl]amino]benzoate | 548.2 | Intermediate C1 and 2-chloropyrimidine |
| Intermediate D3 | tert-butyl 4-(2-chloro-4-(1-methyl-5-(1-(pyrimidin-2-yl)-3-(trifluoromethyl)-pyrazol-4-yl)-imidazole-2-carboxamido)benzoyl)piperazine-1-carboxylate | 660.4 | Intermediate C2 and 2-chloropyrimidine |
| Intermediate D4 | tert-butyl 4-(4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carbonyl)piperidine-1-carboxylate | 815.5 | Intermediate C3 and 2-chloro-5-nitropyridine |
| Intermediate D5 | tert-butyl 4-(4-(2-chloro-4-(5-(1-(5-fluoropyrimidin-2-yl)-3-(trifluoromethyl)-pyrazol-4-yl)-1-methyl-imidazole-2-carboxamido)benzoyl)piperazine-1-carbonyl)piperidine-1-carboxylate | 789.1 | Intermediate C3 and 2-chloro-5-fluoropyrimidine |
| Intermediate D6 | tert-butyl 4-[4-[4-[[5-[1-(5-carbamoyl-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate | 813.4 | Intermediate C3 and 6-chloropyridine-3-carboxamide midine |
| Intermediate D7 | tert-butyl 4-[4-[2-chloro-4-[[1-methyl-5-[1-[5-(methylcarbamoyl)-2-pyridyl]-3-(trifluoromethyl)pyrazol-4-yl]imidazole-2-carbonyl]amino]benzoyl]piperazine-1-carbonyl]piperidine-1-carboxylate | 827.3 | Intermediate C3 and 6-chloro-N-methyl-pyridine-3-carboxamide |
| Intermediate D8 | tert-butyl 4-[4-[2-chloro-4-[5-[1-(5-formyl-2-pyridyl)-3-(trifluoromethyl)pyrazol-4-yl]-1-methyl-imidazole-2-carbonyl]amino]benzoyl]piperazine-1-carbonyl]piperidine-1-carboxylate | 798.3 | Intermediate C3 and 6-chloropyridine-3-carbaldehyde |
| Intermediate D9 | tert-butyl 4-[4-[2-chloro-4-[[5-[1-(6-chloropyridazin-3-yl)-3-(trifluoromethyl)pyrazol-4-yl]-1-methyl-imidazole-2-carbonyl]amino]benzoyl]piperazine-1-carbonyl]piperidine-1-carboxylate | 805.6 | Intermediate C3 and 3,6-dichloropyridazine |
| Intermediate D10 | tert-butyl (3S,4R)-4-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-3-hydroxy-piperidine-1-carboxylate | 831.5 | Intermediate C4 and 2-chloro-5-nitropyridine |

Intermediate E1

N-(3-Chloro-4-(piperazine-1-carbonyl)phenyl)-1-methyl-5-(1-(5-nitropyridin-2-yl)-3-(trifluoromethyl)-pyrazol-4-yl)-imidazole-2-carboxamide Step 1: N-(3-chloro-4-(piperazine-1-carbonyl)phenyl)-1-methyl-5-(1-(5-nitropyridin-2-yl)-3-(trifluoromethyl)-pyrazol-4-yl)-imidazole-2-carboxamide In a 100 mL round-bottomed flask, tert-butyl 4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carboxylate (1.4 g, 1.99 mmol) was combined with THF (8 mL) to give a light brown solution. HCl water solution (6.63 mL, 79.5 mmol) was added. The reaction was stirred at room temperature for 1 h. The crude reaction mixture was concentrated in vacuum. The crude product was directly used to the next step, to afford N-(3-chloro-4-(piperazine-1-carbonyl)phenyl)-1-methyl-5-(1-(5-nitropyridin-2-yl)-3-(trifluoromethyl)-pyrazol-4-yl)-imidazole-2-carboxamide (1.2 g). MS $[M+H]^+$: 604.2.

The following intermediates were prepared in analogy of Intermediate E1.

| Ex# | Name | MS ESI $[M+H]^+$ | Starting Material |
|---|---|---|---|
| Intermediate E2 | 2-chloro-4-[[1-methyl-5-[1-pyrimidin-2-yl-3-(trifluoromethyl)pyrazol-4-yl]imidazole-2-carbonyl]amino]benzoic acid | 419.9 | Intermediate D2 and HCl |
| Intermediate E3 | N-(3-chloro-4-(piperazine-1-carbonyl)phenyl)-1-methyl-5-(1-(pyrimidin-2-yl)-3-(trifluoromethyl)-pyrazol-4-yl)-imidazole-2-carboxamide | 560.7 | Intermediate D3 and HCl |
| Intermediate E4 | N-[3-chloro-4-[4-(piperidine-4-carbonyl)piperazine-1-carbonyl]phenyl]-1-methyl-5-[1-(5-nitro-2-pyridyl)-3-(trifluoromethyl)pyrazol-4-yl]imidazole-2-carboxamide | 715.1 | Intermediate D4 and HCl |
| Intermediate E5 | N-[3-chloro-4-(piperazine-1-carbonyl)phenyl]-5-[1-(5-methoxy-2-pyridyl)-3-(trifluoromethyl)pyrazol-4-yl]-1-methyl-imidazole-2-carboxamide | 589.3 | Intermediate H1 and HCl |
| Intermediate E6 | 1-[2-chloro-4-[[1-methyl-5-[1-(5-nitro-2-pyridyl)-3-(trifluoromethyl)pyrazol-4-yl]imidazole-2-carbonyl]amino]benzoyl]piperidine-4-carboxylic acid | 646.9 | Intermediate D11 and TFA |
| Intermediate E7 | 2-chloro-4-[1-methyl-5-[1-(5-nitro-2-pyridyl)-3-(trifluoromethyl)pyrazol-4-yl]imidazole-2-carbonyl]amino]benzoic acid | 535.8 | Intermediate D12 and TFA |

Intermediate F1

N-[3-chloro-4-[4-[2-(3-hydroxypyrrolidin-1-yl)acetyl]piperazine-1-carbonyl]phenyl]-1-methyl-5-[1-(5-nitro-2-pyridyl)-3-(trifluoromethyl)pyrazol-4-yl]imidazole-2-carboxamide Step 1: N-[3-chloro-4-[4-(2-chloroacetyl)piperazine-1-carbonyl]phenyl]-1-methyl-5-[1-(5-nitro-2-pyridyl)-3-(trifluoromethyl)pyrazol-4-yl]imidazole-2-carboxamide To a solution of N-[3-chloro-4-(piperazine-1-carbonyl)phenyl]-1-methyl-5-[1-(5-nitro-2-pyridyl)-3-(trifluoromethyl)pyrazol-4-yl]imidazole-2-carboxamide. 2,2,2-trifluoroacetic acid (300 mg, 0.42 mmol) in acetonitrile (5 mL) was added sodium carbonate (132.9 mg, 1.3 mmol), then chloroacetyl chloride (47.2 mg, 0.42 mmol) was added dropwise at 0 TC. The reaction was stirred for 2 h and then warmed to room temperature. The reaction mixture was washed with brine and extracted in DCM. The organic layer was dried over anhydrous $Na_2SO_4$ and concentrated in vacuum. The residue was directly used for the next step without further purification. MS $[M+H]^+$: 680.2.

Step 2: N-[3-chloro-4-[4-[2-(3-hydroxypyrrolidin-1-yl)acetyl]piperazine-1-carbonyl]phenyl]-1-methyl-5-[1-(5-nitro-2-pyridyl)-3-(trifluoromethyl)pyrazol-4-yl]imidazole-2-carboxamide To a solution of N-[3-chloro-4-[4-(2-chloroacetyl)piperazine-1-carbonyl]phenyl]-1-methyl-5-[1-(5-nitro-2-pyridyl)-3-(trifluoromethyl)pyrazol-4-yl]imidazole-2-carboxamide (230 mg, 0.34 mmol) in acetonitrile (3 mL) was added 3-pyrrolidinol (29.5 mg, 0.34 mmol) and TEA (68.4 mg, 0.68 mmol), the reaction was stirred for 30 min at 70° C. The reaction mixture was cooled to room temperature. The reaction mixture was washed with brine and extracted in DCM. The organic layer was dried over anhydrous $Na_2SO_4$ and concentrated in vacuum. The residue was directly used for the next step without further purification. MS $[M+H]^+$: 731.2.

Intermediate G1 tert-Butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1-carboxylate Step 1: tert-butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1-carboxylate In a 100 mL round-bottomed flask, tert-butyl 4-(4-(2-chloro-4-(1-methyl-5-(1-(5-nitropyridin-2-yl)-3-(trifluoromethyl)-pyrazol-4-yl)-imidazole-2-carboxamido)benzoyl)piperazine-1-carbonyl)piperidine-1-carboxylate (47 mg, 57.7 μmol) was combined with EtOH (6 mL)/Water (6 mL) to give a light yellow. Zinc (75.4 mg, 1.15 mmol) and $NH_4Cl$ (61.7 mg, 1.15 mmol) were added at rt. The reaction was stirred at room temperature for 1 h. The reaction mixture was filtered through glass fiber paper. The filtrate was poured into 20 mL $H_2O$ and extracted with EtOAc (25 mL×3). The organic layers were combined, washed with sat NaCl (25 mL×1), The organic layers were dried over $Na_2SO_4$ and concentrated in vacuum to afford tert-butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1l-carboxylate (45.3 mg). MS $[M+H]^+$: 785.0.

The following intermediates and compound were prepared in analogy of Intermediate G1.

| Ex# | Name | MS ESI [M + H]+ | Starting Material |
|---|---|---|---|
| Intermediate G2 | tert-butyl (3S,4R)-4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]-3-hydroxy-piperidine-1-carboxylate | 815.7 | Intermediate D10 and zinc |
| Intermediate G3 | tert-butyl 4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]-4-hydroxy-piperidine-1-carboxylate | 801.3 | Intermediate D13 and zinc |
| Intermediate G4 | tert-butyl (2S,3S)-2-[4-[4-[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]-3-hydroxy-pyrrolidine-1-carboxylate | 787.3 | Intermediate D4.4 and zinc |
| Intermediate G5 | 5-[1-(5-amino-2-pyridyl)-3-(trifluoromethyl)pyrazol-4-yl]-N-[3-chloro-4-[4-[2-(3-hydroxypyrrolidin-1-yl)acetyl]piperazine-1-carbonyl]phenyl]-1-methyl-imidazole-2-carboxamide;formic acid | 701.3 | Intermediate F1 and zinc |
| Intermediate G6 | tert-butyl 4-[4-[[[4-[[5-[1-(5-amino-2-pyridyl)-3-(trifluoromethyl)pyrazol-4-yl]-1-methyl-imidazole-2-carbonyl]amino]-2-chloro-benzoyl]amino]methyl]piperidine-1-carbonyl]piperidine-1-carboxylate | 813.5 | Intermediate D17 and zinc |
| Intermediate G7 | tert-butyl (3S)-3-[4-[4-[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]morpholine-4-carboxylate | 787.3 | Intermediate D18 and zinc |
| Intermediate G8 | tert-butyl 4-[4-[4-[[5-[1-(5-amino-2-pyridyl)-3-(trifluoromethyl)pyrazol-4-yl]-1-methyl-imidazole-2-carbonyl]amino]-2-methyl-benzoyl]piperazine-1-carbonyl]piperidine-1-carboxylate | 765.5 | Intermediate D16 and zinc |
| Intermediate G9 | tert-butyl (2S,4R)-2-[4-[4-[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]-4-hydroxy-pyrrolidine-1-carboxylate | 787.5 | Intermediate D19 and zinc |

Intermediate H1

N-[4-[[(1S,5R)-3-Azabicyclo[3.1.0]hexan-6-yl]carbamoyl]-3-chloro-phenyl]-1-methyl-5-[1-pyrimidin-2-yl-3-(trifluoromethyl)pyrazol-4-yl]imidazole-2-carboxamide

Step 1: tert-butyl (1R,5S,6S)-6-(2-chloro-4-(1-methyl-5-(1-(pyrimidin-2-yl)-3-(trifluoromethyl)-pyrazol-4-yl)-imidazole-2-carboxamido)benzamido)-3-azabicyclo[3.1.0]hexane-3-carboxylate In a 50 mL round-bottomed flask, 2-chloro-4-(1-methyl-5-(1-(pyrimidin-2-yl)-3-(trifluoromethyl)-pyrazol-4-yl)-imidazole-2-carboxamido)benzoic acid (340 mg, 691 μmol), tert-butyl (1R,5S,6S)-6-amino-3-azabicyclo[3.1.0]hexane-3-carboxylate (206 mg, 1.04 mmol), 2-(3H-[1,2,3]triazolo[4,5-b]pyridin-3-yl)-1,1,3,3-tetramethylisouronium hexafluorophosphate(V) (394 mg, 1.04 mmol) and DIPEA (179 mg, 1.38 mmol) were combined with DMF (5 mL) to give a light brown solution. The reaction was stirred at room temperature for 1 h. The reaction mixture was poured into 25 mL $H_2O$ and extracted with EtOAc (25 mL×3). The organic layers were combined, washed with sat NaCl (25 mL×1), The organic layers were dried over $Na_2SO_4$ and concentrated in vacuum to afford tert-butyl (1R,5S,6S)-6-(2-chloro-4-(1-methyl-5-(1-(pyrimidin-2-yl)-3-(trifluoromethyl)-pyrazol-4-yl)-imidazole-2-carboxamido)benzamido)-3-azabicyclo[3.1.0]hexane-3-carboxylate (240 mg). MS $[M+H]^+$: 672.2.

Step 2: N-(4-(((1R,5S,6S)-3-azabicyclo[3.1.0]hexan-6-yl)carbamoyl)-3-chlorophenyl)-1-methyl-5-(1-(pyrimidin-2-yl)-3-(trifluoromethyl)-pyrazol-4-yl)-imidazole-2-carboxamide In a 50 mL round-bottomed flask, tert-butyl (1R,5S,6S)-6-(2-chloro-4-(1-methyl-5-(1-(pyrimidin-2-yl)-3-(trifluoromethyl)-pyrazol-4-yl)-imidazole-2-carboxamido)benzamido)-3-azabicyclo[3.1.0]hexane-3-carboxylate (240 mg, 357 μmol) was combined with THF (2 mL) to give a light brown solution. HCl water solution (1.19 mL, 14.3 mmol) was added. The reaction was stirred at room temperature for 1 h. The crude reaction mixture was concentrated in vacuum. The crude product was directly used to the next step, to afford N-(4-(((1R,5S,6S)-3-azabicyclo[3.1.0]hexan-6-yl) carbamoyl)-3-chlorophenyl)-1-methyl-5-(1-(pyrimidin-2-yl)-3-(trifluoromethyl)-pyrazol-4-yl)-imidazole-2-carboxamide (204 mg). MS $[M+H]^+$: 572.7.

Intermediate I1 tert-Butyl 4-[2-chloro-4-[[5-[1-(5-methoxy-2-pyridyl)-3-(trifluoromethyl)pyrazol-4-yl]-1-methyl-imidazole-2 carbonyl]amino]benzoyl]piperazine-1-carboxylate Under $N_2$ protection, a mixture of tert-butyl 4-[2-chloro-4-[[1-methyl-5-[3-(trifluoromethyl)-1H-pyrazol-4-yl]imidazole-2-carbonyl]amino]benzoyl]piperazine-1-carboxylate (600 mg, 1.03 mmol), 2-bromo-5-methoxy-pyriadine (581.54 mg, 3.09 mmol), Cu (196.35 mg, 1.03 mmol) and (1R,2R)—N1,N2-dimethylcyclohexane-1,2-diamine (219.97 mg, 1.55 mmol) in DMF (10 mL) was heated at 100° C. for 16 h. The mixture was concentrated and the residue was purified by flash column to afford the tert-butyl 4-[2-chloro-4-[[5-[1-(5-methoxy-2-pyridyl)-3-(trifluoromethyl)pyrazol-4-yl]-1-methyl-imidazole-2 carbonyl]amino] benzoyl]piperazine-1-carboxylate (500 mg). MS $[M+H^+]$: 689.4.

The following intermediates were prepared in analogy of Intermediate I1.

| Ex# | Name | MS ESI $[M + H]^+$ | Starting Material |
|---|---|---|---|
| Intermediate I2 | tert-butyl 4-[4-[2-chloro-4-[[5-[1-[5-(2-methoxyethylamino)-2-pyridyl]-3-(trifluoromethyl)pyrazol-4-yl]-1-methyl-imidazole-2-carbonyl]amino]benzoyl] piperazine-1-carbonyl] piperidine-1-carboxylate | 843.6 | Intermediate C3 and A10 |
| Intermediate I3 | tert-butyl 4-[4-[4-[[5-[1-[5-[(3-amino-3-oxo-propyl)amino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylate | 856.6 | Intermediate C3 and A7 |

Example A1

N-[3-Chloro-4-[4-(piperidine-4-carbonyl)piperazine-1-carbonyl]phenyl]-1-methyl-5-[1-pyrimidin-2-yl-3-(trifluoromethyl)pyrazol-4-yl]imidazole-2-carboxamide; formic acid

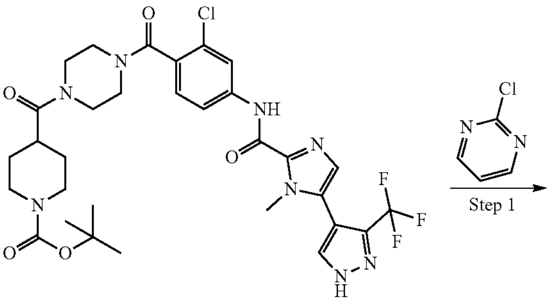

Intermediate C3

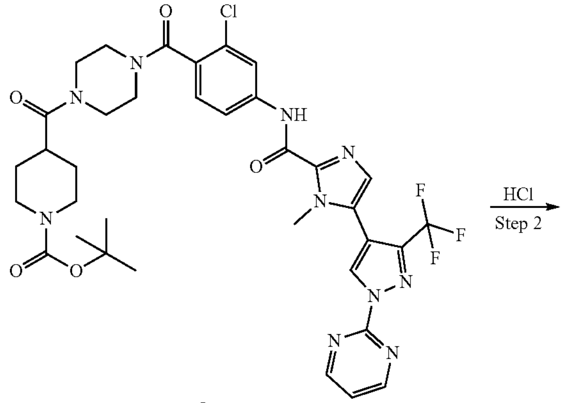

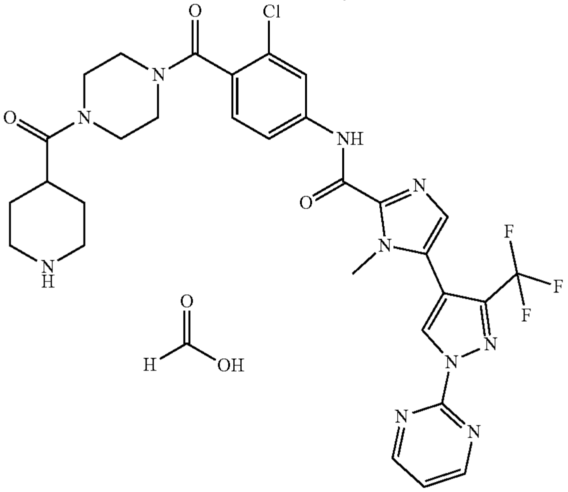

Example A1

Step 1: tert-butyl 4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidine-1-carboxylate To a 5 mL microwave vial was added tert-butyl 4-(4-(2-chloro-4-(1-methyl-5-(3-(trifluoromethyl)-1H-pyrazol-4-yl)-imidazole-2-carboxamido)benzoyl)piperazine-1-carbonyl)piperidine-1-carboxylate (60 mg, 86.6 μmol), 2-chloropyrimidine (14.9 mg, 130 μmol) and $K_2CO_3$ (23.9 mg, 173 μmol) in DMF (2 mL). The vial was capped and heated under microwave at 100° C. for 1 h. The reaction mixture was poured into 25 mL $H_2O$ and extracted with EtOAc (25 mL×3). The organic layers were combined, washed with sat NaCl (25 mL×3), The organic layers were dried over $Na_2SO_4$ and concentrated in vacuum to afford tert-butyl 4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidine-1-carboxylate (66.8 mg). MS [M+H]$^+$: 771.8.

Step 2: N-[3-chloro-4-[4-(piperidine-4-carbonyl) piperazine-1-carbonyl]phenyl]-1-methyl-5-[1-pyrimidin-2-yl-3-(trifluoromethyl)pyrazol-4-yl]imidazole-2-carboxamide; formic acid In a 25 mL round-bottomed flask, tert-butyl 4-(4-(2-chloro-4-(1-methyl-5-(1-(pyrimidin-2-yl)-3-(trifluoromethyl)-pyrazol-4-yl)-imidazole-2-carboxamido)benzoyl) piperazine-1-carbonyl)piperidine-1-carboxylate (66 mg, 85.6 mol) was combined with THF (3 mL) to give a light brown solution. HCl water solution (1.43 mL, 17.1 mmol) was added. The reaction was stirred at room temperature for 1 h. The crude reaction mixture was concentrated in vacuum. The crude material was purified by preparative HPLC. to afford N-[3-chloro-4-[4-(piperidine-4-carbonyl)piperazine-1-carbonyl]phenyl]-1-methyl-5-[1-pyrimidin-2-yl-3-(trifluoromethyl)pyrazol-4-yl]imidazole-2-carboxamide; formic acid (37 mg). MS [M+H]$^+$: 671.4.

The following compounds were prepared in analogy of Example A1

| Ex# | Name | Structure | MS ESI [M + H]$^+$ | Starting Material |
|---|---|---|---|---|
| Example A2 | N-[3-chloro-4-[4-(piperidine-4-carbonyl)piperazine-1-carbonyl]phenyl]-1-methyl-5-[1-(4-pyridyl)-3-(trifluoromethyl)pyrazol-4-yl]imidazole-2-carboxamide; formic acid | 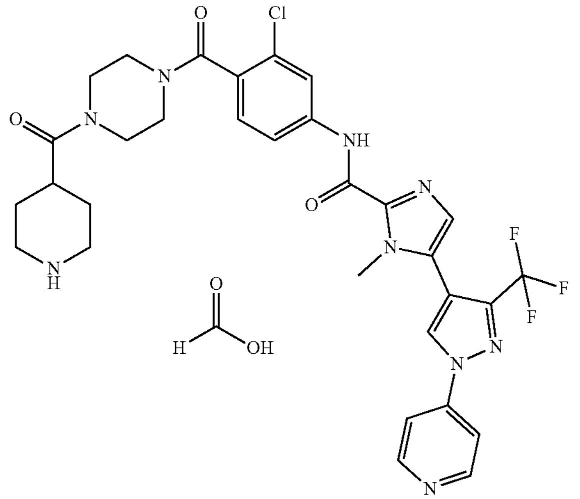 | 670.4 | Intermediate C3 and 4-fluoropyridine and HCl |
| Example A3 | N-[3-chloro-4-[4-(piperidine-4-carbonyl)piperazine-1-carbonyl]phenyl]-5-[1-(5-chloro-2-pyridyl)-3-(trifluoromethyl)pyrazol-4-yl]-1-methyl-imidazole-2-carboxamide; formic acid | 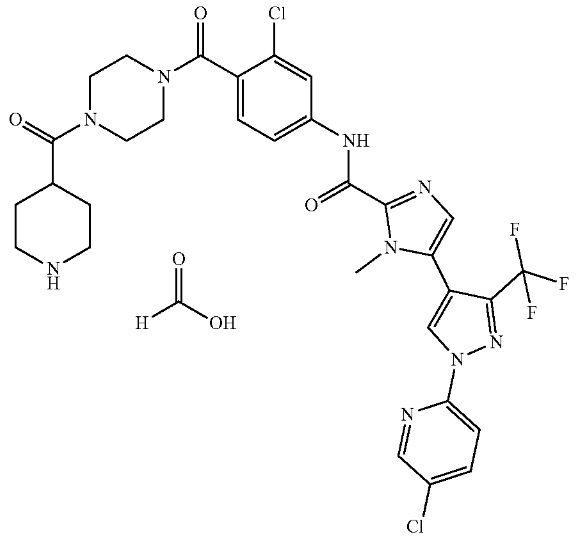 [SMILES: Cn1c(-c2cn(-c3ccc(Cl)cn3)nc2C(F)(F)F)cnc1C(=O)Nc1ccc(C(=O)N2CCN(C(=O)C3CCNCC3)CC2)c(Cl)c1 ; O=CO] | 704.3 | Intermediate C3 and 5-chloro-2-fluoropyridine and HCl |

-continued

| Ex# | Name | Structure | MS ESI [M + H]+ | Starting Material |
|---|---|---|---|---|
| Example A4 | N-[3-chloro-4-[4-(piperidine-4-carbonyl)piperazine-1-carbonyl]phenyl]-5-[1-(5-methoxypyrimidin-2-yl)-3-(trifluoromethyl)pyrazol-4-yl]-1-methyl-imidazole-2-carboxamide; formic acid | 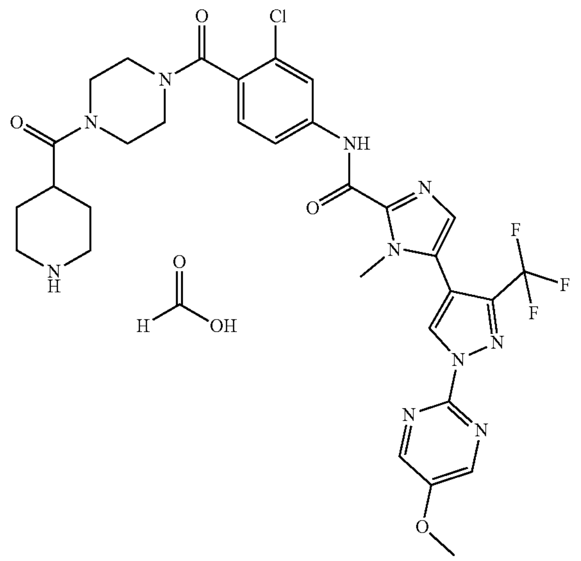 | 701.3 | Intermediate C3 and 2-chloro-5-methoxy-pyrimidine and HCl |
| Example A5 | 5-[1-(5-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 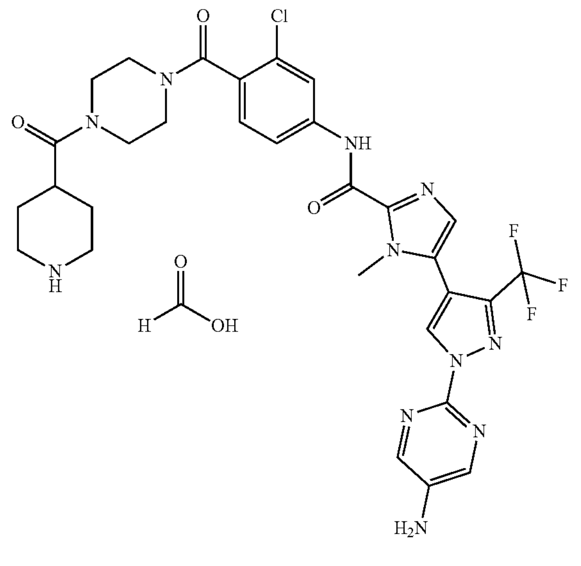 [SMILES: Cn1c(-c2cn(-c3ncc(N)cn3)nc2C(F)(F)F)cnc1C(=O)Nc1ccc(C(=O)N2CCN(C(=O)C3CCNCC3)CC2)c(Cl)c1 ; O=CO] | 686.4 | Intermediate C3 and Intermediate A1 and HCl |

-continued

| Ex# | Name | Structure | MS ESI [M + H]+ | Starting Material |
| --- | --- | --- | --- | --- |
| Example A6 | N-[3-chloro-4-[4-(piperidine-4-carbonyl)piperazine-1-carbonyl]phenyl]-5-[1-[5-(2-methoxyethoxy)pyrimidin-2-yl]-3-(trifluoromethyl)pyrazol-4-yl]-1-methyl-imidazole-2-carboxamide; formic acid | 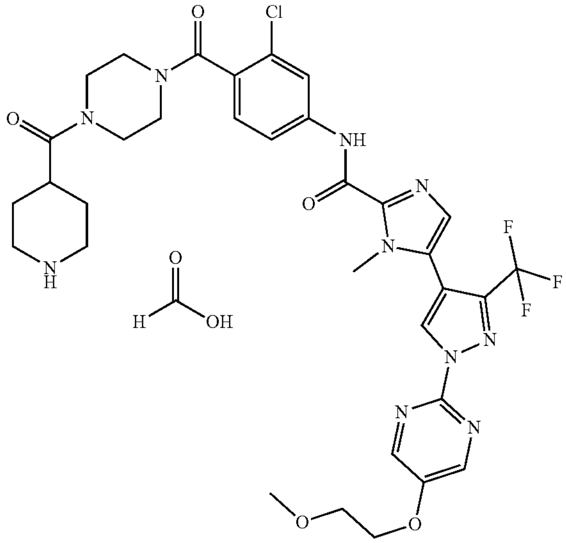 [SMILES: COCCOc1cnc(-n2cc(-c3cnc(C(=O)Nc4ccc(C(=O)N5CCN(C(=O)C6CCNCC6)CC5)c(Cl)c4)n3C)c(C(F)(F)F)n2)nc1 ; O=CO] | 745.3 | Intermediate C3 and Intermediate A2.1 and HCl |
| Example A7 | N-[3-chloro-4-[4-(piperidine-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide; formic acid | 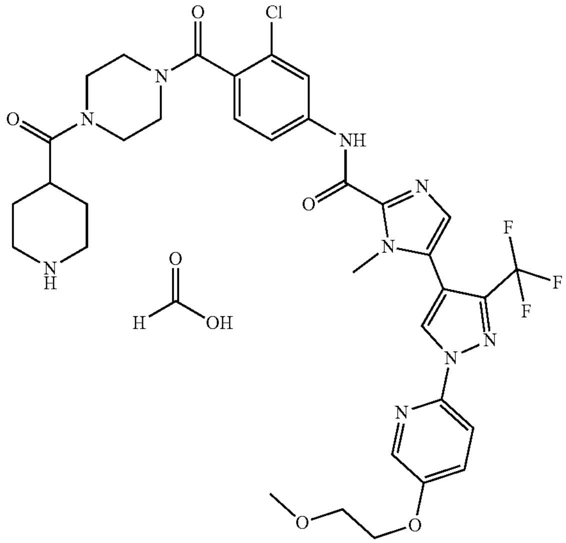 [SMILES: COCCOc1ccc(-n2cc(-c3cnc(C(=O)Nc4ccc(C(=O)N5CCN(C(=O)C6CCNCC6)CC5)c(Cl)c4)n3C)c(C(F)(F)F)n2)nc1 ; O=CO] | 744.3 | Intermediate C3 and Intermediate A2.2 and HCl |

-continued

| Ex# | Name | Structure | MS ESI $[M + H]^+$ | Starting Material |
|---|---|---|---|---|
| Example A8 | N-[3-chloro-4-[4-(piperidine-4-carbonyl)piperazine-1-carbonyl]phenyl]-5-[1-(5-fluoropyrimidin-2-yl)-3-(trifluoromethyl)pyrazol-4-yl]-1-methyl-imidazole-2-carboxamide; formic acid | 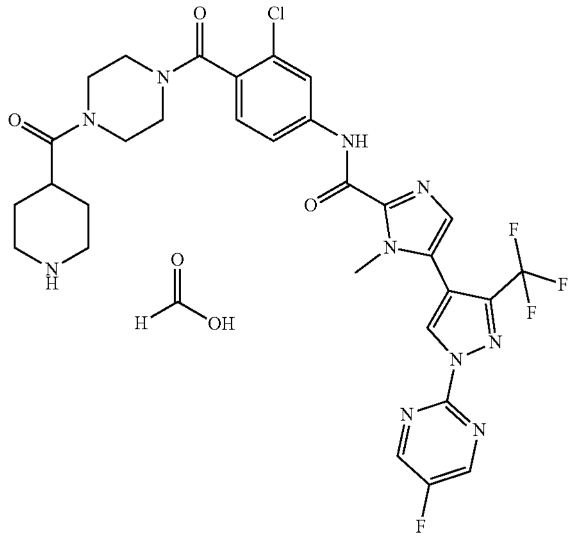 [SMILES: Cn1c(-c2cn(-c3ncc(F)cn3)nc2C(F)(F)F)cnc1C(=O)Nc1ccc(C(=O)N2CCN(C(=O)C3CCNCC3)CC2)c(Cl)c1 ; O=CO] | 689.3 | Intermediate C3 and 2-chloro-5-fluoropyrimidine and HCl |
| Example A9 | N-[3-chloro-4-[4-(piperidine-4-carbonyl)piperazine-1-carbonyl]phenyl]-1-methyl-5-[1-(1h-pyrazolo[3,4-d]pyrimidin-6-yl)-3-(trifluoromethyl)pyrazol-4-yl]imidazole-2-carboxamide; formic acid | 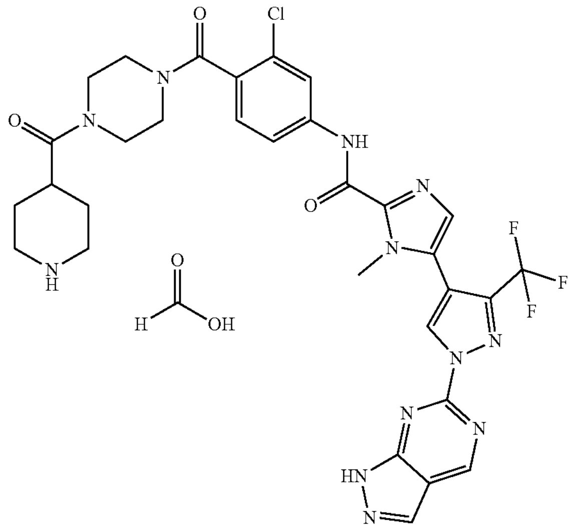 [SMILES: Cn1c(-c2cn(-c3ncc4cn[nH]c4n3)nc2C(F)(F)F)cnc1C(=O)Nc1ccc(C(=O)N2CCN(C(=O)C3CCNCC3)CC2)c(Cl)c1 ; O=CO] | 711.3 | Intermediate C3 and Intermediate A3 and HCl |
| Example A10 | N-[3-chloro-4-[4-(piperidine-4-carbonyl)piperazine-1-carbonyl]phenyl]-1-methyl-5-[3-(trifluoromethyl)-1-[3-(trifluoromethyl)-2-pyridyl]pyrazol-4-yl]imidazole-2-carboxamide; formic acid | 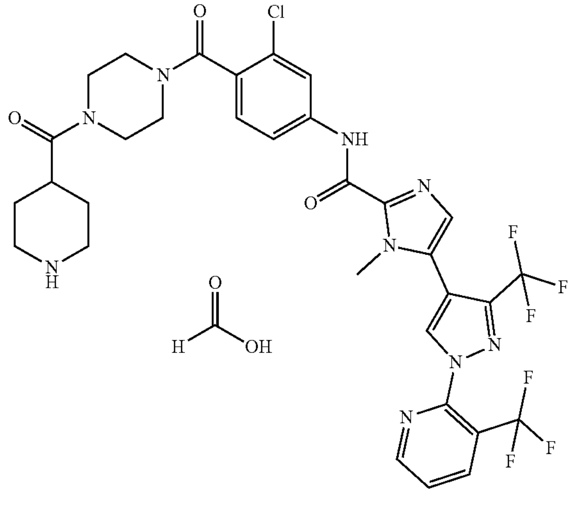 | 738.3 | Intermediate C3 and 2-fluoro-3-(trifluoromethyl) pyridine and HCl |

-continued

| Ex# | Name | Structure | MS ESI $[M + H]^+$ | Starting Material |
| --- | --- | --- | --- | --- |
| Example A11 | N-[3-chloro-4-[4-(piperidine-4-carbonyl)piperazine-1-carbonyl]phenyl]-1-methyl-5-[1-(2-pyridyl)-3-(trifluoromethyl)pyrazol-4-yl]imidazole-2-carboxamide; formic acid | 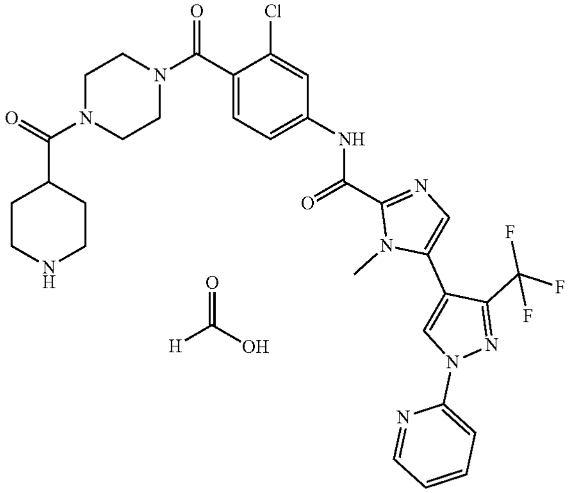 | 670.3 | Intermediate C3 and 2-fluoropyridine and HCl |
| Example A12 | N-[3-chloro-4-[4-(piperidine-4-carbonyl)piperazine-1-carbonyl]phenyl]-5-[1-(4-methoxy-2-pyridyl)-3-(trifluoromethyl)pyrazol-4-yl]-1-methyl-imidazole-2-carboxamide; formic acid | 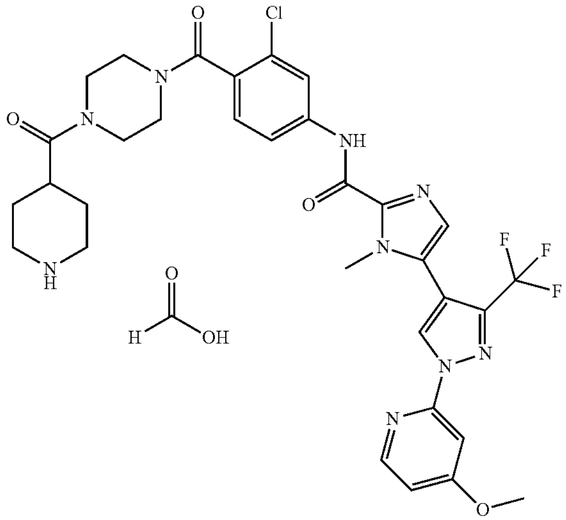 [SMILES: COc1ccnc(-n2cc(-c3cnc(C(=O)Nc4ccc(C(=O)N5CCN(C(=O)C6CCNCC6)CC5)c(Cl)c4)n3C)c(C(F)(F)F)n2)c1 ; O=CO] | 700.2 | Intermediate C3 and 2-fluoro-4-methoxypyridine and HCl |
| Example A13 | N-[3-chloro-4-[4-(piperidine-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide; formic acid | 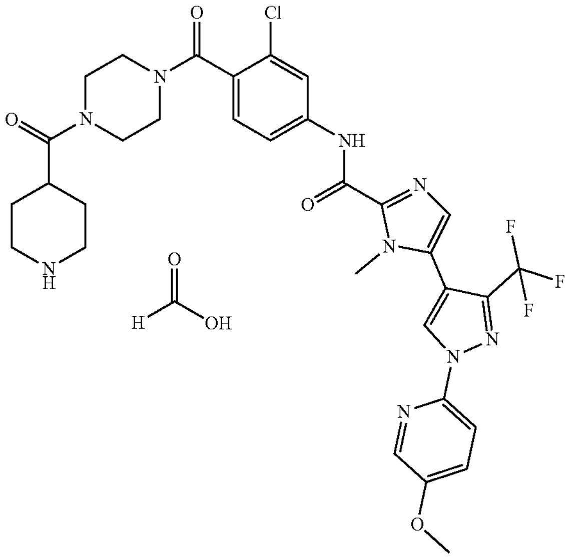 [SMILES: COc1ccc(-n2cc(-c3cnc(C(=O)Nc4ccc(C(=O)N5CCN(C(=O)C6CCNCC6)CC5)c(Cl)c4)n3C)c(C(F)(F)F)n2)nc1 ; O=CO] | 700.2 | Intermediate C3 and 2-fluoro-5-methoxypyridine and HCl |

-continued

| Ex# | Name | Structure | MS ESI [M + H]+ | Starting Material |
|---|---|---|---|---|
| Example A14 | 5-[1-[4-(2-aminoethoxy)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 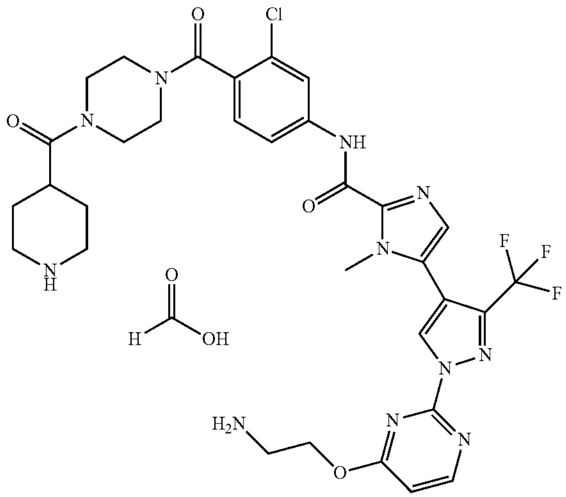 [SMILES: Cn1c(-c2cn(-c3nccc(OCCN)n3)nc2C(F)(F)F)cnc1C(=O)Nc1ccc(C(=O)N2CCN(C(=O)C3CCNCC3)CC2)c(Cl)c1 ; O=CO] | 730.2 | Intermediate C3 and Intermediate A5 and HCl |
| Example A15 | 5-[1-(4-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; 2,2,2-trifluoroacetic acid | 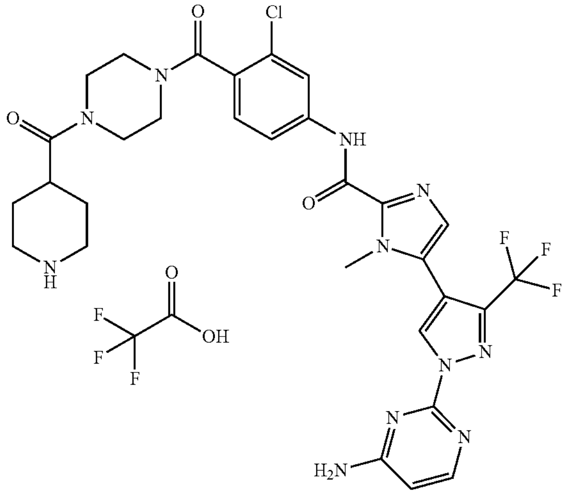 [SMILES: Cn1c(-c2cn(-c3nccc(N)n3)nc2C(F)(F)F)cnc1C(=O)Nc1ccc(C(=O)N2CCN(C(=O)C3CCNCC3)CC2)c(Cl)c1 ; O=C(O)C(F)(F)F] | 686.2 | Intermediate C3 and Intermediate A6.1 and HCl |
| Example A16 | N-[3-chloro-4-[4-(piperidine-4-carbonyl)piperazine-1-carbonyl]phenyl]-1-methyl-5-[1-[4-(methylamino)pyrimidin-2-yl]-3-(trifluoromethyl)pyrazol-4-yl]imidazole-2-carboxamide; 2,2,2-trifluoroacetic acid | 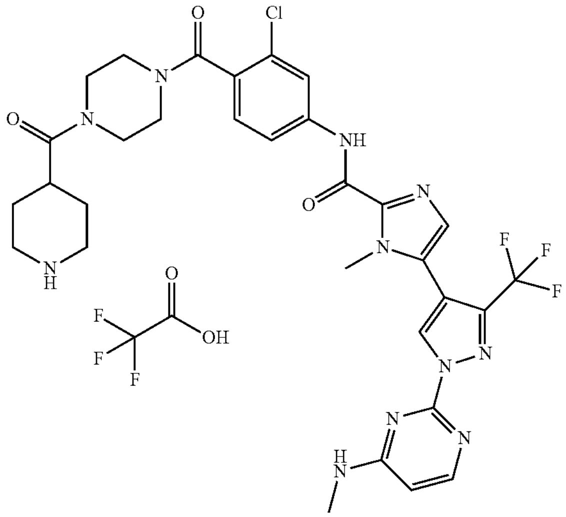 [SMILES: CNc1ccnc(-n2cc(-c3cnc(C(=O)Nc4ccc(C(=O)N5CCN(C(=O)C6CCNCC6)CC5)c(Cl)c4)n3C)c(C(F)(F)F)n2)n1 ; O=C(O)C(F)(F)F] | 700.2 | Intermediate C3 and Intermediate A6.3 and HCl |

-continued

| Ex# | Name | Structure | MS ESI [M + H]+ | Starting Material |
|---|---|---|---|---|
| Example A17 | N-[3-chloro-4-[4-(piperidine-4-carbonyl)piperazine-1-carbonyl]phenyl]-5-[1-[4-(dimethylamino)pyrimidin-2-yl]-3-(trifluoromethyl)pyrazol-4-yl]-1-methyl-imidazole-2-carboxamide; 2,2,2-trifluoroacetic acid | 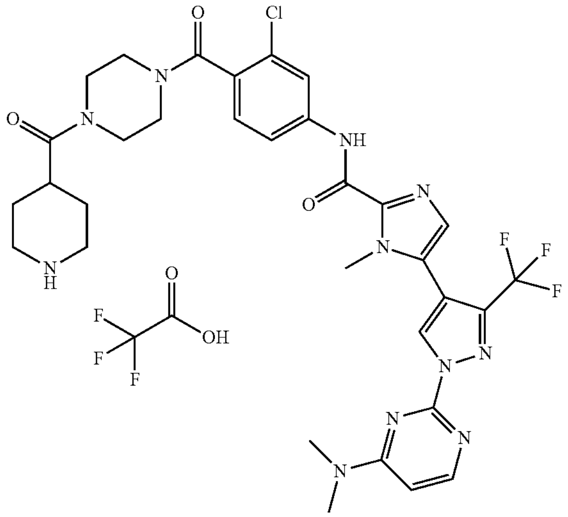 [SMILES: CN(C)c1ccnc(-n2cc(-c3cnc(C(=O)Nc4ccc(C(=O)N5CCN(C(=O)C6CCNCC6)CC5)c(Cl)c4)n3C)c(C(F)(F)F)n2)n1 ; O=C(O)C(F)(F)F] | 714.5 | Intermediate C3 and 2-chloro-N,N-dimethyl-pyrimidin-4-amine and HCl |
| Example A18 | N-[3-chloro-4-[4-(piperidine-4-carbonyl)piperazine-1-carbonyl]phenyl]-5-[1-[4-(dimethylamino)pyrimidin-2-yl]-5-(trifluoromethyl)pyrazol-4-yl]-1-methyl-imidazole-2-carboxamide; 2,2,2-trifluoroacetic acid | 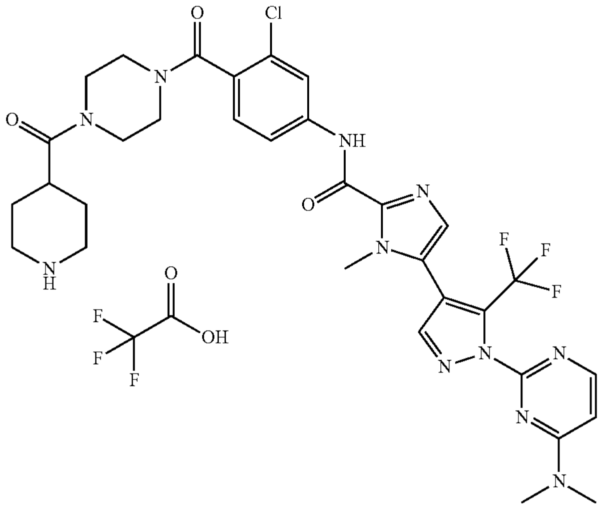 [SMILES: CN(C)c1ccnc(-n2ncc(-c3cnc(C(=O)Nc4ccc(C(=O)N5CCN(C(=O)C6CCNCC6)CC5)c(Cl)c4)n3C)c2C(F)(F)F)n1 ; O=C(O)C(F)(F)F] | 714.2 | Intermediate C3 and 2-chloro-N,N-dimethyl-pyrimidin-4-amine and HCl |
| Example A19 | N-[3-chloro-4-[4-(piperidine-4-carbonyl)piperazine-1-carbonyl]phenyl]-5-[1-[4-(2-methoxyethylamino)pyrimidin-2-yl]-3-(trifluoromethyl)pyrazol-4-yl]-1-methyl-imidazole-2-carboxamide; 2,2,2-trifluoroacetic acid | 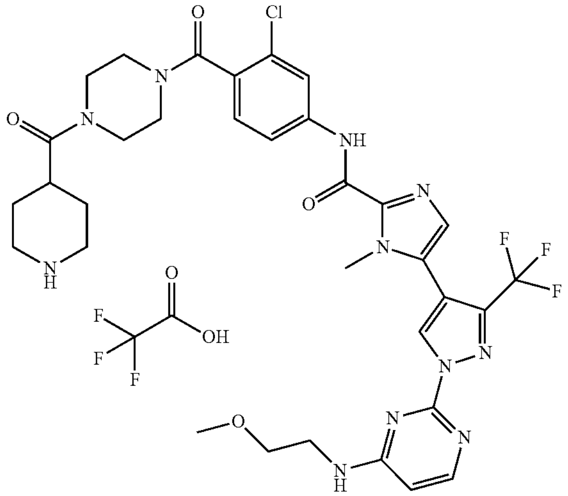 [SMILES: COCCNc1ccnc(-n2cc(-c3cnc(C(=O)Nc4ccc(C(=O)N5CCN(C(=O)C6CCNCC6)CC5)c(Cl)c4)n3C)c(C(F)(F)F)n2)n1 ; O=C(O)C(F)(F)F] | 744.2 | Intermediate C3 and Intermediate A6.2 and HCl |

-continued

| Ex# | Name | Structure | MS ESI [M + H]+ | Starting Material |
|---|---|---|---|---|
| Example A20 | N-[3-chloro-4-[4-(piperidine-4-carbonyl)piperazine-1-carbonyl]phenyl]-1-methyl-5-[1-pyrazin-2-yl-3-(trifluoromethyl)pyrazol-4-yl]imidazole-2-carboxamide; 2,2,2-trifluoroacetic acid | 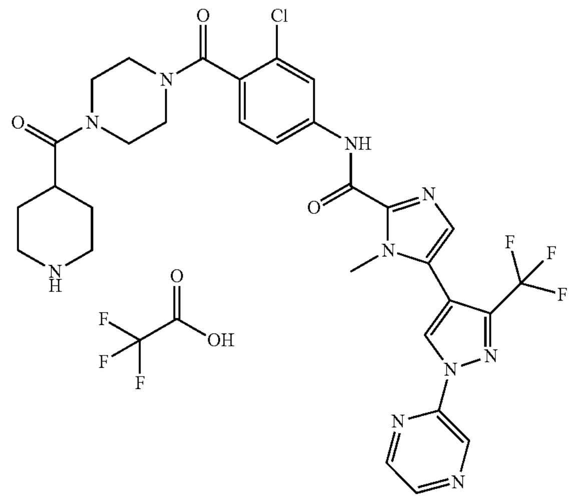 [SMILES: Cn1c(-c2cn(-c3cnccn3)nc2C(F)(F)F)cnc1C(=O)Nc1ccc(C(=O)N2CCN(C(=O)C3CCNCC3)CC2)c(Cl)c1 ; O=C(O)C(F)(F)F] | 671.3 | Intermediate C3 and 2-chloropyrazine and HCl |

Example B1

N-[3-Chloro-4-[4-(piperidine-4-carbonyl)piperazine-1-carbonyl]phenyl]-5-[1-[5-(dimethylamino)pyrimidin-2-yl]-3-(trifluoromethyl)pyrazol-4-yl]-1-methyl-imidazole-2-carboxamide; formic acid

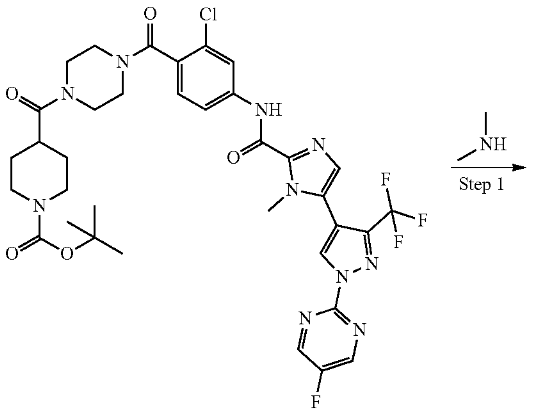

Intermediate D5

-continued

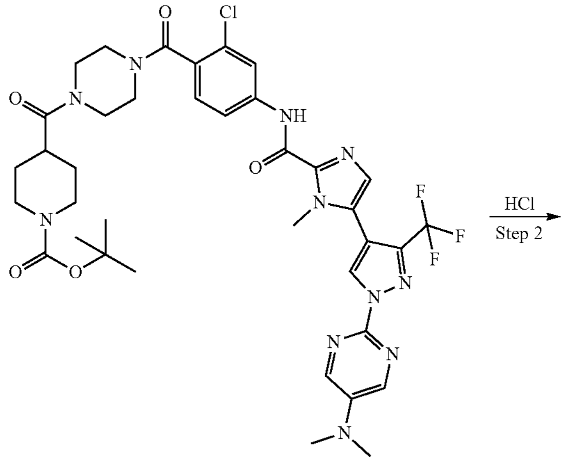

-continued

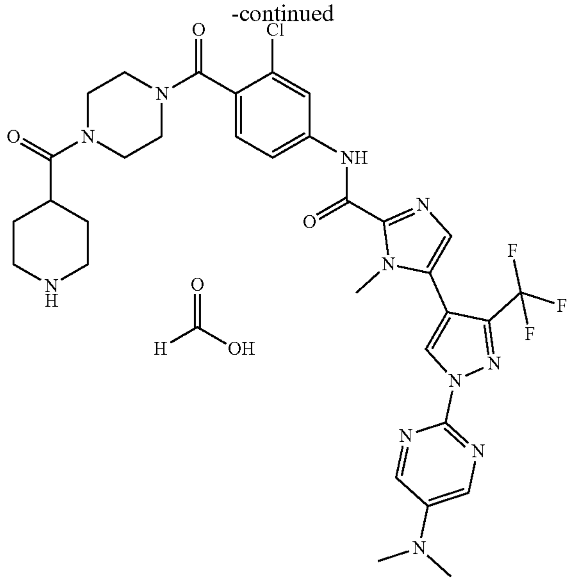

Example B1

Step 1: tert-butyl 4-(4-(2-chloro-4-(5-(1-(5-(dimethylamino)pyrimidin-2-yl)-3-(trifluoromethyl)-pyrazol-4-yl)-1-methyl-imidazole-2-carboxamido)benzoyl)piperazine-1-carbonyl)piperidine-1-carboxylate To a 5 mL microwave vial was added tert-butyl 4-(4-(2-chloro-4-(5-(1-(5-fluoropyrimidin-2-yl)-3-(trifluoromethyl)-pyrazol-4-yl)-1-methyl-imidazole-2-carboxamido)benzoyl)piperazine-1-carbonyl)piperidine-1-carboxylate (50 mg, 63.4 μmol) and dimethylamine (317 μl, 634 μmol) in MeOH (2 mL). The vial was capped and heated under microwave at 100° C. for 2 h. The crude reaction mixture was concentrated in vacuum. The crude product was directly used to the next step, to afford tert-butyl 4-(4-(2-chloro-4-(5-(1-(5-(dimethylamino)pyrimidin-2-yl)-3-(trifluoromethyl)-pyrazol-4-yl)-1-methyl-imidazole-2-carboxamido)benzoyl)piperazine-1-carbonyl)piperidine-1-carboxylate (51 mg). MS $[M+H]^+$: 814.8.

Step 2: N-[3-chloro-4-[4-(piperidine-4-carbonyl)piperazine-1-carbonyl]phenyl]-5-[1-[5-(dimethylamino)pyrimidin-2-yl]-3-(trifluoromethyl)pyrazol-4-yl]-1-methyl-imidazole-2-carboxamide; formic acid In a 50 mL round-bottomed flask, tert-butyl 4-(4-(2-chloro-4-(5-(1-(5-(dimethylamino)pyrimidin-2-yl)-3-(trifluoromethyl)-pyrazol-4-yl)-1-methyl-imidazole-2-carboxamido)benzoyl)piperazine-1-carbonyl)piperidine-1-carboxylate (51 mg, 62.6 μmol) was combined with THF (2 mL) to give a light brown solution. HCl (522 μl, 6.26 mmol) was added. The reaction was stirred at room temperature for 30 min. The crude reaction mixture was concentrated in vacuum. The crude material was purified by preparative HPLC to afford N-[3-chloro-4-[4-(piperidine-4-carbonyl)piperazine-1-carbonyl]phenyl]-5-[1-[5-(dimethylamino)pyrimidin-2-yl]-3-(trifluoromethyl)pyrazol-4-yl]-1-methyl-imidazole-2-carboxamide; formic acid (8.3 mg). MS $[M+H]^+$: 714.3.

The following compounds were prepared in analogy of Example B1.

| Ex# | Name | Structure | MS ESI $[M + H]^+$ | Starting Material |
|---|---|---|---|---|
| Example B2 | 5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;formic acid | 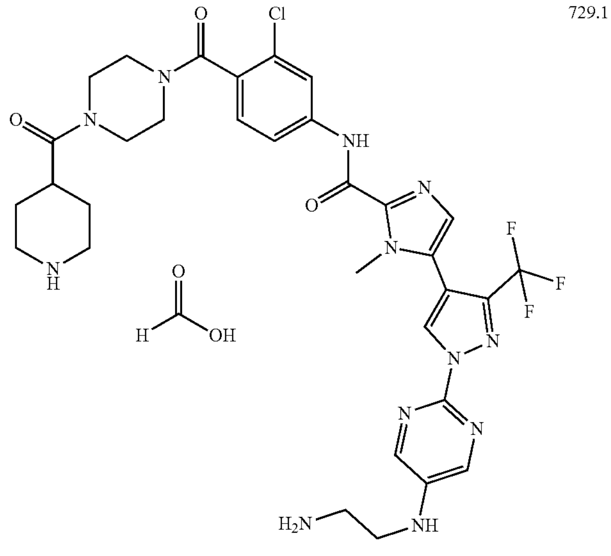 | 729.1 | Intermediate D5 and ethane-1,2-diamine and HCl |

-continued

| Ex# | Name | Structure | MS ESI $[M + H]^+$ | Starting Material |
|---|---|---|---|---|
| Example B3 | N-[3-chloro-4-[4-(piperidine-4-carbonyl)piperazine-1-carbonyl]phenyl]-5-[1-[6-(dimethylamino)pyridazin-3-yl]-3-(trifluoromethyl)pyrazol-4-yl]-1-methyl-imidazole-2-carboxamide;formic acid | 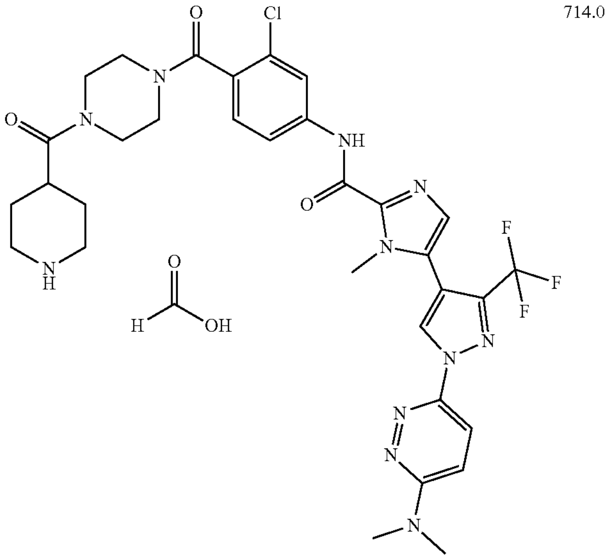 | 714.0 | Intermediate D9 and dimethylamine and HCl |

Example C1

5-[1-(5-Amino-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

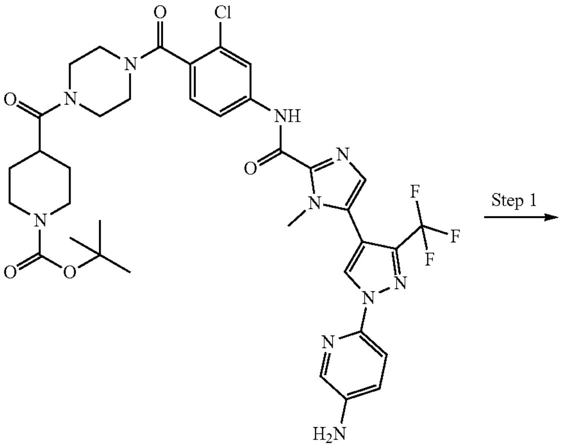

Intermediate G1

-continued

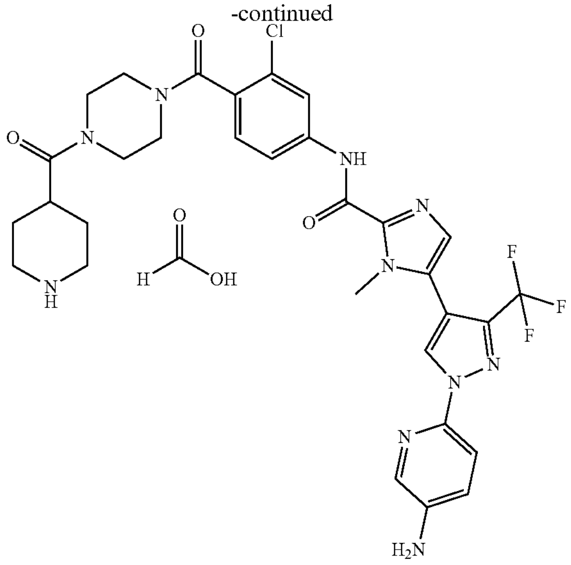

Example C1

Step 1: 5-[1-(5-amino-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid In a 50 mL round-bottomed flask, tert-butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1-carboxylate (45 mg, 57.3 mol) was combined with THF (2 mL) to give a light brown solution. HCl (478 μl, 5.73 mmol) was added. The reaction was stirred at room temperature for 20 min. The crude reaction mixture was concentrated in vacuum. The crude material was purified by preparative HPLC to afford 5-(1-(5-aminopyridin-2-yl)-3-(trifluoromethyl)-pyrazol-4-yl)-N-(3-chloro-4-(4-(piperidine-4-carbonyl)piperazine-1-carbonyl)phenyl)-1-methyl-imidazole-2-carboxamide diformate (14.8 mg). MS $[M+H]^+$: 713.0.

The following compounds were prepared in analogy of Example C1:

| Ex# | Name | Structure | MS ESI $[M + H]^+$ | Starting Material |
|---|---|---|---|---|
| Example C2 | N-[3-chloro-4-[4-(piperidine-4-carbonyl)piperazine-1-carbonyl]phenyl]-5-[1-[5-(2-methoxyethylamino)-2-pyridyl]-3-(trifluoromethyl)pyrazol-4-yl]-1-methyl-imidazole-2-carboxamide;formic acid | 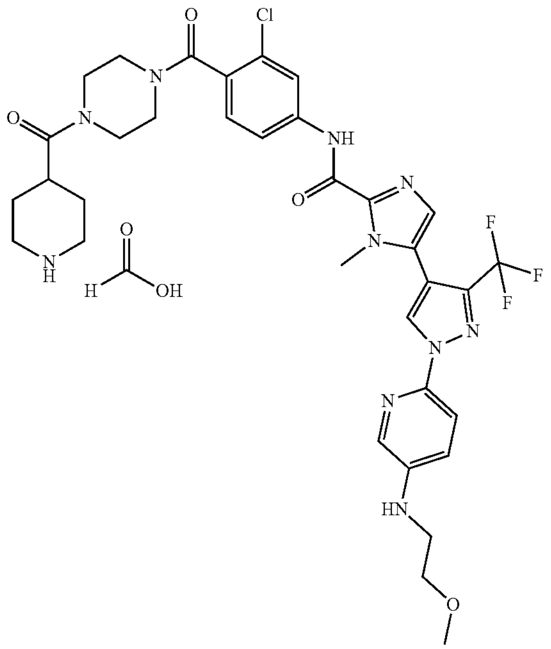 | 743.5 | Intermediate I2 and HCl |
| Example C3 | 5-[1-[5-[(3-amino-3-oxo-propyl)amino]-2-pyridyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;formic acid | 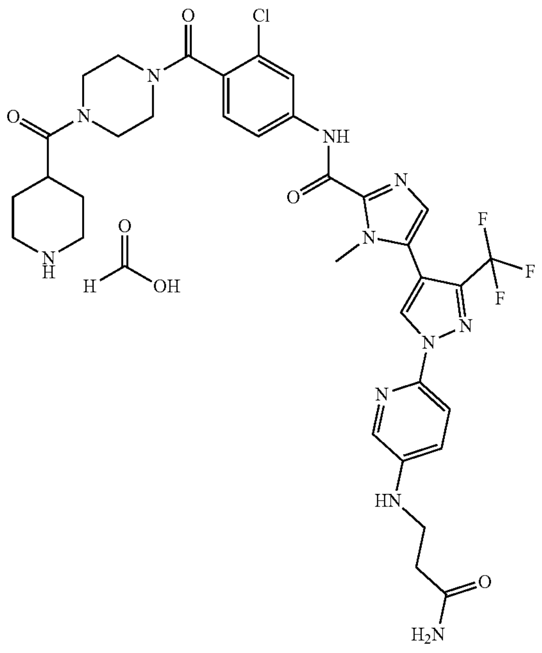 | 756.5 | Intermediate I3 and HCl |

-continued

| Ex# | Name | Structure | MS ESI [M + H]+ | Starting Material |
|---|---|---|---|---|
| Example C4 | 5-[1-(5-amino-2-pyridyl)-3-(trifluoromethyl)pyrazol-4-yl]-N-[3-chloro-4-[4-(4-hydroxypiperidine-4-carbonyl)piperazine-1-carbonyl]phenyl]-1-methyl-imidazole-2-carboxamide;formic acid | 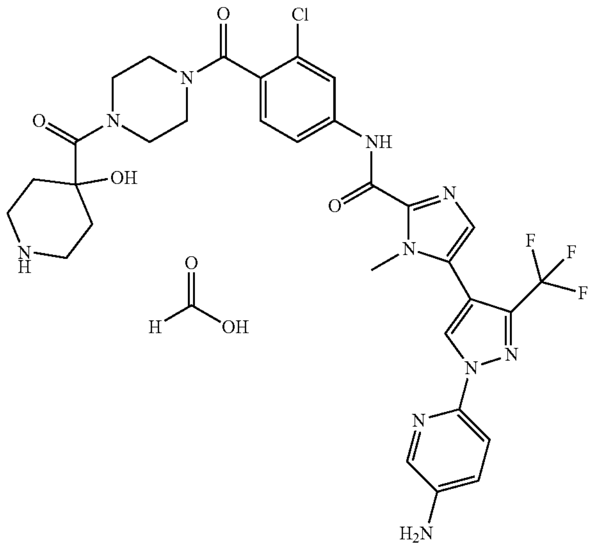 [SMILES: Cn1c(-c2cn(-c3ccc(N)cn3)nc2C(F)(F)F)cnc1C(=O)Nc1ccc(C(=O)N2CCN(C(=O)C3(O)CCNCC3)CC2)c(Cl)c1 ; O=CO] | 701.3 | Intermediate G3 and HCl |
| Example C5 | N-[3-chloro-4-[4-(piperidine-4-carbonyl)piperazine-1-carbonyl]phenyl]-5-[1-(4-methoxypyrimidin-2-yl)-3-(trifluoromethyl)pyrazol-4-yl]-1-methyl-imidazole-2-carboxamide;formic acid | 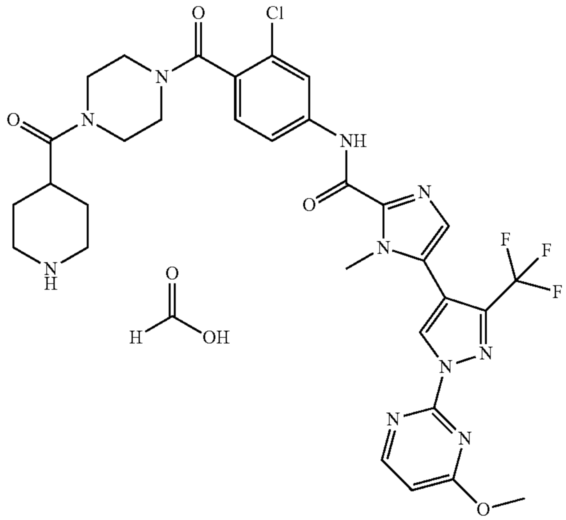 [SMILES: COc1ccnc(-n2cc(-c3cnc(C(=O)Nc4ccc(C(=O)N5CCN(C(=O)C6CCNCC6)CC5)c(Cl)c4)n3C)c(C(F)(F)F)n2)n1 ; O=CO] | 701.2 | Intermediate D14 and HCl |
| Example C6 | N-[3-chloro-4-[4-(piperidine-4-carbonyl)piperazine-1-carbonyl]phenyl]-5-[1-(2-methoxypyrimidin-4-yl)-3-(trifluoromethyl)pyrazol-4-yl]-1-methyl-imidazole-2-carboxamide;formic acid | 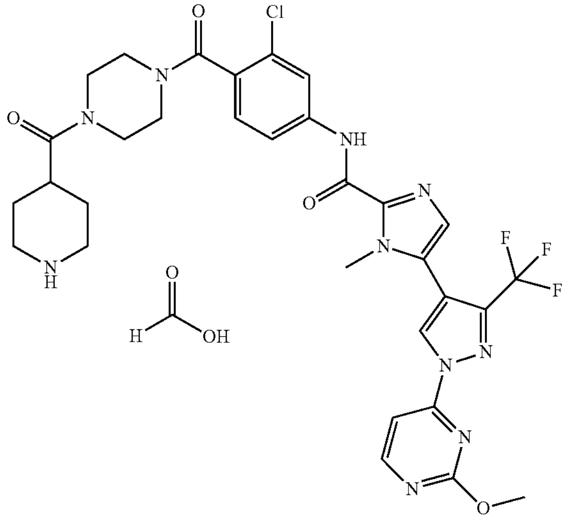 [SMILES: COc1nccc(-n2cc(-c3cnc(C(=O)Nc4ccc(C(=O)N5CCN(C(=O)C6CCNCC6)CC5)c(Cl)c4)n3C)c(C(F)(F)F)n2)n1 ; O=CO] | 701.2 | Intermediate D15 and HCl |

-continued

| Ex# | Name | Structure | MS ESI [M + H]+ | Starting Material |
|---|---|---|---|---|
| Example C7 | 5-[1-(5-amino-2-pyridyl)-3-(trifluoromethyl)pyrazol-4-yl]-N-[3-chloro-4-[[1-(piperidine-4-carbonyl)-4-piperidyl]methylcarbamoyl]phenyl]-1-methyl-imidazole-2-carboxamide;formic acid | 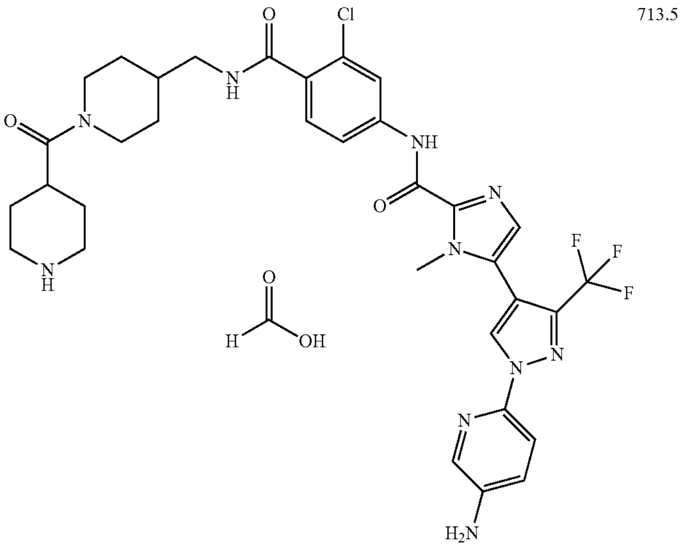 | 713.5 | Intermediate G6 and HCl |
| Example C8 | 5-[1-(5-amino-2-pyridyl)-3-(trifluoromethyl)pyrazol-4-yl]-N-[3-chloro-4-[4-[(3S)-morpholine-3-carbonyl]piperazine-1-carbonyl]phenyl]-1-methyl-imidazole-2-carboxamide;formic acid | 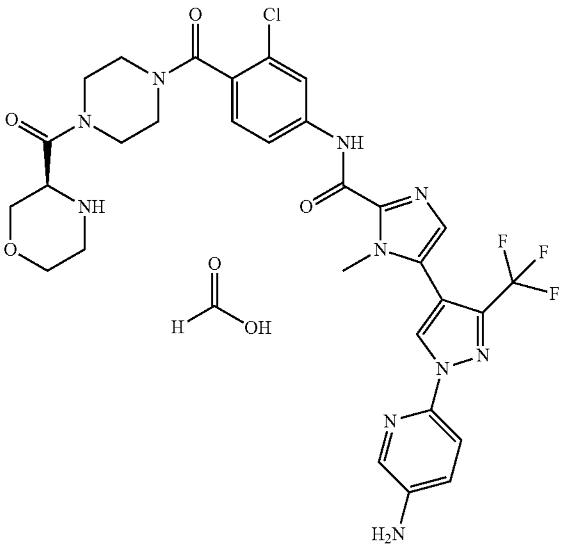 [SMILES: Cn1c(-c2cn(-c3ccc(N)cn3)nc2C(F)(F)F)cnc1C(=O)Nc1ccc(C(=O)N2CCN(C(=O)[C@@H]3COCCN3)CC2)c(Cl)c1 ; O=CO] | 687.2 | Intermediate G7 and HCl |

-continued

| Ex# | Name | Structure | MS ESI $[M + H]^+$ | Starting Material |
|---|---|---|---|---|
| Example C9 | 5-[1-(5-amino-2-pyridyl)-3-(difluoromethyl)pyrazol-4-yl]-N-[3-chloro-4-[4-(1-methylpiperidine-4-carbonyl)piperazine-1-carbonyl]phenyl]-1-methyl-imidazole-2-carboxamide | 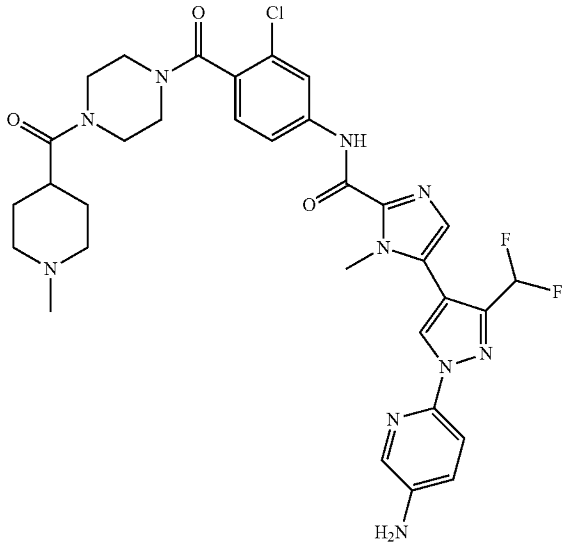 [SMILES: CN1CCC(C(=O)N2CCN(C(=O)c3ccc(NC(=O)c4ncc(-c5cn(-c6ccc(N)cn6)nc5C(F)F)n4C)cc3Cl)CC2)CC1] | 681.2 | Intermediate D20 |
| Example C10 | 5-[1-(5-amino-2-pyridyl)-3-methoxy-pyrazol-4-yl]-N-[3-chloro-4-[4-(1-methylpiperidine-4-carbonyl)piperazine-1-carbonyl]phenyl]-1-methyl-imidazole-2-carboxamide | 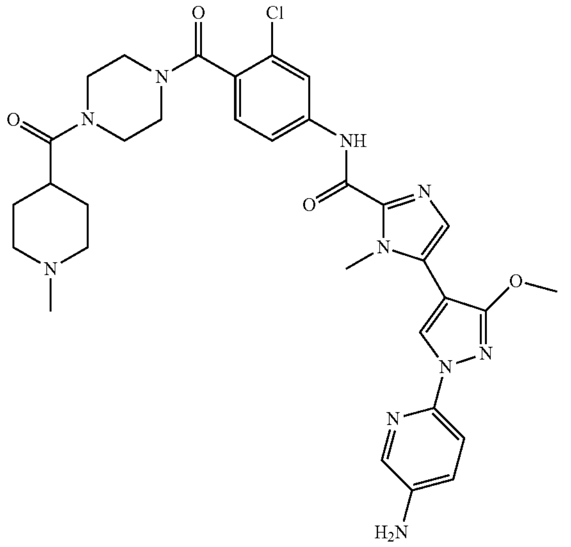 [SMILES: COc1nn(-c2ccc(N)cn2)cc1-c1cnc(C(=O)Nc2ccc(C(=O)N3CCN(C(=O)C4CCN(C)CC4)CC3)c(Cl)c2)n1C] | 661.3 | Intermediate D21 and HCl |

-continued

| Ex# | Name | Structure | MS ESI [M + H]+ | Starting Material |
|---|---|---|---|---|
| Example C11 | 5-[1-(5-amino-2-pyridyl)-3-cyano-pyrazol-4-yl]-N-[3-chloro-4-[4-(1-methylpiperidine-4-carbonyl)piperazine-1-carbonyl]phenyl]-1-methyl-imidazole-2-carboxamide | 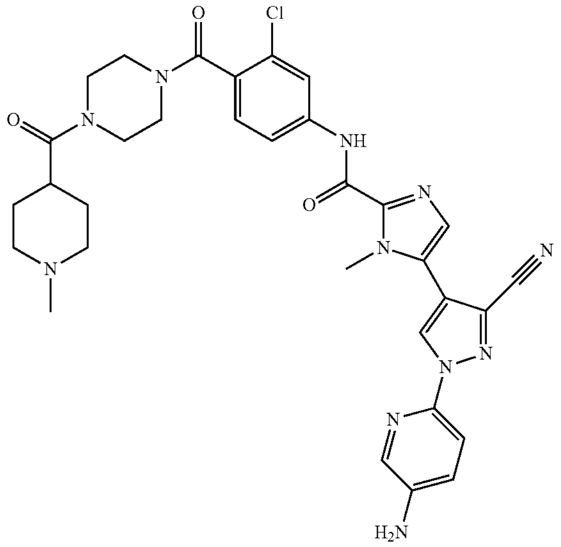 [SMILES: CN1CCC(C(=O)N2CCN(C(=O)c3ccc(NC(=O)c4ncc(-c5cn(-c6ccc(N)cn6)nc5C#N)n4C)cc3Cl)CC2)CC1] | 656.1 | Intermediate D22 and HCl |
| Example C12 | 5-[1-(5-amino-2-pyridyl)-3-methyl-pyrazol-4-yl]-N-[3-chloro-4-[4-(1-methylpiperidine-4-carbonyl)piperazine-1-carbonyl]phenyl]-1-methyl-imidazole-2-carboxamide | 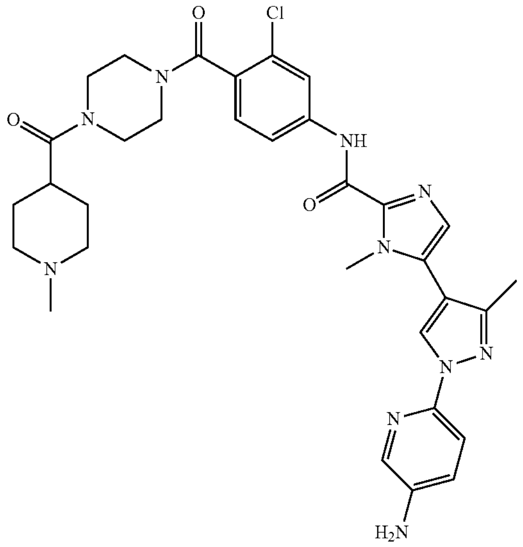 [SMILES: Cc1nn(-c2ccc(N)cn2)cc1-c1cnc(C(=O)Nc2ccc(C(=O)N3CCN(C(=O)C4CCN(C)CC4)CC3)c(Cl)c2)n1C] | 645.3 | Intermediate D23 and HCl |

-continued

| Ex# | Name | Structure | MS ESI [M + H]+ | Starting Material |
|---|---|---|---|---|
| Example C13 | 5-[1-(5-amino-2-pyridyl)-3-ethyl-pyrazol-4-yl]-N-[3-chloro-4-[4-(1-methylpiperidine-4-carbonyl)piperazine-1-carbonyl]phenyl]-1-methyl-imidazole-2-carboxamide;2,2,2-trifluoroacetic acid | 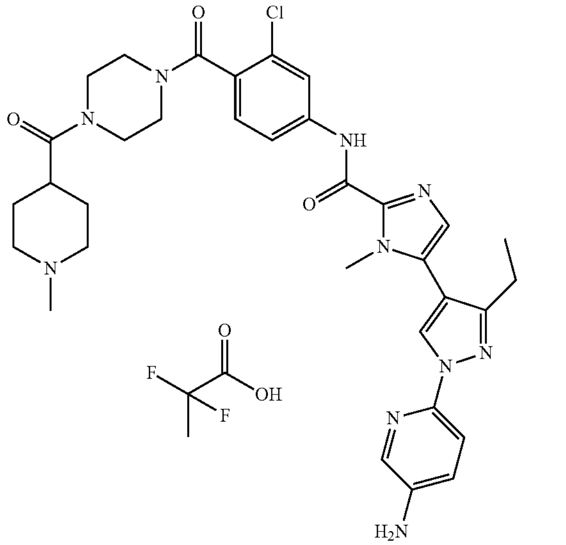 | 659.2 | Intermediate D24 and HCl |
| Example C14 | 5-[1-(6-aminopyridazin-3-yl)-3-(trifluoromethyl)pyrazol-4-yl]-N-[3-chloro-4-[4-(1-methylpiperidine-4-carbonyl)piperazine-1-carbonyl]phenyl]-1-methyl-imidazole-2-carboxamide;2,2,2-trifluoroacetic acid | 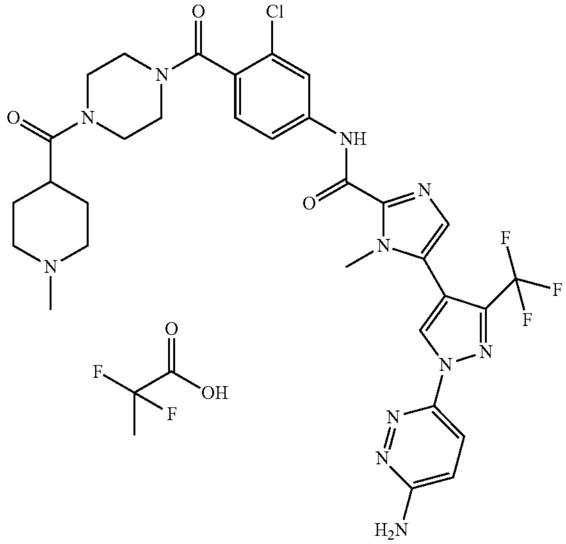 | 700.2 | Intermediate D25 and HCl |
| Example C15 | N-[3-chloro-4-[4-(1-methylpiperidine-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide;2,2,2-trifluoroacetic acid | 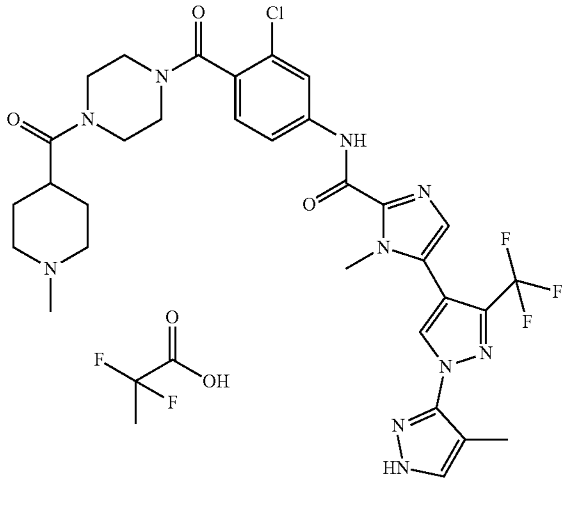 | 687.2 | Intermediate D26 and HCl |

-continued

| Ex# | Name | Structure | MS ESI [M + H]+ | Starting Material |
|---|---|---|---|---|
| Example C16 | 5-[1-(5-amino-2-pyridyl)-3-(trifluoromethyl)pyrazol-4-yl]-N-[3-chloro-4-[4-[2-(3-hydroxypyrrolidin-1-yl)acetyl]piperazine-1-carbonyl]phenyl]-1-methyl-imidazole-2-carboxamide;formic acid | 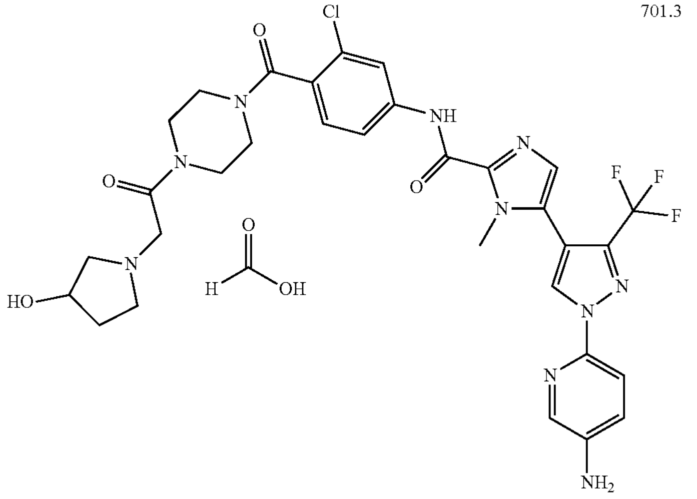 | 701.3 | Intermediate G5 |
| Example C17 | N-[3-chloro-4-[4-[(2S,3S)-3-hydroxypyrrolidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide | 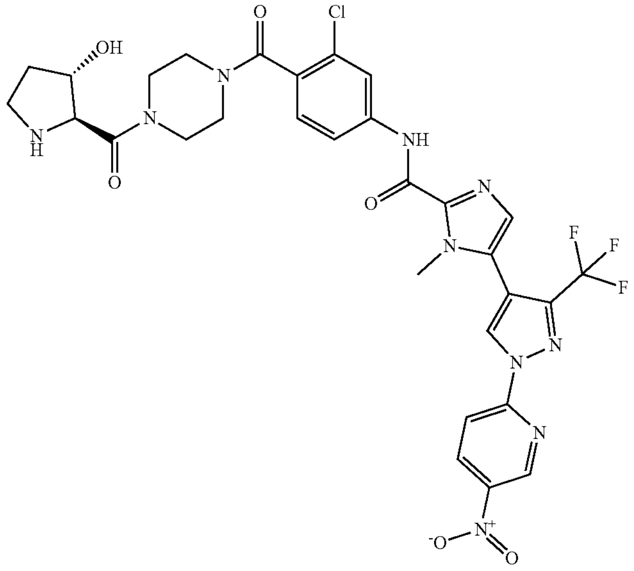 | 717.4 | Intermediate D27 and HCl |

Example D1

N-[3-chloro-4-[4-(piperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formic acid

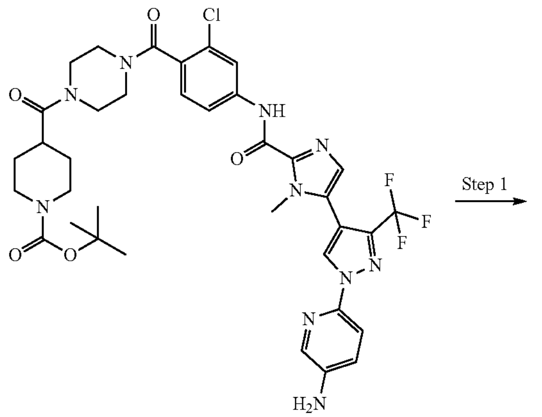

Intermediate G1

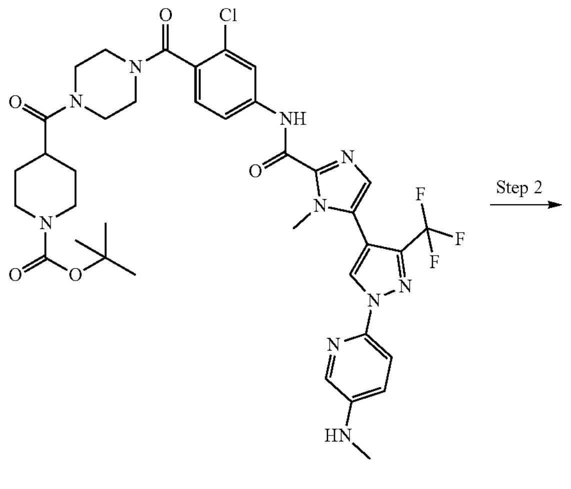

-continued

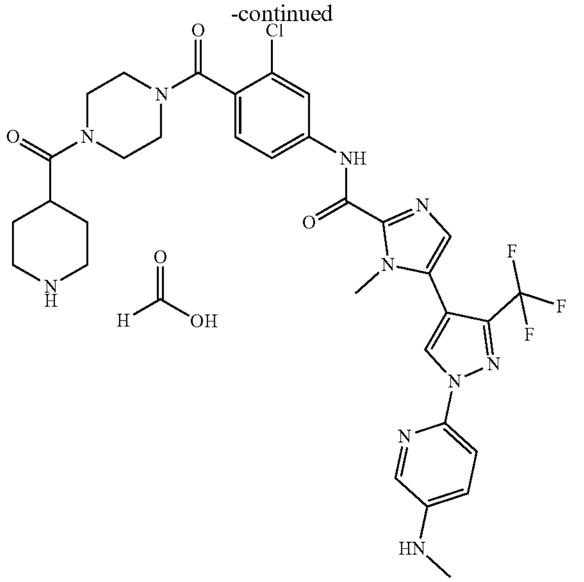

Example D1

Step 1: tert-butyl 4-[4-[2-chloro-4-[[1-methyl-5-[1-[5-(methylamino)-2-pyridyl]-3-(trifluoromethyl)pyrazol-4-yl]imidazole-2-carbonyl]amino]benzoyl]piperazine-1-carbonyl]piperidine-1-carboxylate To a 25 mL microwave vial was added tert-butyl 4-(4-(4-(5-(1-(5-aminopyridin-2-yl)-3-(trifluoromethyl)-pyrazol-4-yl)-1-methyl-imidazole-2-carboxamido)-2-chlorobenzoyl)piperazine-1-carbonyl)piperidine-1-carboxylate (240 mg, 306 μmol), formaldehyde (275 mg, 253 μl, 9.17 mmol) and sodium methoxide (495 mg, 9.17 mmol) in MeOH (10 mL). The vial was capped and heated under microwave at 50° C. for 15 h. The reaction was cooled to the room temperature, $NaBH_4$ (405 mg, 10.7 mmol) was added. The reaction stirred at room temperature for 2 h. The crude reaction mixture was concentrated in vacuum. The reaction mixture was poured into 25 mL sat $NH_4Cl$ and extracted with EtOAc (25 mL×3). The organic layers were combined, washed with sat NaCl (25 mL×1), The organic layers were dried over $Na_2SO_4$ and concentrated in vacuum to afford tert-butyl 4-(4-(2-chloro-4-(1-methyl-5-(1-(5-(methylamino)pyridin-2-yl)-3-(trifluoromethyl)-pyrazol-4-yl)-imidazole-2-carboxamido)benzoyl)piperazine-1-carbonyl)piperidine-1-carboxylate (169 mg). MS $[M+H]^+$: 799.7.

Step 2: N-[3-chloro-4-[4-(piperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formic acid In a 50 mL round-bottomed flask, tert-butyl 4-(4-(2-chloro-4-(1-methyl-5-(1-(5-(methylamino)pyridin-2-yl)-3-(trifluoromethyl)-pyrazol-4-yl)-imidazole-2-carboxamido)benzoyl)piperazine-1-carbonyl)piperidine-1-carboxylate (24 mg, 30 μmol) was combined with THF (2 mL) to give a light brown solution. HCl (500 μl, 6.01 mmol) was added. The reaction was stirred at room temperature for 20 min. The crude reaction mixture was concentrated in vacuum. The crude material was purified by preparative HPLC to afford N-[3-chloro-4-[4-(piperidine-4-carbonyl)piperazine-1-carbonyl]phenyl]-1-methyl-5-[1-[5-(methylamino)-2-pyridyl]-

3-(trifluoromethyl)pyrazol-4-yl]imidazole-2-carboxamide; formic acid (2 mg). MS $[M+H]^+$: 699.2.

The following compounds were prepared in analogy of Example D1.

| Ex# | Name | Structure | MS ESI $[M + H]^+$ | Starting Material |
|---|---|---|---|---|
| Example D2 | 5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 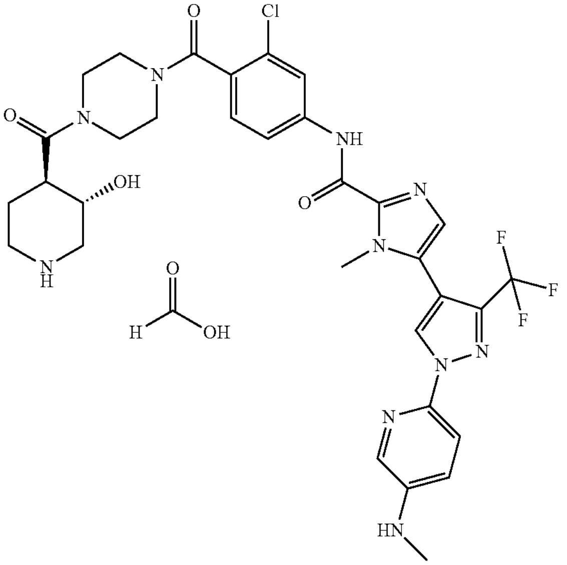 [SMILES: CNc1ccc(-n2cc(-c3cnc(C(=O)Nc4ccc(C(=O)N5CCN(C(=O)[C@@H]6CCNC[C@H]6O)CC5)c(Cl)c4)n3C)c(C(F)(F)F)n2)nc1 ; O=CO] | 715.6 | Intermediate G2 and formaldehyde and HCl |
| Example D3 | N-[3-chloro-4-[4-(4-hydroxypiperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide; formic acid | 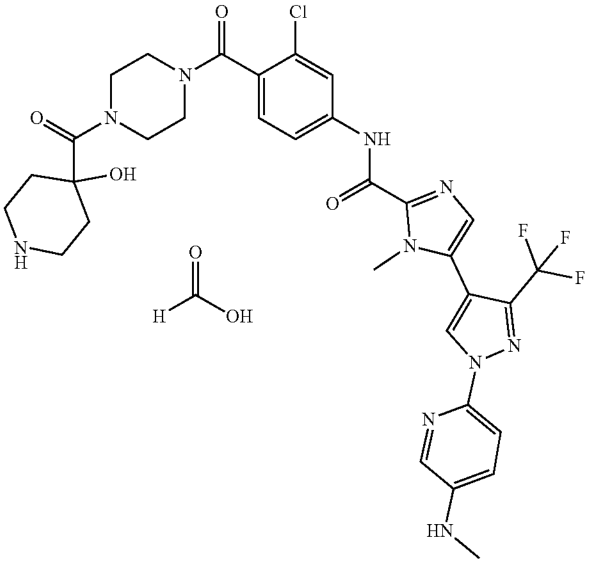 [SMILES: CNc1ccc(-n2cc(-c3cnc(C(=O)Nc4ccc(C(=O)N5CCN(C(=O)C6(O)CCNCC6)CC5)c(Cl)c4)n3C)c(C(F)(F)F)n2)nc1 ; O=CO] | 715.4 | Intermediate G3 and formaldehyde and HCl |

-continued

| Ex# | Name | Structure | MS ESI [M + H]+ | Starting Material |
|---|---|---|---|---|
| Example D4 | N-[3-chloro-4-[4-[(2S,3S)-3-hydroxypyrrolidine-2-carbonyl]piperazine-1-carbonyl]phenyl]-1-methyl-5-[1-[5-(methylamino)-2-pyridyl]-3-(trifluoromethyl) pyrazol-4-yl]imidazole-2-carboxamide; formic acid | 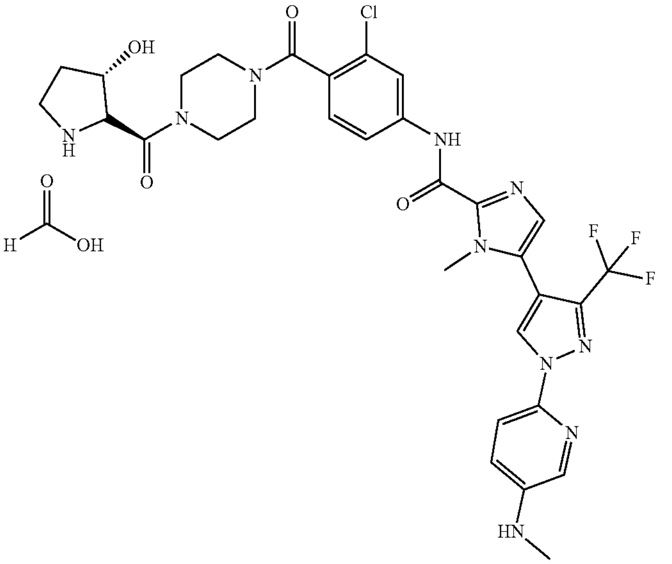 | 701.3 | Intermediate G4 and formaldehyde and HCl |
| Example D5 | N-[3-chloro-4-[4-[2-(3-hydroxypyrrolidin-1-yl)acetyl] piperazine-1-carbonyl]phenyl]-1-methyl-5-[1-[5-(methylamino)-2-pyridyl]-3-(trifluoromethyl) pyrazol-4-yl]imidazole-2-carboxamide; formic acid | 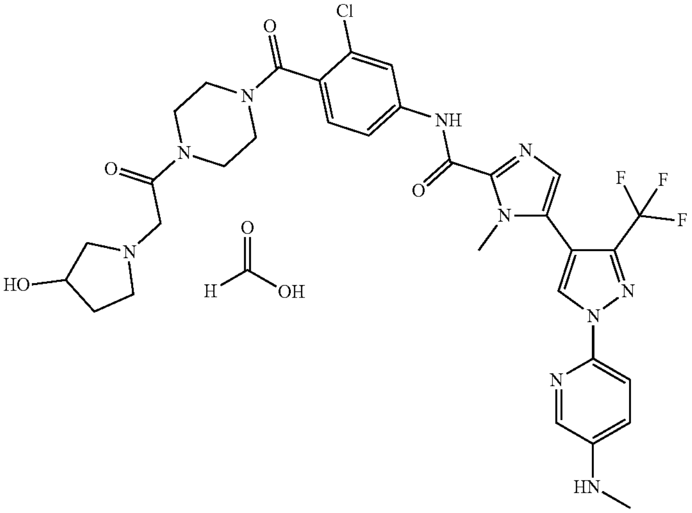 [SMILES: CNc1ccc(-n2cc(-c3cnc(C(=O)Nc4ccc(C(=O)N5CCN(C(=O)CN6CCC(O)C6)CC5)c(Cl)c4)n3C)c(C(F)(F)F)n2)nc1 ; O=CO] | 715.3 | Intermediate G5 and formaldehyde |

-continued

| Ex# | Name | Structure | MS ESI $[M + H]^+$ | Starting Material |
| --- | --- | --- | --- | --- |
| Example D6 | 1-methyl-5-[1-[5-(methylamino)-2-pyridyl]-3-(trifluoromethyl) pyrazol-4-yl]-N-[3-methyl-4-[4-(piperidine-4-carbonyl) piperazine-1-carbonyl]phenyl] imidazole-2-carbox-amide; formic acid | 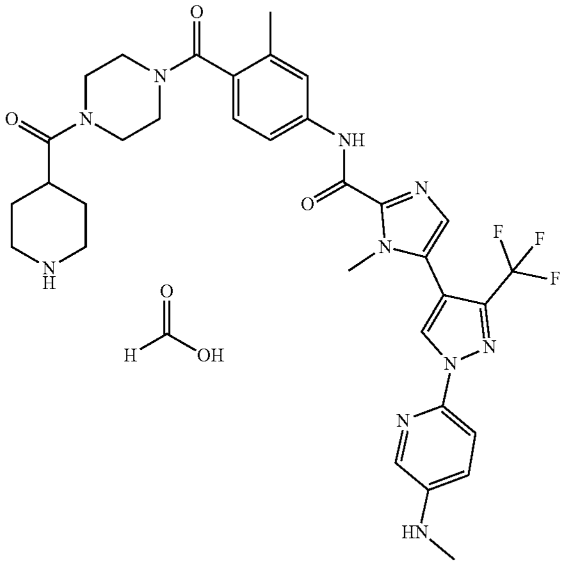 [SMILES: CNc1ccc(-n2cc(-c3cnc(C(=O)Nc4ccc(C(=O)N5CCN(C(=O)C6CCNCC6)CC5)c(C)c4)n3C)c(C(F)(F)F)n2)nc1 ; O=CO] | 679.5 | Intermediate G8 and formaldehyde and HCl |
| Example D7 | N-[3-chloro-4-[4-[(2S,4R)-4-hydroxypyrrolidine-2-carbonyl] piperazine-1-carbonyl] phenyl]-1-methyl-5-[1-[5-(methylamino)-2-pyridyl]-3-(trifluoromethyl) pyrazol-4-yl]imidazole-2-carboxamide; formic acid | 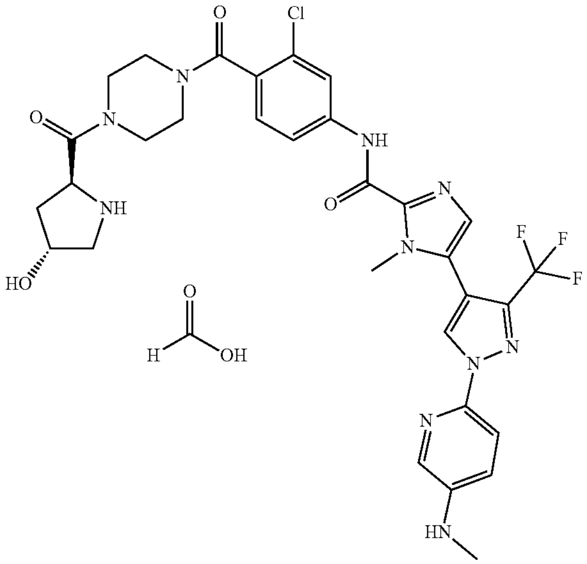 [SMILES: CNc1ccc(-n2cc(-c3cnc(C(=O)Nc4ccc(C(=O)N5CCN(C(=O)[C@@H]6C[C@@H](O)CN6)CC5)c(Cl)c4)n3C)c(C(F)(F)F)n2)nc1 ; O=CO] | 7.701.2 | Intermediate G9 and formaldehyde and HCl |

Example E1
N-[3-chloro-4-[4-(piperidine-4-carbonyl)piperazine-1-carbonyl]phenyl]-5-[1-[1-(2-methoxyethyl)pyrazol-4-yl]-3-(trifluoromethyl)pyrazol-4-yl]-1-methyl-imidazole-2-carboxamide; formic acid
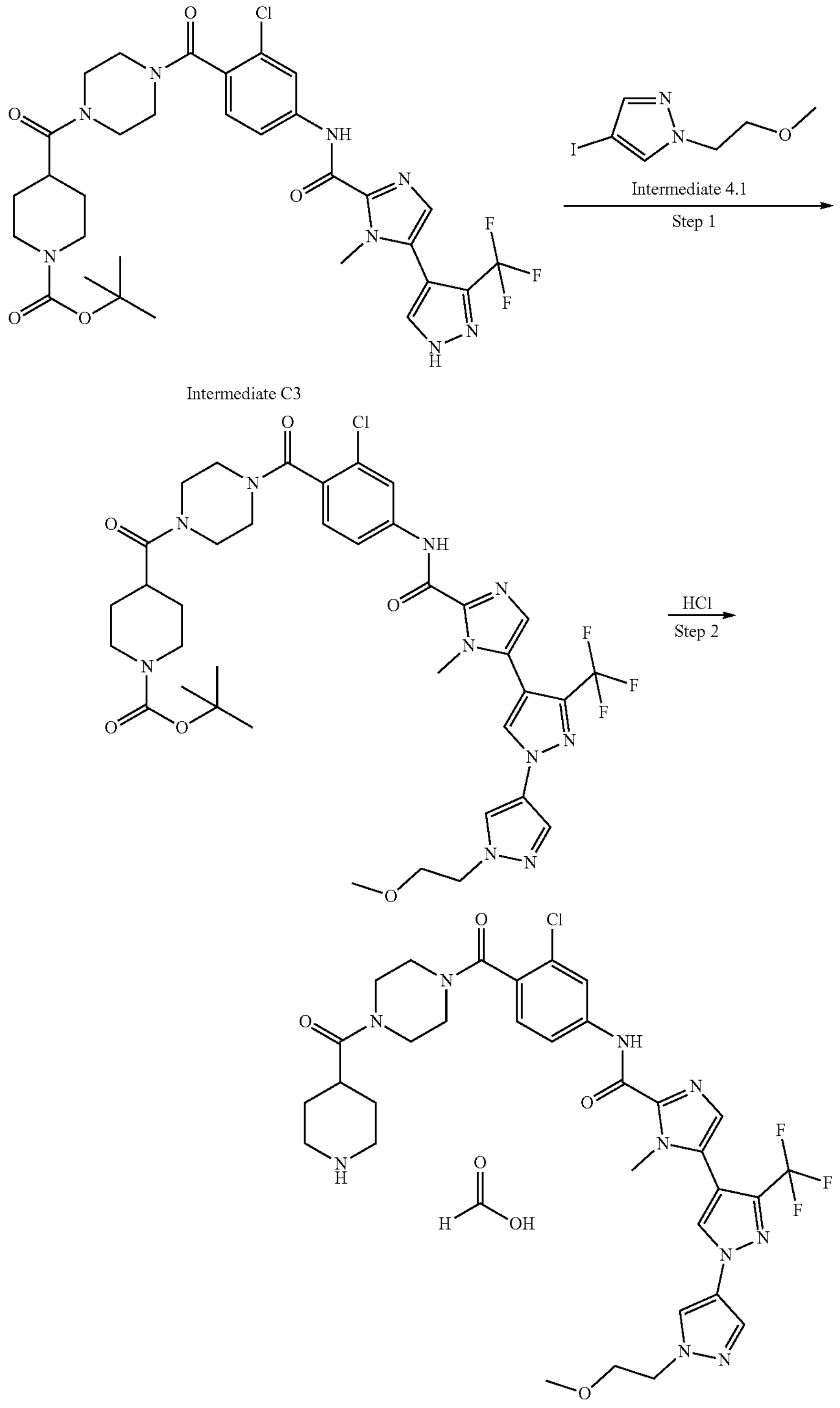
Intermediate C3
Example E1

Step 1: tert-butyl 4-(4-(2-chloro-4-(5-(1'-(2-methoxyethyl)-3-(trifluoromethyl)-1'H-[1,4'-bipyrazol]-4-yl)-1-methyl-imidazole-2-carboxamido)benzoyl)piperazine-1-carbonyl)piperidine-1-carboxylate To a 5 mL microwave vial was added tert-butyl 4-(4-(2-chloro-4-(1-methyl-5-(3-(trifluoromethyl)-1H-pyrazol-4-yl)-imidazole-2-carboxamido)benzoyl)piperazine-1-carbonyl)piperidine-1-carboxylate (60 mg, 86.6 μmol), 4-iodo-1-(2-methoxyethyl)-pyrazole (21.8 mg, 86.6 μmol), copper(I) iodide (1.65 mg, 8.66 μmol), cesium carbonate (56.4 mg, 173 μmol) and Trans-(1R,2R)N,N'-Dimethyl-cyclohexane-1,2-diamine (2.46 mg, 17.3 μmol) in DMF (2 mL). The vial was capped and heated under microwave at 150° C. for 1 h. The reaction mixture was poured into 25 mL $H_2O$ and extracted with EtOAc (25 mL×3). The organic layers were combined, washed with EtOAc (25 mL×3), The organic layers were dried over $Na_2SO_4$ and concentrated in vacuum. The crude material was purified by flash chromatography to afford tert-butyl 4-(4-(2-chloro-4-(5-(1'-(2-methoxyethyl)-3-(trifluoromethyl)-1'H-[1,4'-bipyrazol]-4-yl)-1-methyl-imidazole-2-carboxamido)benzoyl)piperazine-1-carbonyl)piperidine-1-carboxylate (40 mg). MS $[M+H]^+$: 817.8.

Step 2: N-[3-chloro-4-[4-(piperidine-4-carbonyl)piperazine-1-carbonyl]phenyl]-5-[1-[1-(2-methoxyethyl)pyrazol-4-yl]-3-(trifluoromethyl)pyrazol-4-yl]-1-methyl-imidazole-2-carboxamide; formic acid In a 100 mL round-bottomed flask, tert-butyl 4-(4-(2-chloro-4-(5-(1'-(2-methoxyethyl)-3-(trifluoromethyl)-1'H-[1,4'-bipyrazol]-4-yl)-1-methyl-imidazole-2-carboxamido)benzoyl)piperazine-1-carbonyl)piperidine-1-carboxylate (40 mg, 48.9 μmol) was combined with THF (2 mL) to give a light brown solution. HCl (408 μl, 4.89 mmol) was added. The reaction was stirred at room temperature for 1 h. The crude reaction mixture was concentrated in vacuum. The crude material was purified by preparative HPLC to afford N-(3-chloro-4-(4-(piperidine-4-carbonyl)piperazine-1-carbonyl)phenyl)-5-(1'-(2-methoxyethyl)-3-(trifluoromethyl)-1'H-[1,4'-bipyrazol]-4-yl)-1-methyl-imidazole-2-carboxamide formate (6.7 mg). MS $[M+H]^+$: 717.1.

The following compounds were prepared in analogy of Example E1.

| Ex# | Name | Structure | MS ESI $[M + H]^+$ | Starting Material |
|---|---|---|---|---|
| Example E2 | N-[3-chloro-4-[4-(piperidine-4-carbonyl)piperazine-1-carbonyl]phenyl]-5-[1-[1-(2-methoxyethyl)-5-methyl-pyrazol-4-yl]-3-(trifluoromethyl)pyrazol-4-yl]-1-methyl-imidazole-2-carboxamide;formic acid | 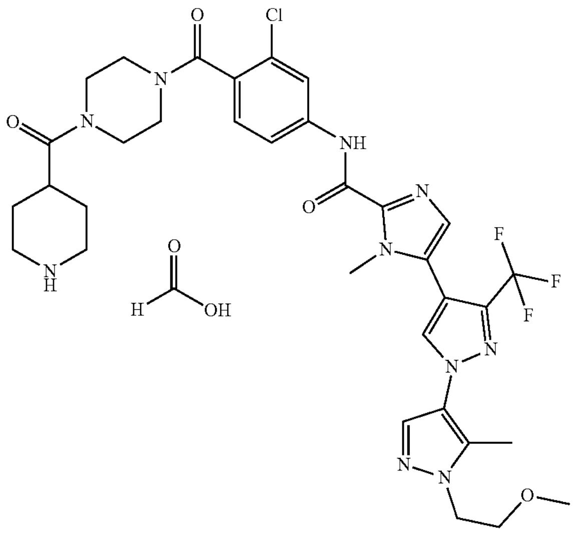 [SMILES: COCCn1ncc(-n2cc(-c3cnc(C(=O)Nc4ccc(C(=O)N5CCN(C(=O)C6CCNCC6)CC5)c(Cl)c4)n3C)c(C(F)(F)F)n2)c1C ; O=CO] | 731.1 | Intermediate C3 and Intermediate A4.2 and HCl |

-continued

| Ex# | Name | Structure | MS ESI $[M + H]^+$ | Starting Material |
| --- | --- | --- | --- | --- |
| Example E3 | N-[3-chloro-4-[4-(piperidine-4-carbonyl)piperazine-1-carbonyl]phenyl]-5-[1-[1-(2-methoxyethyl)imidazol-4-yl]-3-(trifluoromethyl)pyrazol-4-yl]-1-methyl-imidazole-2-carboxamide;formic acid | 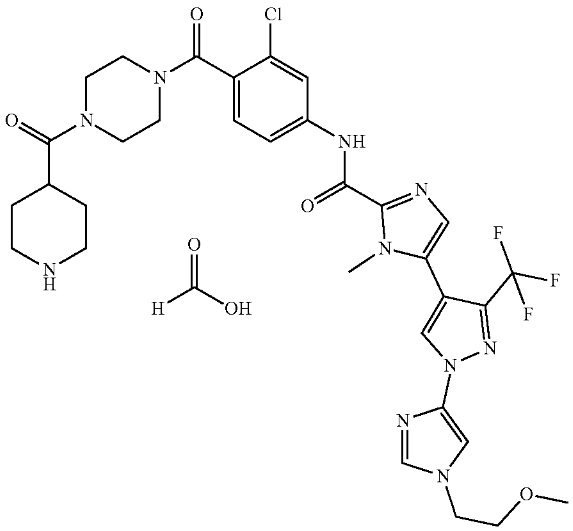 [SMILES: COCCn1cnc(-n2cc(-c3cnc(C(=O)Nc4ccc(C(=O)N5CCN(C(=O)C6CCNCC6)CC5)c(Cl)c4)n3C)c(C(F)(F)F)n2)c1 ; O=CO] | 717.1 | Intermediate B6 and Intermediate A4.3 and HCl |
| Example E4 | N-[3-chloro-4-[4-(piperidine-4-carbonyl)piperazine-1-carbonyl]phenyl]-1-methyl-5-[1-(1-methylimidazol-4-yl)-3-(trifluoromethyl)pyrazol-4-yl]imidazole-2-carboxamide;formic acid | 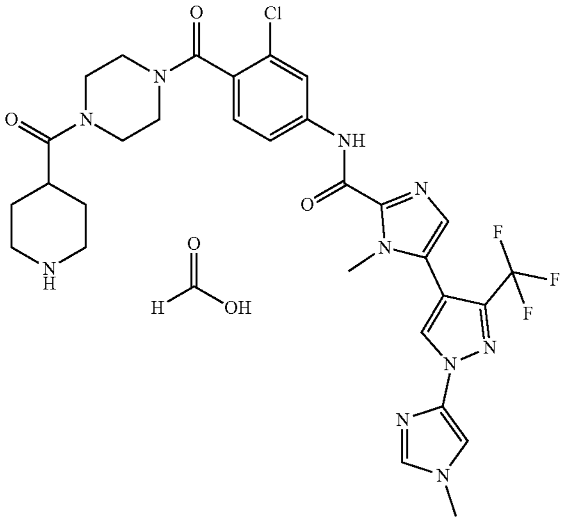 [SMILES: Cn1cnc(-n2cc(-c3cnc(C(=O)Nc4ccc(C(=O)N5CCN(C(=O)C6CCNCC6)CC5)c(Cl)c4)n3C)c(C(F)(F)F)n2)c1 ; O=CO] | 673.2 | Intermediate B6 and 4-iodo-1-methyl-imidazole and HCl |
| Example E5 | N-[3-chloro-4-[4-(piperidine-4-carbonyl)piperazine-1-carbonyl]phenyl]-1-methyl-5-[1-(5-methyl-1H-pyrazol-4-yl)-3-(trifluoromethyl)pyrazol-4-yl]imidazole-2-carboxamide;formic acid | 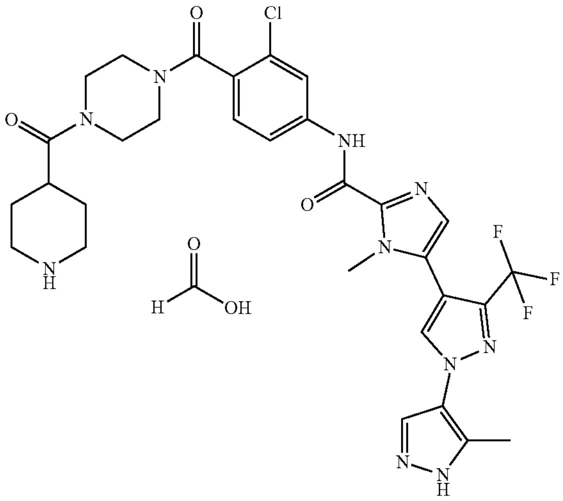 [SMILES: Cc1[nH]ncc1-n1cc(-c2cnc(C(=O)Nc3ccc(C(=O)N4CCN(C(=O)C5CCNCC5)CC4)c(Cl)c3)n2C)c(C(F)(F)F)n1 ; O=CO] | 673.4 | Intermediate C3 and Intermediate A11.2 and TFA |

-continued

| Ex# | Name | Structure | MS ESI [M + H]+ | Starting Material |
| --- | --- | --- | --- | --- |
| Example E6 | N-[3-chloro-4-[4-(piperidine-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide;formic acid | 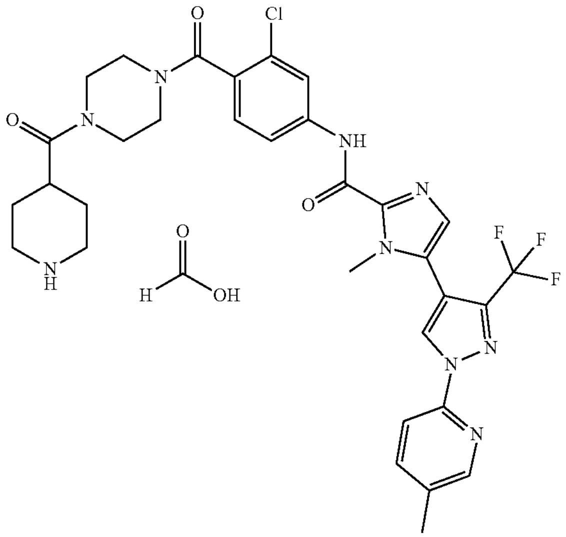 [SMILES: Cc1ccc(-n2cc(-c3cnc(C(=O)Nc4ccc(C(=O)N5CCN(C(=O)C6CCNCC6)CC5)c(Cl)c4)n3C)c(C(F)(F)F)n2)nc1 ; O=CO] | 684.5 | Intermediate C3 and 2-iodo-5-methyl-pyridine and TFA |
| Example E7 | N-[3-chloro-4-[4-(piperidine-4-carbonyl)piperazine-1-carbonyl]phenyl]-1-methyl-5-[1-(4-methyl-1H-pyrazol-5-yl)-3-(trifluoromethyl)pyrazol-4-yl]imidazole-2-carboxamide;2,2,2-trifluoroacetic acid | 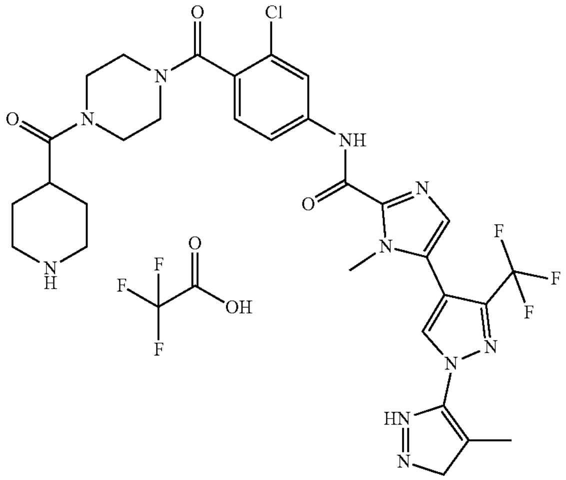 | 673.2 | Intermediate C3 and Intermediate A11.1 and TFA |

Example F1

N-[4-[4-[(1R,5S)-3-Azabicyclo[3.1.0]hexane-6-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formic acid

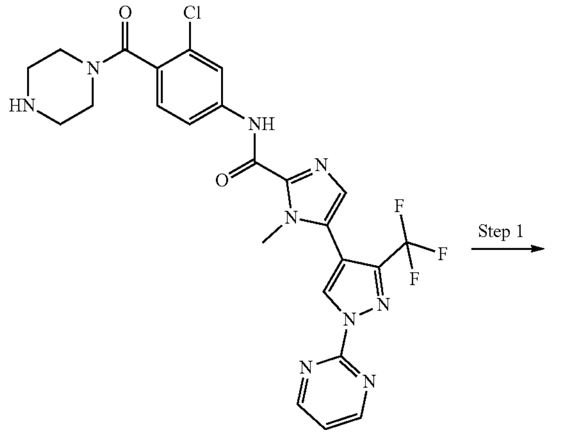

Intermediate E3

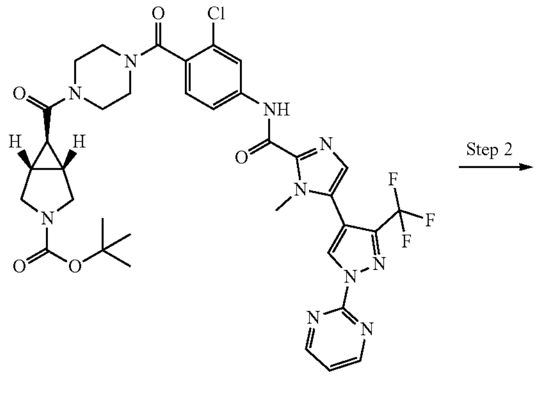

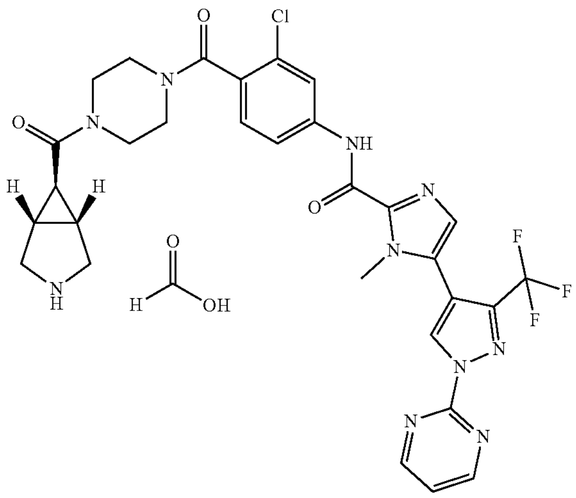

Example F1

Step 1: tert-butyl (1R,5S,6R)-6-(4-(2-chloro-4-(1-methyl-5-(1-(pyrimidin-2-yl)-3-(trifluoromethyl)-pyrazol-4-yl)-imidazole-2-carboxamido)benzoyl) piperazine-1-carbonyl)-3-azabicyclo[3.1.0]hexane-3-carboxylate In a 50 mL round-bottomed flask, N-(3-chloro-4-(piperazine-1-carbonyl)phenyl)-1-methyl-5-(1-(pyrimidin-2-yl)-3-(trifluoromethyl)-pyrazol-4-yl)-imidazole-2-carboxamide (55 mg, 98.2 μmol), (1R,5S,6R)-3-(tert-butoxycarbonyl)-3-azabicyclo[3.1.0]hexane-6-carboxylic acid (29 mg, 128 μmol), 2-(3H-[1,2,3]triazolo[4,5-b]pyridin-3-yl)-1,1,3,3-tetramethylisouronium hexafluorophosphate (V) (48.6 mg, 128 μmol) and DIPEA (25.4 mg, 34.3 μl, 196 μmol) were combined with DMF (3 mL) to give a light brown solution. The reaction mixture was poured into 25 mL $H_2O$ and extracted with EtOAc (3×25 mL). The organic layers were combined, washed with sat NaCl (1×25 mL), The organic layers were dried over $Na_2SO_4$ and concentrated in vacuum to afford tert-butyl (1R,5S,6R)-6-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)-3-azabicyclo[3.1.0]hexane-3-carboxylate (75.6 mg). MS $[M+H]^+$: 769.4.

Step 2: N-[4-[4-[(1R,5S)-3-azabicyclo[3.1.0]hexane-6-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formic acid In a 50 mL round-bottomed flask, tert-butyl (1R,5S,6R)-6-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)-3-azabicyclo[3.1.0]hexane-3-carboxylate (75 mg, 97.5 mol) was combined with THF (2 mL) to give a light brown solution. HCl (813 μl, 9.75 mmol) was added. The reaction was stirred at room temperature for 20 min. The crude reaction mixture was concentrated in vacuum. The crude material was purified by preparative HPLC. to afford N-(4-(4-((1R,5S,6R)-3-azabicyclo[3.1.0]hexane-6-carbonyl)piperazine-1-carbonyl)-3-chlorophenyl)-1-methyl-)-(1-(pyrimidin-2-yl)-3-(trifluoromethyl)-pyrazol-4-yl)-imidazole-2-carboxamide formate (21.7 mg). MS $[M+H]^+$: 669.7.

The following compounds were prepared in analogy of Example FL.

| Ex# | Name | Structure | MS ESI [M + H]+ | Starting Material |
|---|---|---|---|---|
| Example F2 | N-[3-chloro-4-[[(1R,5S)-3-[(2S,4R)-4-hydroxypyrrolidine-2-carbonyl]-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide; formic acid | 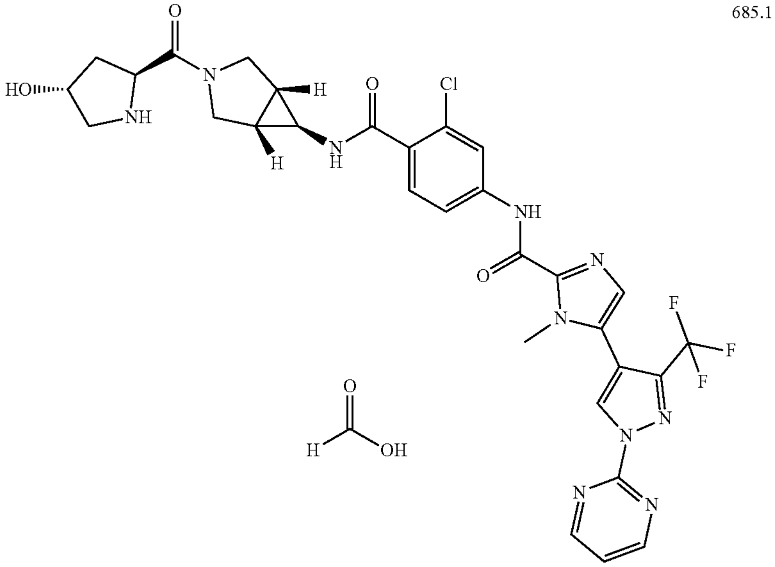 | 685.1 | Intermediate H1 and (2S,4R)-1-(tert-butoxy-carbonyl)-4-hydroxy-pyrrolidine-2-carboxylic acid and HCl |
| Example F3 | N-[3-chloro-4-[[(1S,5R)-3-(piperidine-4-carbonyl)-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide; formic acid | 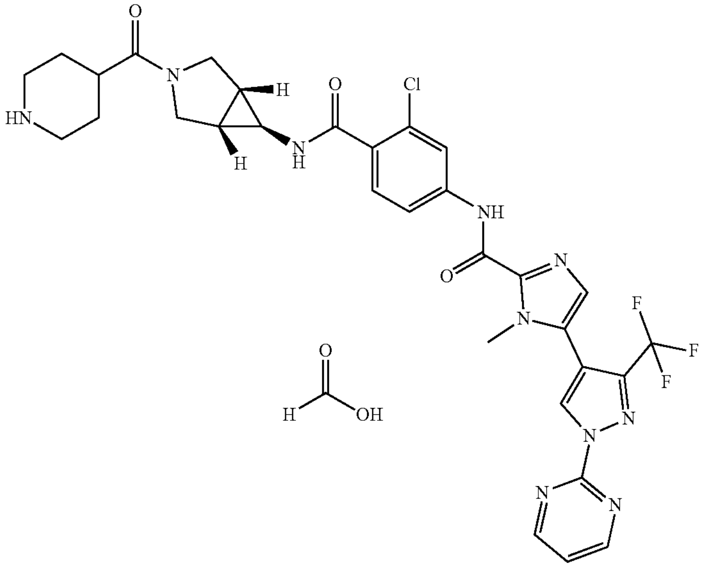 [SMILES: Cn1c(-c2cn(-c3ncccn3)nc2C(F)(F)F)cnc1C(=O)Nc1ccc(C(=O)N[C@H]2[C@@H]3CN(C(=O)C4CCNCC4)C[C@@H]32)c(Cl)c1 ; O=CO] | 683.1 | Intermediate H1 and 1-tert-butoxy carbonyl piperidine-4-carboxylic acid and HCl |

-continued

| Ex# | Name | Structure | MS ESI [M + H]+ | Starting Material |
|---|---|---|---|---|
| Example F4 | N-[3-chloro-4-[4-[(3S,4R)-3-hydroxypiperidine-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide; formic acid | 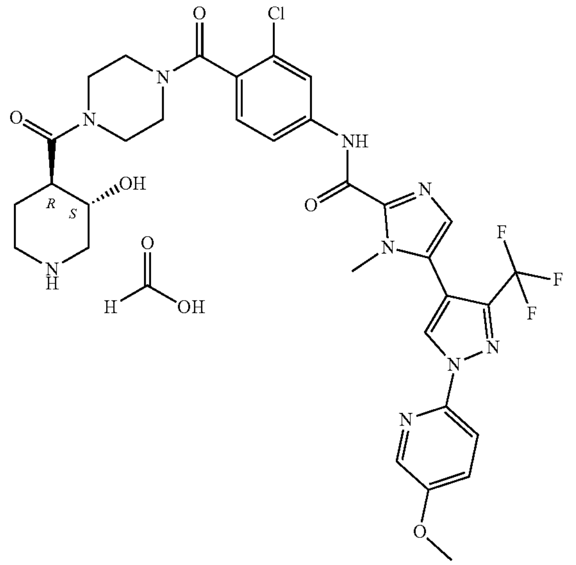 | 716.5 | Intermediate E5 and (3S,4R)-1-tert-butoxy-carbonyl-3-hydroxy-piperidine-4-carboxylic acid and HCl |

Example G1

N-[4-[4-[1-(Azetidin-3-ylmethyl)piperidine-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formic acid

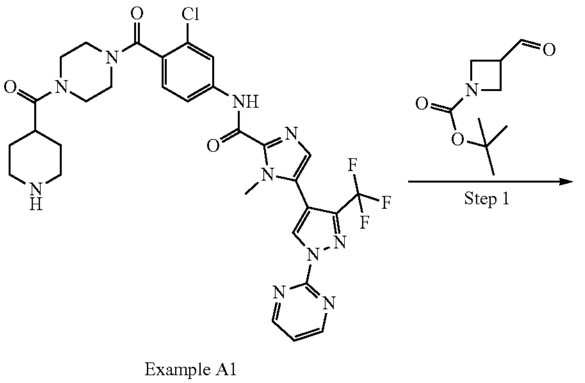

Example A1

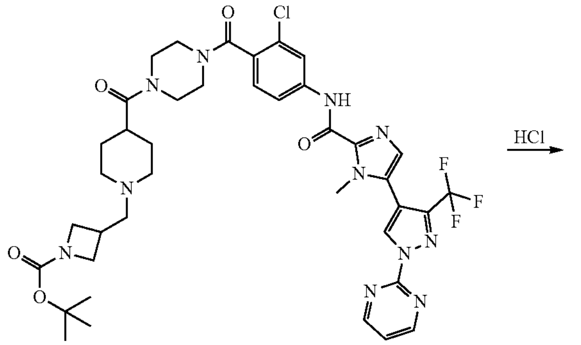

-continued

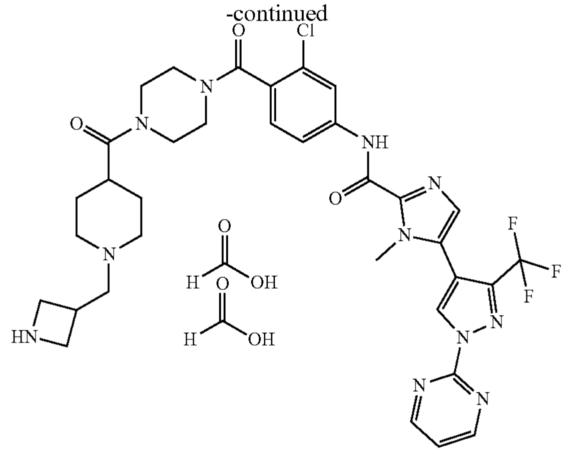

Example G1

Step 1: tert-butyl 3-((4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidin-1-yl)methyl)azetidine-1-carboxylate In a 50 mL round-bottomed flask, N-(3-chloro-4-(4-(piperidine-4-carbonyl)piperazine-1-carbonyl)phenyl)-1-methyl-5-(1-(pyrimidin-2-yl)-3-(trifluoromethyl)-pyrazol-4-yl)-imidazole-2-carboxamide (143 mg, 213 μmol), tert-butyl 3-formylazetidine-1-carboxylate (59.2 mg, 320 μmol) and $NaBH_3CN$ (26.8 mg, 426 μmol) were combined with MeOH (5 mL) to give a light brown solution. The reaction mixture was heated to 45° C. and stirred for 15 h. The crude reaction mixture was concentrated in vacuum. The reaction mixture was poured into 25 mL $H_2O$ and extracted with EtOAc (25 mL×3). The organic layers were combined, washed with sat NaCl (25 mL×1). The organic layers were dried over $Na_2SO_4$ and concentrated in vacuum. to afford tert-butyl 3-((4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidin-1-yl)methyl)azetidine-1-carboxylate (179 mg). MS $[M+H]^+$: 840.5.

Step 2: N-[4-[4-[1-(azetidin-3-ylmethyl)piperidine-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formic acid In a 50 mL round-bottomed flask, tert-butyl 3-((4-(4-(2-chloro-4-(1-methyl-5-(1-(pyrimidin-2-yl)-3-(trifluoromethyl)-pyrazol-4-yl)-imidazole-2-carboxamido)benzoyl)piperazine-1-carbonyl)piperidin-1-yl)methyl)azetidine-1-carboxylate (80 mg, 95.2 μmol) was combined with THF (2 mL) to give a light brown solution. HCl (635 μl, 7.62 mmol) was added. The reaction was stirred at room temperature for 1 h. The crude reaction mixture was concentrated in vacuum. The crude material was purified by preparative HPLC. to afford N-[4-[4-[1-(azetidin-3-ylmethyl)piperidine-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide; formic acid (15.3 mg). MS $[M+H]^+$: 740.1.

Example H1

5-[1-(5-Amino-2-pyridyl)-3-(trifluoromethyl)pyrazol-4-yl]-N-[3-chloro-4-[4-(piperazine-1-carbonyl)piperidine-1-carbonyl]phenyl]-1-methyl-imidazole-2-carboxamide; formic acid

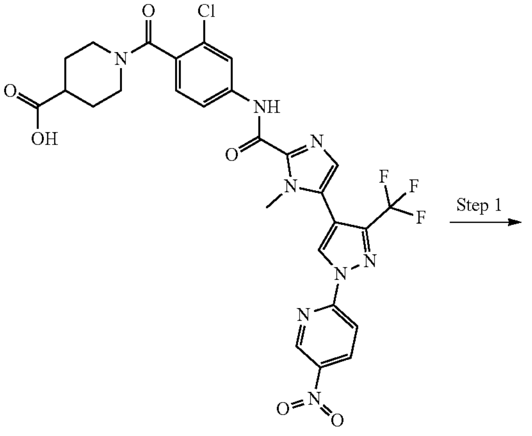

Intermediate E6

-continued

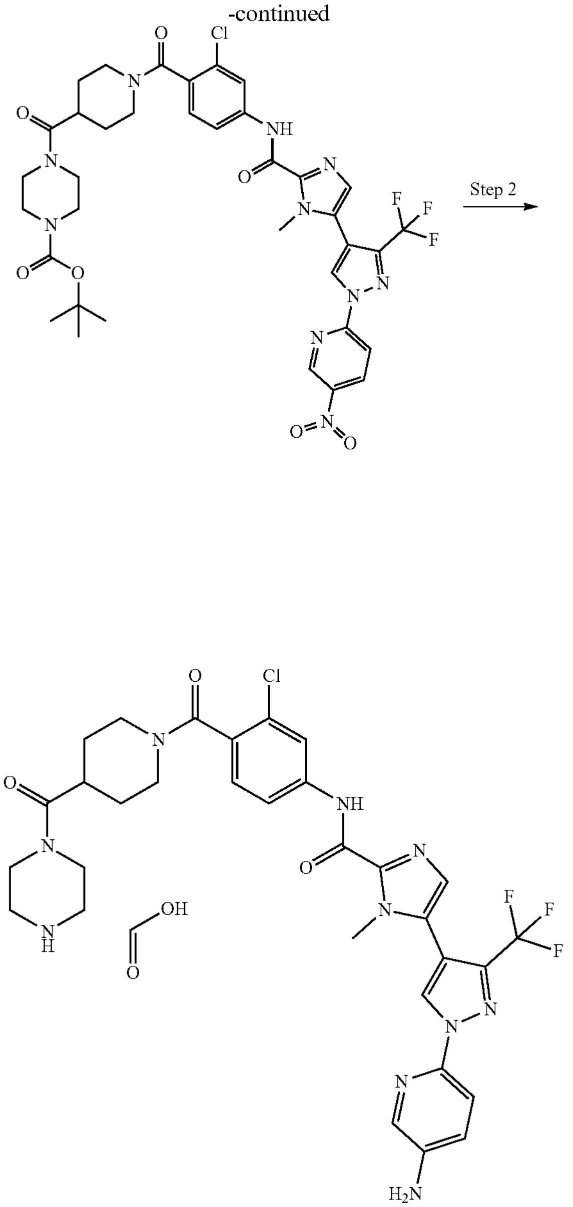

Example H1

Step 1: tert-butyl 4-[1-[2-chloro-4-[[1-methyl-5-[1-(5-nitro-2-pyridyl)-3-(trifluoromethyl)pyrazol-4-yl]imidazole-2-carbonyl]amino]benzoyl]piperidine-4-carbonyl]piperazine-1-carboxylate 1-[2-chloro-4-[[1-methyl-5-[1-(5-nitro-2-pyridyl)-3-(trifluoromethyl)pyrazol-4-yl]imidazole-2-carbonyl]amino]benzoyl]piperidine-4-carboxylic acid (135 mg, 0.2 mmol), tert-butyl piperazine-1-carboxylate (51.8 mg, 0.3 mmol), HATU (97.0 mg, 0.2 mmol) and DIEA (149.8 mg, 202.4 uL, 1.2 mmol) were stirred in acetonitrile (2.3 mL) at 25° C. for 0.5 h. The solvent was removed in vacuum, and the residue was purified by flash chromatography to yield the title compound as light yellow oil. MS $[M+H]^+$: 815.4.

Step 2: 5-[1-(5-amino-2-pyridyl)-3-(trifluoromethyl)pyrazol-4-yl]-N-[3-chloro-4-[4-(piperazine-1-carbonyl)piperidine-1-carbonyl]phenyl]-1-methyl-imidazole-2-carboxamide; formic acid 4-[1-[2-chloro-4-[[1-methyl-5-[1-(5-nitro-2-pyridyl)-3-(trifluoromethyl)pyrazol-4-yl]imidazole-2-carbonyl]amino]benzoyl]isonipecotoyl]piperazine-1-carboxylic acid tert-butyl ester (300 mg, 0.4 mmol) was dissolved in 3 mL 1 M HCl/MeOH solution and stirred at rt for 3 h. The solvent was removed in vacuum, and the residue was dissolved in ethanol (3.7 mL). To this solution were added zinc (481.2 mg, 7.4 mmol) and ammonium chloride (98.4 mg, 1.8 mmol). The mixture was stirred at rt for 1 h. The mixture was filtered, the filtrate was purified by preparative HPLC to yield the title product as light yellow powder, 50 mg. $[M+H]^+$: 685.2.

The following compounds were prepared in analogy of Example H1.

| Ex# | Name | Structure | MS ESI $[M + H]^+$ | Starting Material |
|---|---|---|---|---|
| Example H2 | 5-[1-(5-amino-2-pyridyl)-3-(trifluoromethyl)pyrazol-4-yl]-N-[3-chloro-4-[4-[3-(hydroxymethyl)piperazine-1-carbonyl]piperidine-1-carbonyl]phenyl]-1-methyl-imidazole-2-carboxamide;formic acid | 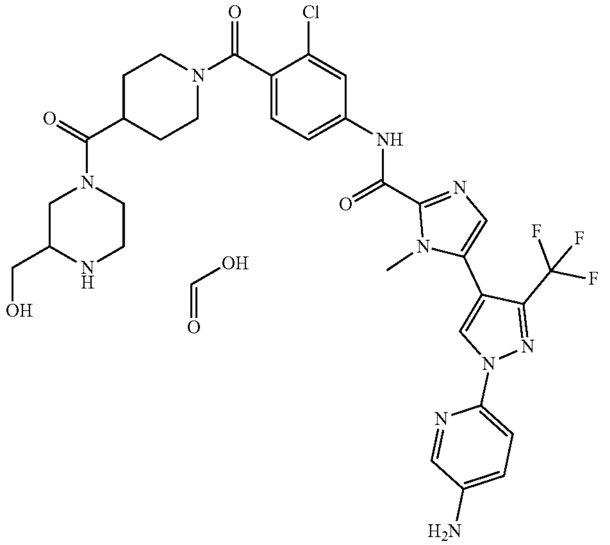 [SMILES: Cn1c(-c2cn(-c3ccc(N)cn3)nc2C(F)(F)F)cnc1C(=O)Nc1ccc(C(=O)N2CCC(C(=O)N3CCNC(CO)C3)CC2)c(Cl)c1 ; O=CO] | 715.6 | Intermediate E6 and 1-boc-(2-hydroxymethyl)piperazine and HCl |

Example I1

5-[1-(5-Amino-2-pyridyl)-3-(trifluoromethyl)pyrazol-4-yl]-N-[3-chloro-4-[4-[(2-oxopiperazin-1-yl)methyl]piperidine-1-carbonyl]phenyl]-1-methyl-imidazole-2-carboxamide; formic acid

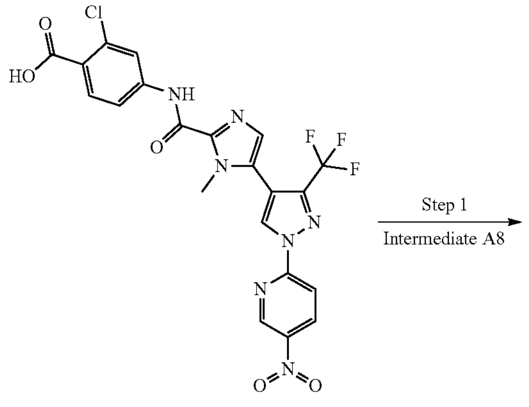

Intermediate E7

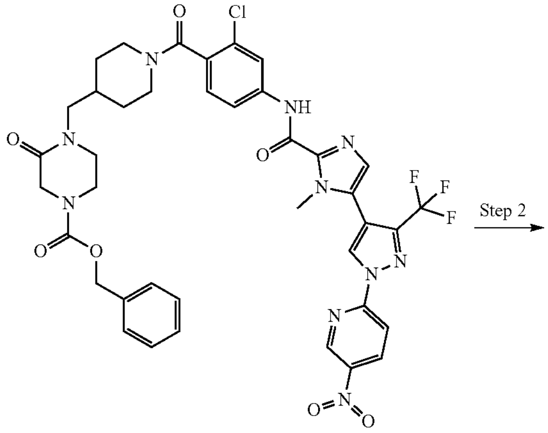

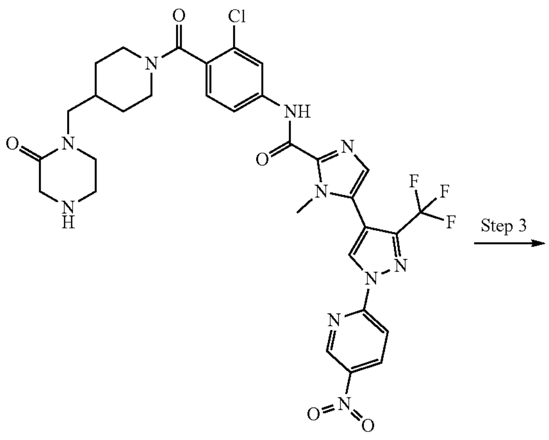

-continued

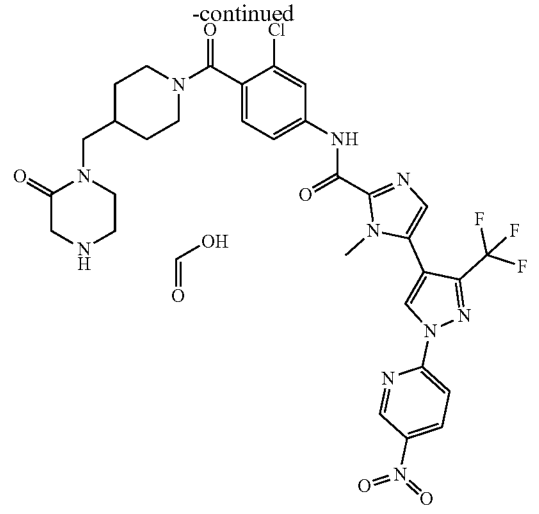

Example I1

Step 1: benzyl 4-[[l-[2-chloro-4-[[1-methyl-5-[1-(5-nitro-2-pyridyl)-3-(trifluoromethyl)pyrazol-4-yl]imidazole-2-carbonyl]amino]benzoyl]-4-piperidyl]methyl]-3-oxo-piperazine-1-carboxylate 2-chloro-4-[[1-methyl-5-[1-(5-nitro-2-pyridyl)-3-(trifluoromethyl)pyrazol-4-yl]imidazole-2-carbonyl]amino]benzoic acid (165 mg, 0.3 mmol), benzyl 2-[3-oxo-4-(4-piperidylmethyl)piperazin-1-yl]acetate (144.7 mg, 0.4 mmol), DIEA (217.1 mg, 293.4 uL, 1.7 mmol) and HATU (153.3 mg, 0.4 mmol) were stirred in acetonitrile (5 mL) at rt for 1 h. The solvent was removed in vacuum, the residue was purified by flash chromatography to give the title compound as light yellow oil, 250 mg. MS $[M+H]^+$: 849.6.

Step 2: N-[3-chloro-4-[4-[(2-oxopiperazin-1-yl)methyl]piperidine-1-carbonyl]phenyl]-1-methyl-5-[1-(5-nitro-2-pyridyl)-3-(trifluoromethyl)pyrazol-4-yl]imidazole-2-carboxamide benzyl 4-[[1-[2-chloro-4-[[1-methyl-5-[1-(5-nitro-2-pyridyl)-3-(trifluoromethyl)pyrazol-4-yl]imidazole-2-carbonyl]amino]benzoyl]-4-piperidyl]methyl]-3-oxo-piperazine-1-carboxylate (250 mg, 0.3 mmol) was heated in TFA (5 mL) under microwave at 100° C. for 1 h. The solvent was removed in vacuum, the residue was used in the next step without purification. MS $[M+H]^+$: 715.4.

Step 3: 5-[1-(5-amino-2-pyridyl)-3-(trifluoromethyl)pyrazol-4-yl]-N-[3-chloro-4-[4-[(2-oxopiperazin-1-yl)methyl]piperidine-1-carbonyl]phenyl]-1-methyl-imidazole-2-carboxamide; formic acid N-[3-chloro-4-[4-[(2-oxopiperazin-1-yl)methyl]piperidine-1-carbonyl]phenyl]-1-methyl-5-[1-(5-nitro-2-pyridyl)-3-(trifluoromethyl)pyrazol-4-yl]imidazole-2-carboxamide (100 mg, 0.1 mmol) was dissolve in ethanol (4 mL) and 1 mL water. To this solution was added ammonium chloride (74.8 mg, 1.4 mmol) and zinc (182.9 mg, 2.8 mmol). The mixture was stirred at rt for 3 h. The mixture was filtered, the filtrate was concentrated in vacuum, the residue was dissolved in DMF and purified by preparative HPLC to give the title compound as light yellow powder, 50 mg. MS $[M+H]^+$: 685.6

The following compounds were prepared in analogy of Example I1.

| Ex# | Name | Structure | MS ESI $[M + H]^+$ | Starting Material |
| --- | --- | --- | --- | --- |
| Example 12 | 5-[1-(5-amino-2-pyridyl)-3-(trifluoromethyl)pyrazol-4-yl]-N-[3-chloro-4-(1H-pyrazol-3-ylmethylcarbamoyl)phenyl]-1-methyl-imidazole-2-carboxamide | 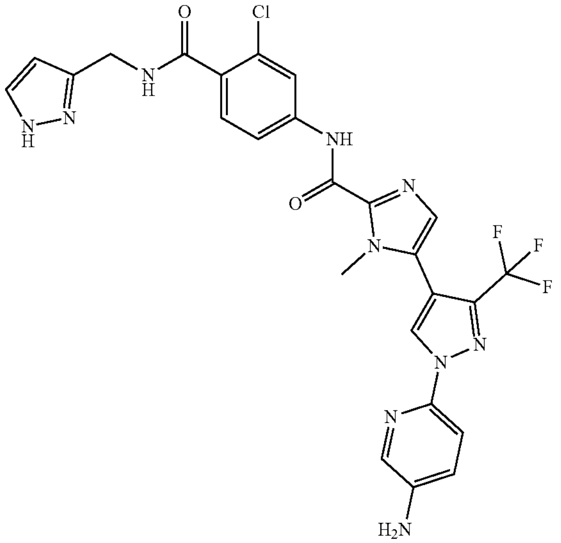 [SMILES: Cn1c(-c2cn(-c3ccc(N)cn3)nc2C(F)(F)F)cnc1C(=O)Nc1ccc(C(=O)NCc2cc[nH]n2)c(Cl)c1] | 585.1 | Intermediate E7 and 1H-pyrazol-3-ylmethanamine and zinc |

Example J1

N-[3-Chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide; formic acid

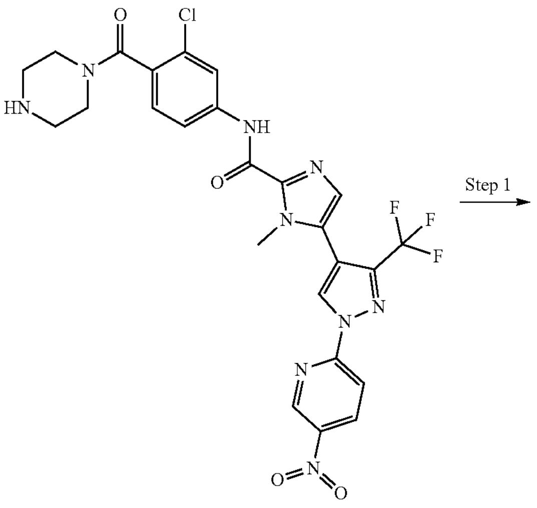

Intermediate E1

-continued

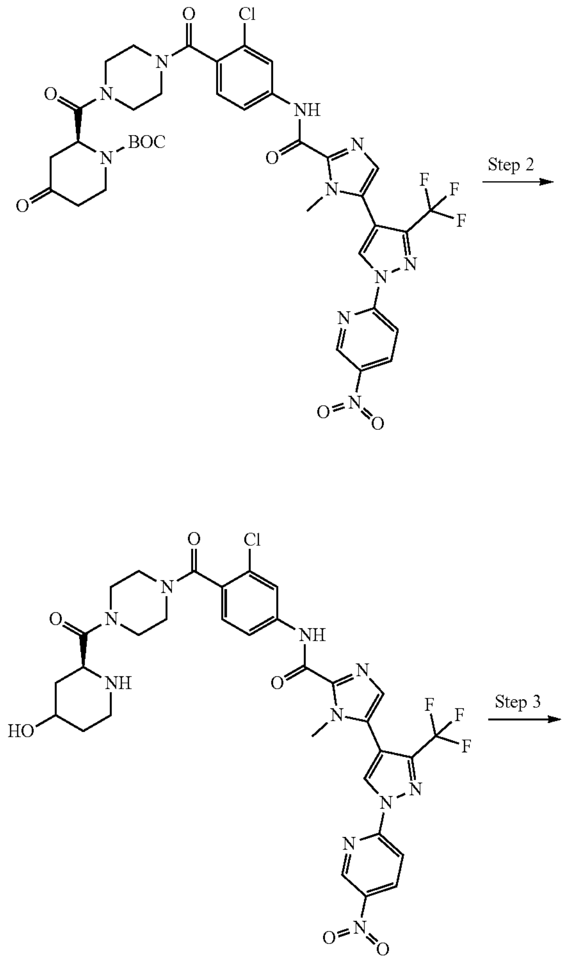

-continued

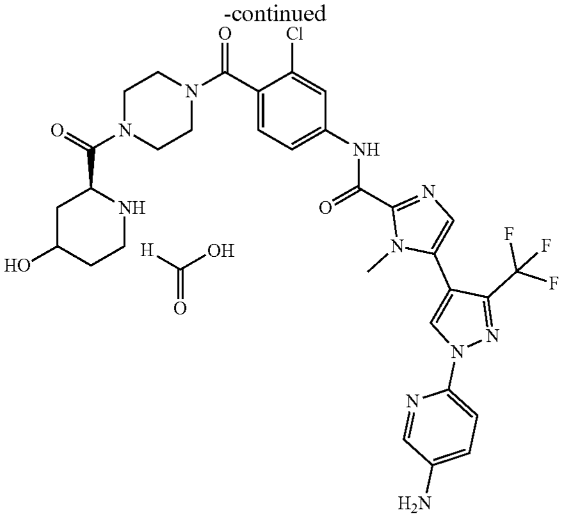

Example J1

Step 1: tert-butyl (2S)-2-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-4-oxo-piperidine-1-carboxylate Intermediate E1 (300 mg, 0.5 mmol), 1-(tert-butoxycarbonyl)-4-oxopiperidine-2-carboxylic acid (135.2 mg, 0.6 mmol), HATU (193.6 mg, 0.5 mmol) and DIEA (299.2 mg, 404.3 uL, 2.3 mmol) were stirred in acetonitrile (4.6 mL) at 25° C. for 0.5 h. The solvent was removed in vacuum, and the residue was purified by flash chromatography to yield the title compound as light yellow oil, 380 mg. MS $[M+H]^+$: 829.9.

Step 2: N-[3-chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide (2S)-2-[4-[2-chloro-4-[[1-methyl-5-[1-(5-nitro-2-pyridyl)-3-(trifluoromethyl)pyrazol-4-yl]imidazole-2-carbonyl]amino]benzoyl]piperazine-1-carbonyl]-4-keto-piperidine-1-carboxylic acid tert-butyl ester (500 mg, 0.6 mmol) was dissolved in methanol (6.0 mL), $NaBH_4$ (22.8 mg, 0.6 mmol) was added in one portion. The mixture was stirred at rt for 30 min. Then 5 mL 1M HCl/MeOH solution was added, and the stirring was continued for 3 h. The solvent was removed in vacuum, the residue was neutralized with TEA and purified by flash chromatography to yield the title compound as light yellow oil, 350 mg. MS $[M+H]^+$: 731.4.

Step 3: N-[3-chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide; formic acid N-[3-chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide (350 mg, 0.5 mmol) was dissolve in ethanol (5.5 mL) and 1 mL water. To this solution was added ammonium chloride (129 mg, 2.4 mmol) and zinc (629 mg, 9.6 mmol). The mixture was stirred at rt for 3 h. The mixture was filtered, the filtrate was concentrated in vacuum, the residue was dissolved in DMF and purified by preparative HPLC to give the title compound as light yellow powder, 50 mg. MS $[M+H]^+$: 701.2.

Example K1

N-[3-chloro-4-[4-(piperidine-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide; formic acid

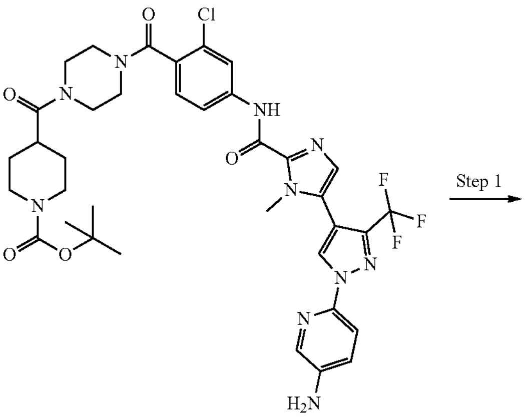

Intermediate G1

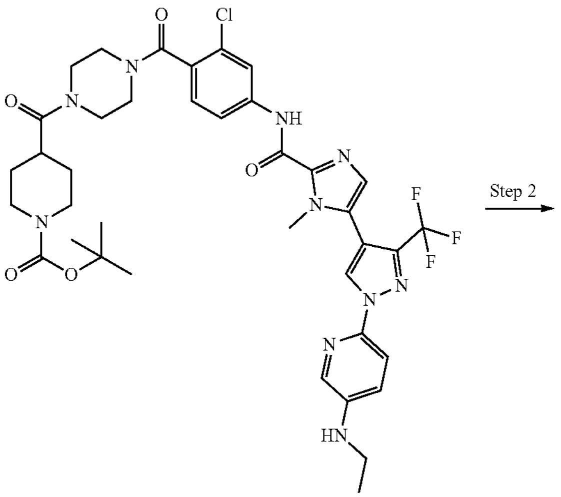

-continued

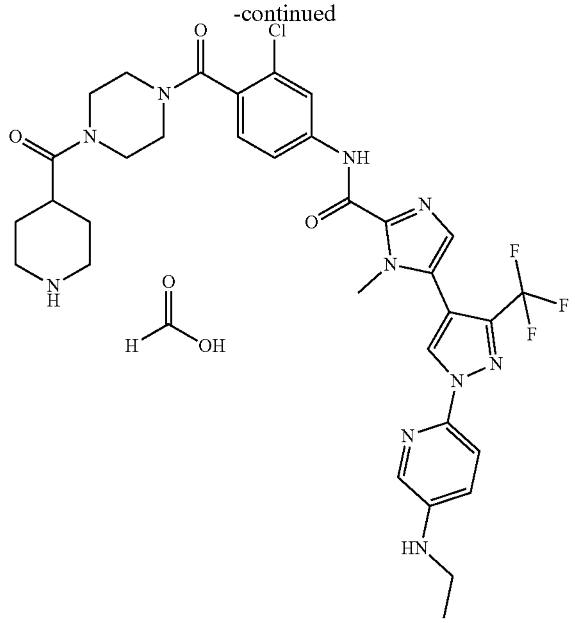

Example K1

Step 1: tert-butyl 4-[4-[2-chloro-4-[[5-[1-[5-(ethylamino)-2-pyridyl]-3-(trifluoromethyl)pyrazol-4-yl]-1-methyl-imidazole-2-carbonyl]amino]benzoyl]piperazine-1-carbonyl]piperidine-1-carboxylate At 0° C., to a solution of tert-butyl 4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (460 mg, 0.586 mmol) in methanol (30 mL) was added 5 M acetaldehyde (228.47 mg, 292.91 uL, 1.46 mmol) in THF and acetic acid (211.07 mg, 201.21 uL, 3.51 mmol). Then the solution was stirred for 30 min at 0° C. Then $NaBH_3CN$ (184.07 mg, 2.93 mmol) was added and was stirred at 0° C. for 2 h. Excess of water was added gradually, and the solution was neutralized (pH=–8) by addition of aqueous 3N sodium hydroxide. The mixture was stirred for 1 h. The water layer was extracted with DCM. The combined organic layers were concentrated and the residue was purified by flash column to afford tert-butyl 4-[4-[2-chloro-4-[[5-[1-[5-(ethylamino)-2-pyridyl]-3-(trifluoromethyl)pyrazol-4-yl]-1-methyl-imidazole-2-carbonyl]amino]benzoyl]piperazine-1-carbonyl]piperidine-1-carboxylate (410 mg) as a yellow solid. MS $[M+H]^+$: 813.6.

Step 2: N-[3-chloro-4-[4-(piperidine-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide; formic acid At r.t, a mixture of tert-butyl 4-[4-[2-chloro-4-[[5-[1-[5-(ethylamino)-2-pyridyl]-3-(trifluoromethyl)pyrazol-4-yl]-1-methyl-imidazole-2-carbonyl]amino]benzoyl]piperazine-1-carbonyl]piperidine-1-carboxylate (100 mg, 0.123 mmol) in tetrahydrofuran (10 mL) and 4 M hydrochloric acid of 1,4-dioxane solution (89.7 mg, 0.62 mL, 20 eq) was stirred for 4 h. Then the mixture was concentrated and the basified by $NH_3 \cdot H_2O$ to PH 8-9. The water layer was extracted with DCM. The organic layer was concentrated and the residue was purified by Prep-HPLC to afford N-[3-chloro-4-[4-(piperidine-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide; formic acid (19 mg) as a light yellow powder. MS $[M+H]^+$: 713.4.

Intermediate Y1

4-[[5-[1-(5-amino-2-pyridyl)-3-(trifluoromethyl)pyrazol-4-yl]-1-methyl-imidazole-2-carbonyl]amino]-2-chloro-benzoic acid

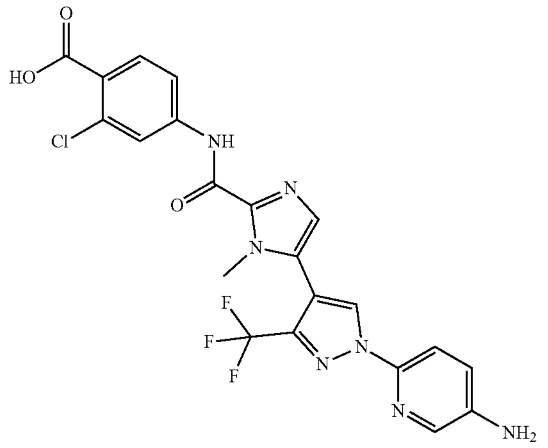 [SMILES: Cn1c(-c2cn(-c3ccc(N)cn3)nc2C(F)(F)F)cnc1C(=O)Nc1ccc(C(=O)O)c(Cl)c1]

Step 1: 2-chloro-4-[[1-methyl-5-[1-(5-nitro-2-pyridyl)-3-(trifluoromethyl)pyrazol-4-yl]imidazole-2-carbonyl]amino]benzoic acid methyl ester In a 250 mL round bottom flask 2-chloro-4-[[1-methyl-5-[3-(trifluoromethyl)-1H-pyrazol-4-yl]imidazole-2-carbonyl]amino]benzoic acid methyl ester [2489205-78-7] (1.88 g, 4.4 mmol, 1 eq), 2-bromo-5-nitropyridine (1.25 g, 6.16 mmol, 1.4 eq) and $K_2CO_3$ (1.83 g, 13.21 mmol, 3 eq) were combined in acetonitrile (70 mL). The mixture was heated to reflux (80° C.) for 1 h. The reaction mixture was filtered and the filtrate was purified by silica gel chromatography (10% to 100% EtOAc in heptane) to afford the title compound (2.76 g, 83.2%) as light brown solid with a purity of 73% by UV. The material was used without further purification. MS: 550.1 $[M+H]^+$, ESI pos.

Step 2: 4-[[5-[1-(5-amino-2-pyridyl)-3-(trifluoromethyl)pyrazol-4-yl]-1-methyl-imidazole-2-carbonyl]amino]-2-chloro-benzoic acid methyl ester 2-chloro-4-[[1-methyl-5-[1-(5-nitro-2-pyridyl)-3-(trifluoromethyl)pyrazol-4-yl]imidazole-2-carbonyl]amino]benzoic acid methyl ester (2730 mg, 3.62 mmol, 1 eq) and ammonium chloride (2.91 g, 54.37 mmol, 15 eq) were combined with ethanol (10 mL) and water (5 mL) to give a off-white solution. Zinc powder (3.55 g, 54.37 mmol, 15 eq) was added and the reaction mixture was stirred under nitrogen at RT for 48h. 200 ml 1M $Na_2CO_3$ were added to the mixture and the suspension filtered. Ethanol was evaporated from the filtrate. The filter cake was washed with ethylacetate and combined with the remaining filtrate. The obtained mixture was extracted 2× with ethylacetate, the combined organic layers dried with $Na_2SO_4$ and evaporated to dryness. The crude material as a drypack on Isolute HM-N was then purified by silica gel chromatography using DCM/MeOH as eluent to afford the title compound (1699 mg, 67.6%) as yellow solid with a purity of 75% by UV. MS: 520.1 $[M+H]^+$, ESI pos.

Step 3: 4-[[5-[1-(5-amino-2-pyridyl)-3-(trifluoromethyl)pyrazol-4-yl]-1-methyl-imidazole-2-carbonyl]amino]-2-chloro-benzoic acid 4-[[5-[1-(5-amino-2-pyridyl)-3-(trifluoromethyl)pyrazol-4-yl]-1-methyl-imidazole-2-carbonyl]amino]-2-chloro-benzoic acid methyl ester (1699 mg, 2.45 mmol, 1 eq) was dissolved in THF (5 mL) and MeOH (5 mL). Lithium hydroxide monohydrate (1.03 g, 24.51 mmol, 10 eq) was added and the reaction was stirred at 22° C. for 24 hr. The clear solution was acidified with 4M HCl solution (pH ~1). Organic solvents were evaporated in vacuo. The residue was diluted with ethyl acetate and water the the mixture extracted 2× with EtOAc. The combined organic layers were dried with sodium sulfate, filtered and evaporated to dryness to afford the title compound (1518 mg, quant) as orange solid, which was used without further purification. MS 504.1 $[M-H]^+$, ESI neg.

Intermediate Y2

2-[[4-(methoxymethyl)-3-[4-(4,4,5,5-tetramethyl-1,3,2-dioxaborolan-2-yl)-3-(trifluoromethyl)pyrazol-1-yl]pyrazol-1-yl]methoxy]ethyl-trimethyl-silane

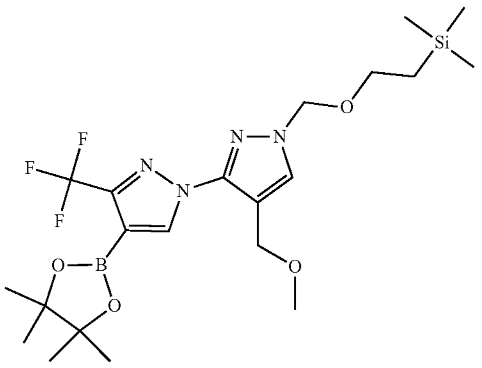

Step 1: 2-[[4-(methoxymethyl)pyrazol-1-yl]methoxy]ethyl-trimethyl-silane

To a solution of [1-(2-trimethylsilylethoxymethyl)pyrazol-4-yl]methanol [1382867-01-7] (5.5 g, 24.08 mmol, 1 eq) in THF (100 mL) was added sodium hydride, 60% in oil (1.44 g, 36.13 mmol, 1.5 eq) slowly at 0° C. After addition, this reaction mixture was stirred at 0° C. for 1 h. Then iodomethane (1.8 mL, 28.9 mmol, 1.2 eq) was added into this mixture at 0° C. This reaction mixture was stirred at 25° C. for 12 h. This reaction was quenched by $NH_4Cl$ (100.0 mL) and was extracted by EtOAc (100.0 mL*2). The combined organic layers were dried over $Na_2SO_4$ and concentrated. This crude product was purified by silica gel chromatography using PE/EtOAc as eluent to afford the title compound (5 g, 20.63 mmol, 78.54% yield) as yellow oil. MS: 243.3, $[M+H]^+$, ESI pos.

Step 2: 2-[[3-bromo-4-(methoxymethyl)pyrazol-1-yl]methoxy]ethyl-trimethyl-silane To a solution of 2-[[4-(methoxymethyl)pyrazol-1-yl]methoxy]ethyl-trimethyl-silane (4.0 g, 16.5 mmol, 1 eq) in THF (60 mL) was added 2M LDA (16.5 mL, 33 mmol, 2 eq) at −78° C. under nitrogen. The mixture was stirred at −78° C. for 1 h. Then 1,2-dibromotetrachloroethane (8.0 g, 24.57 mmol, 1.49 eq) in THF (40 mL) was added at −78° C. The mixture was stirred for 2 h at −78° C. The reaction mixture was poured into aq. HCl (0.5 M, 100 mL) and extracted with EA (100 mL*3). The organics were washed with brine, dried over $Na_2SO_4$ before concentration to dryness. The crude was then purified by flash column (0.1% FA as additive) and dried by lyophilization to afford the title compound (3.5 g, 10.89 mmol, 66.01% yield) as light yellow oil. MS: 219.0 [M−OCH2CH2SiMe3] ESI pos.

Step 3: [4-(methoxymethyl)-1-(2-trimethylsilylethoxymethyl)pyrazol-3-yl]boronic acid A mixture of bis(pinacolato)diboron (2.61 g, 10.27 mmol, 1.1 eq), 2-[[3-bromo-4-(methoxymethyl)pyrazol-1-yl]methoxy]ethyl-trimethyl-silane (3.0 g, 9.34 mmol, 1 eq), potassium acetate (0.88 mL, 14.01 mmol, 1.5 eq) and X-PHOS (890.27 mg, 1.87 mmol, 0.200 eq) in 1,4-dioxane (20 mL) was degassed and purged with $N_2$ for 3 times. Then tris(dibenzylideneacetone)dipalladium (0) (855.04 mg, 0.930 mmol, 0.100 eq) was added into the mixture. The reaction mixture was stirred at 100° C. for 16 h under $N_2$ atmosphere. The mixture was filtered and concentrated under reduced pressure. The crude material was purified by preparative HPLC (0.1% FA as additive) to afford the title compound (1.7 g, 63.6%) as a yellow oil. MS: 287.1 $[M+H]^+$, ESI pos.

Step 4: 2-[[3-[4-bromo-3-(trifluoromethyl)pyrazol-1-yl]-4-(methoxymethyl)pyrazol-1-yl]methoxy]ethyl-trimethyl-silane A mixture of [4-(methoxymethyl)-1-(2-trimethylsilylethoxymethyl)pyrazol-3-yl]boronic acid (1.2 g, 4.19 mmol, 1 eq), 4-bromo-3-(trifluoromethyl)-1H-pyrazole (1.2 g, 5.58 mmol, 1.33 eq), copper(II) acetate monohydrate (0.84 g, 4.19 mmol, 1 eq), and molecular sieves, 4 Å (1.0 g) was degassed and purged with $N_2$ gas for four times. DMF (14 mL) and pyridine (1.7 mL, 20.96 mmol, 5 eq) were added by injector to the mixture. The mixture was stirred under oxygen at 80° C. for 16 h. was detected. The reaction mixture was filtered and the filtrate was concentrated in vacuum. The crude material was purified by flash column (0.1% FA as additive) and dried by lyophilization to give the title compound (1 g, 2.2 mmol, 52.38% yield) as green oil. MS 425.2 [M−30+H] ESI pos.

Step 5: 2-[[4-(methoxymethyl)-3-[4-(4,4,5,5-tetramethyl-1,3,2-dioxaborolan-2-yl)-3-(trifluoromethyl)pyrazol-1-yl]pyrazol-1-yl]methoxy]ethyl-trimethyl-silane A mixture of 2-[[3-[4-bromo-3-(trifluoromethyl)pyrazol-1-yl]-4-(methoxymethyl)pyrazol-1-yl]methoxy]ethyl-trimethyl-silane (900.0 mg, 1.98 mmol, 1 eq) in THF (9 mL) was added 1.3M i-Pr-MgCl·LiCl (3.6 mL, 4.68 mmol, 2.37 eq) under nitrogen at 0° C. The mixture was stirred at 20° C. for 2 h. Then 2-isopropoxy-4,4,5,5-tetramethyl-1,3,2-dioxaborolane (489.6 mg, 2.63 mmol, 1.33 eq) was added to the mixture at 0° C. The mixture was stirred at 20° C. for 2 h. The reaction was poured into 0.5 M HCl (50 mL) and extracted with EtOAc (50 mL*2) and the organics washed with water (50 mL*2) then saturated brine solution (50 mL*1). The organics were then separated and dried ($MgSO_4$) before concentration to dryness afford the title compound (1500 mg, 2.99 mmol, 99.7% yield) as yellow oil which was used without further purification. MS: 471.4 [M−30+H] ESI pos.

Intermediate Y3 tert-butyl 4-[4-[4-[[5-[1-(4-amino-5-nitro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate

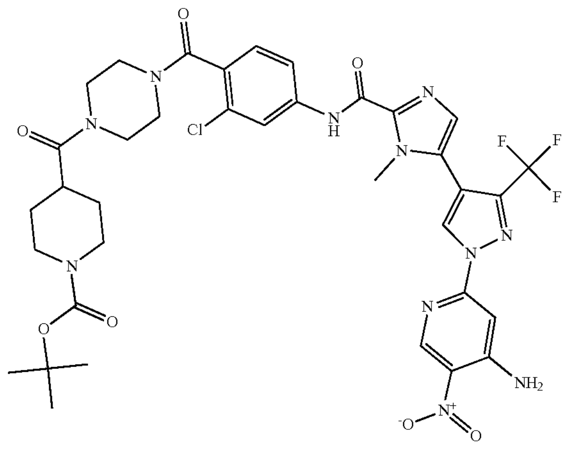

Step 1: N-(2-fluoro-5-nitro-4-pyridyl)-1,1-diphenyl-methanimine

To a solution of 2,4-difluoro-5-nitro-pyridine (480.0 mg, 3 mmol, 1 eq) and triethylamine (0.84 mL, 6 mmol, 2 eq) in ACN (10 mL) was added diphenylmethanimine (0.6 mL, 3.6 mmol, 1.2 eq). The mixture was stirred at 20° C. for 4 h. The mixture was diluted with EA (40 mL) and then washed with brine (20 mL*2). The organic layer was dried over sodium sulfate, filtered, the filtrate was concentrated under vacuum to give the title compound (1.2 g, 3.73 mmol, quant yield) as a red gum, which was used without further purification. MS: 322.1, $[M+H]^+$, ESI pos.

Step 2: tert-butyl 4-[4-[4-[[5-[1-[4-(benzhydrylideneamino)-5-nitro-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate [2489205-74-3] (400.0 mg, 0.580 mmol, 1 eq) and triethylamine (0.24 mL, 1.73 mmol, 3 eq) in DMSO (6 mL) was added N-(2-fluoro-5-nitro-4-pyridyl)-1,1-diphenyl-methanimine (463.57 mg, 0.870 mmol, 1.5 eq). The mixture was stirred at 80° C. for 16 h. The mixture was diluted with EA (100 mL) and then washed with brine (30 mL*3). The organic layer was dried over sodium sulfate, filtered, and the filtrate was concentrated under vacuum to give the title compound (800 mg, 0.800 mmol, quant yield) as a light yellow solid, which was used without further purification. MS: 894.4, $[M\text{-}Boc+H]^+$, ESI pos.

Step 3: tert-butyl 4-[4-[4-[[5-[1-(4-amino-5-nitro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[4-[[5-[1-[4-(benzhydrylideneamino)-5-nitro-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylate (800.0 mg, 0.560 mmol, 1 eq) and sodium acetate (462 mg, 5.63 mmol, 10 eq) in methanol (10 mL) was added hydroxylamine hydrochloride (313 mg, 4.51 mmol, 8 eq). The mixture was stirred at 20° C. for 5 h. The mixture was concentrated under vacuum. The residue was purified by prep-HPLC (FA condition) to the title compound (440 mg, 0.530 mmol, 94.11% yield) as a light yellow solid. MS 730.4, $[M\text{−}Boc+H]^+$, ESI pos.

Example Z14

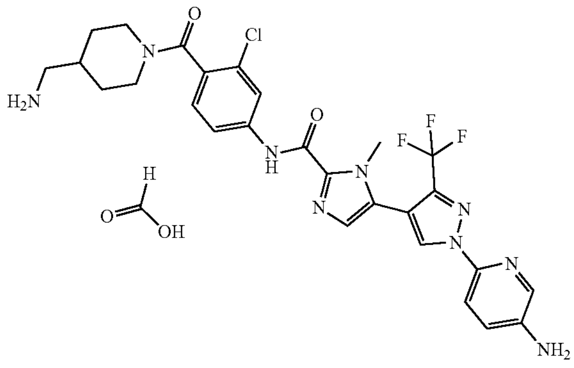 [SMILES: Cn1c(-c2cn(-c3ccc(N)cn3)nc2C(F)(F)F)cnc1C(=O)Nc1ccc(C(=O)N2CCC(CN)CC2)c(Cl)c1 ; O=CO]

Step 1: N-[4-[4-(aminomethyl)piperidine-1-carbonyl]-3-chloro-phenyl]-5-[1-(5-amino-2-pyridyl)-3-(trifluoromethyl)pyrazol-4-yl]-1-methyl-imidazole-2-carboxamide; 1:1 formic acid To a solution of 4-[[5-[1-(5-amino-2-pyridyl)-3-(trifluoromethyl)pyrazol-4-yl]-1-methyl-imidazole-2-carbonyl]amino]-2-chloro-benzoic acid (15.7 mg, 0.031 mmol, 1 eq) in N,N-dimethylformamide (1 mL) were added HATU (14.1 mg, 0.037 mmol, 1.2 eq) and $Et_3N$ (21.6 uL, 0.155 mmol, 5 eq). The mixture was stirred at RT for 10 min added to N-(4-piperidylmethyl)carbamic acid tert-butyl ester (10.6 mg, 0.050 mmol, 1.6 eq). The reaction mixture was stirred at RT overnight. The mixture was then evaporated to dryness, dissolved in dichloromethane (1 mL), and treated with 4 M HCl (77.5 uL, 0.310 mmol, 10 eq) over night at RT. The mixture was concentrated to dryness, dissolved in 1.5 ml of MeOH and purified by preparative HPLC using a Gemini 5um C18 75x30 column and water (+0.05% formic acid)/acetonitrile as eluent to afford the title compound (12.4 mg, 65.9%). MS: 602.3 $[M+H]^+$, ESI pos.

The following compounds were prepared in analogy to example Z14.

| Structure | Ex | Name | Yield % | Reactant Name | MS |
|---|---|---|---|---|---|
| 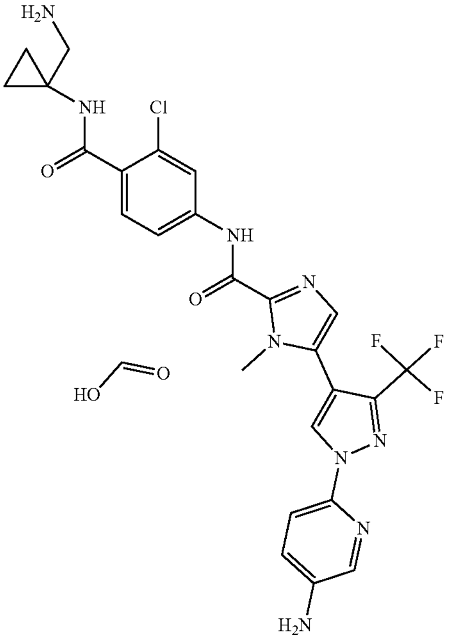 [SMILES: Cn1c(-c2cn(-c3ccc(N)cn3)nc2C(F)(F)F)cnc1C(=O)Nc1ccc(C(=O)NC2(CN)CC2)c(Cl)c1 ; O=CO] | Z6 | N-[4-[[1-(aminomethyl)cyclopropyl]carbamoyl]-3-chloro-phenyl]-5-[1-(5-amino-2-pyridyl)-3-(trifluoromethyl)pyrazol-4-yl]-1-methyl-imidazole-2-carboxamide .1:1 formic acid | 62.3 | N-[1-(aminomethyl) cyclopropyl] carbamic acid tert-butyl ester | 574.3 $[M + H]^+$, ESI pos |
| 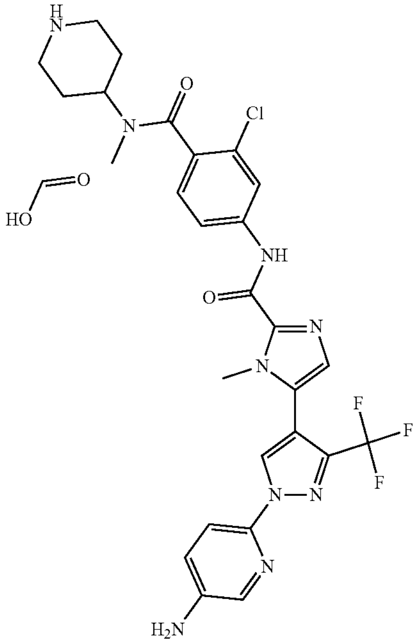 | Z13 | 5-[1-(5-amino-2-pyridyl)-3-(trifluoromethyl)pyrazol-4-yl]-N-[3-chloro-4-[methyl(4-piperidyl)carbamoyl]phenyl]-1-methyl-imidazole-2-carboxamide .1:1 formic acid | 64.2 | 4-(methylamino) piperidine-1-carboxylic | 602.3 $[M + H]^+$, ESI pos |

-continued

| Structure | Ex | Name | Yield % | Reactant Name | MS |
|---|---|---|---|---|---|
| 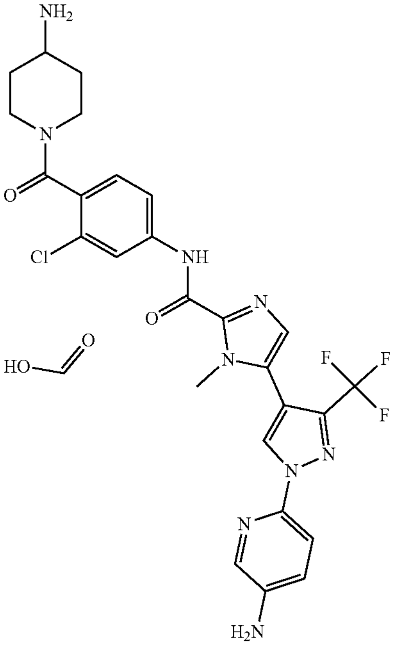 [SMILES: Cn1c(-c2cn(-c3ccc(N)cn3)nc2C(F)(F)F)cnc1C(=O)Nc1ccc(C(=O)N2CCC(N)CC2)c(Cl)c1 ; O=CO] | Z20 | N-[4-(4-aminopiperidine-1-carbonyl)-3-chloro-phenyl]-5-[1-(5-amino-2-pyridyl)-3-(trifluoromethyl)pyrazol-4-yl]-1-methyl-imidazole-2-carboxamide .1:1 formic acid | 63.1 | N-[(1S,3S)-3-aminocyclopentyl] carbamic acid tert-butyl ester | 588.3 $[M + H]^+$, ESI pos |
| 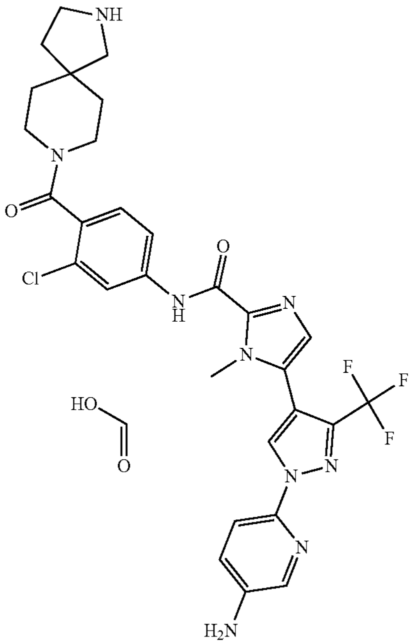 [SMILES: Cn1c(-c2cn(-c3ccc(N)cn3)nc2C(F)(F)F)cnc1C(=O)Nc1ccc(C(=O)N2CCC3(CCNC3)CC2)c(Cl)c1 ; O=CO] | Z8 | 5-[1-(5-amino-2-pyridyl)-3-(trifluoromethyl)pyrazol-4-yl]-N-[3-chloro-4-(2,8-diazaspiro[4.5]decane-8-carbonyl)phenyl]-1-methyl-imidazole-2-carboxamide .1:1 formic acid | 65.1 | 2,8-diazaspiro[4.5] decane-2-carboxylic acid tert-butyl ester | 628.3 $[M + H]^+$, ESI pos |

-continued

| Structure | Ex | Name | Yield % | Reactant Name | MS |
|---|---|---|---|---|---|
| 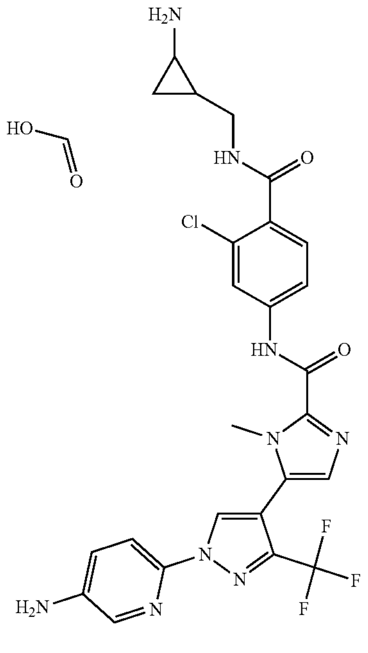 [SMILES: O=CO ; Cn1c(-c2cn(-c3ccc(N)cn3)nc2C(F)(F)F)cnc1C(=O)Nc1ccc(C(=O)NCC2CC2N)c(Cl)c1] | Z18 | N-[4-[(2-aminocyclopropyl)methylcarbamoyl]-3-chloro-phenyl]-5-[1-(5-amino-2-pyridyl)-3-(trifluoromethyl)pyrazol-4-yl]-1-methyl-imidazole-2-carboxamide .1:1 formic acid | 52.7 | N-[2-(aminomethyl) cyclopropyl] carbamic acid tert-butyl ester | 574.3 [M + H]$^+$, ESI pos |
| 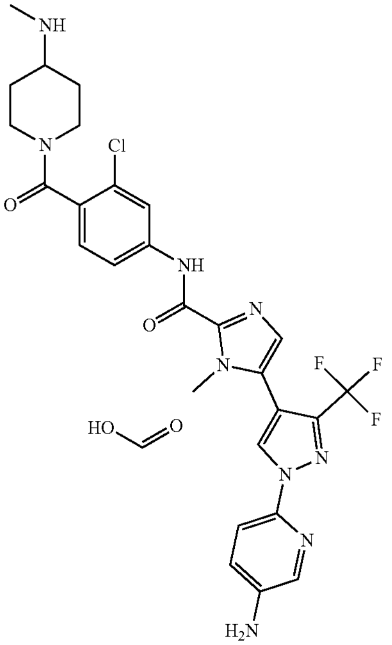 | Z4 | 5-[1-(5-amino-2-pyridyl)-3-(trifluoromethyl)pyrazol-4-yl]-N-[3-chloro-4-[4-(methylamino)piperidine-1-carbonyl]phenyl]-1-methyl-imidazole-2-carboxamide .1:1 formic acid | 69.5 | N-methyl-N-(4-piperidyl) carbamic acid tert-butyl ester | 602.3 [M + H]$^+$, ESI pos |

-continued

| Structure | Ex | Name | Yield % | Reactant Name | MS |
|---|---|---|---|---|---|
| 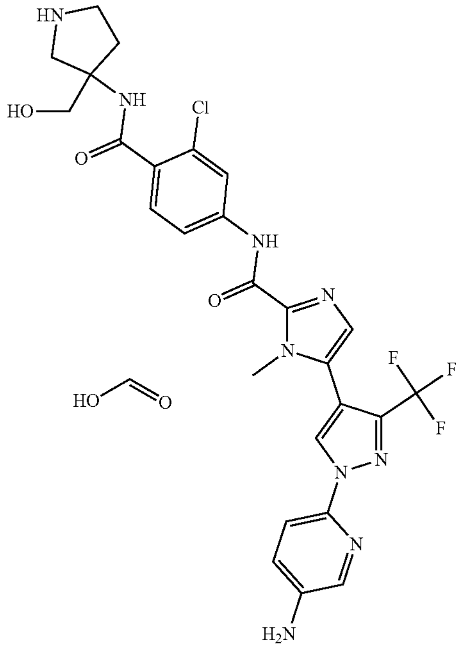 [SMILES: Cn1c(-c2cn(-c3ccc(N)cn3)nc2C(F)(F)F)cnc1C(=O)Nc1ccc(C(=O)NC2(CO)CCNC2)c(Cl)c1 ; O=CO] | Z5 | 5-[1-(5-amino-2-pyridyl)-3-(trifluoromethyl)pyrazol-4-yl]-N-[3-chloro-4-[(3-methylolpyrrolidin-3-yl)carbamoyl]phenyl]-1-methyl-imidazole-2-carboxamide .1:1 formic acid | 62.3 | 3-amino-3-methylol-pyrrolidine-1-carboxylic acid tert-butyl ester | 604.3 $[M + H]^+$, ESI pos |
| 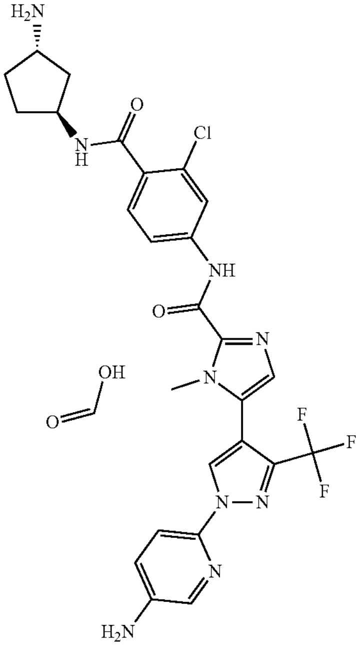 [SMILES: Cn1c(-c2cn(-c3ccc(N)cn3)nc2C(F)(F)F)cnc1C(=O)Nc1ccc(C(=O)N[C@H]2CC[C@H](N)C2)c(Cl)c1 ; O=CO] | Z16 | N-[4-[[(trans-3-aminocyclopentyl]carbamoyl]-3-chloro-phenyl]-5-[1-(5-amino-2-pyridyl)-3-(trifluoromethyl)pyrazol-4-yl]-1-methyl-imidazole-2-carboxamide .1:1 formic acid | 59.3 | N-[[(3S)-pyrrolidin-3-yl]methyl] carbamic acid tert-butyl | 588.3 $[M + H]^+$, ESI pos |

-continued

| Structure | Ex | Name | Yield % | Reactant Name | MS |
|---|---|---|---|---|---|
| 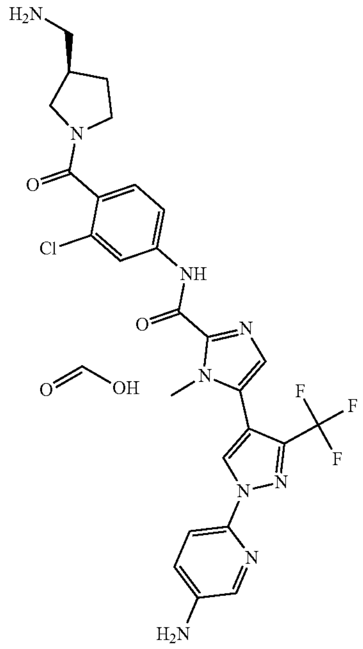 | Z1 | N-[4-[(3R)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide .1:1 formic acid | 36.9 | N-(4-piperidyl) carbamic acid tert-butyl ester | 588.3 $[M + H]^+$, ESI pos |
| 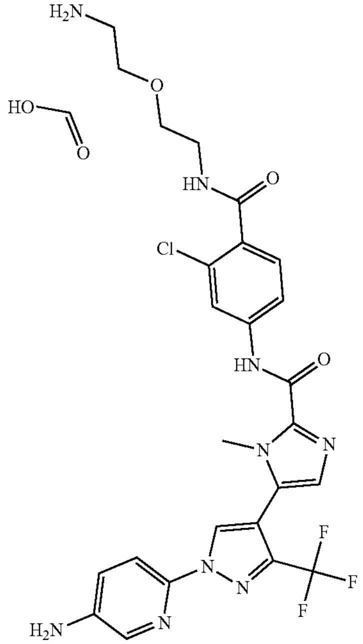 [SMILES: O=CO ; Cn1c(-c2cn(-c3ccc(N)cn3)nc2C(F)(F)F)cnc1C(=O)Nc1ccc(C(=O)NCCOCCN)c(Cl)c1] | Z21 | N-[4-[2-(2-aminoethoxy)ethylcarbamoyl]-3-chloro-phenyl]-5-[1-(5-amino-2-pyridyl)-3-(trifluoromethyl)pyrazol-4-yl]-1-methyl-imidazole-2-carboxamide .1:1 formic acid | 62.7 | N-[2-(2-aminoethoxy) ethyl]carbamic acid tert-butyl ester | 592.3 $[M + H]^+$, ESI pos |

-continued

| Structure | Ex | Name | Yield % | Reactant Name | MS |
|---|---|---|---|---|---|
| 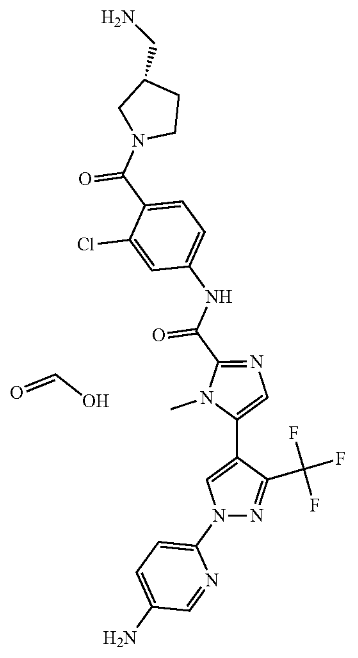 [SMILES: O=CO ; Cn1c(-c2cn(-c3ccc(N)cn3)nc2C(F)(F)F)cnc1C(=O)Nc1ccc(C(=O)N2CC[C@@H](CN)C2)c(Cl)c1] | Z7 | N-[4-[(3S)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide .1:1 formic acid | 61.5 | N-[[(3R)-pyrrolidin-3-yl]methyl] carbamic acid tert-butyl ester | 588.3 $[M + H]^+$, ESI pos |
| 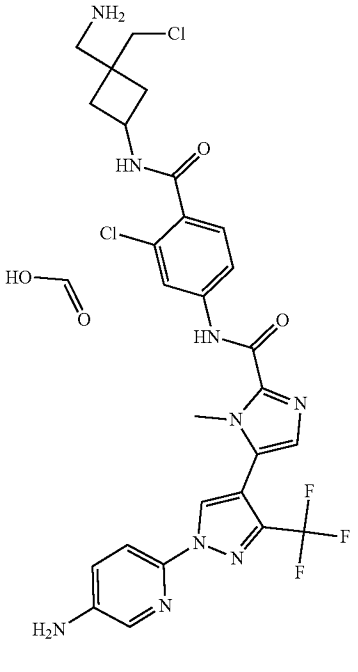 [SMILES: O=CO ; Cn1c(-c2cn(-c3ccc(N)cn3)nc2C(F)(F)F)cnc1C(=O)Nc1ccc(C(=O)NC2CC(CN)(CCl)C2)c(Cl)c1] | Z15 | N-[4-[3-(aminomethyl)-3-(chloromethyl)cyclobutyl]carbamoyl]-3-chloro-phenyl]-5-[1-(5-amino-2-pyridyl)-3-(trifluoromethyl)pyrazol-4-yl]-1-methyl-imidazole-2-carboxamide .1:1 formic acid | 12.5 | 6-amino-2-azaspiro[3.3] heptane-2-carboxylic acid tert-butyl ester | 636.3 $[M + H]^+$, ESI pos |

-continued

| Structure | Ex | Name | Yield % | Reactant Name | MS |
|---|---|---|---|---|---|
| 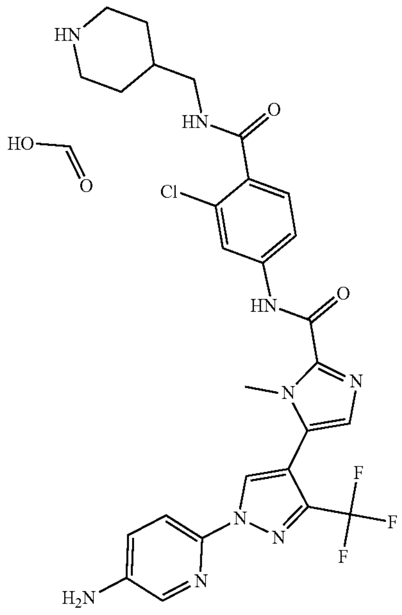 [SMILES: O=CO ; Cn1c(-c2cn(-c3ccc(N)cn3)nc2C(F)(F)F)cnc1C(=O)Nc1ccc(C(=O)NCC2CCNCC2)c(Cl)c1] | Z3 | 5-[1-(5-amino-2-pyridyl)-3-(trifluoromethyl)pyrazol-4-yl]-N-[3-chloro-4-(4-piperidylmethylcarbamoyl)phenyl]-1-methyl-imidazole-2-carboxamide .1:1 formic acid | 71.1 | 4-(aminomethyl) piperidine-1-carboxylic acid tert-butyl ester | 602.3 [M + H]$^+$, ESI pos |
| 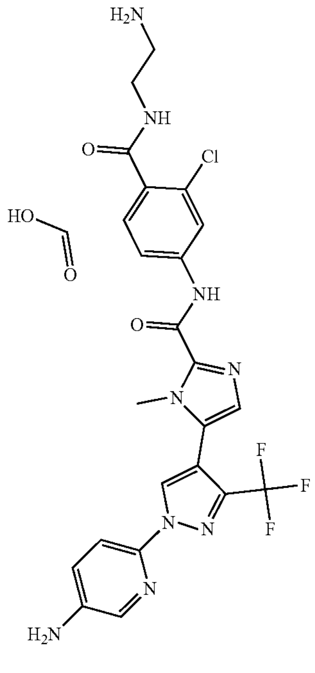 [SMILES: O=CO ; Cn1c(-c2cn(-c3ccc(N)cn3)nc2C(F)(F)F)cnc1C(=O)Nc1ccc(C(=O)NCCN)c(Cl)c1] | Z17 | N-[4-(2-aminoethylcarbamoyl)-3-chloro-phenyl]-5-[1-(5-amino-2-pyridyl)-3-(trifluoromethyl)pyrazol-4-yl]-1-methyl-imidazole-2-carboxamide .1:1 formic acid | 46.9 | N-(2-aminoethyl) carbamic acid tert-butyl ester | 548.2 [M + H]$^+$, ESI pos |

-continued

| Structure | Ex | Name | Yield % | Reactant Name | MS |
|---|---|---|---|---|---|
| 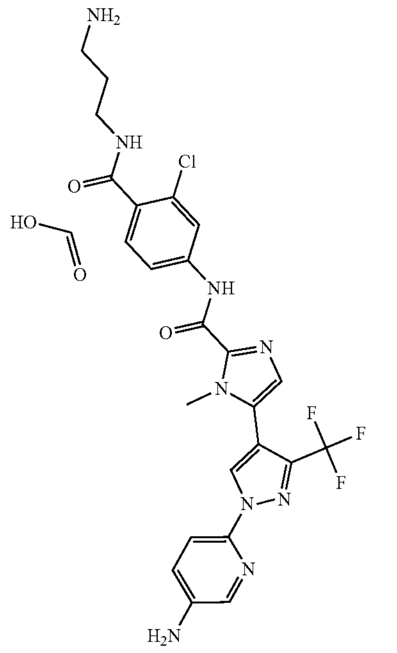 | Z2 | N-[4-(3-aminopropylcarbamoyl)-3-chloro-phenyl]-5-[1-(5-amino-2-pyridyl)-3-(trifluoromethyl)pyrazol-4-yl]-1-methyl-imidazole-2-carboxamide .1:1 formic acid | 45.4 | N-(3-aminopropyl) carbamic acid tert-butyl ester | 562.3 $[M + H]^+$, ESI pos |
| 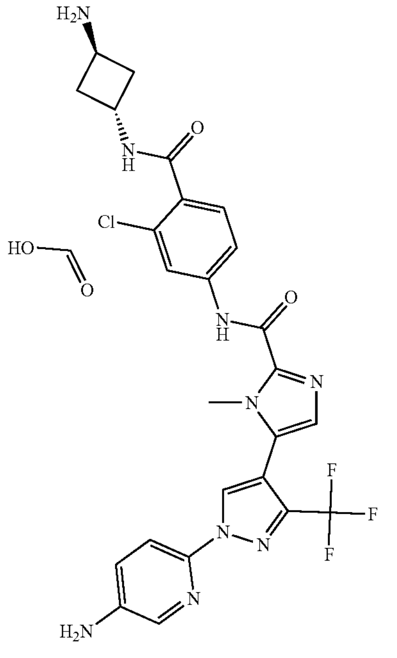 | Z19 | N-[4-[trans-(3-aminocyclobutyl)carbamoyl]-3-chloro-phenyl]-5-[1-(5-amino-2-pyridyl)-3-(trifluoromethyl)pyrazol-4-yl]-1-methyl-imidazole-2-carboxamide .1:1 formic acid | 60.8 | trans-N-(3-aminocyclobutyl) carbamic acid tert-butyl ester | 574.2 $[M + H]^+$, ESI pos |

-continued

| Structure | Ex | Name | Yield % | Reactant Name | MS |
|---|---|---|---|---|---|
| 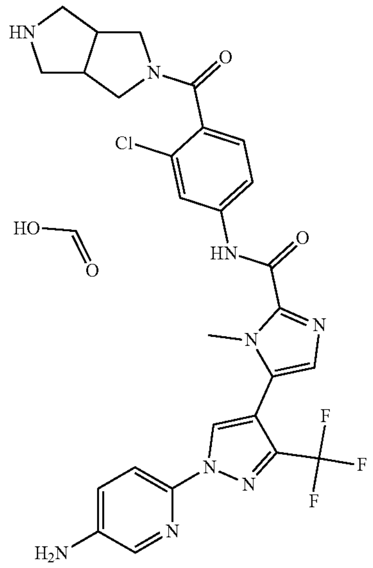 [SMILES: Cn1c(-c2cn(-c3ccc(N)cn3)nc2C(F)(F)F)cnc1C(=O)Nc1ccc(C(=O)N2CC3CNCC3C2)c(Cl)c1 ; O=CO] | Z12 | N-[4-(2,3,3a,4,6,6a-hexahydro-1H-pyrrolo[3,4-c]pyrrole-5-carbonyl)-3-chloro-phenyl]-5-[1-(5-amino-2-pyridyl)-3-(trifluoromethyl)pyrazol-4-yl]-1-methyl-imidazole-2-carboxamide .1:1 formic acid | 59.2 | 2,3,3a,4,6,6a-hexahydro-1H-pyrrolo[3,4-c]pyrrole-5-carboxylic acid tert-butyl ester | 600.3 $[M + H]^+$, ESI pos |
| 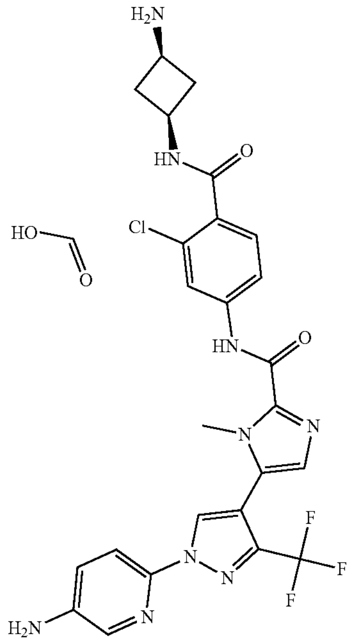 [SMILES: O=CO ; Cn1c(-c2cn(-c3ccc(N)cn3)nc2C(F)(F)F)cnc1C(=O)Nc1ccc(C(=O)N[C@H]2C[C@@H](N)C2)c(Cl)c1] | Z11 | N-[4-[cis-(3-aminocyclobutyl)carbamoyl]-3-chloro-phenyl]-5-[1-(5-amino-2-pyridyl)-3-(trifluoromethyl)pyrazol-4-yl]-1-methyl-imidazole-2-carboxamide .1:1 formic acid | 60.2 | cis-N-(3-aminocyclobutyl) carbamic acid tert-butyl ester | 574.2 $[M + H]^+$, ESI pos |

-continued

| Structure | Ex | Name | Yield % | Reactant Name | MS |
|---|---|---|---|---|---|
| 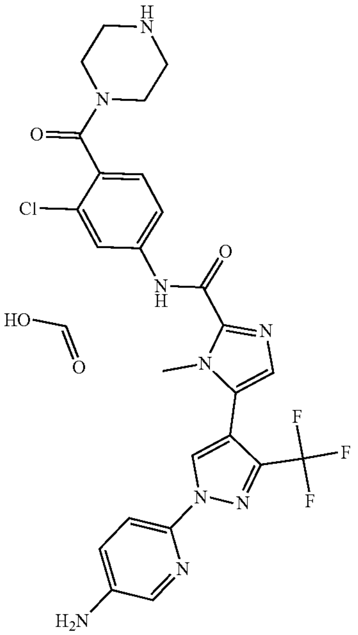 [SMILES: O=CO ; Cn1c(-c2cn(-c3ccc(N)cn3)nc2C(F)(F)F)cnc1C(=O)Nc1ccc(C(=O)N2CCNCC2)c(Cl)c1] | Z32 | 5-[1-(5-amino-2-pyridyl)-3-(trifluoromethyl)pyrazol-4-yl]-N-[3-chloro-4-(piperazine-1-carbonyl)phenyl]-1-methyl-imidazole-2-carboxamide .1:1 formic acid | 4.29 | piperazine-1-carboxylic acid tert-butyl ester | 574.2 $[M + H]^+$, ESI pos |
| 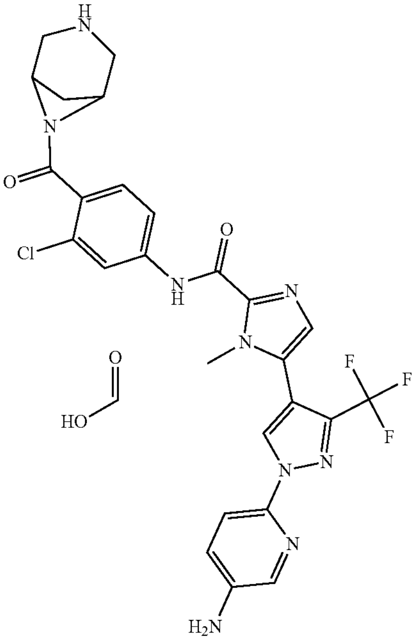 [SMILES: Cn1c(-c2cn(-c3ccc(N)cn3)nc2C(F)(F)F)cnc1C(=O)Nc1ccc(C(=O)N2C3CNCC2C3)c(Cl)c1 ; O=CO] | Z55 | 5-[1-(5-amino-2-pyridyl)-3-(trifluoromethyl)pyrazol-4-yl]-N-[3-chloro-4-(3,6-diazabicyclo[3.1.1]heptane-6-carbonyl)phenyl]-1-methyl-imidazole-2-carboxamide .1:1 formic acid | 27.3 | 3,6-diazabicyclo [3.1.1]heptane-3-carboxylic acid tert-butyl ester | 586.2 $[M + H]^+$, ESI pos |

-continued

| Structure | Ex | Name | Yield % | Reactant Name | MS |
|---|---|---|---|---|---|
| 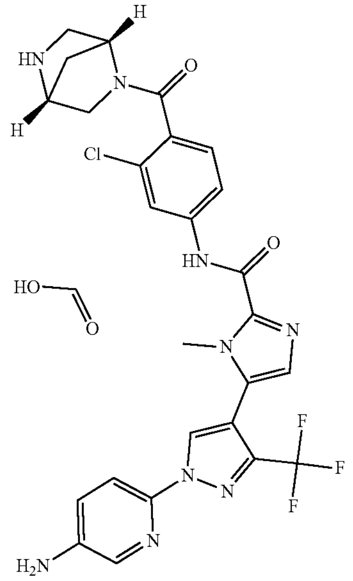 [SMILES: Cn1c(-c2cn(-c3ccc(N)cn3)nc2C(F)(F)F)cnc1C(=O)Nc1ccc(C(=O)N2C[C@H]3C[C@@H]2CN3)c(Cl)c1 ; O=CO] | Z66 | 5-[1-(5-amino-2-pyridyl)-3-(trifluoromethyl)pyrazol-4-yl]-N-[3-chloro-4-[(1R,4R)-2,5-diazabicyclo[2.2.1]heptane-2-carbonyl]phenyl]-1-methyl-imidazole-2-carboxamide .1:1 formic acid | 59.3 | (1R,4R)-2,5-diazabicyclo [2.2.1]]heptane-2-carboxylic acid tert-butyl ester | 586.2 [M + H]$^+$, ESI pos |
| 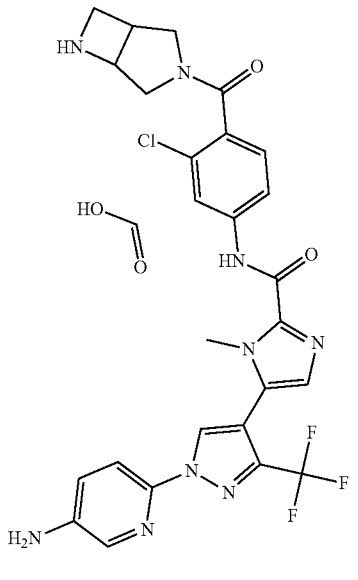 [SMILES: Cn1c(-c2cn(-c3ccc(N)cn3)nc2C(F)(F)F)cnc1C(=O)Nc1ccc(C(=O)N2CC3CNC3C2)c(Cl)c1 ; O=CO] | Z59 | 5-[1-(5-amino-2-pyridyl)-3-(trifluoromethyl)pyrazol-4-yl]-N-[3-chloro-4-(3,6-diazabicyclo[3.2.0]heptane-3-carbonyl)phenyl]-1-methyl-imidazole-2-carboxamide .1:1 formic acid | 45.8 | 3,6-diazabicyclo [3.2.0]heptane-6-carboxylic acid tert-butyl ester | 586.2 [M + H]$^+$, ESI pos |

-continued

| Structure | Ex | Name | Yield % | Reactant Name | MS |
|---|---|---|---|---|---|
| 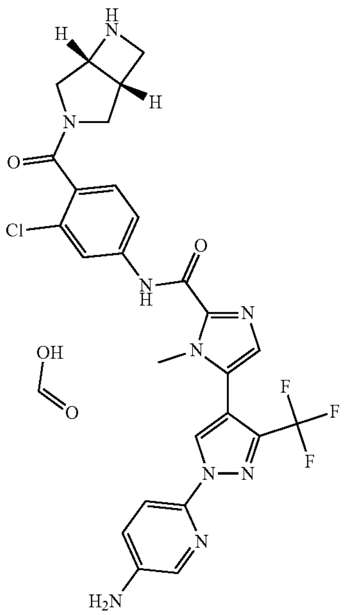 Chiral | Z70 | 5-[1-(5-amino-2-pyridyl)-3-(trifluoromethyl)pyrazol-4-yl]-N-[3-chloro-4-[(1R,5R)-3,6-diazabicyclo[3.2.0]heptane-3-carbonyl]phenyl]-1-methyl-imidazole-2-carboxamide .1:1 formic acid | 22.3 | (1S,5R)-3,6-diazabicyclo [3.2.0]heptane-6-carboxylic acid tert-butyl ester | 586.2 $[M + H]^+$, ESI pos |
| 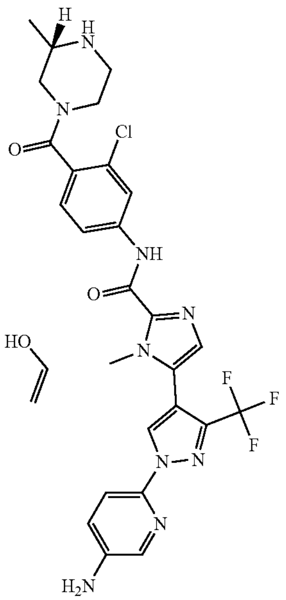 Chiral | Z61 | 5-[1-(5-amino-2-pyridyl)-3-(trifluoromethyl)pyrazol-4-yl]-N-[3-chloro-4-[(3S)-3-methylpiperazine-1-carbonyl]phenyl]-1-methyl-imidazole-2-carboxamide .1:1 formic acid | 52.3 | (2S)-2-methylpiper-azine-1-carboxylic acid tert-butyl ester | 588.2 $[M + H]^+$, ESI pos |

-continued

| Structure | Ex | Name | Yield % | Reactant Name | MS |
|---|---|---|---|---|---|
| Chiral 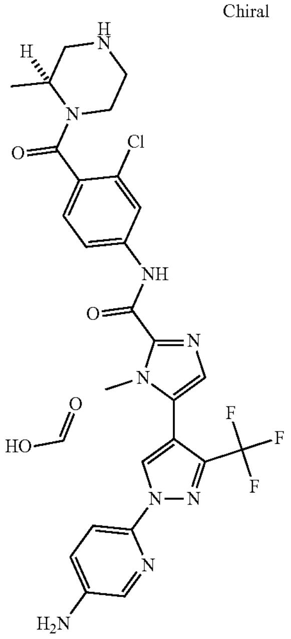 | Z56 | 5-[1-(5-amino-2-pyridyl)-3-(trifluoromethyl)pyrazol-4-yl]-N-[3-chloro-4-[(2S)-2-methylpiperazine-1-carbonyl]phenyl]-1-methyl-imidazole-2-carboxamide .1:1 formic acid | 43.4 | (3S)-3-methylpiper-azine-1-carboxylic acid tert-butyl ester | 588.2 $[M + H]^+$, ESI pos |
| 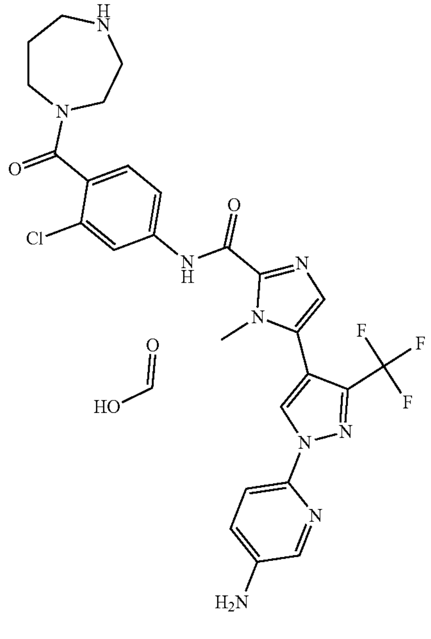 [SMILES: Cn1c(-c2cn(-c3ccc(N)cn3)nc2C(F)(F)F)cnc1C(=O)Nc1ccc(C(=O)N2CCCNCC2)c(Cl)c1 ; O=CO] | Z60 | 5-[1-(5-amino-2-pyridyl)-3-(trifluoromethyl)pyrazol-4-yl]-N-[3-chloro-4-(1,4-diazepane-1-carbonyl)phenyl]-1-methyl-imidazole-2-carboxamide .1:1 formic acid | 45.5 | 1,4-diazepane-1-carboxylic acid tert-butyl ester | 588.2 $[M + H]^+$, ESI pos |

-continued

| Structure | Ex | Name | Yield % | Reactant Name | MS |
|---|---|---|---|---|---|
| 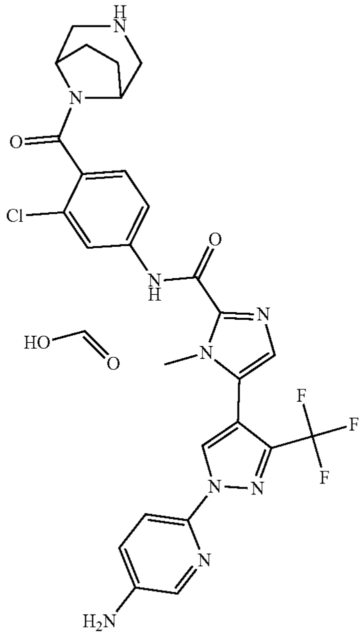 | Z62 | 5-[1-(5-amino-2-pyridyl)-3-(trifluoromethyl)pyrazol-4-yl]-N-[3-chloro-4-(3,8-diazabicyclo[3.2.1]octane-8-carbonyl)phenyl]-1-methyl-imidazole-2-carboxamide .1:1 formic acid | 39.2 | 3,8-diazabicyclo [3.2.1]octane-3-carboxylic acid tert-butyl ester | 600.2 $[M + H]^+$, ESI pos |
| 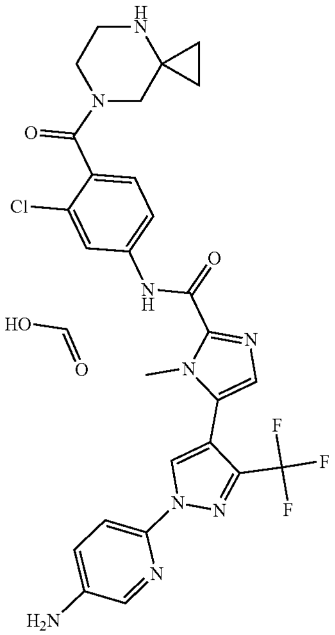 [SMILES: O=CO ; Cn1c(-c2cn(-c3ccc(N)cn3)nc2C(F)(F)F)cnc1C(=O)Nc1ccc(C(=O)N2CCNC3(CC3)C2)c(Cl)c1] | Z51 | 5-[1-(5-amino-2-pyridyl)-3-(trifluoromethyl)pyrazol-4-yl]-N-[3-chloro-4-(4,7-diazaspiro[2.5]octane-7-carbonyl)phenyl]-1-methyl-imidazole-2-carboxamide .1:1 formic acid | 28.5 | 4,7-diazaspiro[2.5] octane-4-carboxylic acid tert-butyl ester | 598.3 $[M - H]^-$, ESI neg |

-continued

| Structure | Ex | Name | Yield % | Reactant Name | MS |
|---|---|---|---|---|---|
| 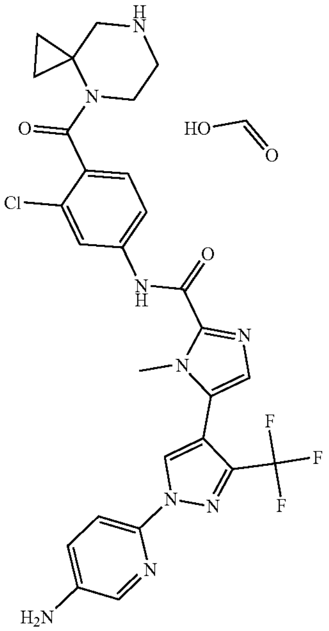 [SMILES: Cn1c(-c2cn(-c3ccc(N)cn3)nc2C(F)(F)F)cnc1C(=O)Nc1ccc(C(=O)N2CCNCC23CC3)c(Cl)c1 ; O=CO] | Z67 | 5-[1-(5-amino-2-pyridyl)-3-(trifluoromethyl)pyrazol-4-yl]-N-[3-chloro-4-(4,7-diazaspiro[2.5]octane-4-carbonyl)phenyl]-1-methyl-imidazole-2-carboxamide .1:1 formic acid | 50.4 | 4,7-diazaspiro[2.5]octane-7-carboxylic acid tert-butyl ester | 600.2 $[M + H]^+$, ESI pos |
| 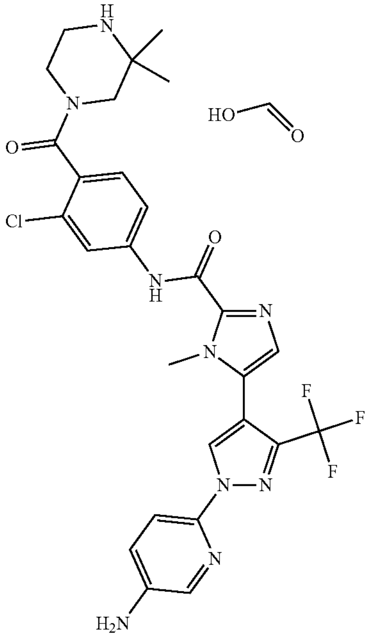 [SMILES: Cn1c(-c2cn(-c3ccc(N)cn3)nc2C(F)(F)F)cnc1C(=O)Nc1ccc(C(=O)N2CCNC(C)(C)C2)c(Cl)c1 ; O=CO] | Z57 | 5-[1-(5-amino-2-pyridyl)-3-(trifluoromethyl)pyrazol-4-yl]-N-[3-chloro-4-(3,3-dimethylpiperazine-1-carbonyl)phenyl]-1-methyl-imidazole-2-carboxamide .1:1 formic acid | 29.7 | 2,2-dimethylpiperazine-1-carboxylic acid tert-butyl ester | 602.3 $[M + H]^+$, ESI pos |

-continued

| Structure | Ex | Name | Yield % | Reactant Name | MS |
|---|---|---|---|---|---|
| 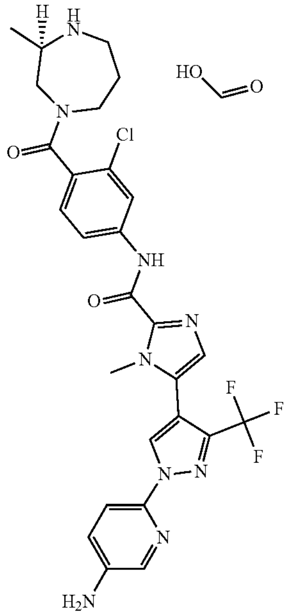 Chiral | Z52 | 5-[1-(5-amino-2-pyridyl)-3-(trifluoromethyl)pyrazol-4-yl]-N-[3-chloro-4-[(3R)-3-methyl-1,4-diazepane-1-carbonyl]phenyl]-1-methyl-imidazole-2-carboxamide .1:1 formic acid | 54.9 | (2R)-2-methyl-1,4-diazepane-1-carboxylic acid tert-butyl ester | 602.3 $[M + H]^+$, ESI pos |
| 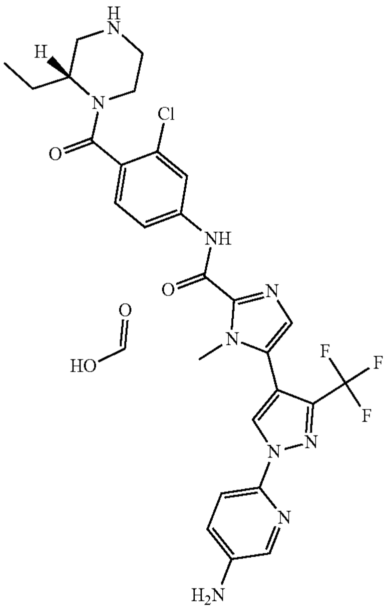 Chiral | Z63 | 5-[1-(5-amino-2-pyridyl)-3-(trifluoromethyl)pyrazol-4-yl]-N-[3-chloro-4-[(2R)-2-ethylpiperazine-1-carbonyl]phenyl]-1-methyl-imidazole-2-carboxamide .1:1 formic acid | 23 | (3R)-3-ethylpiperazine-1-carboxylic acid tert-butyl ester | 602.3 $[M + H]^+$, ESI pos |

-continued

| Structure | Ex | Name | Yield % | Reactant Name | MS |
|---|---|---|---|---|---|
| Chiral 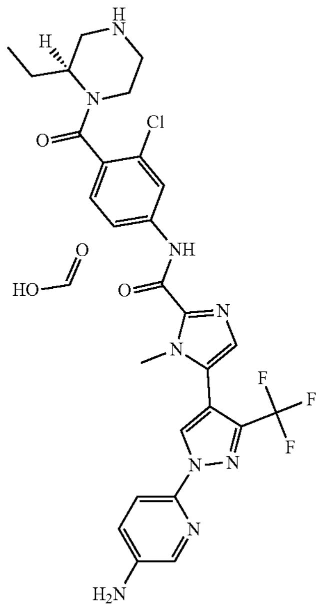 | Z64 | 5-[1-(5-amino-2-pyridyl)-3-(trifluoromethyl)pyrazol-4-yl]-N-[3-chloro-4-[(2S)-2-ethylpiperazine-1-carbonyl]phenyl]-1-methyl-imidazole-2-carboxamide .1:1 formic acid | 22.9 | (3S)-3-ethylpiperazine-1-carboxylic acid tert-butyl ester | 602.3 [M + H]$^+$, ESI pos |
| 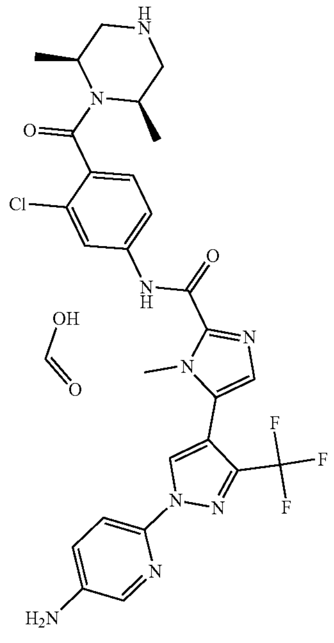 [SMILES: C[C@@H]1CNC[C@H](C)N1C(=O)c1ccc(NC(=O)c2ncc(-c3cn(-c4ccc(N)cn4)nc3C(F)(F)F)n2C)cc1Cl ; O=CO] | Z54 | 5-[1-(5-amino-2-pyridyl)-3-(trifluoromethyl)pyrazol-4-yl]-N-[3-chloro-4-[(2S,6R)-2,6-dimethylpiperazine-1-carbonyl]phenyl]-1-methyl-imidazole-2-carboxamide .1:1 formic acid | 5.27 | (3S,5R)-3,5-dimethylpiperazine-1-carboxylic acid tert-butyl ester | 602.2 [M + H]$^+$, ESI pos |

-continued

| Structure | Ex | Name | Yield % | Reactant Name | MS |
|---|---|---|---|---|---|
| 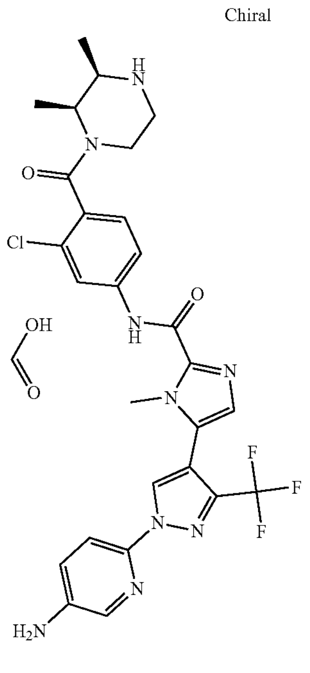 [SMILES: O=CO ; C[C@H]1NCCN(C(=O)c2ccc(NC(=O)c3ncc(-c4cn(-c5ccc(N)cn5)nc4C(F)(F)F)n3C)cc2Cl)[C@H]1C] | Z68 | 5-[1-(5-amino-2-pyridyl)-3-(trifluoromethyl)pyrazol-4-yl]-N-[3-chloro-4-[(2S,3R)-2,3-dimethylpiperazine-1-carbonyl]phenyl]-1-methyl-imidazole-2-carboxamide .1:1 formic acid | 24.4 | (2R,3S)-2,3-dimethylpiperazine-1-carboxylic acid tert-butyl ester | 602.3 $[M + H]^+$, ESI pos |
| 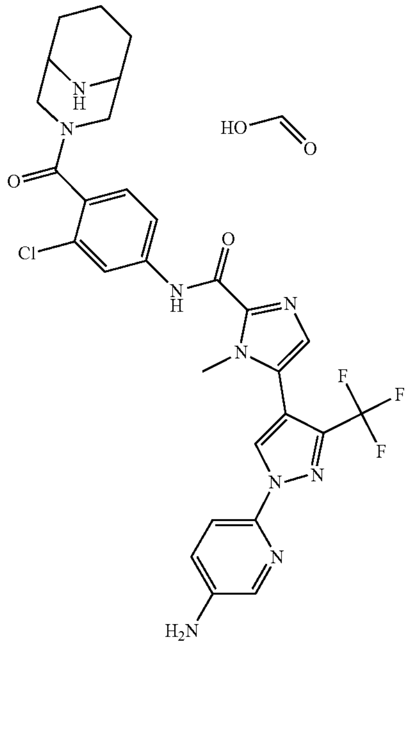 [SMILES: Cn1c(-c2cn(-c3ccc(N)cn3)nc2C(F)(F)F)cnc1C(=O)Nc1ccc(C(=O)N2CC3CCCC(C2)N3)c(Cl)c1 ; O=CO] | Z53 | 5-[1-(5-amino-2-pyridyl)-3-(trifluoromethyl)pyrazol-4-yl]-N-[3-chloro-4-(3,9-diazabicyclo[3.3.1]]nonane-3-carbonyl)phenyl]-1-methyl-imidazole-2-carboxamide .1:1 formic acid | 31.5 | 3,9-diazabicyclo [3.3.1]nonane-9-carboxylic acid tert-butyl ester | 614.2 $[M + H]^+$, ESI pos |

-continued

| Structure | Ex | Name | Yield % | Reactant Name | MS |
|---|---|---|---|---|---|
| 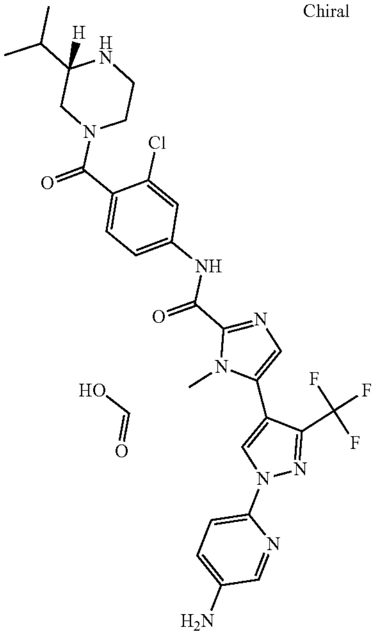 [SMILES: CC(C)[C@H]1CN(C(=O)c2ccc(NC(=O)c3ncc(-c4cn(-c5ccc(N)cn5)nc4C(F)(F)F)n3C)cc2Cl)CCN1 ; O=CO] Chiral | Z58 | 5-[1-(5-amino-2-pyridyl)-3-(trifluoromethyl)pyrazol-4-yl]-N-[3-chloro-4-[(3S)-3-isopropylpiperazine-1-carbonyl]phenyl]-1-methyl-imidazole-2-carboxamide .1:1 formic acid | 45.9 | (2S)-2-isopropylpiperazine-1-carboxylic acid tert-butyl ester | 616.3 [M + H]$^+$, ESI pos |
| 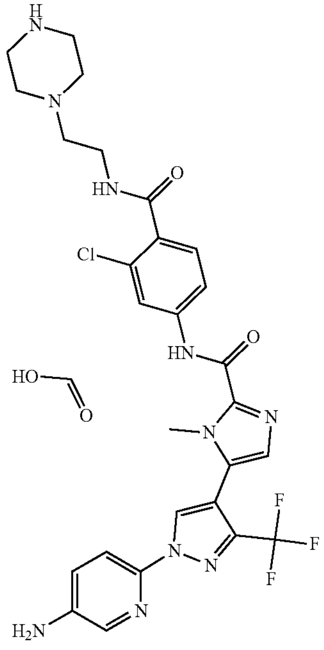 [SMILES: Cn1c(-c2cn(-c3ccc(N)cn3)nc2C(F)(F)F)cnc1C(=O)Nc1ccc(C(=O)NCCN2CCNCC2)c(Cl)c1 ; O=CO] | Z65 | 5-[1-(5-amino-2-pyridyl)-3-(trifluoromethyl)pyrazol-4-yl]-N-[3-chloro-4-(2-piperazinoethylcarbamoyl)phenyl]-1-methyl-imidazole-2-carboxamide .1:2 formic acid | 9.73 | 4-(2-aminoethyl) piperazine-1-carboxylic acid tert-butyl ester | 617.3 [M + H]$^+$, ESI pos |

-continued

| Structure | Ex | Name | Yield % | Reactant Name | MS |
|---|---|---|---|---|---|
| 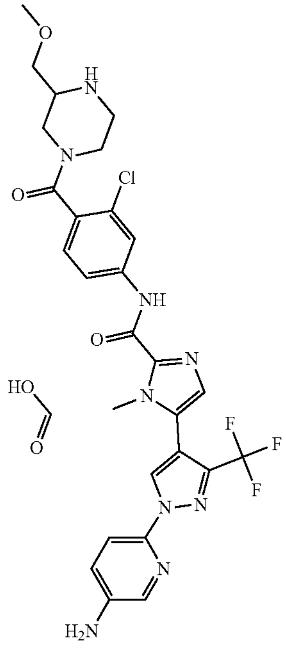 [SMILES: COCC1CN(C(=O)c2ccc(NC(=O)c3ncc(-c4cn(-c5ccc(N)cn5)nc4C(F)(F)F)n3C)cc2Cl)CCN1 ; O=CO] | Z69 | 5-[1-(5-amino-2-pyridyl)-3-(trifluoromethyl)pyrazol-4-yl]-N-[3-chloro-4-[3-(methoxymethyl)piperazine-1-carbonyl]phenyl]-1-methyl-imidazole-2-carboxamide .1:1 formic acid | 21.5 | 2-(methoxymethyl) piperazine-1-carboxylic acid tert-butyl ester | 618.3 $[M + H]^+$, ESI pos |

Example Z22

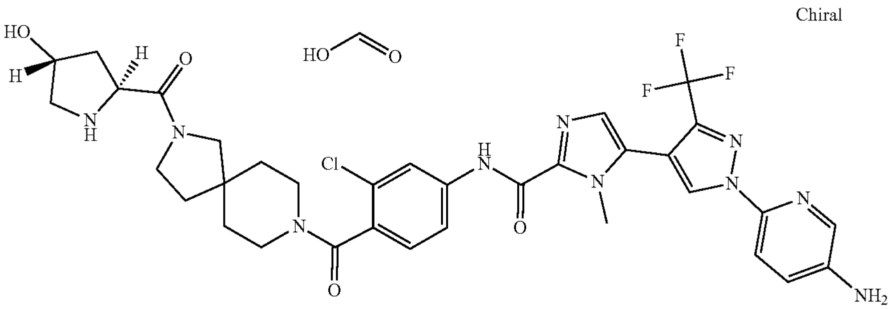 [SMILES: Cn1c(-c2cn(-c3ccc(N)cn3)nc2C(F)(F)F)cnc1C(=O)Nc1ccc(C(=O)N2CCC3(CC2)CCN(C(=O)[C@@H]2C[C@@H](O)CN2)C3)c(Cl)c1 ; O=CO]

Step 1: 5-[1-(5-amino-2-pyridyl)-3-(trifluoromethyl) pyrazol-4-yl]-N-[3-chloro-4-[2-[(2S,4R)-4-hydroxy-prolyl]-2,8-diazaspiro[4.5]decane-8-carbonyl]phenyl]-1-methyl-imidazole-2-carboxamide; 1:1 formic acid To (2S,4R)-1-tert-butoxycarbonyl-4-hydroxy-proline (6.24 mg, 0.027 mmol, 1.5 eq) dissolved in DMF, was added HATU (10.27 mg, 0.027 mmol, 1.5 eq) and $Et_3N$ (7.53 uL, 0.054 mmol, 3 eq). The mixture was stirred at RT for 10 min and then added to 5-[1-(5-amino-2-pyridyl)-3-(trifluoromethyl)pyrazol-4-yl]-N-[3-chloro-4-(2,8-diazaspiro[4.5]decane-8-carbonyl)phenyl]-1-methyl-imidazole-2-carboxamide 0.1:1 formic acid (11.3 mg, 0.018 mmol, 1 eq). The mixture was stirred at RT over night and then evaporated to dryness. The residue was then dissolved in 1 ml DCM and treated with 4 M HCl (180 uL, 0.720 mmol, 40 eq) over night at RT. The mixtures were then evaporated to dryness, dissolved in 1 ml of MeOH and directly purified by preparative HPLC using a Gemini 5um C18 75x30 column and water (+0.05% formic acid)/acetonitrile as eluent to afford the title compound (4.2 mg, 29.3%). MS: 739.5 $[M-H]^-$, ESI neg.

The following compounds were prepared in analogy to example Z22.

If the preparation of the reagents are not already described, they can be prepared in analogy to example Z14.

| Structure | Ex | Product Name | Yield % | Reagent | MS |
|---|---|---|---|---|---|
| 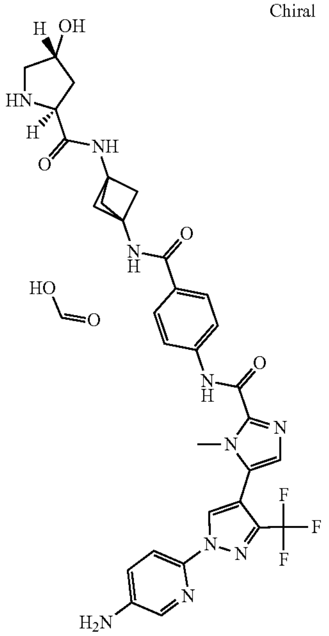 Chiral | Z47 | 5-[1-(5-amino-2-pyridyl)-3-(trifluoromethyl)pyrazol-4-yl]-N-[3-chloro-4-[[3-[[(2S,4R)-4-hydroxyprolyl]amino]-1-bicyclo[1.1.1]pentanyl]carbamoyl]phenyl]-1-methyl-imidazole-2-carboxamide .1:1 formic acid | 31.1 | N-[4-[(3-amino-1-bicyclo[1.1.1]pentanyl)carbamoyl]-3-chloro-phenyl]-5-[1-(5-amino-2-pyridyl)-3-(trifluoromethyl)pyrazol-4-yl]-1-methyl-imidazole-2-carboxamide | 697.5 $[M-H]^-$, ESI neg |
| 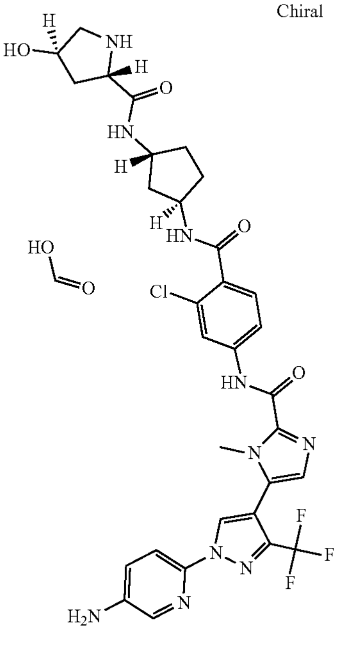 [SMILES: Cn1c(-c2cn(-c3ccc(N)cn3)nc2C(F)(F)F)cnc1C(=O)Nc1ccc(C(=O)N[C@@H]2CC[C@@H](NC(=O)[C@@H]3C[C@@H](O)CN3)C2)c(Cl)c1 ; O=CO] Chiral | Z23 | 5-[1-(5-amino-2-pyridyl)-3-(trifluoromethyl)pyrazol-4-yl]-N-[3-chloro-4-[[(1R,3R)-3-[[(2S,4R)-4-hydroxyprolyl]amino]cyclopentyl]carbamoyl]phenyl]-1-methyl-imidazole-2-carboxamide .1:1 formic acid | 8.48 | N-[4-[(1R,3R)-3-aminocyclopentyl]carbamoyl]-3-chloro-phenyl]-5-[1-(5-amino-2-pyridyl)-3-(trifluoromethyl)pyrazol-4-yl]-1-methyl-imidazole-2-carboxamide | 699.5 $[M-H]^-$, ESI neg |

-continued

| Structure | Ex | Product Name | Yield % | Reagent | MS |
|---|---|---|---|---|---|
| 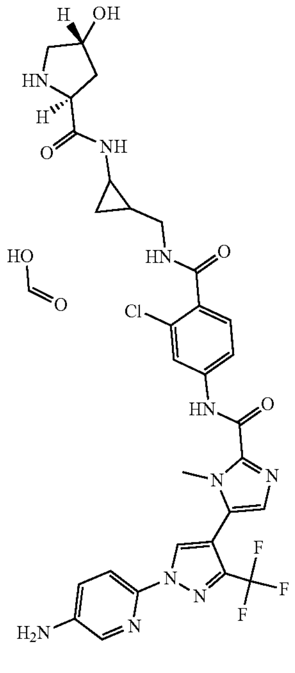 [SMILES: O=CO ; Cn1c(-c2cn(-c3ccc(N)cn3)nc2C(F)(F)F)cnc1C(=O)Nc1ccc(C(=O)NCC2CC2NC(=O)[C@@H]2C[C@@H](O)CN2)c(Cl)c1] | Z36 | 5-[1-(5-amino-2-pyridyl)-3-(trifluoromethyl)pyrazol-4-yl]-N-[3-chloro-4-[[2-[[(2S,4R)-4-hydroxyprolyl]amino]cyclopropyl]methylcarbamoyl]phenyl]-1-methyl-imidazole-2-carboxamide .1:1 formic acid | 24.9 | N-[4-[(2-aminocyclopropyl)methylcarbamoyl]-3-chloro-phenyl]-5-[1-(5-amino-2-pyridyl)-3-(trifluoromethyl)pyrazol-4-yl]-1-methyl-imidazole-2-carboxamide | 685.4 $[M-H]^-$, ESI neg |
| 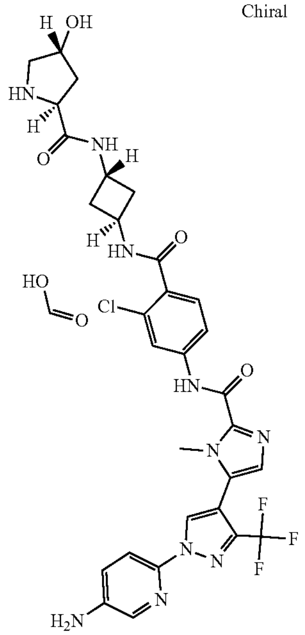 Chiral | Z38 | 5-[1-(5-amino-2-pyridyl)-3-(trifluoromethyl)pyrazol-4-yl]-N-[3-chloro-4-[trans-[3-[[(2S,4R)-4-hydroxyprolyl]amino]cyclobutyl]carbamoyl]phenyl]-1-methyl-imidazole-2-carboxamide .1:1 formic acid | 34.9 | N-[4-[trans-(3-aminocyclobutyl)carbamoyl]-3-chloro-phenyl]-5-[1-(5-amino-2-pyridyl)-3-(trifluoromethyl)pyrazol-4-yl]-1-methyl-imidazole-2-carboxamide | 685.5 $[M-H]^-$, ESI neg |

-continued

| Structure | Ex | Product Name | Yield % | Reagent | MS |
|---|---|---|---|---|---|
| 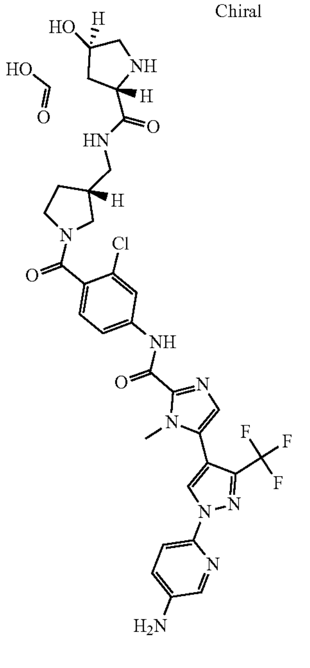 Chiral | Z44 | 5-[1-(5-amino-2-pyridyl)-3-(trifluoromethyl)pyrazol-4-yl]-N-[3-chloro-4-[(3R)-3-[[[(2S,4R)-4-hydroxyprolyl]amino]methyl]pyrrolidine-1-carbonyl]phenyl]-1-methyl-imidazole-2-carboxamide .1:1 formic acid | 31.1 | N-[4-[(3R)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide | 699.5 [M − H]⁻, ESI neg |
| 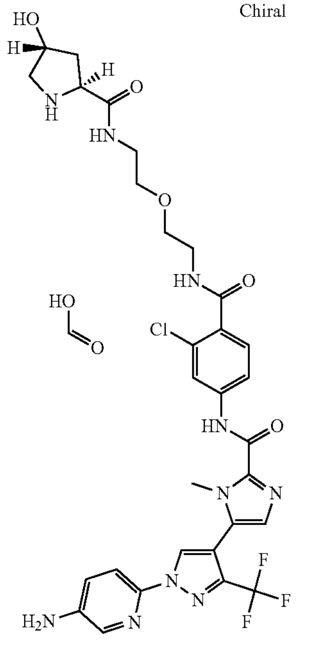 [SMILES: Cn1c(-c2cn(-c3ccc(N)cn3)nc2C(F)(F)F)cnc1C(=O)Nc1ccc(C(=O)NCCOCCNC(=O)[C@@H]2C[C@@H](O)CN2)c(Cl)c1 ; O=CO] Chiral | Z40 | 5-[1-(5-amino-2-pyridyl)-3-(trifluoromethyl)pyrazol-4-yl]-N-[3-chloro-4-[2-[2-[[(2S,4R)-4-hydroxyprolyl]amino]ethoxy]ethylcarbamoyl]phenyl]-1-methyl-imidazole-2-carboxamide .1:1 formic acid | 23.1 | N-[4-[2-(2-aminoethoxy)ethylcarbamoyl]-3-chloro-phenyl]-5-[1-(5-amino-2-pyridyl)-3-(trifluoromethyl)pyrazol-4-yl]-1-methyl-imidazole-2-carboxamide | 703.5 [M − H]⁻, ESI neg |

-continued

| Structure | Ex | Product Name | Yield % | Reagent | MS |
|---|---|---|---|---|---|
| 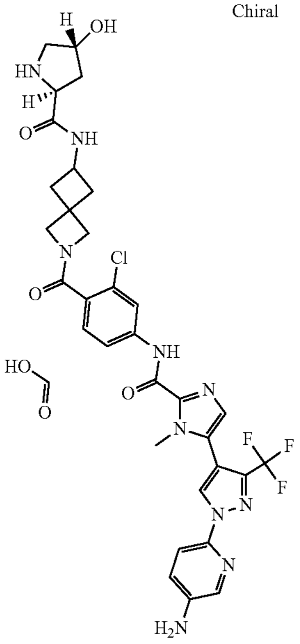 [SMILES: O=CO ; Cn1c(-c2cn(-c3ccc(N)cn3)nc2C(F)(F)F)cnc1C(=O)Nc1ccc(C(=O)N2CC3(CC(NC(=O)[C@@H]4C[C@@H](O)CN4)C3)C2)c(Cl)c1] Chiral | Z25 | 5-[1-(5-amino-2-pyridyl)-3-(trifluoromethyl)pyrazol-4-yl]-N-[3-chloro-4-[6-[[(2S,4R)-4-hydroxyprolyl]amino]-2-azaspiro[3.3]heptane-2-carbonyl]phenyl]-1-methyl-imidazole-2-carboxamide .1:1 formic acid | 21 | N-[4-(6-amino-2-azaspiro[3.3]heptane-2-carbonyl)-3-chloro-phenyl]-5-[1-(5-amino-2-pyridyl)-3-(trifluoromethyl)pyrazol-4-yl]-1-methyl-imidazole-2-carboxamide | 711.5 [M − H]⁻, ESI neg |
| 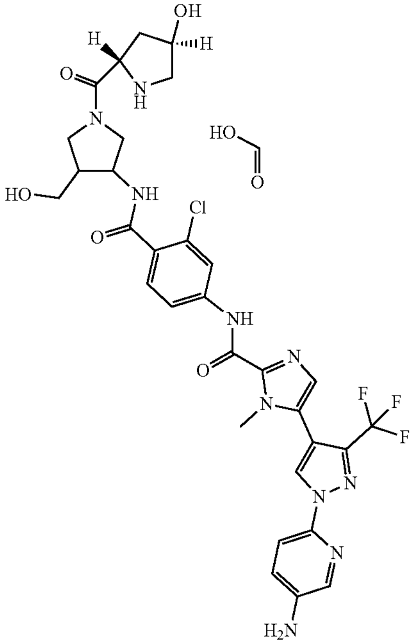 [SMILES: Cn1c(-c2cn(-c3ccc(N)cn3)nc2C(F)(F)F)cnc1C(=O)Nc1ccc(C(=O)NC2CN(C(=O)[C@@H]3C[C@@H](O)CN3)CC2CO)c(Cl)c1 ; O=CO] | Z27 | 5-[1-(5-amino-2-pyridyl)-3-(trifluoromethyl)pyrazol-4-yl]-N-[3-chloro-4-[[1-[(2S,4R)-4-hydroxyprolyl]-4-methylol-pyrrolidin-3-yl]carbamoyl]phenyl]-1-methyl-imidazole-2-carboxamide .1:1 formic acid | 29.1 | 5-[1-(5-amino-2-pyridyl)-3-(trifluoromethyl)pyrazol-4-yl]-N-[3-chloro-4-[(3-methylolpyrrolidin-3-yl)carbamoyl]phenyl]-1-methyl-imidazole-2-carboxamide | 715.5 [M − H]⁻, ESI neg |

-continued

| Structure | Ex | Product Name | Yield % | Reagent | MS |
|---|---|---|---|---|---|
| 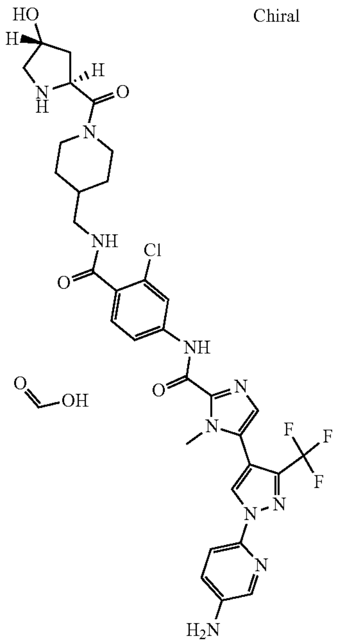 [SMILES: Cn1c(-c2cn(-c3ccc(N)cn3)nc2C(F)(F)F)cnc1C(=O)Nc1ccc(C(=O)NCC2CCN(C(=O)[C@@H]3C[C@@H](O)CN3)CC2)c(Cl)c1 ; O=CO] Chiral | Z34 | 5-[1-(5-amino-2-pyridyl)-3-(trifluoromethyl)pyrazol-4-yl]-N-[3-chloro-4-[[1-[(2S,4R)-4-hydroxyprolyl]-4-piperidyl]methylcarbamoyl]phenyl]-1-methyl-imidazole-2-carboxamide .1:1 formic acid | 32.2 | 5-[1-(5-amino-2-pyridyl)-3-(trifluoromethyl)pyrazol-4-yl]-N-[3-chloro-4-(4-piperidylmethylcarbamoyl)phenyl]-1-methyl-imidazole-2-carboxamide | 713.5 [M − H]⁻, ESI neg |
| 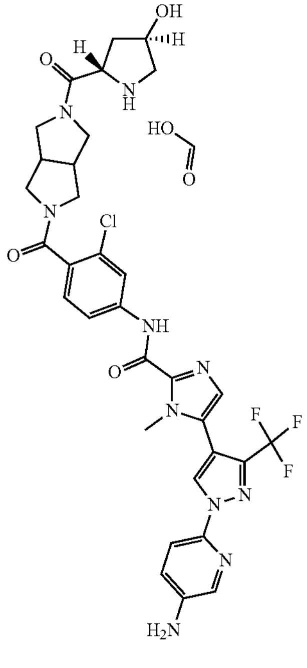 [SMILES: Cn1c(-c2cn(-c3ccc(N)cn3)nc2C(F)(F)F)cnc1C(=O)Nc1ccc(C(=O)N2CC3CN(C(=O)[C@@H]4C[C@@H](O)CN4)CC3C2)c(Cl)c1 ; O=CO] | Z37 | 5-[1-(5-amino-2-pyridyl)-3-(trifluoromethyl)pyrazol-4-yl]-N-[3-chloro-4-[5-[(2S,4R)-4-hydroxyprolyl]-1,3,3a,4,6,6a-hexahydropyrrolo[3,4-c]pyrrole-2-carbonyl]phenyl]-1-methyl-imidazole-2-carboxamide .1:1 formic acid | 19.8 | N-[4-(2,3,3a,4,6,6a-hexahydro-1H-pyrrolo[3,4-c]pyrrole-5-carbonyl)-3-chloro-phenyl]-5-[1-(5-amino-2-pyridyl)-3-(trifluoromethyl)pyrazol-4-yl]-1-methyl-imidazole-2-carboxamide | 711.4 [M − H]⁻, ESI neg |

-continued

| Structure | Ex | Product Name | Yield % | Reagent | MS |
|---|---|---|---|---|---|
| 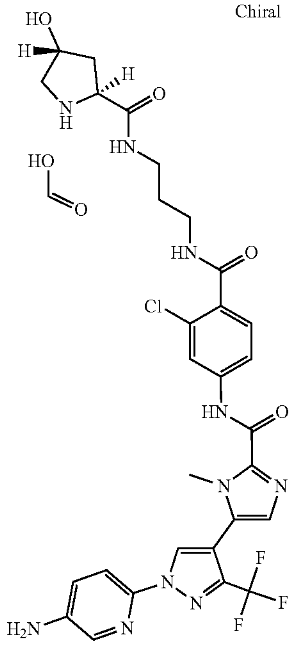 [SMILES: Cn1c(-c2cn(-c3ccc(N)cn3)nc2C(F)(F)F)cnc1C(=O)Nc1ccc(C(=O)NCCCNC(=O)[C@@H]2C[C@@H](O)CN2)c(Cl)c1 ; O=CO] Chiral | Z26 | 5-[1-(5-amino-2-pyridyl)-3-(trifluoromethyl)pyrazol-4-yl]-N-[3-chloro-4-[3-[[(2S,4R)-4-hydroxyprolyl]amino]propyl-carbamoyl]phenyl]-1-methyl-imidazole-2-carboxamide .1:1 formic acid | 25 | N-[4-(3-aminopropylcarbamoyl)-3-chloro-phenyl]-5-[1-(5-amino-2-pyridyl)-3-(trifluoromethyl)pyrazol-4-yl]-1-methyl-imidazole-2-carboxamide | 673.5 $[M-H]^-$, ESI neg |
| 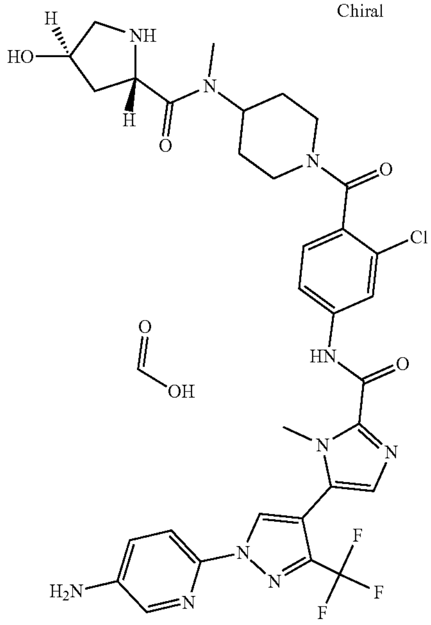 [SMILES: CN(C(=O)[C@@H]1C[C@@H](O)CN1)C1CCN(C(=O)c2ccc(NC(=O)c3ncc(-c4cn(-c5ccc(N)cn5)nc4C(F)(F)F)n3C)cc2Cl)CC1 ; O=CO] Chiral | Z46 | 5-[1-(5-amino-2-pyridyl)-3-(trifluoromethyl)pyrazol-4-yl]-N-[3-chloro-4-[4-[[(2S,4R)-4-hydroxyprolyl]-methyl-amino]piperidine-1-carbonyl]phenyl]-1-methyl-imidazole-2-carboxamide .1:1 formic acid | 39.4 | 5-[1-(5-amino-2-pyridyl)-3-(trifluoromethyl)pyrazol-4-yl]-N-[3-chloro-4-[4-(methylamino)piperidine-1-carbonyl]phenyl]-1-methyl-imidazole-2-carboxamide | 713.5 $[M-H]^-$, ESI neg |

-continued

| Structure | Ex | Product Name | Yield % | Reagent | MS |
|---|---|---|---|---|---|
| 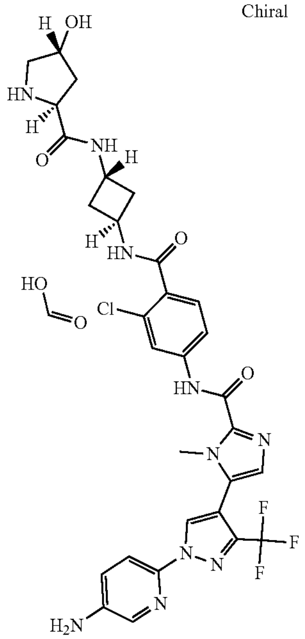 Chiral | Z42 | 5-[1-(5-amino-2-pyridyl)-3-(trifluoromethyl)pyrazol-4-yl]-N-[3-chloro-4-[cis-[3-[[(2S,4R)-4-hydroxyprolyl]amino]cyclo-butyl]carbamoyl]phenyl]-1-methyl-imidazole-2-carboxamide .1:1 formic acid | 33.5 | N-[4-[cis-(3-aminocyclobutyl)car-bamoyl]-3-chloro-phenyl]-5-[1-(5-amino-2-pyridyl)-3-(trifluoromethyl) pyrazol-4-yl]-1-methyl-imidazole-2-carboxamide | 685.4 [M − H]⁻, ESI neg |
| 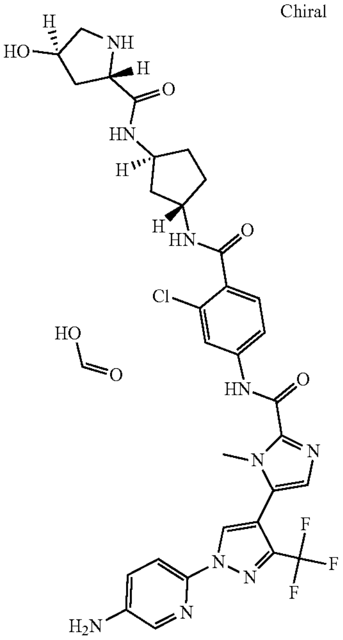 [SMILES: Cn1c(-c2cn(-c3ccc(N)cn3)nc2C(F)(F)F)cnc1C(=O)Nc1ccc(C(=O)N[C@H]2CC[C@H](NC(=O)[C@@H]3C[C@@H](O)CN3)C2)c(Cl)c1 ; O=CO] Chiral | Z48 | 5-[1-(5-amino-2-pyridyl)-3-(trifluoromethyl)pyrazol-4-yl]-N-[3-chloro-4-[[(1S,3S)-3-[(2S,4R)-4-hydroxyprolyl]amino]cyclo-pentyl]carbamoyl]phenyl]-1-methyl-imidazole-2-carboxamide .1:1 formic acid | 29.7 | N-[4-[[(1S,3S)-3-aminocyclopentyl] carbamoyl]-3-chloro-phenyl]-5-[1-(5-amino-2-pyridyl)-3-(trifluoromethyl)pyrazol-4-yl]-1-methyl-imidazole-2-carboxamide | 699.5 [M − H]⁻, ESI neg |

-continued

| Structure | Ex | Product Name | Yield % | Reagent | MS |
|---|---|---|---|---|---|
| Chiral 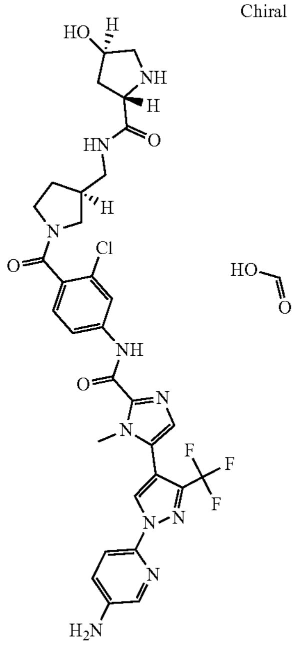 [SMILES: Cn1c(-c2cn(-c3ccc(N)cn3)nc2C(F)(F)F)cnc1C(=O)Nc1ccc(C(=O)N2CC[C@@H](CNC(=O)[C@@H]3C[C@@H](O)CN3)C2)c(Cl)c1 ; O=CO] | Z39 | 5-[1-(5-amino-2-pyridyl)-3-(trifluoromethyl)pyrazol-4-yl]-N-[3-chloro-4-[(3S)-3-[[[(2S,4R)-4-hydroxyprolyl]amino]methyl]pyrrolidine-1-carbonyl]phenyl]-1-methyl-imidazole-2-carboxamide .1:1 formic acid | 34.9 | N-[4-[(3S)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide | 699.5 [M − H]$^-$, ESI neg |
| Chiral 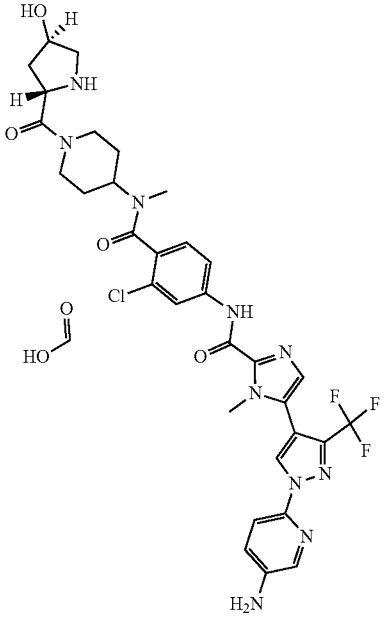 | Z35 | 5-[1-(5-amino-2-pyridyl)-3-(trifluoromethyl)pyrazol-4-yl]-N-[3-chloro-4-[[1-[(2S,4R)-4-hydroxyprolyl]-4-piperidyl]-methyl-carbamoyl]phenyl]-1-methyl-imidazole-2-carboxamide .1:1 formic acid | 13 | 5-[1-(5-amino-2-pyridyl)-3-(trifluoromethyl)pyrazol-4-yl]-N-[3-chloro-4-[methyl(4-piperidyl)carbamoyl]phenyl]-1-methyl-imidazole-2-carboxamide | 713.5 [M − H]$^-$, ESI neg |

-continued

| Structure | | Ex | Product Name | Yield % | Reagent | MS |
|---|---|---|---|---|---|---|
| 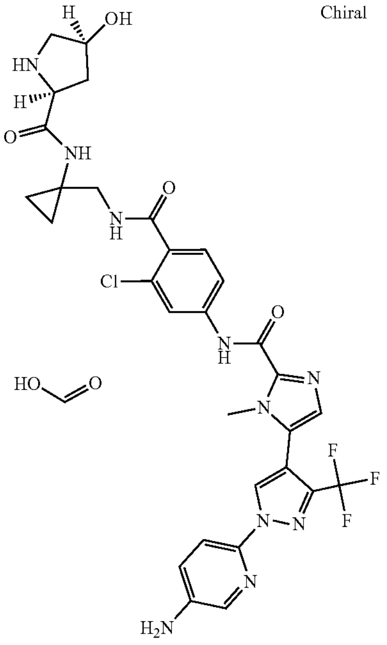 [SMILES: Cn1c(-c2cn(-c3ccc(N)cn3)nc2C(F)(F)F)cnc1C(=O)Nc1ccc(C(=O)NCC2(NC(=O)[C@@H]3C[C@H](O)CN3)CC2)c(Cl)c1 ; O=CO] | Chiral | Z43 | 5-[1-(5-amino-2-pyridyl)-3-(trifluoromethyl)pyrazol-4-yl]-N-[3-chloro-4-[[1-[[(2S,4R)-4-hydroxyprolyl]amino]cyclo-propyl]methylcarbamoyl]phenyl]-1-methyl-imidazole-2-carboxamide .1:1 formic acid | 29.7 | N-[4-[(1-aminocyclopropyl)methylcarbamoyl]-3-chloro-phenyl]-5-[1-(5-amino-2-pyridyl)-3-(trifluoromethyl)pyrazol-4-yl]-1-methyl-imidazole-2-carboxamide | 685.5 [M − H]$^-$, ESI neg |
| 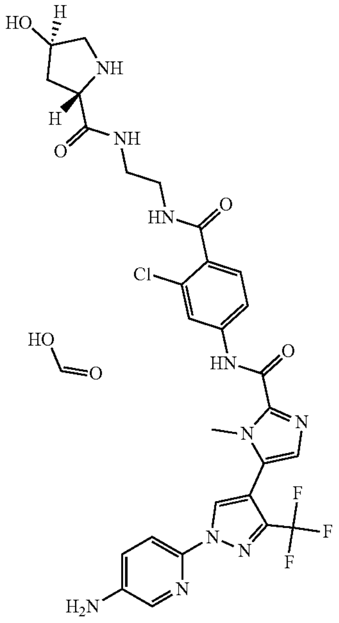 | Chiral | Z33 | 5-[1-(5-amino-2-pyridyl)-3-(trifluoromethyl)pyrazol-4-yl]-N-[3-chloro-4-[2-[[(2S,4R)-4-hydroxyprolyl]amino]ethyl carbamoyl]phenyl]-1-methyl-imidazole-2-carboxamide .1:1 formic acid | 28.3 | N-[4-(2-aminoethylcarbamoyl)-3-chloro-phenyl]-5-[1-(5-amino-2-pyridyl)-3-(trifluoromethyl)pyrazol-4-yl]-1-methyl-imidazole-2-carboxamide | 659.4 [M − H]$^-$, ESI neg |

-continued

| Structure | Ex | Product Name | Yield % | Reagent | MS |
|---|---|---|---|---|---|
| 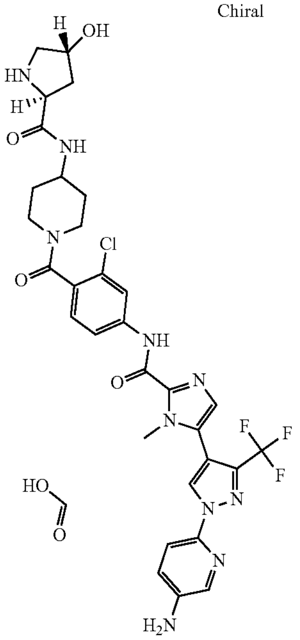 [SMILES: Cn1c(-c2cn(-c3ccc(N)cn3)nc2C(F)(F)F)cnc1C(=O)Nc1ccc(C(=O)N2CCC(NC(=O)[C@@H]3C[C@@H](O)CN3)CC2)c(Cl)c1 ; O=CO] Chiral | Z24 | 5-[1-(5-amino-2-pyridyl)-3-(trifluoromethyl)pyrazol-4-yl]-N-[3-chloro-4-[4-[[(2S,4R)-4-hydroxyprolyl]amino]piperidine-1-carbonyl]phenyl]-1-methyl-imidazole-2-carboxamide .1:1 formic acid | 13 | N-[4-(4-aminopiperidine-1-carbonyl)-3-chloro-phenyl]-5-[1-(5-amino-2-pyridyl)-3-(trifluoromethyl) pyrazol-4-yl]-1-methyl-imidazole-2-carboxamide | 699.5 $[M-H]^-$, ESI neg |
| 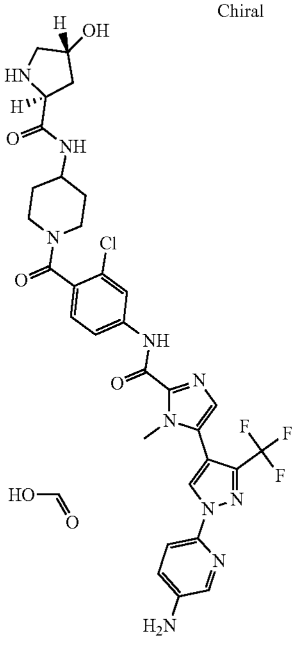 Chiral | Z45 | 5-[1-(5-amino-2-pyridyl)-3-(trifluoromethyl)pyrazol-4-yl]-N-[3-chloro-4-[4-[[[(2S,4R)-4-hydroxyprolyl]amino] methyl]piperidine-1-carbonyl]phenyl]-1-methyl-imidazole-2-carboxamide .1:1 formic acid | 34 | N-[4-[4-(aminomethyl)piperidine-1-carbonyl]-3-chloro-phenyl]-5-[1-(5-amino-2-pyridyl)-3-(trifluoromethyl) pyrazol-4-yl]-1-methyl-imidazole-2-carboxamide | 713.5 $[M-H]^-$, ESI neg |

-continued

| Structure | Ex | Product Name | Yield % | Reagent | MS |
|---|---|---|---|---|---|
| 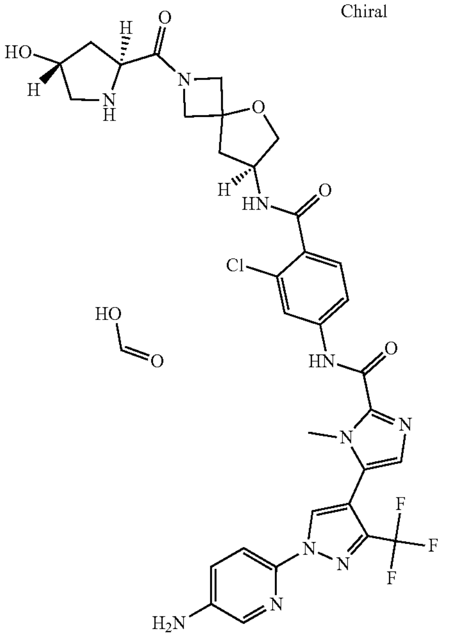 [SMILES: Cn1c(-c2cn(-c3ccc(N)cn3)nc2C(F)(F)F)cnc1C(=O)Nc1ccc(C(=O)N[C@@H]2COC3(C2)CN(C(=O)[C@@H]2C[C@@H](O)CN2)C3)c(Cl)c1 ; O=CO] | Z41 | 5-[1-(5-amino-2-pyridyl)-3-(trifluoromethyl)pyrazol-4-yl]-N-[3-chloro-4-[(7S)-2-[(2S,4R)-4-hydroxyprolyl]-5-oxa-2-azaspiro[3.4]octan-7-yl]carbamoyl]phenyl]-1-methyl-imidazole-2-carboxamide .1:1 formic acid | 11.6 | 5-[1-(5-amino-2-pyridyl)-3-(trifluoromethyl) pyrazol-4-yl]-N-[3-chloro-4-[[(7S)-5-oxa-2-azaspiro[3.4]octan-7-yl]carbamoyl]phenyl]-1-methyl-imidazole-2-carboxamide | 727.5 [M − H]$^-$, ESI neg |

Example Z31

N-[3-chloro-4-(4-isonipecotoylpiperazine-1-carbonyl)phenyl]-5-[1-(6-methoxy-2-pyridyl)-3-(trifluoromethyl)pyrazol-4-yl]-1-methyl-imidazole-2-carboxamide

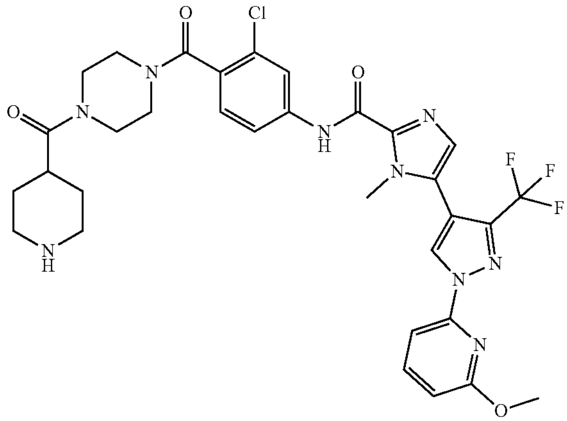 [SMILES: COc1cccc(-n2cc(-c3cnc(C(=O)Nc4ccc(C(=O)N5CCN(C(=O)C6CCNCC6)CC5)c(Cl)c4)n3C)c(C(F)(F)F)n2)n1]

Step 1: 4-[4-[2-chloro-4-[[5-[1-(6-methoxy-2-pyridyl)-3-(trifluoromethyl)pyrazol-4-yl]-1-methyl-imidazole-2-carbonyl]amino]benzoyl]piperazine-1-carbonyl]piperidine-1-carboxylic acid tert-butyl ester A mixture of 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylic acid tert-butyl ester [2489205-74-3] (50 mg, 0.072 mmol, 1 eq) in N,N-dimethylformamide, extra dry (1.6 mL) was treated with $K_2CO_3$ (19.94 mg, 0.144 mmol, 2 eq), stirred for 5 min at RT. Then 2-fluoro-6-methoxy-pyridine (28.6 mg, 26 µL, 0.225 mmol, 3.12 eq) was added. The mixture was stirred under micro wave irradiation at 125° C. for 30 min. Then again $K_2CO_3$ (19.94 mg, 0.144 mmol, 2 eq) and 2-fluoro-6-methoxy-pyridine (28.6 mg, 26 µL, 0.225 mmol, 3.12 eq) were added, and the heating under micro wave irradiation was repeated at 125° C. for 30 min. The reaction mixture was diluted with half-sat. aq. $NH_4Cl$ (40 mL), and extracted with EtOAc (3x20 mL). The combined organic layers were washed with brine (15 mL), dried over sodium sulphate, filtered, and evaporated. The crude material was purified by silica gel chromatography using DCM/MeOH as eluent to afford the title compound (22 mg, 38.11) as off-white solid. MS: 798.5, [M−H]$^-$, ESI neg.

Step 2: N-[3-chloro-4-(4-isonipecotoylpiperazine-1-carbonyl)phenyl]-5-[1-(6-methoxy-2-pyridyl)-3-(trifluoromethyl)pyrazol-4-yl]-1-methyl-imidazole-2-carboxamide A mixture of 4-[4-[2-chloro-4-[[5-[-1-(6-methoxy-2-pyridyl)-3-(trifluoromethyl)pyrazol-4-yl]-1-methyl-imidazole-2-carbonyl]amino]benzoyl]piperazine-1-carbonyl]piperidine-1-carboxylic acid tert-butyl ester (22 mg, 0.027 mmol, 1 eq) in dichloromethane (5 mL) and TFA (1 mL, 12.98 mmol, 472.14 eq) was stirred at RT for 5 h, then concentrated in vacuo. The crude material was purified by reversed phase HPLC to afford the title compound (7 mg, 36.37%) as white lyoph powder. MS: 698.3, [M−H]$^-$, ESI neg.

The following compounds were prepared in analogy to example Z31.

| | Ex | Product Name | Reactant | MS |
|---|---|---|---|---|
| 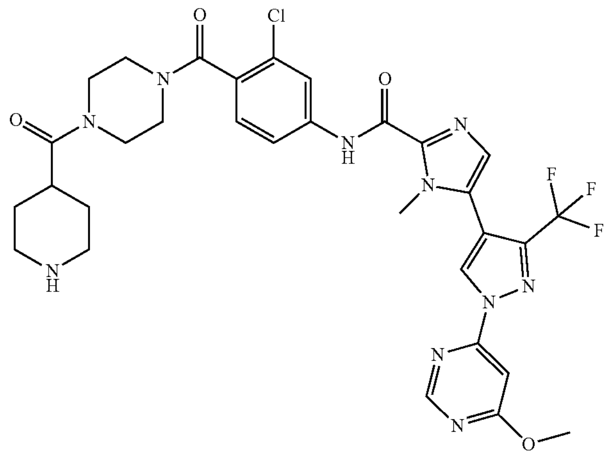 [SMILES: COc1cc(-n2cc(-c3cnc(C(=O)Nc4ccc(C(=O)N5CCN(C(=O)C6CCNCC6)CC5)c(Cl)c4)n3C)c(C(F)(F)F)n2)ncn1] | Z49 | N-[3-chloro-4-(4-isonipecotoylpiperazine-1-carbonyl)phenyl]-5-[1-(6-methoxypyrimidin-4-yl)-3-(trifluoromethyl)pyrazol-4-yl]-1-methyl-imidazole-2-carboxamide | 4-chloro-6-methoxy-pyrimidine | 699.5, [M −H]⁻, ESI neg |
| 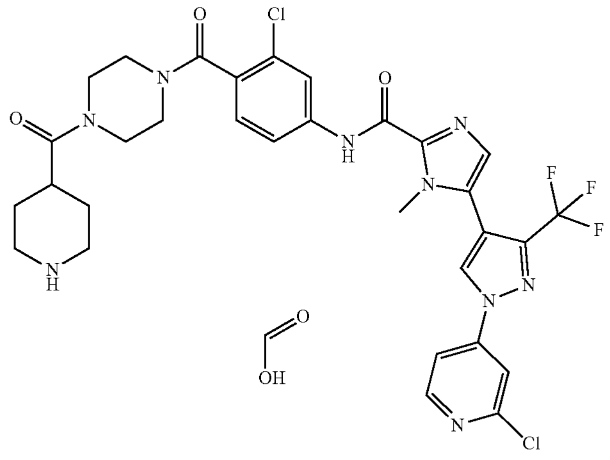 [SMILES: Cn1c(-c2cn(-c3ccnc(Cl)c3)nc2C(F)(F)F)cnc1C(=O)Nc1ccc(C(=O)N2CCN(C(=O)C3CCNCC3)CC2)c(Cl)c1 ; O=CO] | Z50 | N-[3-chloro-4-(4-isonipecotoylpiperazine-1-carbonyl)phenyl]-5-[1-(2-chloro-4-pyridyl)-3-(trifluoromethyl)pyrazol-4-yl]-1-methyl-imidazole-2-carboxamide .1:1 formic acid | 2-chloro-4-fluoro-pyridine | 702.4, [M −H]⁻, ESI neg |
| 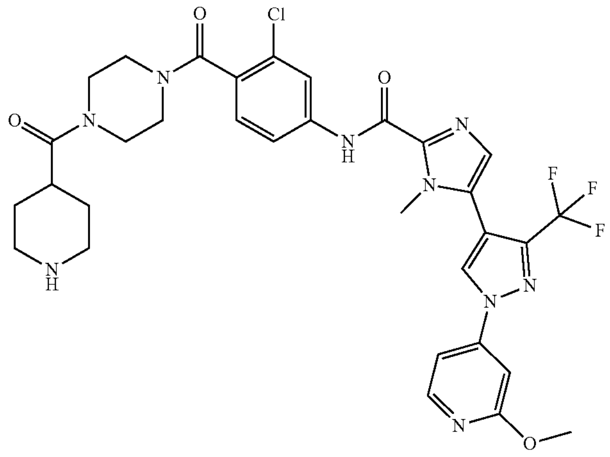 | Z73 | N-[3-chloro-4-(4-isonipecotoylpiperazine-1-carbonyl)phenyl]-5-[1-(2-methoxy-4-pyridyl)-3-(trifluoromethyl)pyrazol-4-yl]-1-methyl-imidazole-2-carboxamide | 4-fluoro-2-methoxy-pyridine | 744.4, [M + HCOO]⁻, ESI neg |

Example Z10

5-[1-(6-amino-3-pyridyl)-3-(trifluoromethyl)pyrazol-4-yl]-N-[3-chloro-4-(4-isonipecotoylpiperazine-1-carbonyl)phenyl]-1-methyl-imidazole-2-carboxamide; 1:1 formic acid

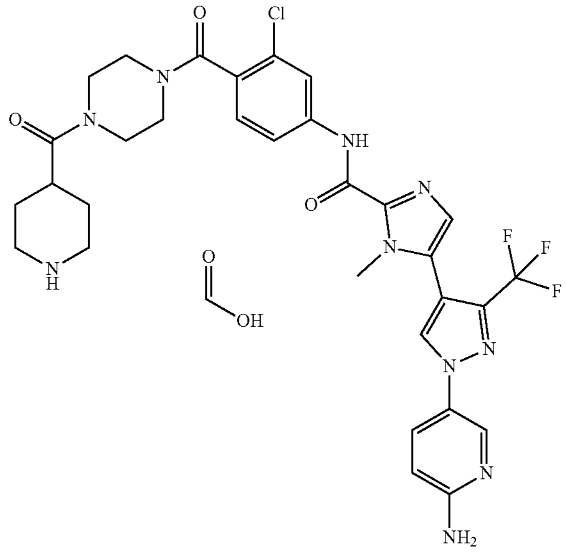 [SMILES: Cn1c(-c2cn(-c3ccc(N)nc3)nc2C(F)(F)F)cnc1C(=O)Nc1ccc(C(=O)N2CCN(C(=O)C3CCNCC3)CC2)c(Cl)c1 ; O=CO]

Step 1: 4-[4-[2-chloro-4-[[1-methyl-5-[1-(6-nitro-3-pyridyl)-3-(trifluoromethyl)pyrazol-4-yl]imidazole-2-carbonyl]amino]benzoyl]piperazine-1-carbonyl]piperidine-1-carboxylic acid tert-butyl ester To a 5 ml microwave vial was added 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylic acid tert-butyl ester [2489205-74-3] (100 mg, 0.144 mmol, 1 eq), potassium carbonate (59.82 mg, 0.433 mmol, 3 eq) and 5-chloro-2-nitro-pyridine (34.31 mg, 0.216 mmol, 1.5 eq) in N-methyl-2-pyrrolidinone (1.5 mL). The vial was capped and heated in the microwave at 120° C. for 60 min. To the reaction was added water and the product was extracted with AcOEt. The crude material was purified by column chromatography on silica gel using MeOH/DCM as eluent to give the title compound (98.3 mg, 48.48%) as brown solid, which was used without further purification. MS: 815.3 [M+H]+, ESI pos.

Step 2: 5-[1-(6-amino-3-pyridyl)-3-(trifluoromethyl)pyrazol-4-yl]-N-[3-chloro-4-(4-isonipecotoylpiperazine-1-carbonyl)phenyl]-1-methyl-imidazole-2-carboxamide; 1:1 formic acid To a mixture of 4-[4-[2-chloro-4-[[1-methyl-5-[1-(6-nitro-3-pyridyl)-3-(trifluoromethyl)pyrazol-4-yl]imidazole-2-carbonyl]amino]benzoyl]piperazine-1-carbonyl]piperidine-1-carboxylic acid tert-butyl ester (98.3 mg, 0.070 mmol, 1 eq) in ethanol (900 uL) and water (300 uL) were added ammonium chloride (187.06 mg, 3.5 mmol, 50 eq) and zinc (91.49 mg, 1.4 mmol, 20 eq) and the reaction mixture was stirred at RT for 1 hour. Then the reaction mixture was filtered, the solvents evaporated and the residue dried under high vacuum. The residue was dissolved in dichloromethane (1 ml) and 4 M HCl in dioxane (87.42 uL, 0.350 mmol, 5 eq) was added. The reaction mixture was stirred at RT for 1 hour. The reaction mixture was concentrated to dryness, then purified by prep HPLC to afford the title compound (9.2 mg, 17.27%) as light yellow lyoph solid. MS: 685.2[M+H]+, ESI pos.

Example Z29

5-[1-(5-aminopyrazin-2-yl)-3-(trifluoromethyl)pyrazol-4-yl]-N-[3-chloro-4-(4-isonipecotoylpiperazine-1-carbonyl)phenyl]-1-methyl-imidazole-2-carboxamide; 1:1 formic acid

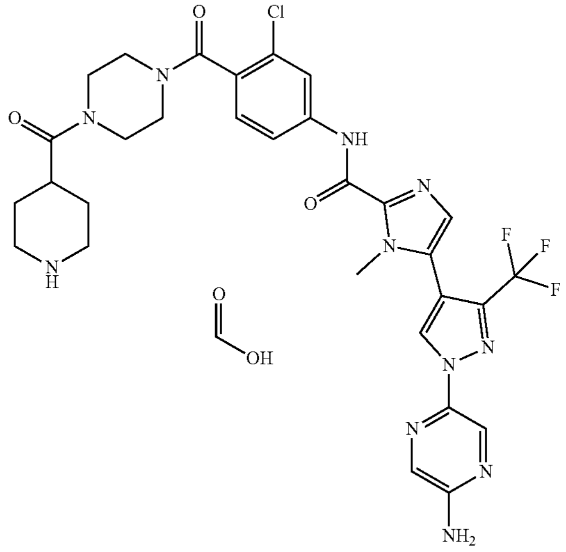 [SMILES: Cn1c(-c2cn(-c3cnc(N)cn3)nc2C(F)(F)F)cnc1C(=O)Nc1ccc(C(=O)N2CCN(C(=O)C3CCNCC3)CC2)c(Cl)c1 ; O=CO]

This example was prepared in analogy to example Z10 using 2-bromo-5-nitro-pyrazine in acetonitrile at 80° C. in the first step. The title compound was obtained as off white lyoph solid (4.2 mg). MS: 686.2 [M+H]+, ESI pos.

Example Z28

N-[4-(5-aminopentylcarbamoyl)-3-chloro-phenyl]-5-[1-(5-amino-2-pyridyl)-3-(trifluoromethyl)pyrazol-4-yl]-1-methyl-imidazole-2-carboxamide; 1:1 hydrogen chloride

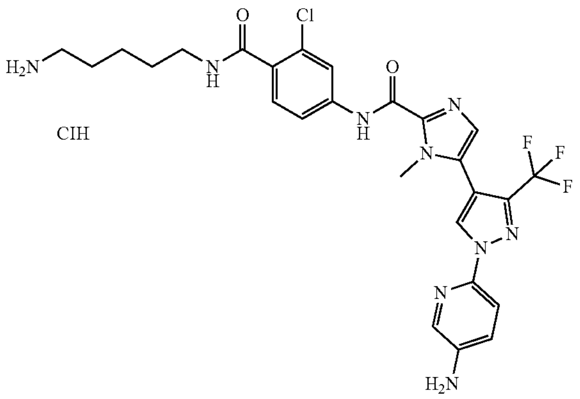 [SMILES: Cn1c(-c2cn(-c3ccc(N)cn3)nc2C(F)(F)F)cnc1C(=O)Nc1ccc(C(=O)NCCCCCN)c(Cl)c1 ; "CIH"]

Step 1: N-[5-[[2-chloro-4-[[1-methyl-5-[3-(trifluoromethyl)-1H-pyrazol-4-yl]imidazole-2-carbonyl]amino]benzoyl]amino]pentyl]carbamic acid tert-butyl ester 2-Chloro-4-[[1-methyl-5-[3-(trifluoromethyl)-1H-pyrazol-4-yl]imidazole-2-carbonyl]amino]benzoic acid [2489205-74-3] (200 mg, 0.483 mmol, 1 eq) was combined with N,N-dimethylformamide (4 mL) to give a light yellow suspension. DIPEA (187 mg, 253.29 uL, 1.45 mmol, 3 eq) and N-(5-aminopentyl)carbamic acid tert-butyl ester (147 mg, 150.9 uL, 0.725 mmol, 1.5 eq) were added, followed by addition of HATU (275.7 mg, 0.725 mmol, 1.5 eq). The reaction mixture was stirred at Rt overnight Water was added and the mixture extracted with AcOEt. The organic layer was washed with a 5% LiCl solution, with brine and then dried over $Na_2SO_4$. After filtration and evaporation of the solvents, the residue was purified by column chromatography on silica gel using DCM/MeOH as eluent to give the title compound (212 mg, 68.94%) as brown foam. MS: 596 $[M-H]^-$, ESI neg.

Step 2+3: N-[4-(5-aminopentylcarbamoyl)-3-chloro-phenyl]-5-[1-(5-amino-2-pyridyl)-3-(trifluoromethyl)pyrazol-4-yl]-1-methyl-imidazole-2-carboxamide; 1:1 hydrogen chloride The title compound was prepared in analogy to example Z10 using 2-bromo-5-nitropyridine in acetonitrile at 80° C. in the first step and was obtained as yellow solid (177 mg with 77% purity by UV). MS: 590.2 $[M+H]^+$, ESI pos.

Example Z75

N-[3-chloro-4-(4-isonipecotoylpiperazine-1-carbonyl)phenyl]-5-[1-(6-methoxy-3-pyridyl)-3-(trifluoromethyl)pyrazol-4-yl]-1-methyl-imidazole-2-carboxamide

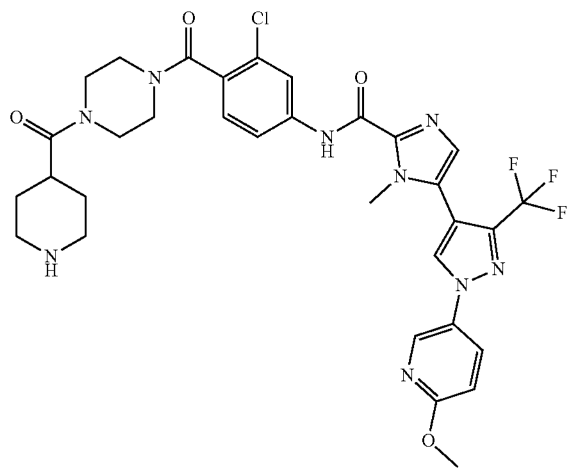 [SMILES: COc1ccc(-n2cc(-c3cnc(C(=O)Nc4ccc(C(=O)N5CCN(C(=O)C6CCNCC6)CC5)c(Cl)c4)n3C)c(C(F)(F)F)n2)cn1]

Step 1: 4-[4-[2-chloro-4-[[5-[1-(6-methoxy-3-pyridyl)-3-(trifluoromethyl)pyrazol-4-yl]-1-methyl-imidazole-2-carbonyl]amino]benzoyl]piperazine-1-carbonyl]piperidine-1-carboxylic acid tert-butyl ester A mixture of 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylic acid tert-butyl ester [2489205-74-3] (56 mg, 0.081 mmol, 1 eq) and (6-methoxy-3-pyridyl)boronic acid (22.24 mg, 0.145 mmol, 1.8 eq) in N,N-dimethylformamide, extra dry (1.25 mL) was treated with cupric acetate (30.82 mg, 0.170 mmol, 2.1 eq) and pyridine (12.78 mg, 13.07 uL, 0.162 mmol, 2 eq), and the mixture was stirred at 50° C. for 20.5 h under air. The reaction mixture was suspended in aq. $NaHCO_3$ (15 mL) and 5% aq. EDTA (5 mL), and extracted with EtOAc (3×10 mL). The organic layers were washed with brine (10 mL), dried ($Na_2SO_4$), filtered, and evaporated. Purification by MPLC using Heptane/EtOAc/EtOH as eluent afforded the title compound (21 mg, 29.88%) as off-white solid. MS 798.5, $[M-H]^-$, ESI neg.

Step 2: N-[3-chloro-4-(4-isonipecotoylpiperazine-1-carbonyl)phenyl]-5-[1-(6-methoxy-3-pyridyl)-3-(trifluoromethyl)pyrazol-4-yl]-1-methyl-imidazole-2-carboxamide A mixture of 4-[4-[2-chloro-4-[[5-[1-(6-methoxy-3-pyridyl)-3-(trifluoromethyl)pyrazol-4-yl]-1-methyl-imidazole-2-carbonyl]amino]benzoyl]piperazine-1-carbonyl]piperidine-1-carboxylic acid tert-butyl ester (31 mg, 0.036 mmol, 1 eq) in dichloromethane (4 mL) and TFA (1.18 g, 0.800 mL, 10.38 mmol, 291.36 eq) was stirred at RT for 3 h, and concentrated. Purification by reversed phase HPLC afforded the title compound (3.1 mg, 11.8%) as white lyoph solid. MS: 744.4, $[M+HCOO]^-$, ESI neg.

Example Z30

N-[3-chloro-4-[4-[(2S,4R)-4-hydroxyprolyl]piperazine-1-carbonyl]phenyl]-5-[1-(6-chloro-3-pyridyl)-3-(trifluoromethyl)pyrazol-4-yl]-1-methyl-imidazole-2-carboxamide; 1:1 hydrogen chloride

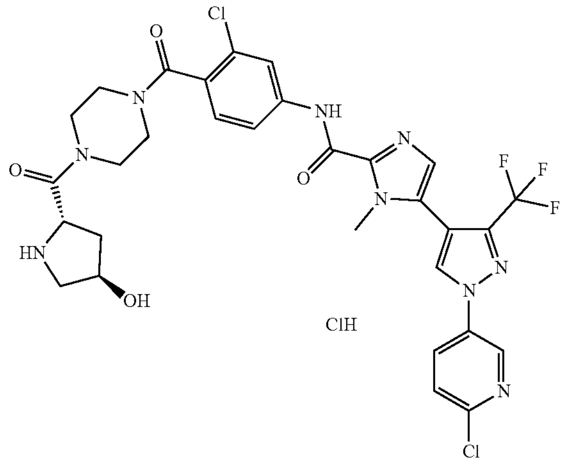 [SMILES: Cn1c(-c2cn(-c3ccc(Cl)nc3)nc2C(F)(F)F)cnc1C(=O)Nc1ccc(C(=O)N2CCN(C(=O)[C@@H]3C[C@@H](O)CN3)CC2)c(Cl)c1 ; Cl]

Step 1: methyl 2-chloro-4-(1-methyl-5-(3-(trifluoromethyl)-1H-pyrazol-4-yl)-1H-imidazole-2-carboxamido)benzoate Methyl 4-(5-bromo-1-methyl-1H-imidazole-2-carboxamido)-2-chlorobenzoate [2489205-77-6] (3.3 g, 8.86 mmol, Eq: 1), (3-(trifluoromethyl)-1H-pyrazol-4-yl)boronic acid (1.59 g, 8.86 mmol, Eq: 1) and Na2CO3 (2.16 g, 20.4 mmol, Eq: 2.30) in dioxane (20 ml) and water (2 ml) were sparged with argon for 2 minutes. Then 1,1'-bis(di-tert-butylphosphino)ferrocene palladium dichloride (dtbpf) (577 mg, 886 μmol, Eq: 0.1) was added. The mixture was split between 3 pressure tubes which were sealed and then heated to 100° C. for 60 min under microwave irradiation. Again (3-(trifluoromethyl)-1H-pyrazol-4-yl)boronic acid (797 mg, 4.43 mmol, Eq: 0.5) and 1,1'-bis(di-tert-butylphosphino) ferrocene palladium dichloride (dtbpf) (289 mg, 443 μmol, Eq: 0.05) were added and the reaction heated to 100° C. for 30 minutes under microwave irradiation. The reaction mixture was filtered over dicalite and washed with MeOH. The obtained solution was concentrated in vacuo and the residue was purified by silica gel chromatography using MeOH in DCM as eluent to afford the title compound (2.85 g, 6.33 mmol, 71.5% yield) as a brown solid. MS: 428.2 [M+H]+.

Step 2: 2-chloro-4-[[1-methyl-5-[1-(6-nitro-3-pyridyl)-3-(trifluoromethyl)pyrazol-4-yl]imidazole-2-carbonyl]amino]benzoic acid methyl ester/2-chloro-4-[[5-[1-(6-chloro-3-pyridyl)-3-(trifluoromethyl)pyrazol-4-yl]-1-methyl-imidazole-2-carbonyl]amino]benzoic acid methyl ester The title compound was prepared in analogy to example Z10 starting from 2-chloro-4-[[1-methyl-5-[3-(trifluoromethyl)-1H-pyrazol-4-yl]imidazole-2-carbonyl]amino]benzoic acid methyl ester (800 mg) using and 5-chloro-2-nitropyridine and was obtained (215.5 mg, 11.02%) as light yellow solid, in mixture ~2:1 with 2-chloro-4-[[5-[1-(6-chloro-3-pyridyl)-3-(trifluoromethyl)pyrazol-4-yl]-1-methyl-imidazole-2-carbonyl]amino]benzoic acid methyl ester. The obtained material was used without further purification. MS: 550.1 $[M+H]^+$, ESI pos.

Step 3: 2-chloro-4-[[5-[1-(6-chloro-3-pyridyl)-3-(trifluoromethyl)pyrazol-4-yl]-1-methyl-imidazole-2-carbonyl]amino]benzoic acid The obtained mixture of 2-chloro-4-[[5-[1-(6-chloro-3-pyridyl)-3-(trifluoromethyl)pyrazol-4-yl]-1-methyl-imidazole-2-carbonyl]amino]benzoic acid methyl ester and 2-chloro-4-[[1-methyl-5-[1-(6-nitro-3-pyridyl)-3-(trifluoromethyl)pyrazol-4-yl]imidazole-2-carbonyl]amino]benzoic acid methyl ester (215 mg, 0.197 mmol, 1 eq) was combined with methanol (0.500 mL) and tetrahydrofuran (1 mL) to give a yellow solution. 1 M LiOH (493.51 uL, 0.494 mmol, 2.5 eq) was added and the reaction mixture was stirred at RT overnight, then for another 24 h at 40° C. After cooling down to RT, the volatiles were removed. The residue was diluted with water and acidified with a 1M HCl solution. The resulting suspension was filtered and washed with water. The obtained light brown solid were purified by preparative reversed phase HPLC to afford 2-chloro-4-[[5-[1-(6-chloro-3-pyridyl)-3-(trifluoromethyl)pyrazol-4-yl]-1-methyl-imidazole-2-carbonyl]amino]benzoic acid (23.4 mg, 18.05%) as light yellow solid. MS: 525.0 $[M+H]^+$, ESI pos.

Step 4: (2S,4R)-2-[4-[2-chloro-4-[[5-[1-(6-chloro-3-pyridyl)-3-(trifluoromethyl)pyrazol-4-yl]-1-methyl-imidazole-2-carbonyl]amino]benzoyl]piperazine-1-carbonyl]-4-hydroxy-pyrrolidine-1-carboxylic acid tert-butyl ester 2-chloro-4-[[5-[1-(6-chloro-3-pyridyl)-3-(trifluoromethyl)pyrazol-4-yl]-1-methyl-imidazole-2-carbonyl]amino] benzoic acid (23 mg, 0.035 mmol, 1 eq) was combined with N,N-dimethylformamide (400 uL) to give a light yellow solution. (2S,4R)-4-hydroxy-2-(piperazine-1-carbonyl)pyrrolidine-1-carboxylic acid tert-butyl ester (15.7 mg, 0.053 mmol, 1.5 eq), DIPEA (13.6 mg, 18.3 uL, 0.105 mmol, 3 eq) and HATU (19.98 mg, 0.053 mmol, 1.5 eq) were added and the reaction was stirred at RT for 1 h. Then water was added to the reaction mixture and the product was extracted with AcOEt. The organic layer was washed with a 5% LiCl solution, brine and dried over $Na_2SO_4$. After filtration and evaporation to dryness, the crude material was purified by silica gel chromatography using DCM:MeOH as eluent to afford the title compound (29 mg, 99.56%) as off-white foam. MS: 806.2 $[M+H]^+$, ESI pos.

Step 5: N-[3-chloro-4-[4-[(2S,4R)-4-hydroxyprolyl]piperazine-1-carbonyl]phenyl]-5-[1-(6-chloro-3-pyridyl)-3-(trifluoromethyl)pyrazol-4-yl]-1-methyl-imidazole-2-carboxamide; 1:1 hydrogen chloride In a 5 ml round-bottomed flask, (2S,4R)-2-[4-[2-chloro-4-[[5-[1-(6-chloro-3-pyridyl)-3-(trifluoromethyl)pyrazol-4-yl]-1-methyl-imidazole-2-carbonyl]amino]benzoyl]piperazine-1-carbonyl]-4-hydroxy-pyrrolidine-1-carboxylic acid tert-butyl ester (5 mg, 0.006 mmol, 1 eq) was combined with dichloromethane (100 uL) to give a colorless solution. 4 M HCl in dioxane (7.52 uL, 0.030 mmol, 5 eq) was added and the reaction mixture was stirred at RT for 1 h. After removal of the volatiles, the residue was lyophilized to afford the title compound (3.4 mg, 68.5%) as white lyoph solid. MS: 706.2 $[M+H]^+$, ESI pos.

Example Z89

5-[1-[5-(2-aminoethylamino)-2-pyridyl]-3-(trifluoromethyl)pyrazol-4-yl]-N-[3-chloro-4-(4-isonipecotoylpiperazine-1-carbonyl)phenyl]-1-methyl-imidazole-2-carboxamide; 1:2 2,2,2-trifluoroacetic acid

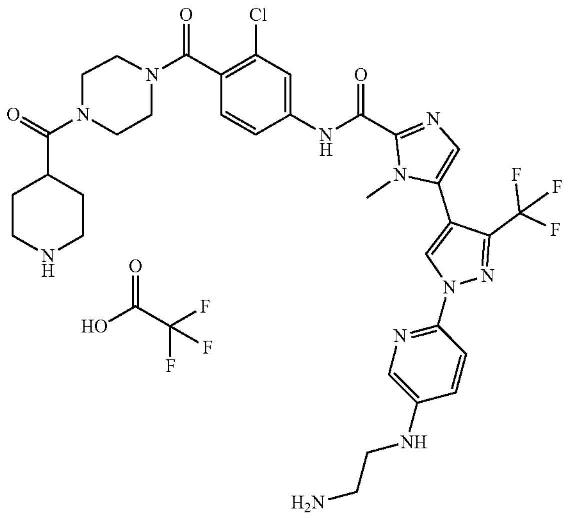 [SMILES: Cn1c(-c2cn(-c3ccc(NCCN)cn3)nc2C(F)(F)F)cnc1C(=O)Nc1ccc(C(=O)N2CCN(C(=O)C3CCNCC3)CC2)c(Cl)c1 ; O=C(O)C(F)(F)F]

Step 1: 4-[4-[4-[[5-[1-(5-amino-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylic acid 9H-fluoren-9-ylmethyl ester A mixture of 5-[1-(5-amino-2-pyridyl)-3-(trifluoromethyl)pyrazol-4-yl]-N-[3-chloro-4-(piperazine-1-carbonyl)

phenyl]-1-methyl-imidazole-2-carboxamide 0.1:1 hydrogen chloride (100 mg, 0.162 mmol, 1 eq) and 1-[(9h-fluoren-9-ylmethoxy)carbonyl]piperidine-4-carboxylic acid (59.8 mg, 0.170 mmol, 1.05 eq) in N,N-dimethylformamide (2 mL) was treated with N-ethyldiisopropylamine (83.8 mg, 113. uL, 0.649 mmol, 4 eq), and subsequently with PyAOP (101.5 mg, 0.195 mmol, 1.2 eq), and the mixture was stirred at RT for 2.5 h. The reaction mixture was transferred into half-sat. $NaHCO_3$ (50 mL), and extracted with EtOAc (3×22 mL). The combined organics were washed with brine (20 mL), dried ($Na_2SO_4$), filtered, and evaporated. Purification by MPLC using heptane/EtOAc/EtOH as eluent afforded the title compound (137 mg, 85.65%) as light yellow solid. MS: 454.6, $[M+2H]^{2+}$, ESI pos.

Step 2: 4-[4-[4-[[5-[1-[5-[2-(tert-butoxycarbonylamino)ethylamino]-2-pyridyl]-3-(trifluoromethyl) pyrazol-4-yl]-1-methyl-imidazole-2-carbonyl] amino]-2-chloro-benzoyl]piperazine-1-carbonyl] piperidine-1-carboxylic acid 9H-fluoren-9-ylmethyl ester A mixture of 4-[4-[4-[[5-[1-(5-amino-2-pyridyl)-3-(trifluoromethyl)pyrazol-4-yl]-1-methyl-imidazole-2-carbonyl] amino]-2-chloro-benzoyl]piperazine-1-carbonyl]piperidine-1-carboxylic acid 9H-fluoren-9-ylmethyl ester (137 mg, 0.139 mmol, 1 eq) in dichloromethane (2 mL) was treated with molecular sieves, 3 Å, N-(2-ketoethyl)carbamic acid tert-butyl ester (33.2 mg, 0.208 mmol, 1.5 eq), and acetic acid (15.9 uL, 0.278 mmol, 2 eq), cooled to 0° C., and stirred for 10 min. Subsequently, sodium triacetoxyborohydride (51.5 mg, 0.243 mmol, 1.75 eq) was added portionwise during 30 min, after which stirring was continued at RT for 2 h. The mixture was diluted with EtOAc and half-sat. $NaHCO_3$ (50 mL) and extracted with EtOAc (3×20 mL). The combined organics were washed with brine (20 mL), dried ($Na_2SO_4$), filtered, and evaporated. Purification by MPLC using heptane/EtOAc/EtOH as eluent afforded the title compound (128 mg, 78.94%) as off-white solid, which was used without further purification. MS: 1094.9, $[M+HCOO]^-$, ESI neg.

Step 3: N-[2-[[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]amino]ethyl]carbamic acid tert-butyl ester A mixture of 4-[4-[4-[[5-[1-[5-[2-(tert-butoxycarbonylamino)ethylamino]-2-pyridyl]-3-(trifluoromethyl)pyrazol-4-yl]-1-methyl-imidazole-2-carbonyl]amino]-2-chloro-benzoyl]piperazine-1-carbonyl]piperidine-1-carboxylic acid 9H-fluoren-9-ylmethyl ester (128 mg, 0.110 mmol, 1 eq) in acetonitrile (2.5 mL) was treated with 2 M dimethylamine in THF (548.3 uL, 1.1 mmol, 10 eq), and the mixture was stirred at RT for 3 h, and evaporated. Purification by MPLC using DCM/MeOH/$Et_3N$ as eluent afforded a residue, which was dissolved in 0.1 M NaOH (25 mL), and extracted with EtOAc (3×12 mL). The combined organics were washed with brine (12 mL), dried ($Na_2SO_4$), filtered, and evaporated to afford the title compound (60 mg, 60.77%) as white solid. MS: 872.6, $[M+HCOO]^-$, ESI neg.

Step 4: 5-[1-[5-(2-aminoethylamino)-2-pyridyl]-3-(trifluoromethyl)pyrazol-4-yl]-N-[3-chloro-4-(4-isonipecotoylpiperazine-1-carbonyl)phenyl]-1-methyl-imidazole-2-carboxamide; 1:2 2,2,2-trifluoroacetic acid A mixture of N-[2-[[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl] amino]ethyl]carbamic acid tert-butyl ester (23 mg, 0.026 mmol, 1 eq) in dichloromethane (0.958 mL) and 4 M HCl (613.13 mg, 510.94 uL, 2.04 mmol, 80 eq) was stirred at RT for 4.5 h, and evaporated. Purification by reversed phase HPLC afforded the title compound (12 mg, 49.12%) as white lyoph solid. 772.7, $[M+HCOO]^-$, ESI neg.

Example Z76

5-[1-(5-amino-2-pyridyl)-3-(trifluoromethyl)pyrazol-4-yl]-N-[3-chloro-4-(diethylcarbamoyl)phenyl]-1-methyl-imidazole-2-carboxamide

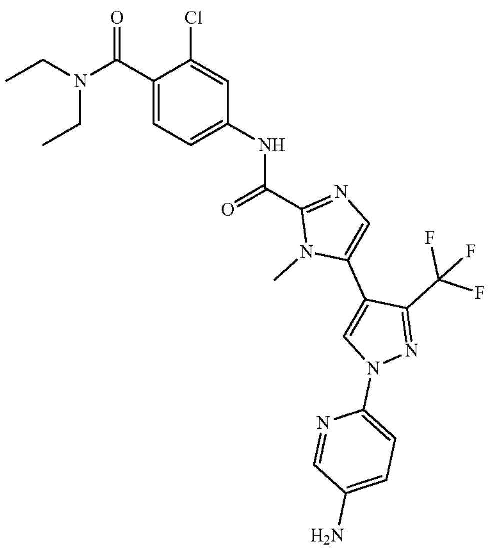 [SMILES: CCN(CC)C(=O)c1ccc(NC(=O)c2ncc(-c3cn(-c4ccc(N)cn4)nc3C(F)(F)F)n2C)cc1Cl]

To 4-[[5-[1-(5-amino-2-pyridyl)-3-(trifluoromethyl)pyrazol-4-yl]-1-methyl-imidazole-2-carbonyl]amino]-2-chloro-benzoic acid (18 mg, 0.029 mmol, 1 eq) in N,N-dimethylformamide (2 mL) and Et3N (14.58 mg, 20.09 uL, 0.144 mmol, 5 eq) was added TBTU (12.03 mg, 0.037 mmol, 1.3 eq) and DSPE-PEG-2K-amine [47922-26-4] (104.48 mg, 0.037 mmol, 1.3 eq) and the reaction mixture was stirred at RT. The mixture was purified by preparative HPLC to afford the title compound (5.6 mg, 33.94%) as light yellow powder and unexpected byproduct. MS: 559.3 $[M-H]^-$, ESI neg.

Example Z88

N-[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]isonipecotamide; 1:2 hydrogen chloride

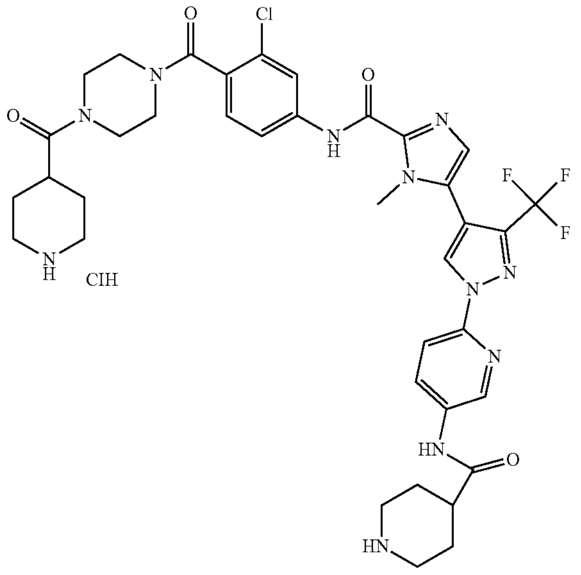

Step 1: 4-[[6-[4-[2-[[4-[4-(1-tert-butoxycarbonylisonipecotoyl)piperazine-1-carbonyl]-3-chloro-phenyl]carbamoyl]-3-methyl-imidazol-4-yl]-3-(trifluoromethyl)pyrazol-1-yl]-3-pyridyl]carbamoyl]piperidine-1-carboxylic acid tert-butyl ester 1-tert-butoxycarbonylisonipecotic acid (264.2 mg, 1.15 mmol, 1.05 eq) and 5-[1-(5-amino-2-pyridyl)-3-(trifluoromethyl)pyrazol-4-yl]-N-[3-chloro-4-(piperazine-1-carbonyl)phenyl]-1-methyl-imidazole-2-carboxamide (630 mg, 1.1 mmol, 1 eq) were dissolved in N,N-dimethylformamide, extra dry (5.49 mL). DIEA (425.6 mg, 575.1 uL, 3.29 mmol, 3 eq) was added and the mixture cooled to 0° C. HATU (500.8 mg, 1.32 mmol, 1.2 eq) was added and the mixture stirred at rt overnight. The mixture was diluted with DCM and washed with 2×30 mL of water and brine. The aqueous layer was extracted with 2×30 mL of DCM. The combined organic phases were dried and concentrated in vacuo. The crude material was purified by silica gel chromatography the title compound (110 mg, 9.35%) as pink waxy solid. MS: 896.4 $[M+H-BOC]^+$, ESI pos.

Step 2: N-[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]isonipecotamide; 1:2 hydrogen chloride 4-[[6-[4-[2-[[4-[4-(1-tert-butoxycarbonylisonipecotoyl)piperazine-1-carbonyl]-3-chloro-phenyl]carbamoyl]-3-methyl-imidazol-4-yl]-3-(trifluoromethyl)pyrazol-1-yl]-3-pyridyl]carbamoyl]piperidine-1-carboxylic acid tert-butyl ester (110 mg, 0.103 mmol, 1 eq) was dissolved in 4 M hydrochloric acid in 1,4-dioxane (769.97 uL, 3.08 mmol, 30 eq) and the mixture stirred at rt overnight The mixture was triturated with diethyl ether (6×50 mL), the solid collected and concentrated in vacuo to afford the title compound (79 mg, 81.45%) as light brown crystalline solid. MS: 794.5 $[M-H]^-$, ESI neg.

Example Z9

N-[3-chloro-4-[4-(1-methylpiperidine-4-carbonyl)piperazine-1-carbonyl]phenyl]-5-[1-[4-(methoxymethyl)-1H-pyrazol-3-yl]-3-(trifluoromethyl)pyrazol-4-yl]-1-methyl-imidazole-2-carboxamide; formic acid

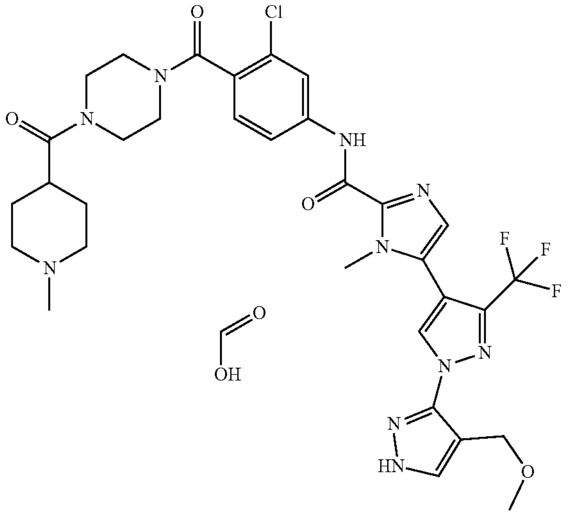 [SMILES: COCc1c[nH]nc1-n1cc(-c2cnc(C(=O)Nc3ccc(C(=O)N4CCN(C(=O)C5CCN(C)CC5)CC4)c(Cl)c3)n2C)c(C(F)(F)F)n1 ; O=CO]

Step 1: 5-bromo-N-[3-chloro-4-[4-(1-methylpiperidine-4-carbonyl)piperazine-1-carbonyl]phenyl]-1-methyl-imidazole-2-carboxamide To a solution of 1-methylpiperidine-4-carboxylic acid (3301.83 mg, 23.06 mmol, 1.2 eq) in DMF (80 mL) was added N,N-diisopropylethylamine (10.04 mL, 57.65 mmol, 3 eq), 0-(7-azabenzotriazol-1-yl)-N,N,N',N'-tetramethyluronium hexafluorophosphate (8768.37 mg, 23.06 mmol, 1.2 eq) and 5-bromo-N-[3-chloro-4-(piperazine-1-carbonyl)phenyl]-1-methyl-imidazole-2-carboxamide [2489205-92-5] (8.2 g, 19.2 mmol, 1 eq) at 0° C. The mixture was stirred at 0° C. for 2 h under $N_2$. The mixture was directly purified by reversed-phase chromatography (FA as additive) and dried by lyophilization to give the title compound (7 g, 12.68 mmol, 66.01% yield) as a white solid. MS: 553.1 $[M+H]^+$, ESI pos.

Step 2: N-[3-chloro-4-[4-(1-methylpiperidine-4-carbonyl)piperazine-1-carbonyl]phenyl]-5-[1-[4-(methoxymethyl)-1-(2-trimethylsilylethoxymethyl)pyrazol-3-yl]-3-(trifluoromethyl)pyrazol-4-yl]-1-methyl-imidazole-2-carboxamide To a solution of 5-bromo-N-[3-chloro-4-[4-(1-methylpiperidine-4-carbonyl)piperazine-1-carbonyl]phenyl]-1-methyl-imidazole-2-carboxamide (144.99 mg, 0.260 mmol, 1 eq) and 2-[[4-(methoxymethyl)-3-[4-(4,4,5,5-tetramethyl-1,3,2-dioxaborolan-2-yl)-3-(trifluoromethyl)pyrazol-1-yl]pyrazol-1-yl]methoxy]ethyl-trimethyl-silane (200.0 mg, 0.260 mmol, 1 eq) in 1,4-dioxane (5 mL) and water (0.500 mL) was added sodium carbonate (55.69 mg, 0.530 mmol, 2 eq) and CyJohnPhos Pd(crotyl)Cl (Pd-188 [692782-19-7]) (25.69 mg, 0.040 mmol, 0.150 eq) under argon in a glove box. The mixture was stirred at 90° C. for 2 h. The reaction mixture was filtered and the filtrate was concentrated in vacuum to give a residue, which was purified by flash column (0.1% FA as additive) and dried by lyophilization to give the title compound (100 mg, 0.120 mmol, 44.92% yield) as a yellow solid. MS: 847.6, [M+H], ESI pos.

Step 3: N-[3-chloro-4-[4-(1-methylpiperidine-4-carbonyl)piperazine-1-carbonyl]phenyl]-5-[1-[4-(methoxymethyl)-1H-pyrazol-3-yl]-3-(trifluoromethyl)pyrazol-4-yl]-1-methyl-imidazole-2-carboxamide; formic acid To a solution of N-[3-chloro-4-[4-(1-methylpiperidine-4-carbonyl)piperazine-1-carbonyl]phenyl]-5-[1-[4-(methoxymethyl)-1-(2-trimethylsilylethoxymethyl)pyrazol-3-yl]-3-(trifluoromethyl)pyrazol-4-yl]-1-methyl-imidazole-2-carboxamide (100.0 mg, 0.120 mmol, 1 eq) in DCM (2.5 mL) was added TFA (0.3 mL). The mixture was stirred at 20° C. for 1 h. Then the mixture was concentrated in vacuum. The residue was dissolved in 1,4-dioxane (2.5 mL) and then NH3·H2O (0.5 mL) was added. The mixture was stirred at 20° C. for 1 h. The reaction mixture was filtered and the filtrate was concentrated in vacuum. The residue was purified by Prep-HPLC (0.1% FA as additive) and dried by lyophilization to give the title compound (50 mg, 0.070 mmol, 52.82% yield) as a white solid. MS: 717.2, [M+H], ESI pos.

Example Z77

5-[1-(6-amino-5-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

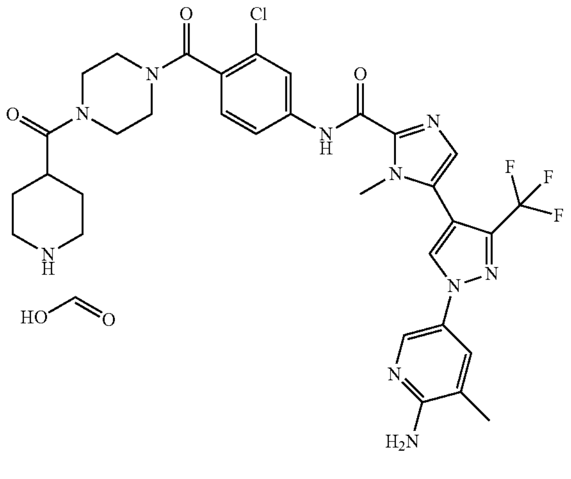

Step 1: tert-butyl 4-[4-[4-[[5-[1-(6-amino-5-methyl-3-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate [2489205-74-3] (50.0 mg, 0.070 mmol, 1 eq), 2-amino-5-iodo-3-methylpyridine (25.32 mg, 0.110 mmol, 1.5 eq), 2-(2,6-dimethylanilino)-2-oxo-acetic acid (6.97 mg, 0.040 mmol, 0.500 eq), phosphoric acid, potassium salt (45.9 mg, 0.220 mmol, 3 eq) in DMSO (2 mL) was added copper(I) iodide (13.7 mg, 0.070 mmol, 1 eq) under N2. The mixture was degassed and then stirred at 120° C. for 16 h under N2. The reaction mixture was cooled to room temperature. EtOAc (5 ml) and water (10 ml) were added and layers were separated. The aqueous phase was extracted with EtOAc (10 ml*2). Combined extracts were washed with brine (30 ml), dried over MgSO4, filtered and concentrated in vacuum. The residue was purified by reversed phase HPLC (FA condition) to afford the title compound (50 mg, 86.7% yield) as yellow solid. MS: 799.5[M+H]$^+$, ESI pos.

Step 2: 5-[1-(6-amino-5-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid To a solution of tert-butyl 4-[4-[4-[[5-[1-(6-amino-5-methyl-3-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (50.0 mg, 0.060 mmol, 1 eq) in DCM (2 mL) was added trifluoroacetic acid (2.0 mL, 25.96 mmol, 414.96 eq). The mixture was stirred at 10° C. for 1 h. The mixture was concentrated in vacuum. The residue was purified by Prep-HPLC (FA condition) to afford the title compound (22.2 mg, 0.030 mmol, 47.6200 yield) as white solid. MS: 699.3 [M+H]$^+$, ESI pos.

The following compounds were prepared in analogy to example Z77.

| Structure | Ex | Product name | reactants | MS |
|---|---|---|---|---|
| 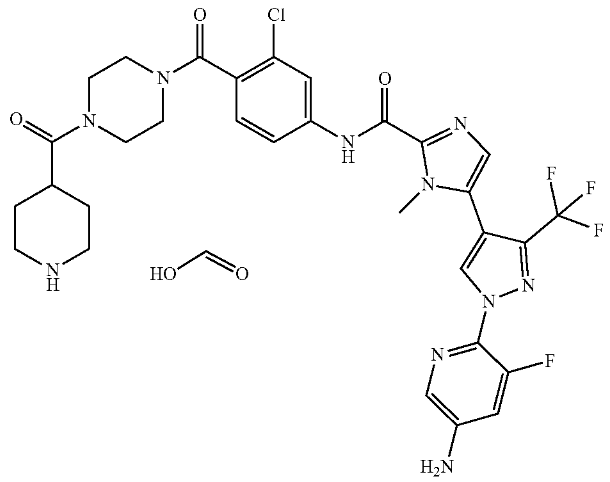 [SMILES: Cn1c(-c2cn(-c3ncc(N)cc3F)nc2C(F)(F)F)cnc1C(=O)Nc1ccc(C(=O)N2CCN(C(=O)C3CCNCC3)CC2)c(Cl)c1 ; O=CO] | Z71 | 5-[1-(5-amino-3-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 6-bromo-5-fluoro-pyridin-3-amine; deprotection with hydrochloric acid in dioxane | 703.1, $[M + H]^+$, ESI pos |
| 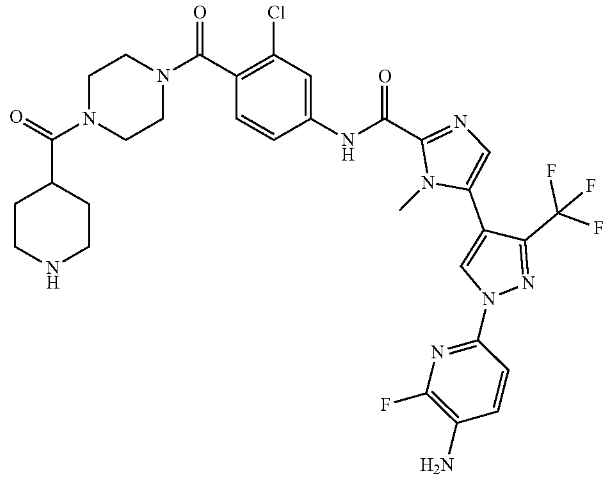 [SMILES: Cn1c(-c2cn(-c3ccc(N)c(F)n3)nc2C(F)(F)F)cnc1C(=O)Nc1ccc(C(=O)N2CCN(C(=O)C3CCNCC3)CC2)c(Cl)c1] | Z72 | 5-[1-(5-amino-6-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 6-bromo-2-fluoro-pyridin-3-amine; deprotection with hydrochloric acid in dioxane | 703.3, $[M + H]^+$, ESI pos |
| 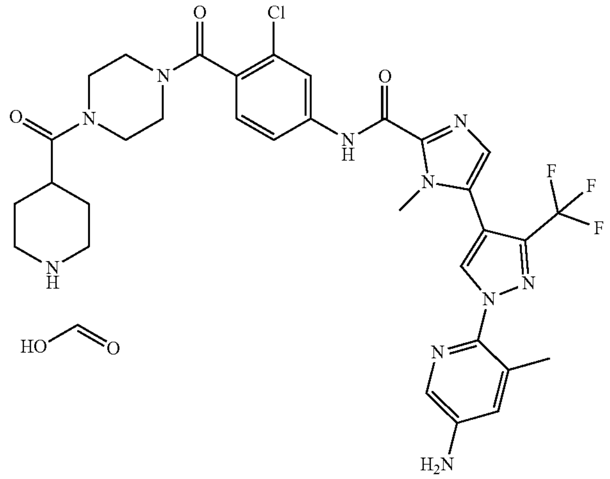 [SMILES: Cc1cc(N)cnc1-n1cc(-c2cnc(C(=O)Nc3ccc(C(=O)N4CCN(C(=O)C5CCNCC5)CC4)c(Cl)c3)n2C)c(C(F)(F)F)n1 ; O=CO] | Z78 | 5-[1-(6-amino-4-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid | 5-iodo-4-methyl-pyridin-2-amine | 699.4 $[M + H]^+$, ESI pos |

Example Z74

5-[1-(6-amino-5-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide

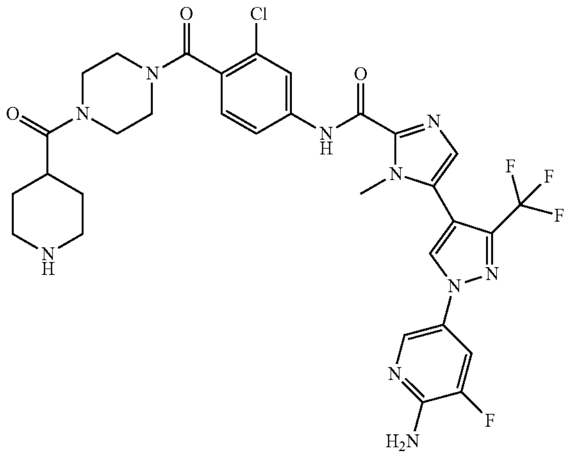 [SMILES: Cn1c(-c2cn(-c3cnc(N)c(F)c3)nc2C(F)(F)F)cnc1C(=O)Nc1ccc(C(=O)N2CCN(C(=O)C3CCNCC3)CC2)c(Cl)c1]

Step 1: tert-butyl 4-[4-[4-[[5-[1-(6-amino-5-fluoro-3-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate [2489205-74-3] (200.0 mg, 0.290 mmol, 1 eq), trans-(1r,2r)-N,N'-bismethyl-1,2-cyclohexanediamine (16.42 mg, 0.120 mmol, 0.400 eq), 5-bromo-3-fluoropyridin-2-amine (66.14 mg, 0.350 mmol, 1.2 eq) and phosphoric acid, potassium salt (0.07 mL, 0.870 mmol, 3 eq) in DMSO (5 mL) was added copper(I) iodide (0.01 mL, 0.290 mmol, 1 eq). The mixture was degassed and then stirred at 120° C. for 16 h under N2. Then water (20 mL) and EA (20 mL) were added, the mixture was filtered through celite pad, and the solid was washed with EA (10 mL*2). The organic layer was separated from the filtrate. The aqueous layer was extracted with EA (20 mL*2). The combined organic layers were washed with brine (20 mL*2), dried over sodium sulfate, filtered, and the filtrate was concentrated under vacuum. The residue was purified by prep-HPLC (FA condition) to give the title compound (40 mg, 0.050 mmol, 17.26% yield) as a light yellow solid. MS: 803.0 $[M+H]^+$, ESI pos.

Step 2: 5-[1-(6-amino-5-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide To a solution of tert-butyl 4-[4-[4-[[5-[1-(6-amino-5-fluoro-3-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (40.0 mg, 0.050 mmol, 1 eq) in DCM (2 mL) was added trifluoroacetic acid (1.0 mL, 12.98 mmol, 260.64 eq). The mixture was stirred at 15° C. for 1 h. The mixture was concentrated under vacuum. The residue was purified by prep-HPLC (FA condition) to give the title compound (14.8 mg, 0.020 mmol, 40.42% yield) as a white solid. MS 703.2, $[M+H]^+$, ESI pos.

Example Z79

5-[1-(6-amino-2-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

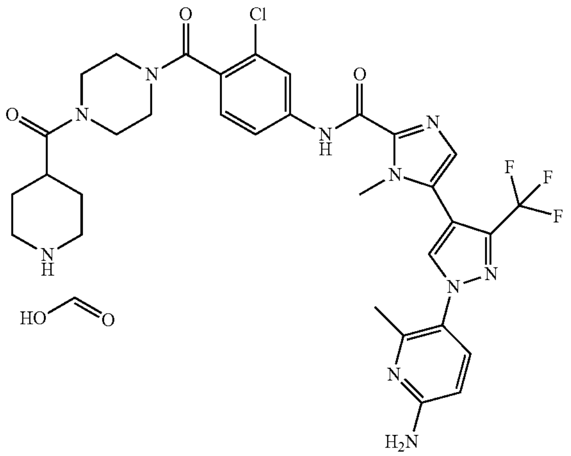

This example was prepared in analogy to example Z74 using 5-iodo-6-methyl-pyridin-2-amine and was obtained as white solid (20.4 mg. MS: 699.4 $[M+H]^+$, ESI pos.

Example Z81

5-[1-(5-amino-3-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide

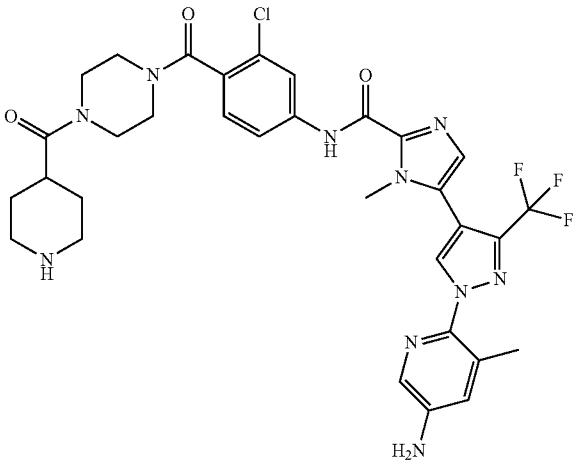 [SMILES: Cc1cc(N)cnc1-n1cc(-c2cnc(C(=O)Nc3ccc(C(=O)N4CCN(C(=O)C5CCNCC5)CC4)c(Cl)c3)n2C)c(C(F)(F)F)n1]

Step 1: tert-butyl 4-[4-[2-chloro-4-[[1-methyl-5-[1-(3-methyl-5-nitro-2-pyridyl)-3-(trifluoromethyl) pyrazol-4-yl]imidazole-2-carbonyl]amino]benzoyl] piperazine-1-carbonyl]piperidine-1-carboxylate To a solution of tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate [2489205-74-3] (100.0 mg, 0.140 mmol, 1 eq), N,N-diisopropylethylamine (0.1 mL, 0.580 mmol, 4 eq) in DMF (2 mL) was added 2-chloro-3-methyl-5-nitro-pyridine (37.35 mg, 0.220 mmol, 1.5 eq). The mixture was stirred at 120° C. for 16 h The mixture was purified by prep-HPLC (FA condition) to give the title compound (92 mg, 0.110 mmol, 76.9% yield) as a light brown solid. MS: 829.4, $[M+H]^+$, ESI pos.

Step 2: tert-butyl 4-[4-[4-[[5-[1-(5-amino-3-methyl-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[1-(3-methyl-5-nitro-2-pyridyl)-3-(trifluoromethyl)pyrazol-4-yl]imidazole-2-carbonyl]amino]benzoyl]piperazine-1-carbonyl]piperidine-1-carboxylate (72.0 mg, 0.090 mmol, 1 eq) and saturated NH4Cl in water (2.0 mL) and methanol (2 mL) and was added iron (96.98 mg, 1.74 mmol, 20 eq) powder. The mixture was stirred at 30° C. for 16 h. The mixture was diluted with water (20 mL) and EA (20 mL) and then filtered. The filtrate was extracted with EA (30 mL*2). The combined organic layers were washed with brine (30 mL), dried over sodium sulfate, filtered, the filtrate was concentrated under vacuum to give the title compound (80 mg, 0.100 mmol, 115.28% yield) as a light yellow solid. MS: 799.4, $[M+H]^+$, ESI pos.

Step 3: 5-[1-(5-amino-3-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide To a solution of tert-butyl 4-[4-[4-[[5-[1-(5-amino-3-methyl-2-pyridyl)-3-(trifluoromethyl)pyrazol-4-yl]-1-methyl-imidazole-2-carbonyl]amino]-2-chloro-benzoyl] piperazine-1-carbonyl]piperidine-1-carboxylate (80.0 mg, 0.100 mmol, 1 eq) in DCM (2 mL) was added trifluoroacetic acid (1.0 mL, 12.98 mmol, 129.68 eq). The mixture was stirred at 15° C. for 2 h. The mixture was concentrated under vacuum. The residue was purified by prep-HPLC (FA condition) to give the title compound (40.7 mg, 0.060 mmol, 56.88% yield) as an off-white solid. MS: 699.2, $[M+H]^+$, ESI pos.

Example Z86

5-[1-(5-amino-6-methylpyridin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

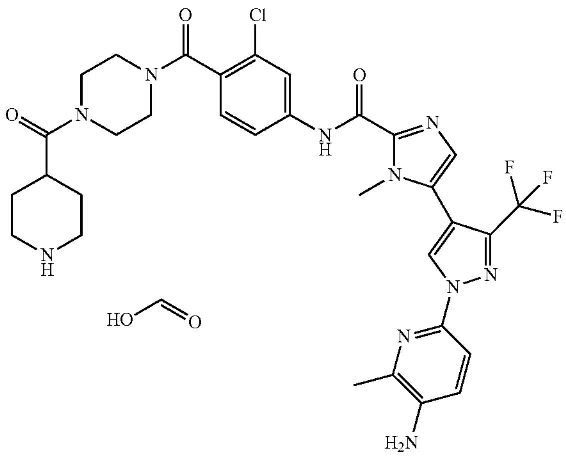 [SMILES: Cc1nc(-n2cc(-c3cnc(C(=O)Nc4ccc(C(=O)N5CCN(C(=O)C6CCNCC6)CC5)c(Cl)c4)n3C)c(C(F)(F)F)n2)ccc1N ; O=CO]

This compound was prepared in analogy to Z81 using 6-chloro-2-methyl-3-nitro-pyridine in the first step. The title compound was obtained as off white solid (42.7 mg). MS: 699.4, $[M+H]^+$, ESI pos.

Example Z82

5-[1-(5-amino-4-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide

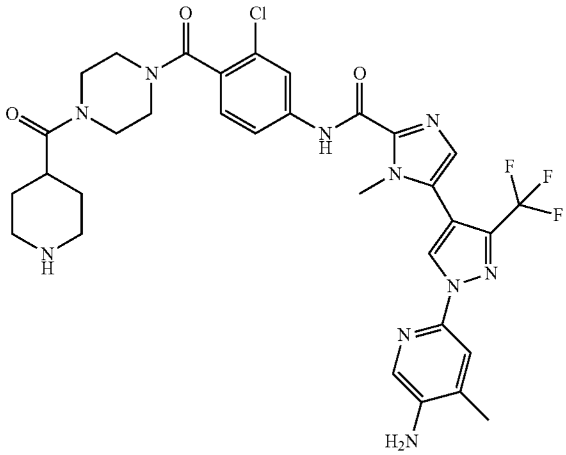 [SMILES: Cc1cc(-n2cc(-c3cnc(C(=O)Nc4ccc(C(=O)N5CCN(C(=O)C6CCNCC6)CC5)c(Cl)c4)n3C)c(C(F)(F)F)n2)ncc1N]

This compound was prepared in analogy to Z81 using 2-chloro-4-methyl-5-nitro-pyridine and DMSO as solvent in the first step. The title compound was obtained as light yellow solid (33.7 mg). MS: 699.2, $[M+H]^+$, ESI pos.

Example Z83

5-[1-(5-amino-2-fluoro-4-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

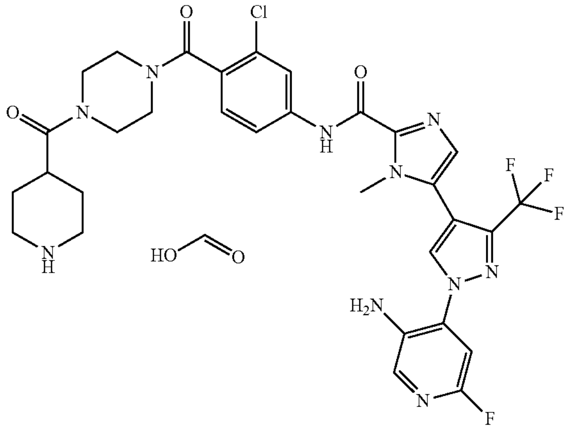 [SMILES: Cn1c(-c2cn(-c3cc(F)ncc3N)nc2C(F)(F)F)cnc1C(=O)Nc1ccc(C(=O)N2CCN(C(=O)C3CCNCC3)CC2)c(Cl)c1 ; O=CO]

This compound was prepared in analogy to Z81 using 2,4-difluoro-5-nitro-pyridine and trimethylamine as the base at 15° C. in the first step. The title compound was obtained grey solid (15.5 mg). MS: 703.2, $[M+H]^+$, ESI pos.

Example Z80

5-[1-(5-amino-4-chloro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

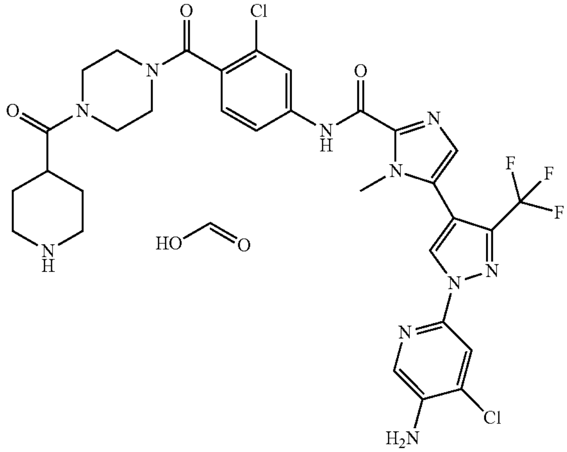 [SMILES: Cn1c(-c2cn(-c3cc(Cl)c(N)cn3)nc2C(F)(F)F)cnc1C(=O)Nc1ccc(C(=O)N2CCN(C(=O)C3CCNCC3)CC2)c(Cl)c1 ; O=CO]

Step 1: tert-butyl 4-[4-[4-[[5-[1-(5-amino-4-chloro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate [2489205-74-3] (100.0 mg, 0.140 mmol, 1 eq) and tert-butyl N-(4-chloro-6-fluoro-3-pyridyl)carbamate (49.82 mg, 0.200 mmol, 1.4 eq) in DMF (1 mL) was added cesium carbonate (70.51 mg, 0.220 mmol, 1.5 eq). The mixture was stirred at 80° C. for 16 h. The mixture was filtered, concentrated and purified by reversed phase-HPLC (FA) to afford the title compound (60 mg, 0.070 mmol, 45.21% yield) as yellow oil. MS: 919.4, $[M+H]^+$, ESI pos.

Step 2: 5-[1-(5-amino-4-chloro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid To a solution of tert-butyl 4-[4-[4-[[5-[1-(5-amino-4-chloro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (20.0 mg, 0.020 mmol, 1 eq) in DCM (0.500 mL) was added trifluoroacetic acid (0.5 mL, 6.49 mmol, 265.98 eq). The mixture was stirred at 15° C. for 2 h. The mixture was concentrated under vacuum and the residue was purified by prep-HPLC (FA condition) to give the title compound (13.6 mg, 0.020 mmol, 72.52% yield) as a white solid. MS: 719.2, $[M+H]^+$, ESI pos.

Example Z84

5-[1-(6-amino-2-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

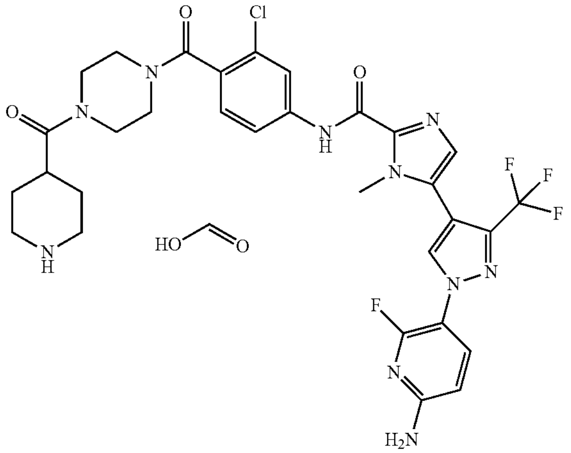 [SMILES: Cn1c(-c2cn(-c3ccc(N)nc3F)nc2C(F)(F)F)cnc1C(=O)Nc1ccc(C(=O)N2CCN(C(=O)C3CCNCC3)CC2)c(Cl)c1 ; O=CO]

Step 1: 6-fluoro-5-(4,4,5,5-tetramethyl-1,3,2-dioxaborolan-2-yl)pyridin-2-amine

To a solution of 6-fluoro-5-iodo-pyridin-2-amine (670.0 mg, 2.82 mmol, 1 eq), bis(pinacolato)diboron (1072 mg, 4.22 mmol, 1.5 eq), potassium acetate (829 mg, 8.45 mmol, 3 eq) in 1,4-Dioxane (6 mL) was added 1,1'-bis(diphenylphosphino)ferrocene-palladium(II)dichloride dichloromethane complex (229.71 mg, 0.280 mmol, 0.100 eq) under $N_2$. The mixture was degassed and then stirred at 90° C. for 18 h under N2. The mixture was cooled and then filtered through celite pad. The solid was washed with EA (10 mL*3). The filtrate was concentrated under vacuum. The residue was purified by column (PE:EA=1:0~2:1) to the title compound (620 mg, 2.6 mmol, 46.26% yield) as a light brown solid and was used without further purification. MS: 239.2, $[M+H]^+$, ESI pos.

Step 2: tert-butyl 4-[4-[4-[[5-[1-(6-amino-2-fluoro-3-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate To a solution of tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate [2489205-74-3] (120.0 mg, 0.170 mmol, 1 eq), 6-fluoro-5-(4,4,5,5-tetramethyl-1,3,2-dioxaborolan-2-yl)pyridin-2-amine (82.43 mg, 0.350 mmol, 2 eq) and 4-dimethylaminopyridine (42.3 mg, 0.350 mmol, 2 eq) in ACN (1.5 mL) and methanol (1.5 mL) was added cupric acetate (62.89 mg, 0.350 mmol, 2 eq). The mixture was stirred at 50° C. for 16 h under $O_2$. Again tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate (120.0 mg, 0.170 mmol, 1 eq) was added into the mixture. The mixture was stirred at 50° C. for another 24h. Again tert-butyl 4-[4-[2-chloro-4-[[1-methyl-5-[3-(trifluoromethyl)-1H-pyrazol-4-yl]imidazole-2-carbonyl]amino]benzoyl]piperazine-1-carbonyl]piperidine-1-carboxylate (120.0 mg, 0.170 mmol, 1 eq) was added into the mixture. The mixture was stirred at 50° C. for another 24 h. Then the mixture was diluted with EA (20 mL). The mixture was filtered through celite pad. The cake was washed with EA (5 mL*4). The combined filtrate was concentrated under vacuum. The residue was purified by prep-HPLC (FA condition) to the title compound (20 mg, 0.020 mmol, 14.38% yield) as a light brown solid. MS: 703.1, $[M\text{-}Boc+H]^+$, ESI pos.

Step 3: 5-[1-(6-amino-2-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid To a solution of tert-butyl 4-[4-[4-[[5-[1-(6-amino-2-fluoro-3-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (15.0 mg, 0.020 mmol, 1 eq) in DCM (0.400 mL) was added trifluoroacetic acid (0.6 mL, 7.79 mmol, 417.02 eq). The mixture was stirred at 15° C. for 1 h. The mixture was concentrated under vacuum. The residue was purified by prep-HPLC (FA condition) to give the title compound (11.2 mg, 0.010 mmol, 78.42% yield) as a white solid. MS: 703.1, $[M+H]^+$, ESI pos.

Example Z85

5-[1-(4-amino-5-nitro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide; formic acid

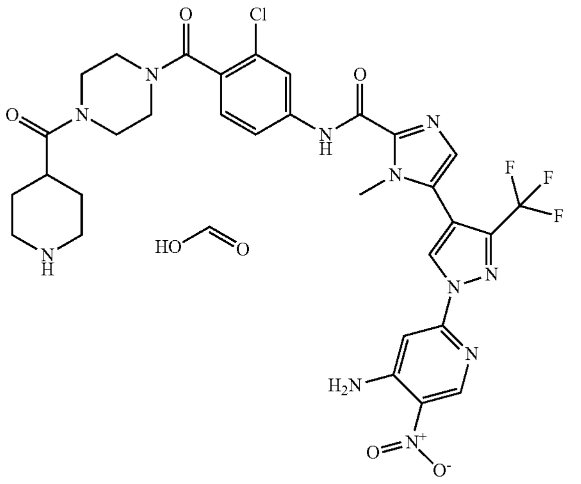 [SMILES: Cn1c(-c2cn(-c3cc(N)c([N+](=O)[O-])cn3)nc2C(F)(F)F)cnc1C(=O)Nc1ccc(C(=O)N2CCN(C(=O)C3CCNCC3)CC2)c(Cl)c1 ; O=CO]

To a solution of tert-butyl 4-[4-[4-[[5-[1-(4-amino-5-nitro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (50.0 mg, 0.060 mmol, 1 eq) in DCM (1 mL) was added trifluoroacetic acid (0.06 mL, 0.060 mmol, 1 eq). The mixture was stirred at 25° C. for 1 h. The mixture was concentrated under vacuum. The residue was purified by prep-HPLC (FA condition) to give the title compound (28.1 mg, 0.040 mmol, 59.88% yield) as a white solid. MS: 730.1, $[M+H]^+$, ESI pos.

Example Z87

N-[3-chloro-4-[4-(piperidine-4-carbonyl)piperazine-1-carbonyl]phenyl]-5-[1-(4,5-diamino-2-pyridyl)-3-(trifluoromethyl)pyrazol-4-yl]-1-methyl-imidazole-2-carboxamide

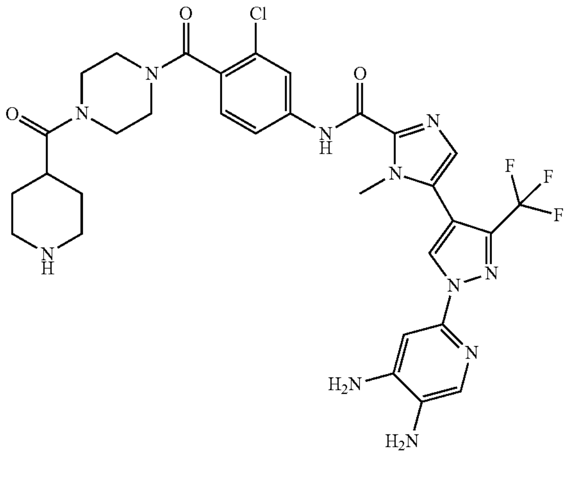 [SMILES: Cn1c(-c2cn(-c3cc(N)c(N)cn3)nc2C(F)(F)F)cnc1C(=O)Nc1ccc(C(=O)N2CCN(C(=O)C3CCNCC3)CC2)c(Cl)c1]

Step 1: tert-butyl 4-[4-[2-chloro-4-[[5-[1-(4,5-diamino-2-pyridyl)-3-(trifluoromethyl)pyrazol-4-yl]-1-methyl-imidazole-2-carbonyl]amino]benzoyl]piperazine-1-carbonyl]piperidine-1-carboxylate To a solution of tert-butyl 4-[4-[4-[[5-[1-(4-amino-5-nitro-2-pyridyl)-3-(trifluoromethyl)pyrazol-4-yl]-1-methyl-imidazole-2-carbonyl]amino]-2-chloro-benzoyl]piperazine-1-carbonyl]piperidine-1-carboxylate (50.0 mg, 0.060 mmol, 1 eq) in methanol (1 mL) and saturated ammonium chloride in water (0.06 mL, 0.060 mmol, 1 eq) was added iron powder (33.63 mg, 0.600 mmol, 10 eq). The mixture was stirred at 25° C. for 16 h. The mixture was diluted with water (20 mL) and EA (10 mL). The mixture was filtered through a celite pad, the solid was washed with EA (5 mL*3). The combined filtrate was extracted with EA (20 mL*3). The combined organic layers were washed with brine (30 mL), dried over sodium sulfate, and filtered. The filtrate was concentrated under vacuum to give the title compound (40 mg, 0.050 mmol, 83% yield) as a light yellow solid. MS: 800.2, $[M+H]^+$, ESI pos.

Step 2: N-[3-chloro-4-[4-(piperidine-4-carbonyl)piperazine-1-carbonyl]phenyl]-5-[1-(4,5-diamino-2-pyridyl)-3-(trifluoromethyl)pyrazol-4-yl]-1-methyl-imidazole-2-carboxamide To a solution of tert-butyl 4-[4-[2-chloro-4-[[5-[1-(4,5-diamino-2-pyridyl)-3-(trifluoromethyl)pyrazol-4-yl]-1-methyl-imidazole-2-carbonyl]amino]benzoyl]piperazine-1-carbonyl]piperidine-1-carboxylate (40.0 mg, 0.050 mmol, 1 eq) in DCM (1 mL) was added trifluoroacetic acid (0.5 mL, 6.49 mmol, 129.84 eq). The mixture was stirred at 25° C. for 1 h. The mixture was concentrated under vacuum. The residue was dissolved in EtOH (3 mL) and water (1 mL). NaOH (30 mg) was added into the mixture. The mixture was stirred at 20° C. for 16 h. The mixture was adjusted to pH=6 with 4 M HCl (in MeOH) and then concentrated under vacuum. The residue was purified by prep-HPLC (FA condition) to give the title compound (10.4 mg, 0.010 mmol, 29.07% yield) as a white solid. MS: 700.1, $[M+H]^+$, ESI pos.

Assay Procedures

Antimicrobial Susceptibility Testing:

90% Growth Inhibitory Concentration (IC90) Determination

The in vitro antimicrobial activity of the compounds was determined according to the following procedure:

The assay used a 10-points Iso-Sensitest broth medium to measure quantitatively the in vitro activity of the compounds against *Acinetobacter baumannii* ATCC17961.

Stock compounds in DMSO were serially twofold diluted (e.g. range from 50 to 0.097 μM final concentration) in 384 wells microtiter plates and inoculated with 49 μl the bacterial suspension in Iso-Sensitest medium to have a final cell concentration of ~$5\times10^{(5)}$ CFU/ml in a final volume/well of 50 ul/well. Microtiter plates were incubated at 35±2° C.

Bacterial cell growth was determined with the measurement of optical density at λ=600 nm each 20 minutes over a time course of 16h. Growth inhibition was calculated during the logarithmic growth of the bacterial cells with determination of the concentration inhibiting 50% (IC50) and 90% (IC90) of the growth.

Table 1 provides the 90% growth inhibitory concentrations (IC90) in micromoles per liter of the compounds of present invention obtained against the strain *Acinetobacter baumannii* ATCC17961.

Particular compounds of the present invention exhibit an IC90 (*Acinetobacter baumannii* ATCC17961)≤25 μmol/l.

More particular compounds of the present invention exhibit an IC90 (*Acinetobacter baumannii* ATCC17961)≤5 μmol/l.

Most particular compounds of the present invention exhibit an IC90 (*Acinetobacter baumannii* ATCC17961)≤1 μmol/l.

TABLE 1

| Example | ATCC 17961 IC90 [μM] |
|---|---|
| Example A1 | 0.69 |
| Example A2 | 0.71 |
| Example A3 | 0.37 |
| Example A4 | — |
| Example A5 | 1.0 |
| Example A6 | 0.54 |
| Example A7 | — |
| Example A8 | 0.91 |
| Example A9 | 0.51 |
| Example A10 | 0.83 |
| Example A11 | 0.24 |
| Example A12 | 0.25 |
| Example A13 | 0.21 |
| Example A14 | 2.2 |
| Example A15 | 0.59 |
| Example A16 | 0.68 |
| Example A17 | 0.5 |
| Example A18 | — |
| Example A19 | 1.2 |
| Example A20 | 0.48 |
| Example B1 | 0.23 |
| Example B2 | 0.17 |
| Example B3 | 0.48 |
| Example C1 | 0.22 |
| Example C2 | 0.34 |
| Example C3 | 1.2 |
| Example C4 | 0.31 |
| Example C5 | 0.93 |
| Example C6 | 0.89 |
| Example C7 | 0.66 |
| Example C8 | 0.82 |
| Example C9 | 0.42 |
| Example C10 | 7 |
| Example C11 | 2 |
| Example C12 | — |
| Example C13 | — |
| Example C14 | — |
| Example C15 | 0.91 |
| Example C16 | 0.26 |
| Example C17 | 0.79 |
| Example D1 | — |
| Example D2 | — |
| Example D3 | — |
| Example D4 | 0.52 |
| Example D5 | 0.31 |
| Example D6 | 0.37 |
| Example D7 | 0.28 |
| Example E1 | 0.88 |
| Example E2 | 0.47 |
| Example E3 | 0.5 |
| Example E4 | 0.68 |
| Example E5 | 1.4 |
| Example E6 | 0.35 |
| Example E7 | 0.29 |
| Example F1 | 0.45 |
| Example F2 | — |
| Example F3 | — |
| Example F4 | 0.31 |
| Example G1 | 0.39 |
| Example H1 | 0.48 |
| Example H2 | 0.88 |
| Example I1 | 1.5 |
| Example I2 | 0.4 |
| Example J1 | 0.58 |
| Example K1 | 0.5 |
| Z1 | 0.48 |

TABLE 1-continued

| Example | ATCC 17961 IC90 [μM] |
|---|---|
| Z2 | 0.98 |
| Z3 | 0.50 |
| Z4 | 0.22 |
| Z5 | 1.80 |
| Z6 | 0.93 |
| Z7 | 0.25 |
| Z8 | 0.37 |
| Z9 | 1.08 |
| Z10 | 0.33 |
| Z11 | 0.95 |
| Z12 | 0.93 |
| Z13 | 0.42 |
| Z14 | 0.85 |
| Z15 | 0.91 |
| Z16 | 0.86 |
| Z17 | 0.99 |
| Z18 | 1.59 |
| Z19 | 0.95 |
| Z20 | 0.33 |
| Z21 | 0.67 |
| Z22 | 0.51 |
| Z23 | 0.36 |
| Z24 | 0.46 |
| Z25 | 0.54 |
| Z26 | 0.69 |
| Z27 | 1.18 |
| Z28 | 0.36 |
| Z29 | 0.60 |
| Z30 | 0.78 |
| Z31 | 0.86 |
| Z32 | 0.39 |
| Z33 | 1.22 |
| Z34 | 0.41 |
| Z35 | 0.27 |
| Z36 | 1.18 |
| Z37 | 0.50 |
| Z38 | 0.66 |
| Z39 | 0.58 |
| Z40 | 0.78 |
| Z41 | 0.30 |
| Z42 | 0.63 |
| Z43 | 1.22 |
| Z44 | 0.81 |
| Z45 | 0.65 |
| Z46 | 0.39 |
| Z47 | 0.58 |
| Z48 | 0.51 |
| Z49 | 0.84 |
| Z50 | 0.80 |
| Z51 | 0.99 |
| Z52 | 1.27 |
| Z53 | 0.50 |
| Z54 | 0.35 |
| Z55 | 0.34 |
| Z56 | 0.40 |
| Z57 | 1.29 |
| Z58 | 0.56 |
| Z59 | 1.31 |
| Z60 | 0.40 |
| Z61 | 0.70 |
| Z62 | 0.38 |
| Z63 | 1.17 |
| Z64 | 0.44 |
| Z65 | 0.76 |
| Z66 | 1.16 |
| Z67 | 0.89 |
| Z68 | 0.65 |
| Z69 | 1.31 |
| Z70 | 1.37 |
| Z71 | 0.31 |
| Z72 | 0.25 |
| Z73 | 0.95 |
| Z74 | 0.75 |
| Z75 | 1.11 |
| Z76 | 1.14 |

TABLE 1-continued

| Example | ATCC 17961 IC90 [μM] |
|---|---|
| Z77 | 0.41 |
| Z78 | 1.44 |
| Z79 | 1.20 |
| Z80 | 0.38 |
| Z81 | 0.75 |
| Z82 | 0.34 |
| Z83 | 1.22 |
| Z84 | 0.23 |
| Z85 | 0.17 |
| Z86 | 0.29 |
| Z87 | 0.54 |
| Z88 | 0.98 |
| Z89 | 0.10 |

Minimal Inhibitory Concentration Protocol (MIC) Assay:

Table 2 provides the in vitro potency of the compounds of present invention obtained against the strain *Acinetobacter baumannii* ATCC17978, which was assessed by an MIC (Minimal Inhibitory Concentration) assay as follows.

Test compounds were prepared from 10 mM DMSO stock solutions. The top dose was diluted from 10 mM to 2.5 mM by DMSO, followed by serial 2-fold 11 points dilutions in DMSO in a master plate (Greiner, Cat No: 651201). 2 μL compounds were transferred from the master plate into a new 96-well assay plate (Costar, 3599).

The growth medium Caution-Adjusted Mueller Hinton Broth (CAMHB) was prepared by adding 22 g powder (BD, 212322) in 1 L purified water, autoclaved, and supplemented with sterilized $CaCl_2$) (20 mg per liter) and $MgCl_2$ (10 mg per liter).

Vials of each of the test microorganisms were maintained frozen in the vapor phase of a liquid nitrogen freezer. Took out the bacterial strain ATCC 17978 from liquid nitrogen freezer, thawed it at room temperature, and diluted the bacterial in the CAMHB medium to achieve a final inoculum of $2\times10^5$ CFU/mL. 98 μL of the adjusted bacteria suspension was dispensed to the assay plate and pipetted 5 times.

Then the assay plates were incubated for 20 hours at 35±2° C. in ambient air with humidity. Following incubation, MIC (μg/mL) value, the lowest concentration of drug that inhibits visible growth of the microorganism, was recorded by visual judgment of bacterial growth through magnification mirror of MIC reader, and the assay plates were photographed with Qcount system as image raw data. Meanwhile, the OD600 of assay plates was recorded with SpectraMax Plus384 as OD raw data.

TABLE 2

| Example | ATCC 17978 MIC [μg/mL] |
|---|---|
| Example A4 | 2.19 |
| Example A7 | 1.16 |
| Example A18 | 2.23 |
| Example D1 | 0.55 |
| Example F2 | 4.43 |
| Example F3 | 4.41 |
| Example D2 | 1.12 |
| Example D3 | 1.16 |
| Example C12 | 37.96 |
| Example C14 | 5.09 |

TABLE 2-continued

| Example | ATCC 17978 MIC [μg/mL] |
|---|---|
| Example C13 | 16.48 |

Example 1

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 2

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Example 3

A compound of formula (I) can be used in a manner known per se as the active ingredient for the production of an infusion solution of the following composition:

Active ingredient 100 mg

Lactic acid 90% 100 mg

NaOH q.s. or HCl q.s. for adjustment to pH 4.0

Sodium chloride q.s. or glucose q.s. for adjustment of the osmolality to 290 mOsm/kg Water for injection (WFI) ad 100 ml

Example 4

A compound of formula (I) can be used in a manner known per se as the active ingredient for the production of an infusion solution of the following composition:

Active ingredient 100 mg

Hydroxypropyl-beta-cyclodextrin 10 g

NaOH q.s. or HCl q.s. for adjustment to pH 7.4

Sodium chloride q.s. or glucose q.s. for adjustment of the osmolality to 290 mOsm/kg Water for injection (WFI) ad 100 ml

The invention claimed is:

1. A compound of formula (I):

(I)

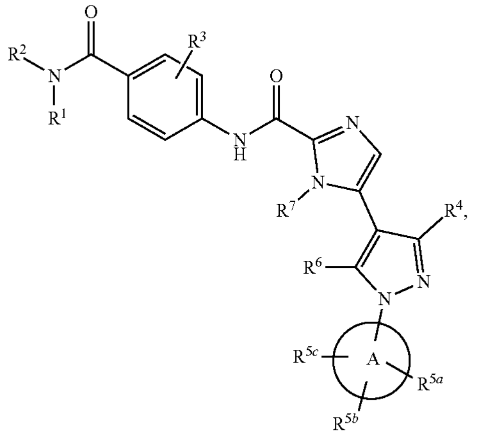

or a pharmaceutically acceptable salt thereof, wherein:

$R^1$ and $R^2$, taken together with the nitrogen atom to which they are attached, form a group of formula (II), (III) or (IV):

(II)

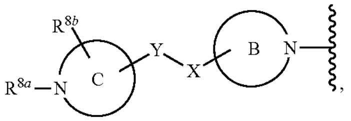

(III)

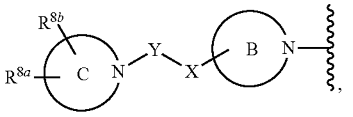

(IV)

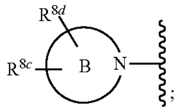

or $R^1$ is selected from the group consisting of $C_1$-$C_6$-alkyl, amino-$C_1$-$C_6$-alkyl, amino-$C_1$-$C_6$-alkoxy-$C_1$-$C_6$-alkyl, and

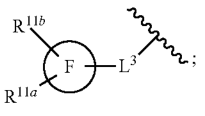

and $R^2$ is hydrogen or $C_1$-$C_6$-alkyl;

$R^3$ is selected from hydrogen, halogen, $C_1$-$C_6$-alkyl and $C_1$-$C_6$-alkoxy;

$R^4$ and $R^6$ are each independently selected from the group consisting of hydrogen, $C_1$-$C_6$-alkyl, $C_1$-$C_6$-alkoxy, cyano, halo-$C_1$-$C_6$-alkyl and halo-$C_6$-alkoxy;

$R^{5a}$, $R^{5b}$ and $R^{5c}$ are each independently selected from the group consisting of hydrogen, halogen, hydroxy, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, ($C_1$-$C_6$-alkyl)$_2$N—, $C_1$-$C_6$-alkyl-NH—C(O)—, amino-$C_1$-$C_6$-alkyl-NH—, $C_1$-C6-alkoxy-$C_1$-$C_6$-alkyl-NH—, carbamoyl-$C_1$-$C_6$-alkyl-NH—, (3- to 14-membered heterocyclyl)-C(O)—NH—, carbamoyl, and nitro;

$R^7$ is selected from the group consisting of hydrogen, $C_1$-$C_6$-alkyl and halo-$C_1$-$C_6$-alkyl;

$R^{8a}$ is selected from the group consisting of hydrogen, $C_1$-$C_6$-alkyl, carbamoyl-$C_1$-$C_6$-alkyl, and;

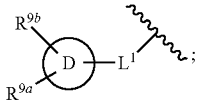

$R^{8b}$ is selected from the group consisting of hydrogen, hydroxy, oxo, hydroxy-$C_1$-$C_6$-alkyl, and

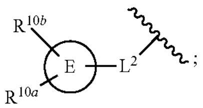

$R^{8c}$ is selected from the group consisting of hydrogen, $C_1$-$C_6$-alkyl, amino-$C_1$-$C_6$-alkyl, amino, $C_1$-$C_6$-alkyl-NH—, and $C_1$-$C_6$-alkoxy-$C_1$-$C_6$-alkyl;

$R^{8d}$ is hydrogen or $C_1$-$C_6$-alkyl;

$R^{9a}$, $R^{9b}$, $R^{10a}$, $R^{10b}$, $R^{12a}$ and $R^{12b}$ are each independently selected from the group consisting of hydrogen, halogen, $C_1$-$C_6$-alkyl, $C_1$-$C_6$-alkoxy, halo-$C_1$-$C_6$-alkyl, halo-$C_1$-$C_6$-alkoxy, amino, nitro and hydroxy;

$R^{11a}$ and $R^{11b}$ are each independently selected from the group consisting of hydrogen, halogen, $C_1$-$C_6$-alkyl, $C_1$-$C_6$-alkoxy, halo-$C_1$-$C_6$-alkyl, amino-$C_1$-$C_6$-alkyl, hydroxy-$C_1$-$C_6$-alkyl, halo-$C_1$-$C_6$-alkoxy, amino, nitro, hydroxy and

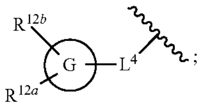

Y is carbonyl and X is selected from the group consisting of a covalent bond, NH, N($C_1$-$C_6$-alkyl), NH—$C_1$-$C_6$-alkyldiyl, and $C_1$-$C_6$-alkyldiyl; or X is carbonyl and Y is selected from the group consisting of a covalent bond, NH, N($C_1$-$C_6$-alkyl), NH—$C_1$-$C_6$-alkyldiyl, and $C_1$-$C_6$-alkyldiyl;

X is $C_1$-$C_6$-alkyldiyl and Y is a covalent bond;

$L^1$ and $L^3$ are each independently selected from the group consisting of a covalent bond, —C(O)—NH—$C_1$-$C_6$-alkyldiyl-, —$C_1$-$C_6$-alkyldiyl-NH—C(O)—, —C(O)—NH—$C_1$-$C_6$-alkoxy-$C_1$-$C_6$-alkyldiyl-, —$C_1$-$C_6$-alkoxy-$C_1$-$C_6$-alkyldiyl-NH—C(O)—, carbonyl and $C_1$-$C_6$-alkyldiyl;

$L^2$ and $L^4$ are each independently selected from the group consisting of a covalent bond, carbonyl, —O—, —NH—C(O)—, —C(O)—NH—, —C(O)—NH—$C_1$-$C_6$-alkyldiyl-, —$C_1$-$C_6$-alkyldiyl-NH—C(O)—, and $C_1$-$C_6$-alkyldiyl;

A is 5- to 14-membered heteroaryl;

B, C, D, E and G are each independently 3- to 14-membered heterocyclyl and 5- to 14-membered heteroaryl; and F is 3- to 14-membered heterocyclyl or $C_3$-$C_{10}$-cycloalkyl.

2. The compound of claim 1, or a pharmaceutically acceptable salt thereof, wherein the compound is a compound of formula (I-I):

(I-I)

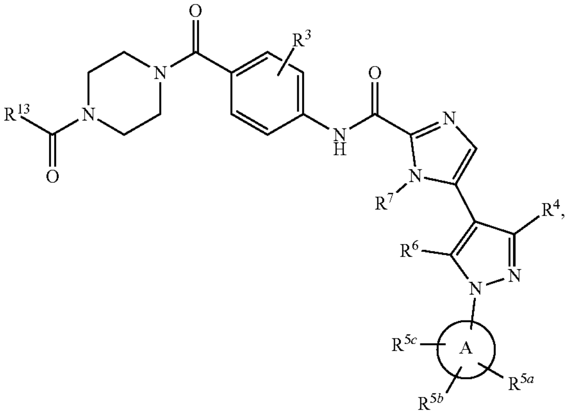

wherein:

$R^{13}$ is

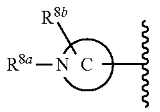

or

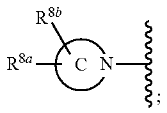

and

A, C, $R^3$, $R^4$, $R^{5a}$, $R^{5b}$, $R^{5c}$, $R^6$, $R^7$, $R^{8a}$ and $R^{8b}$ are as defined in claim 1.

3. The compound of claim 1, or a pharmaceutically acceptable salt thereof, wherein the compound is a compound of formula (I-II):

(I-II)

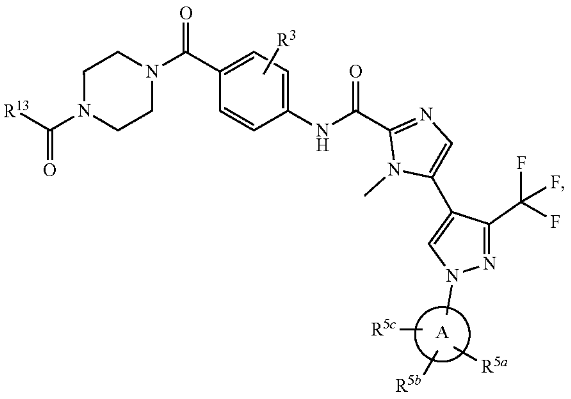

wherein:

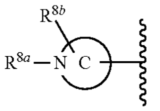

or

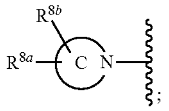

and

A, C, $R^3$, $R^{5a}$, $R^{5b}$, $R^{5c}$, $R^{8a}$ and $R^{8b}$ are as defined in claim 1.

4. The compound of claim 1, or a pharmaceutically acceptable salt thereof, wherein:

$R^1$ and $R^2$, taken together with the nitrogen atom to which they are attached, form a group of formula (II), (III) or (IV):

(II)

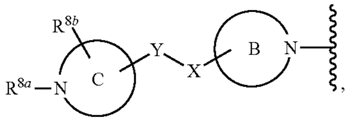

(III)

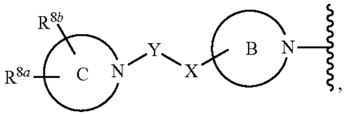

(IV)

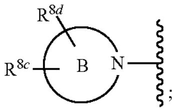

or $R^1$ is selected from the group consisting of $C_1$-$C_6$-alkyl, amino-$C_1$-$C_6$-alkyl, amino-$C_1$-$C_6$-alkoxy-$C_1$-$C_6$-alkyl, and

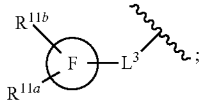

and $R^2$ is hydrogen or $C_1$-$C_6$-alkyl;

$R^{9a}$ is hydrogen or hydroxy;

$R^{9b}$, $R^{10b}$, and $R^{12b}$ are each hydrogen;

$R^{8a}$ is selected from the group consisting of hydrogen, $C_1$-$C_6$-alkyl, carbamoyl-$C_1$-$C_6$-alkyl and

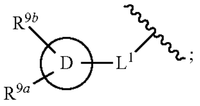

$R^{8b}$ is selected from the group consisting of hydrogen, hydroxy, oxo, hydroxy-$C_1$-$C_6$-alkyl, and

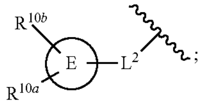

$R^{8c}$ is selected from the group consisting of hydrogen, $C_1$-$C_6$-alkyl, amino-$C_1$-$C_6$-alkyl, amino, $C_1$-$C_6$-alkyl-NH—, and $C_1$-$C_6$-alkoxy-$C_1$-$C_6$-alkyl;

$R^{8d}$ is hydrogen or $C_1$-$C_6$-alkyl;

$R^{10a}$ is amino or nitro;

$R^{11a}$ is selected from the group consisting of hydrogen, amino-$C_1$-$C_6$-alkyl, hydroxy-$C_1$-$C_6$-alkyl, amino, hydroxy and

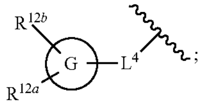

$R^{11b}$ is selected from the group consisting of hydrogen, halo-$C_1$-$C_6$-alkyl, and hydroxy-$C_1$-$C_6$-alkyl;

$R^{12a}$ is hydrogen or hydroxy;

X is carbonyl and Y is a covalent bond or $C_1$-$C_6$-alkyldiyl; or

X is selected from the group consisting of NH, N($C_1$-$C_6$-alkyl), and NH—$C_1$-$C_6$-alkyldiyl;

and Y is carbonyl; or

X is $C_1$-$C_6$-alkyldiyl and Y is a covalent bond;

$L^1$ is $C_1$-$C_6$-alkyldiyl;

$L^2$ is —O—;

$L^3$ is selected from the group consisting of a covalent bond, C(O)—NH—$C_1$-$C_6$-alkyldiyl-, —C(O)—NH—$C_1$-$C_6$-alkoxy-$C_1$-$C_6$-alkyldiyl-, and $C_1$-$C_6$-alkyldiyl;

$L^4$ is selected from the group consisting of carbonyl, —C(O)—NH—, and —C(O)—NH—$C_1$-$C_6$-alkyldiyl-;

B, C, D and G are each independently 3- to 14-membered heterocyclyl;

E is 5- to 14-membered heteroaryl; and

F is 3- to 14-membered heterocyclyl.

5. The compound of claim 4, or a pharmaceutically acceptable salt thereof, wherein:

$R^1$ and $R^2$, taken together with the nitrogen atom to which they are attached, form a group of formula (II), (III) or (IV):

(II)

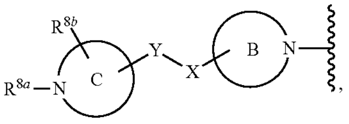

(III)

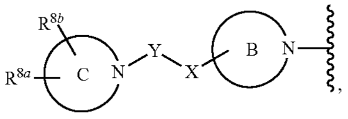

(IV)

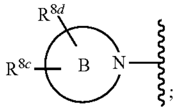

or $R^1$ is

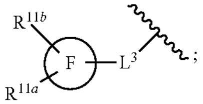

and $R^2$ is $C_1$-$C_6$-alkyl;

$R^{8a}$ is hydrogen or $C_1$-$C_6$-alkyl;

$R^{8b}$ is hydrogen or hydroxy;

$R^{8c}$ is hydrogen or $C_1$-$C_6$-alkyl-NH—;

$R^{8d}$ is hydrogen;

$R^{11a}$ is

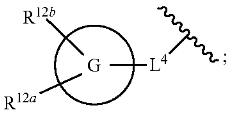

$R^{11b}$ is hydrogen;

$R^{12a}$ is hydroxy;

$R^{12b}$ is hydrogen;

X is carbonyl;

Y is a covalent bond or $C_1$-$C_6$-alkyldiyl;

$L^3$ is a covalent bond;

$L^4$ is carbonyl; and

B, C, F and G are each independently 3- to 14-membered heterocyclyl.

6. The compound of claim 5, or a pharmaceutically acceptable salt thereof, wherein:

$R^1$ and $R^2$, taken together with the nitrogen atom to which they are attached, form a group of formula (II), (III) or (IV):

(II)

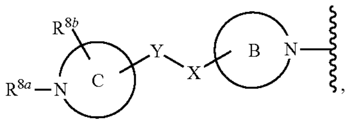

(III)

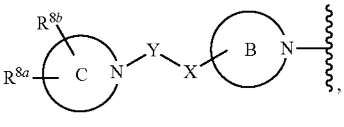

(IV)

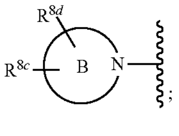

or $R^1$ is

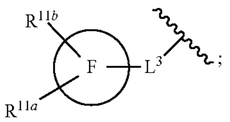

and $R^2$ is methyl;

$R^{8a}$ is hydrogen or methyl;

$R^{8b}$ is hydrogen or hydroxy;

$R^{8c}$ is hydrogen or methyl-NH—;

$R^{8d}$ is hydrogen;

$R^{11a}$ is

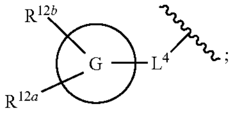

$R^{11b}$ is hydrogen $R^{12a}$ is hydroxy;

$R^{12b}$ is hydrogen;

X is carbonyl;

Y is a covalent bond or —$CH_2$—;

$L^3$ is a covalent bond;

$L^4$ is carbonyl;

B is selected from the group consisting of piperazinyl, piperidyl, and 2,8-diazaspiro[4.5]decan-8-yl;

C is piperidyl or pyrrolidinyl;

F is piperidyl; and

G is pyrrolidinyl.

7. The compound of claim 1, or a pharmaceutically acceptable salt thereof, wherein $R^3$ is halogen or $C_1$-$C_6$-alkyl.

8. The compound of formula (I) according to claim 7, or a pharmaceutically acceptable salt thereof, wherein $R^3$ is halogen.

9. The compound of formula (I) claim 1, or a pharmaceutically acceptable salt thereof, wherein:

$R^4$ is selected from the group consisting of $C_1$-$C_6$-alkyl, $C_1$-$C_6$-alkoxy, cyano and halo-$C_1$-$C_6$-alkyl; and $R^6$ is hydrogen or halo-$C_1$-$C_6$-alkyl.

10. The compound of claim 9, or a pharmaceutically acceptable salt thereof, wherein:

$R^4$ is halo-$C_1$-$C_6$-alkyl; and $R^6$ is hydrogen.

11. The compound of claim 1, or a pharmaceutically acceptable salt thereof, wherein:

A is 5- to 14-membered heteroaryl;

$R^{5a}$ is selected from the group consisting of hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, (3- to 14-membered heterocyclyl)-C(O)—NH—, carbamoyl and nitro;

$R^{5b}$ is selected from the group consisting of hydrogen, halogen, and amino; and $R^{5c}$ is hydrogen.

12. The compound of claim 11, or a pharmaceutically acceptable salt thereof, wherein:

A is 5- to 14-membered heteroaryl;

$R^{5a}$ is selected from the group consisting of halogen, $C_1$-$C_6$-alkyl, $C_1$-$C_6$-alkoxy, hydroxy-$C_1$-$C_6$-alkyl, amino-$C_1$-$C_6$-alkyl, $C_1$-$C_6$-alkyl-NH—, amino-$C_1$-$C_6$-alkyl-NH—, and amino;

$R^{5b}$ is hydrogen or amino; and $R^{5c}$ is hydrogen.

13. The compound of claim 12, or a pharmaceutically acceptable salt thereof, wherein:

A is pyridyl;

$R^{5a}$ is selected from the group consisting of fluoro, methyl, methoxy, hydroxymethyl, methylamino, 2-aminoethyl-NH—, and amino;

$R^{5b}$ is hydrogen or amino; and $R^{5c}$ is hydrogen.

14. The compound of claim 1, or a pharmaceutically acceptable salt thereof, wherein $R^7$ is $C_1$-$C_6$-alkyl.

15. The compound of claim 1, or a pharmaceutically acceptable salt thereof, wherein:

$R^1$ and $R^2$, taken together with the nitrogen atom to which they are attached, form a group of formula (II), (III) or (IV):

(II)

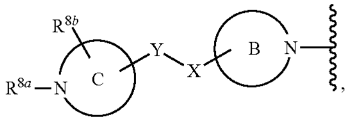

(III)

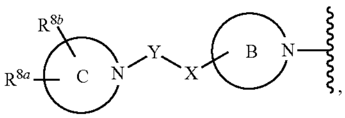

(IV)

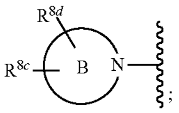

or $R^1$ is selected from the group consisting of $C_1$-$C_6$-alkyl, amino-$C_1$-$C_6$-alkyl, amino-$C_1$-$C_6$-alkoxy-$C_1$-$C_6$-alkyl, and

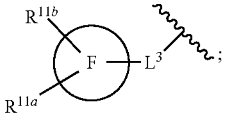

and $R^2$ is hydrogen or $C_1$-$C_6$-alkyl;

$R^3$ is halogen or $C_1$-$C_6$-alkyl;

$R^4$ is selected from the group consisting of $C_1$-$C_6$-alkyl, $C_1$-$C_6$-alkoxy, cyano and halo-$C_1$-$C_6$-alkyl;

$R^{5a}$ is selected from the group consisting of hydrogen, halogen, $C_1$-$C_6$-alkyl, $C_1$-$C_6$-alkoxy, amino-$C_1$-$C_6$-alkoxy, hydroxy-$C_1$-$C_6$-alkyl, halo-$C_1$-$C_6$-alkyl, $C_1$-$C_6$-alkoxy-$C_1$-$C_6$-alkyl-, $C_1$-$C_6$-alkoxy-$C_1$-$C_6$-alkoxy-, amino, $C_1$-$C_6$-alkyl-NH—, $(C_1$-$C_6$-alkyl$)_2$N—, $C_1$-$C_6$-alkyl-NH—C(O)—, amino-$C_1$-$C_6$-alkyl-NH—, $C_1$-$C_6$-alkoxy-$C_1$-$C_6$-alkyl-NH—, carbamoyl-$C_1$-$C_6$-alkyl-NH—, (3- to 14-membered heterocyclyl)-C(O)—NH—, carbamoyl and nitro;

$R^{5b}$ is selected from the group consisting of hydrogen, halogen, and amino;

$R^{5c}$ is hydrogen;

$R^6$ is hydrogen or halo-$C_1$-$C_6$-alkyl;

$R^7$ is $C_1$-$C_6$-alkyl;

$R^{8a}$ is selected from the group consisting of hydrogen, $C_1$-$C_6$-alkyl, carbamoyl-$C_1$-$C_6$-alkyl and

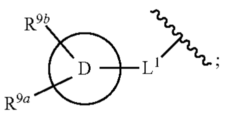

$R^{8b}$ is selected from the group consisting of hydrogen, hydroxy, oxo, hydroxy-$C_1$-$C_6$-alkyl, and

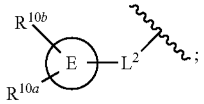

$R^{8c}$ is selected from the group consisting of hydrogen, $C_1$-$C_6$-alkyl, amino-$C_1$-$C_6$-alkyl, amino, $C_1$-$C_6$-alkyl-NH—, and $C_1$-$C_6$-alkoxy-$C_1$-$C_6$-alkyl;

$R^{8d}$ is hydrogen or $C_1$-$C_6$-alkyl;

$R^{9a}$ is hydrogen or hydroxy;

$R^{9b}$, $R^{10b}$, and $R^{12b}$ are each hydrogen;

$R^{10a}$ is amino or nitro;

$R^{11a}$ is selected from the group consisting of hydrogen, amino-$C_1$-$C_6$-alkyl, hydroxy-$C_1$-$C_6$-alkyl, amino, hydroxy and

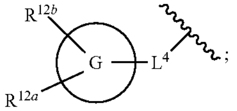

$R^{11b}$ is selected from the group consisting of hydrogen, halo-$C_1$-$C_6$-alkyl, and hydroxy-$C_1$-$C_6$-alkyl;

$R^{12a}$ is hydrogen or hydroxy;

X is carbonyl and Y is a covalent bond or $C_1$-$C_6$-alkyldiyl; or

X is selected from the group consisting of NH, N($C_1$-$C_6$-alkyl), and NH—$C_1$-$C_6$-alkyldiyl;

and Y is carbonyl; or

X is $C_1$-$C_6$-alkyldiyl and Y is a covalent bond;

$L^1$ is $C_1$-$C_6$-alkyldiyl;

$L^2$ is —O—;

$L^3$ is selected from the group consisting of a covalent bond, C(O)—NH—$C_1$-$C_6$-alkyldiyl-, —C(O)—NH—$C_1$-$C_6$-alkoxy-$C_1$-$C_6$-alkyldiyl-, and $C_1$-$C_6$-alkyldiyl;

$L^4$ is selected from the group consisting of carbonyl, —C(O)—NH—, and —C(O)—NH—$C_1$-$C_6$-alkyldiyl-;

A is 5- to 14-membered heteroaryl;

B, C, D and G are each independently 3- to 14-membered heterocyclyl;

E is 5- to 14-membered heteroaryl; and

F is selected from the group consisting of 5- to 14-membered heteroaryl, C3-C10-cycloalkyl, and 3- to 14-membered heterocyclyl.

16. The compound of claim 15, or a pharmaceutically acceptable salt thereof, wherein:

$R^1$ and $R^2$, taken together with the nitrogen atom to which they are attached, form a group of formula (II), (III) or (IV):

(II)

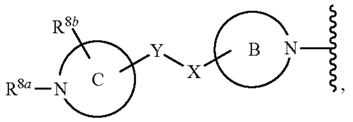

(III)

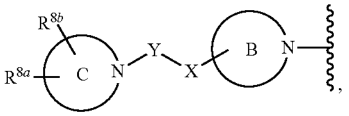

(IV)

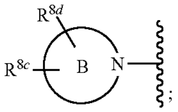

or $R^1$ is

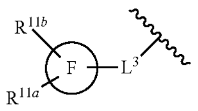

and $R^2$ is $C_1$-$C_6$-alkyl;

$R^3$ is halogen;

$R^4$ is halo-$C_1$-$C_6$-alkyl;

$R^{5a}$ is selected from the group consisting of halogen, $C_1$-$C_6$-alkyl, $C_1$-$C_6$-alkoxy, hydroxy-$C_1$-$C_6$-alkyl, amino-$C_1$-$C_6$-alkyl, $C_1$-$C_6$-alkyl-NH—, amino-$C_1$-$C_6$-alkyl-NH—, and amino;

$R^{5b}$ is hydrogen or amino;

$R^{5c}$ and $R^6$ are hydrogen;

$R^7$ is $C_1$-$C_6$-alkyl;

$R^{8a}$ is hydrogen or $C_1$-$C_6$-alkyl;

$R^{5b}$ is hydrogen or hydroxy;

$R^{8c}$ is hydrogen or $C_1$-$C_6$-alkyl-NH—;

$R^{8d}$ is hydrogen;

$R^{11a}$ is

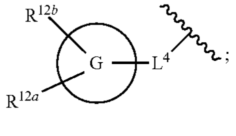

$R^{11b}$ is hydrogen;

$R^{12a}$ is hydroxy;

$R^{12b}$ is hydrogen;

X is carbonyl;

Y is a covalent bond or $C_1$-$C_6$-alkyldiyl;

$L^3$ is a covalent bond;

$L^4$ is carbonyl;

A is 5- to 14-membered heteroaryl;

B, C, F and G are each independently 3- to 14-membered heterocyclyl.

17. The compound of claim 16, or a pharmaceutically acceptable salt thereof, wherein:

$R^1$ and $R^2$, taken together with the nitrogen atom to which they are attached, form a group of formula (II), (III) or (IV):

(II)

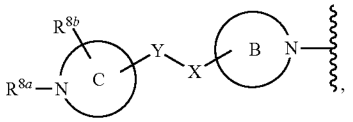

(III)

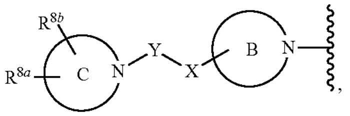

(IV)

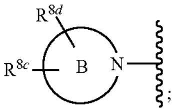

or $R^1$ is

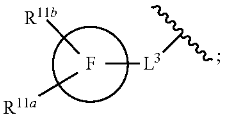

and $R^2$ is methyl;

$R^3$ is chloro;

$R^4$ is $CF_3$;

$R^{5a}$ is selected from the group consisting of fluoro, methyl, methoxy, hydroxymethyl, methylamino, 2-aminoethyl-NH—, and amino;

$R^{5b}$ is hydrogen or amino;

$R^{5c}$ and $R^6$ are hydrogen;

$R^7$ is methyl;

$R^{8a}$ is hydrogen or methyl;

$R^{8b}$ is hydrogen or hydroxy;

$R^{8c}$ is hydrogen or methyl-NH—;

$R^{8d}$ is hydrogen;

$R^{11a}$ is

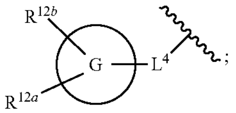

$R^{11b}$ is hydrogen $R^{12a}$ is hydroxy;

$R^{12b}$ is hydrogen;

X is carbonyl;

Y is a covalent bond or —$CH_2$—;

$L^3$ is a covalent bond;

$L^4$ is carbonyl;

A is pyridyl;

B is selected from the group consisting of piperazinyl, piperidyl, and 2,8-diazaspiro[4.5]decan-8-yl;

C is piperidyl or pyrrolidinyl;

F is piperidyl; and

G is pyrrolidinyl.

18. The compound of claim 1, or a pharmaceutically acceptable salt thereof, wherein the compound is selected from the group consisting of:

N-[3-Chloro-4-[4-(piperidine-4-carbonyl)piperazine-1-carbonyl]phenyl]-1-methyl-5-[1-pyrimidin-2-yl-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(4-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-(5-chloro-2-pyridyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(5-methoxypyrimidin-2-yl)-3-(trifluoromethyl)pyrazol-4-yl]-1-methyl-imidazole-2-carboxamide;

5-[1-(5-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-[5-(2-methoxyethoxy)pyrimidin-2-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[5-(2-methoxyethoxy)-2-pyridyl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(5-fluoropyrimidin-2-yl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-(1h-pyrazolo[3,4-d]pyrimidin-6-yl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[3-(trifluoromethyl)-1-[3-(trifluoromethyl)-2-pyridyl]pyrazol-4-yl]imidazole-2-carboxamide;

N-[3-chloro-4-[4-(piperidine-4-carbonyl)piperazine-1-carbonyl]phenyl]-1-methyl-5-[1-(2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-(4-methoxy-2-pyridyl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(5-methoxy-2-pyridyl)-3-(trifluoromethyl)pyrazol-4-yl]-1-methyl-imidazole-2-carboxamide;

5-[1-[4-(2-aminoethoxy)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(4-aminopyrimidin-2-yl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-1-methyl-5-[1-[4-(methylamino)pyrimidin-2-yl]-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[4-(dimethylamino)pyrimidin-2-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[4-(dimethylamino)pyrimidin-2-yl]-5-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[4-(2-methoxyethylamino)pyrimidin-2-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-pyrazin-2-yl-3-(trifluoromethyl)pyrazol-4-yl]imidazole-2-carboxamide;

N-[3-Chloro-4-[4-(piperidine-4-carbonyl)piperazine-1-carbonyl]phenyl]-5-[1-[5-(dimethylamino)pyrimidin-2-yl]-3-(trifluoromethyl)pyrazol-4-yl]-1-methyl-imidazole-2-carboxamide;

5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-[6-(dimethylamino)pyridazin-3-yl]-3-(trifluoromethyl)pyrazol-4-yl]-1-methyl-imidazole-2-carboxamide;

5-[1-(5-Amino-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-[5-(2-methoxyethylamino)-2-pyridyl]-3-(trifluoromethyl)pyrazol-4-yl]-1-methyl-imidazole-2-carboxamide;

5-[1-[5-[(3-amino-3-oxo-propyl)amino]-2-pyridyl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-(4-hydroxypiperidine-4-carbonyl)piperazine-1-carbonyl]phenyl]-1-methyl-imidazole-2-carboxamide;

N-[3-chloro-4-[4-(piperidine-4-carbonyl)piperazine-1-carbonyl]phenyl]-5-[1-(4-methoxypyrimidin-2-yl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(2-methoxypyrimidin-4-yl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[[1-(piperidine-4-carbonyl)-4-piperidyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[4-[(3S)-morpholine-3-carbonyl]piperazine-1-carbonyl]phenyl]-1-methyl-imidazole-2-carboxamide;

5-[1-(5-amino-2-pyridyl)-3-(difluoromethyl)pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-methoxy-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-cyano-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-methyl-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(5-amino-2-pyridyl)-3-ethyl-pyrazol-4-yl]-N-[3-chloro-4-[4-(1-methylpiperidine-4-carbonyl)piperazine-1-carbonyl]phenyl]-1-methyl-imidazole-2-carboxamide;

5-[1-(6-aminopyridazin-3-yl)-3-(trifluoromethyl)pyrazol-4-yl]-N-[3-chloro-4-[4-(1-methylpiperidine-4-carbonyl)piperazine-1-carbonyl]phenyl]-1-methyl-imidazole-2-carboxamide;

N-[3-chloro-4-[4-(1-methylpiperidine-4-carbonyl)piperazine-1-carbonyl]phenyl]-1-methyl-5-[1-(4-methyl-1H-pyrazol-3-yl)-3-(trifluoromethyl)pyrazol-4-yl]imidazole-2-carboxamide;

5-[1-(5-amino-2-pyridyl)-3-(trifluoromethyl)pyrazol-4-yl]-N-[3-chloro-4-[4-[2-(3-hydroxypyrrolidin-1-yl)acetyl]piperazine-1-carbonyl]phenyl]-1-methyl-imidazole-2-carboxamide;

N-[3-chloro-4-[4-[(2S,3S)-3-hydroxypyrrolidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

5-[1-[5-(2-aminoethylamino)pyrimidin-2-yl]-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-[4-(4-hydroxypiperidine-4-carbonyl)piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[(2S,3S)-3-hydroxypyrrolidine-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-[2-(3-hydroxypyrrolidin-1-yl)acetyl]piperazine-1-carbonyl]phenyl]-1-methyl-5-[1-[5-(methylamino)-2-pyridyl]-3-(trifluoromethyl)pyrazol-4-yl]imidazole-2-carboxamide;

1-methyl-5-[1-[5-(methylamino)-2-pyridyl]-3-(trifluoromethyl)pyrazol-4-yl]-N-[3-methyl-4-[4-(piperidine-4-carbonyl)piperazine-1-carbonyl]phenyl]imidazole-2-carboxamide;

N-[3-chloro-4-[4-[(2S,4R)-4-hydroxypyrrolidine-2-carbonyl]piperazine-1-carbonyl]phenyl]-1-methyl-5-[1-[5-(methylamino)-2-pyridyl]-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[1-(2-methoxyethyl)pyrazol-4-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[1-(2-methoxyethyl)-5-methyl-pyrazol-4-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-[1-(2-methoxyethyl)imidazol-4-yl]-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-1-methyl-5-[1-(1-methylimidazol-4-yl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(5-methyl-1H-pyrazol-4-yl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(5-methyl-2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-1-methyl-5-[1-(4-methyl-1H-pyrazol-5-yl)-3-(trifluoromethyl)pyrazol-4-yl]imidazole-2-carboxamide;

N-[4-[4-[(1R,5S)-3-Azabicyclo[3.1.0]hexane-6-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

N-[3-chloro-4-[[(1R,5S)-3-[(2S,4R)-4-hydroxypyrrolidine-2-carbonyl]-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide;

N-[3-chloro-4-[[(1S,5R)-3-(piperidine-4-carbonyl)-3-azabicyclo[3.1.0]hexan-6-yl]carbamoyl]phenyl]-1-methyl-5-[1-pyrimidin-2-yl-3-(trifluoromethyl)pyrazol-4-yl]imidazole-2-carboxamide;

N-[3-chloro-4-[4-[(3S,4R)-3-hydroxypiperidine-4-carbonyl]piperazine-1-carbonyl]phenyl]-5-[1-(5-methoxy-2-pyridyl)-3-(trifluoromethyl)pyrazol-4-yl]-1-methyl-imidazole-2-carboxamide;

N-[4-[4-[1-(Azetidin-3-ylmethyl)piperidine-4-carbonyl]piperazine-1-carbonyl]-3-chloro-phenyl]-1-methyl-5-[1-pyrimidin-2-yl-3-(trifluoromethyl)pyrazol-4-yl]imidazole-2-carboxamide;

5-[1-(5-Amino-2-pyridyl)-3-(trifluoromethyl)pyrazol-4-yl]-N-[3-chloro-4-[4-(piperazine-1-carbonyl)piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[3-(hydroxymethyl)piperazine-1-carbonyl]piperidine-1-carbonyl]phenyl]-1-methyl-imidazole-2-carboxamide;

5-[1-(5-Amino-2-pyridyl)-3-(trifluoromethyl)pyrazol-4-yl]-N-[3-chloro-4-[4-[(2-oxopiperazin-1-yl)methyl]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(1H-pyrazol-3-ylmethylcarbamoyl)phenyl]-1-methyl-imidazole-2-carboxamide;

N-[3-Chloro-4-[4-[(2S)-4-hydroxypiperidine-2-carbonyl]piperazine-1-carbonyl]phenyl]-1-methyl-5-[1-(5-nitro-2-pyridyl)-3-(trifluoromethyl)pyrazol-4-yl]imidazole-2-carboxamide;

N-[3-chloro-4-[4-(piperidine-4-carbonyl)piperazine-1-carbonyl]phenyl]-5-[1-[5-(ethylamino)-2-pyridyl]-3-(trifluoromethyl)pyrazol-4-yl]-1-methyl-imidazole-2-carboxamide;

N-[4-[(3R)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide;

N-[4-(3-aminopropylcarbamoyl)-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(4-piperidylmethylcarbamoyl)phenyl]-1-methyl-imidazole-2-carboxamide;

5-[1-(5-amino-2-pyridyl)-3-(trifluoromethyl)pyrazol-4-yl]-N-[3-chloro-4-(4-piperidylmethylcarbamoyl)phenyl]-1-methyl-imidazole-2-carboxamide;

5-[1-(5-amino-2-pyridyl)-3-(trifluoromethyl)pyrazol-4-yl]-N-[3-chloro-4-[4-(methylamino)piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[(3-methylolpyrrolidin-3-yl)carbamoyl]phenyl]-1-methyl-imidazole-2-carboxamide;

N-[4-[[1-(aminomethyl)cyclopropyl]carbamoyl]-3-chloro-phenyl]-5-[1-(5-amino-2-pyridyl)-3-(trifluoromethyl)pyrazol-4-yl]-1-methyl-imidazole-2-carboxamide;

N-[4-[(3S)-3-(aminomethyl)pyrrolidine-1-carbonyl]-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(2,8-diazaspiro[4.5]decane-8-carbonyl)phenyl]-1-methyl-imidazole-2-carboxamide;

N-[3-chloro-4-[4-(1-methylpiperidine-4-carbonyl)piperazine-1-carbonyl]phenyl]-5-[1-[4-(methoxymethyl)-1H-pyrazol-3-yl]-3-(trifluoromethyl)pyrazol-4-yl]-1-methyl-imidazole-2-carboxamide;

5-[1-(6-amino-3-pyridyl)-3-(trifluoromethyl)pyrazol-4-yl]-N-[3-chloro-4-(4-isonipecotoylpiperazine-1-carbonyl)phenyl]-1-methyl-imidazole-2-carboxamide;

N-[4-[cis-(3-aminocyclobutyl)carbamoyl]-3-chloro-phenyl]-5-[1-(5-amino-2-pyridyl)-3-(trifluoromethyl)pyrazol-4-yl]-1-methyl-imidazole-2-carboxamide;

N-[4-(2,3,3a,4,6,6a-hexahydro-1H-pyrrolo[3,4-c]pyrrole-5-carbonyl)-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[methyl(4-piperidyl)carbamoyl]phenyl]-1-methyl-imidazole-2-carboxamide;

N-[4-[4-(aminomethyl)piperidine-1-carbonyl]-3-chloro-phenyl]-5-[1-(5-amino-2-pyridyl)-3-(trifluoromethyl)pyrazol-4-yl]-1-methyl-imidazole-2-carboxamide;

N-[4-[[3-(aminomethyl)-3-(chloromethyl)cyclobutyl]carbamoyl]-3-chloro-phenyl]-5-[1-(5-amino-2-pyridyl)-3-(trifluoromethyl)pyrazol-4-yl]-1-methyl-imidazole-2-carboxamide;

N-[4-[[(trans-3-aminocyclopentyl]carbamoyl]-3-chloro-phenyl]-5-[1-(5-amino-2-pyridyl)-3-(trifluoromethyl)pyrazol-4-yl]-1-methyl-imidazole-2-carboxamide;

N-[4-(2-aminoethylcarbamoyl)-3-chloro-phenyl]-5-[1-(5-amino-2-pyridyl)-3-(trifluoromethyl)pyrazol-4-yl]-1-methyl-imidazole-2-carboxamide;

N-[4-[(2-aminocyclopropyl)methylcarbamoyl]-3-chloro-phenyl]-5-[1-(5-amino-2-pyridyl)-3-(trifluoromethyl)pyrazol-4-yl]-1-methyl-imidazole-2-carboxamide;

N-[4-[trans-(3-aminocyclobutyl)carbamoyl]-3-chloro-phenyl]-5-[1-(5-amino-2-pyridyl)-3-(trifluoromethyl)pyrazol-4-yl]-1-methyl-imidazole-2-carboxamide;

N-[4-(4-aminopiperidine-1-carbonyl)-3-chloro-phenyl]-5-[1-(5-amino-2-pyridyl)-3-(trifluoromethyl)pyrazol-4-yl]-1-methyl-imidazole-2-carboxamide;

N-[4-[2-(2-aminoethoxy)ethylcarbamoyl]-3-chloro-phenyl]-5-[1-(5-amino-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-[2-[(2S,4R)-4-hydroxyprolyl]-2,8-diazaspiro[4.5]decane-8-carbonyl]phenyl]-1-methyl-imidazole-2-carboxamide;

5-[1-(5-amino-2-pyridyl)-3-(trifluoromethyl)pyrazol-4-yl]-N-[3-chloro-4-[[(1R,3R)-3-[[(2S,4R)-4-hydroxyprolyl]amino]cyclopentyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[4-[[(2S,4R)-4-hydroxyprolyl]amino]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[6-[[(2S,4R)-4-hydroxyprolyl]amino]-2-azaspiro[3.3]heptane-2-carbonyl]phenyl]-1-methyl-imidazole-2-carboxamide;

5-[1-(5-amino-2-pyridyl)-3-(trifluoromethyl)pyrazol-4-yl]-N-[3-chloro-4-[3-[[(2S,4R)-4-hydroxyprolyl]amino]propylcarbamoyl]phenyl]-1-methyl-imidazole-2-carboxamide;

5-[1-(5-aminopyridin-2-yl)-3-(trifluoromethyl)pyrazol-4-yl]-N-[3-chloro-4-[[4-(hydroxymethyl)-1-[rac-(2R,4S)-4-hydroxypyrrolidine-2-carbonyl]pyrrolidin-3-yl]carbamoyl]phenyl]-1-methylimidazole-2-carboxamide;

N-[4-(5-aminopentylcarbamoyl)-3-chloro-phenyl]-5-[1-(5-amino-2-pyridyl)-3-(trifluoromethyl)pyrazol-4-yl]-1-methyl-imidazole-2-carboxamide;

5-[1-(5-aminopyrazin-2-yl)-3-(trifluoromethyl)pyrazol-4-yl]-N-[3-chloro-4-(4-isonipecotoylpiperazine-1-carbonyl)phenyl]-1-methyl-imidazole-2-carboxamide;

N-[3-chloro-4-[4-[(2S,4R)-4-hydroxyprolyl]piperazine-1-carbonyl]phenyl]-5-[1-(6-chloro-3-pyridyl)-3-(trifluoromethyl)pyrazol-4-yl]-1-methyl-imidazole-2-carboxamide;

N-[3-chloro-4-(4-isonipecotoylpiperazine-1-carbonyl)phenyl]-5-[1-(6-methoxy-2-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(piperazine-1-carbonyl)phenyl]-1-methyl-imidazole-2-carboxamide;

5-[1-(5-amino-2-pyridyl)-3-(trifluoromethyl)pyrazol-4-yl]-N-[3-chloro-4-[2-[[(2S,4R)-4-hydroxyprolyl]amino]ethylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[[1-[(2S,4R)-4-hydroxyprolyl]-4-piperidyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[[1-[(2S,4R)-4-hydroxyprolyl]-4-piperidyl]-methyl-carbamoyl]phenyl]-1-methyl-imidazole-2-carboxamide;

5-[1-(5-amino-2-pyridyl)-3-(trifluoromethyl)pyrazol-4-yl]-N-[3-chloro-4-[[2-[[(2S,4R)-4-hydroxyprolyl]amino]cyclopropyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[5-[(2S,4R)-4-hydroxyprolyl]-1,3,3a,4,6,6a-hexahydropyrrolo[3,4-c]pyrrole-2-carbonyl]phenyl]-1-methyl-imidazole-2-carboxamide;

5-[1-(5-amino-2-pyridyl)-3-(trifluoromethyl)pyrazol-4-yl]-N-[3-chloro-4-[trans-[3-[[(2S,4R)-4-hydroxyprolyl]amino]cyclobutyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[(3S)-3-[[[(2S,4R)-4-hydroxyprolyl]amino]methyl]pyrrolidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[2-[2-[[(2S,4R)-4-hydroxyprolyl]amino]ethoxy]ethylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[[(7S)-2-[(2S,4R)-4-hydroxyprolyl]-5-oxa-2-azaspiro[3.4]octan-7-yl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[cis-[3-[[(2S,4R)-4-hydroxyprolyl]amino]cyclobutyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[[1-[[(2S,4R)-4-hydroxyprolyl]amino]cyclopropyl]methylcarbamoyl]phenyl]-1-methyl-imidazole-2-carboxamide;

5-[1-(5-amino-2-pyridyl)-3-(trifluoromethyl)pyrazol-4-yl]-N-[3-chloro-4-[(3R)-3-[[[(2S,4R)-4-hydroxyprolyl]amino]methyl]pyrrolidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[[[(2S,4R)-4-hydroxyprolyl]amino]methyl]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[4-[[(2S,4R)-4-hydroxyprolyl]-methyl-amino]piperidine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[[3-[[(2S,4R)-4-hydroxyprolyl]amino]-1-bicyclo[1.1.1]pentanyl]carbamoyl]phenyl]-1-methyl-imidazole-2-carboxamide;

5-[1-(5-amino-2-pyridyl)-3-(trifluoromethyl)pyrazol-4-yl]-N-[3-chloro-4-[[(1S,3S)-3-[[(2S,4R)-4-hydroxyprolyl]amino]cyclopentyl]carbamoyl]phenyl]-1-methyl-imidazole-2-carboxamide;

N-[3-chloro-4-(4-isonipecotoylpiperazine-1-carbonyl)phenyl]-5-[1-(6-methoxypyrimidin-4-yl)-3-(trifluoromethyl)pyrazol-4-yl]-1-methyl-imidazole-2-carboxamide;

N-[3-chloro-4-[4-(piperidine-4-carbonyl)piperazine-1-carbonyl]phenyl]-5-[1-(2-chloropyridin-4-yl)-3-(trifluoromethyl)pyrazol-4-yl]-1-methylimidazole-2-carboxamide;

5-[1-(5-amino-2-pyridyl)-3-(trifluoromethyl)pyrazol-4-yl]-N-[3-chloro-4-(4,7-diazaspiro[2.5]octane-7-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(3R)-3-methyl-1,4-diazepane-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,9-diazabicyclo[3.3.1]nonane-3-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2S,6R)-2,6-dimethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,6-diazabicyclo[3.1.1]heptane-6-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2S)-2-methylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,3-dimethylpiperazine-1-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(3S)-3-isopropylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,6-diazabicyclo[3.2.0]heptane-3-carbonyl)phenyl]-1-methyl-imidazole-2-carboxamide;

5-[1-(5-amino-2-pyridyl)-3-(trifluoromethyl)pyrazol-4-yl]-N-[3-chloro-4-(1,4-diazepane-1-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(3S)-3-methylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(3,8-diazabicyclo[3.2.1]octane-8-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2R)-2-ethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[(2S)-2-ethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-(2-piperazinoethylcarbamoyl)phenyl]-1-methyl-imidazole-2-carboxamide;

5-[1-(5-amino-2-pyridyl)-3-(trifluoromethyl)pyrazol-4-yl]-N-[3-chloro-4-[(1R,4R)-2,5-diazabicyclo[2.2.1]heptane-2-carbonyl]phenyl]-1-methyl-imidazole-2-carboxamide;

5-[1-(5-amino-2-pyridyl)-3-(trifluoromethyl)pyrazol-4-yl]-N-[3-chloro-4-(4,7-diazaspiro[2.5]octane-4-carbonyl)phenyl]-1-methyl-imidazole-2-carboxamide;

5-[1-(5-amino-2-pyridyl)-3-(trifluoromethyl)pyrazol-4-yl]-N-[3-chloro-4-[(2S,3R)-2,3-dimethylpiperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[3-(methoxymethyl)piperazine-1-carbonyl]phenyl]-1-methyl-imidazole-2-carboxamide;

5-[1-(5-amino-2-pyridyl)-3-(trifluoromethyl)pyrazol-4-yl]-N-[3-chloro-4-[(1R,5R)-3,6-diazabicyclo[3.2.0]heptane-3-carbonyl]phenyl]-1-methyl-imidazole-2-carboxamide;

5-[1-(5-amino-3-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-6-fluoro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-(4-isonipecotoylpiperazine-1-carbonyl)phenyl]-5-[1-(2-methoxy-4-pyridyl)-3-(trifluoromethyl)pyrazol-4-yl]-1-methyl-imidazole-2-carboxamide;

5-[1-(6-amino-5-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

N-[3-chloro-4-(4-isonipecotoylpiperazine-1-carbonyl)phenyl]-5-[1-(6-methoxy-3-pyridyl)-3-(trifluoromethyl)pyrazol-4-yl]-1-methyl-imidazole-2-carboxamide;

5-[1-(5-amino-2-pyridyl)-3-(trifluoromethyl)pyrazol-4-yl]-N-[3-chloro-4-(diethylcarbamoyl)phenyl]-1-methyl-imidazole-2-carboxamide;

5-[1-(6-amino-5-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(6-amino-4-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(6-amino-2-methyl-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-4-chloro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-4-chloro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide";

5-[1-(5-amino-3-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-4-methyl-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-2-fluoro-4-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(6-amino-2-fluoro-3-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(4-amino-5-nitro-2-pyridyl)-3-(trifluoromethyl)pyrazol-4-yl]-N-[3-chloro-4-[4-(piperidine-4-carbonyl)piperazine-1-carbonyl]phenyl]-1-methyl-imidazole-2-carboxamide;

5-[1-(5-amino-6-methylpyridin-2-yl)-3-(trifluoromethyl)pyrazol-4-yl]-N-[3-chloro-4-[4-(piperidine-4-carbonyl)piperazine-1-carbonyl]phenyl]-1-methylimidazole-2-carboxamide;

N-[3-chloro-4-[4-(piperidine-4-carbonyl)piperazine-1-carbonyl]phenyl]-5-[1-(4,5-diamino-2-pyridyl)-3-(trifluoromethyl)pyrazol-4-yl]-1-methyl-imidazole-2-carboxamide;

N-[6-[4-[2-[[3-chloro-4-(4-isonipecotoylpiperazine-1-carbonyl)phenyl]carbamoyl]-3-methyl-imidazol-4-yl]-3-(trifluoromethyl)pyrazol-1-yl]-3-pyridyl]isonipecotamide; and 5-[1-[5-(2-aminoethylamino)-2-pyridyl]-3-(trifluoromethyl)pyrazol-4-yl]-N-[3-chloro-4-(4-isonipecotoylpiperazine-1-carbonyl)phenyl]-1-methyl-imidazole-2-carboxamide.

19. A pharmaceutical composition comprising a compound of claim 1, or a pharmaceutically acceptable salt thereof, and a therapeutically inert carrier.

20. A method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, the method comprising administering a compound of claim 1, or a pharmaceutically acceptable salt thereof, to a mammal in need thereof.

* * * * *